(12) United States Patent
Fujiwara et al.

(10) Patent No.: US 9,645,491 B2
(45) Date of Patent: May 9, 2017

(54) SULFONIUM SALT, CHEMICALLY AMPLIFIED RESIST COMPOSITION, AND PATTERNING PROCESS

(71) Applicant: SHIN-ETSU CHEMICAL CO., LTD., Tokyo (JP)

(72) Inventors: Takayuki Fujiwara, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/163,553

(22) Filed: May 24, 2016

(65) Prior Publication Data

US 2016/0349612 A1  Dec. 1, 2016

(30) Foreign Application Priority Data

May 27, 2015 (JP) .................. 2015-107652

(51) Int. Cl.
*G03F 7/004* (2006.01)
*G03F 7/038* (2006.01)
(Continued)

(52) U.S. Cl.
CPC .......... *G03F 7/0045* (2013.01); *C07C 309/06* (2013.01); *C07C 309/12* (2013.01); *C07C 323/20* (2013.01); *C07C 381/12* (2013.01); *C07D 333/46* (2013.01); *C07D 335/02* (2013.01); *C08F 220/18* (2013.01); *C08F 220/28* (2013.01); *C08F 220/30* (2013.01); *C08F 220/38* (2013.01);
(Continued)

(58) Field of Classification Search
CPC ...... G03F 7/004; G03F 7/0045; G03F 7/0046; G03F 7/0397; G03F 7/26; G03F 7/325; G03F 7/2041; H01L 21/0274; C07C 381/12; C07C 309/12; C07C 309/06; C08F 220/38; C08F 220/18; C08F 220/28; C08F 220/30; C08F 220/36
USPC .... 430/270.1, 322, 325, 329, 330, 331, 396, 430/913, 942, 296; 526/243, 268, 281; 562/108
See application file for complete search history.

(56) References Cited

U.S. PATENT DOCUMENTS 7,511,169 B2  3/2009  Ohsawa et al.
7,875,746 B2  1/2011  Wada
(Continued)

FOREIGN PATENT DOCUMENTS

EP  1635 218 A2  3/2006
JP  2006-84530 A  3/2006
(Continued)

OTHER PUBLICATIONS

Dammel et al., "193 nm Immersion Lithography—Taking the Plunge". Journal of Photopolymer Science and Technology, vol. 17, No. 4, pp. 587-601 (2004).

*Primary Examiner* — Amanda C Walke
(74) *Attorney, Agent, or Firm* — Westerman, Hattori, Daniels & Adrian, LLP

(57) ABSTRACT

A sulfonium salt having both anion and cation moieties in the molecule functions as a photoacid generator and is compatible with other components. A resist composition comprising the sulfonium salt has the advantages of reduced acid diffusion and forms a pattern with a good balance of sensitivity, MEF and DOF, less outgassing, and minimal defects.

17 Claims, 1 Drawing Sheet

(51) Int. Cl.

| | | |
|---|---|---|
| *G03F 7/16* | (2006.01) | |
| *G03F 7/20* | (2006.01) | |
| *G03F 7/38* | (2006.01) | |
| *G03F 7/32* | (2006.01) | |
| *G03F 7/039* | (2006.01) | |
| *C07C 323/20* | (2006.01) | |
| *C07D 333/46* | (2006.01) | |
| *C07D 335/02* | (2006.01) | |
| *C08F 220/38* | (2006.01) | |
| *C07C 309/12* | (2006.01) | |
| *H01L 21/027* | (2006.01) | |
| *C07C 381/12* | (2006.01) | |
| *C07C 309/06* | (2006.01) | |
| *C08F 220/18* | (2006.01) | |
| *C08F 220/30* | (2006.01) | |
| *C08F 220/28* | (2006.01) | |

(52) U.S. Cl.
CPC .......... *G03F 7/0382* (2013.01); *G03F 7/0395* (2013.01); *G03F 7/168* (2013.01); *G03F 7/2041* (2013.01); *G03F 7/2053* (2013.01); *G03F 7/322* (2013.01); *G03F 7/325* (2013.01); *G03F 7/38* (2013.01); *H01L 21/0274* (2013.01)

(56) References Cited

U.S. PATENT DOCUMENTS

| | | |
|---|---|---|
| 7,919,226 B2 | 4/2011 | Ohsawa et al. |
| 8,034,547 B2 | 10/2011 | Tsubaki et al. |
| 8,173,354 B2 | 5/2012 | Ohsawa et al. |
| 8,227,183 B2 | 7/2012 | Tsubaki et al. |
| 8,241,840 B2 | 8/2012 | Tsubaki et al. |
| 8,853,441 B2 * | 10/2014 | Oh .................. C07C 309/06 430/270.1 |
| 8,865,919 B2 * | 10/2014 | Joo .................. C07D 307/64 549/60 |
| 2010/0063302 A1 * | 3/2010 | Muraoka .......... C07D 327/10 549/18 |
| 2014/0005301 A1 * | 1/2014 | Kunimoto .......... C07D 333/50 523/400 |
| 2014/0315130 A1 * | 10/2014 | Gonsalves .......... C07C 309/65 430/281.1 |
| 2015/0044509 A1 * | 2/2015 | Kunimoto .......... C09D 11/02 428/704 |
| 2015/0301449 A1 * | 10/2015 | Ohashi .................. G03F 7/027 430/285.1 |

FOREIGN PATENT DOCUMENTS

| | | |
|---|---|---|
| JP | 2006-84660 A | 3/2006 |
| JP | 2006-330098 A | 12/2006 |
| JP | 2007-145797 A | 6/2007 |
| JP | 2008-281974 A | 11/2008 |
| JP | 2008-281975 A | 11/2008 |
| JP | 2010-8912 A | 1/2010 |
| JP | 4554665 B2 | 9/2010 |
| JP | 2011-16746 A | 1/2011 |

* cited by examiner

SULFONIUM SALT, CHEMICALLY AMPLIFIED RESIST COMPOSITION, AND PATTERNING PROCESS

CROSS-REFERENCE TO RELATED APPLICATION

This non-provisional application claims priority under 35 U.S.C. §119(a) on Patent Application No. 2015-107652 filed to in Japan on May 27, 2015, the entire contents of which are hereby incorporated by reference.

TECHNICAL FIELD

This invention relates to a sulfonium salt of specific structure, a chemically amplified resist composition comprising the salt, and a pattern forming process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using an ArF excimer laser as the light source is requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkali development and organic solvent development is under study. As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perflucrooctanesulfonic acid (PFOS), which are considered problematic with respect to their non-degradability. biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 refers to the is prior art PAGs capable of generating α,α-difluoroalkanesulfonic acid, such as di(4-t-butylphenyl)-iodonium 1,1-difluoro-2-(1-naphthyl)ethanesulfonate and PAGs capable of generating α,α,ββ-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

Incorporating a bulky substituent or polar group into PAG is effective for suppressing acid diffusion. Patent Document 4 describes a PAG having 2-acyloxy-1,1,3,3,3-pentafluoropropane-1-sulfonic acid which is fully soluble and stable in resist solvents and allows for a wide span of molecular design. In particular, a PAG having incorporated therein a bulky substituent, 2-(1-adamantyloxy)-1,1,3,3,3-pentafluoropropane-1-sulfonic acid is characterized by slow acid diffusion. A resist composition comprising this PAG, however, is still insufficient in precise control of acid diffusion, and its lithography performance is unsatisfactory when evaluated totally in terms of MEF, pattern profile and sensitivity.

As resist patterns with high resolution are currently required, not only lithography characteristics including pattern profile, contrast, MEEF and roughness are necessary, but improvements in (surface) defects of resist patterns as developed become more requisite. The surface defects refer to all faults which are detected when the resist pattern as developed is observed from just above by a surface flaw detector (trade name KLA by KLA-Tencor Co., Ltd.). Such faults include scum, foam, debris, and bridges between resist pattern features after development. These defects form because PAG or other resist components have low solubility in casting solvent and leave undissolved residues after developer immersion.

As the PAG which is effective for controlling acid diffusion, for example, Patent Document 5 describes a PAG of betaine structure (having both cation and anion structures in one molecule) capable of generating perfluoroalkanesulfonic acid. When the PAG of betaine structure generates an acid, it becomes an apparently giant compound by forming a salt compound between molecules or with another PAG if added concurrently. As a result, there are presumably obtained advantages including improved dissolution contrast, suppressed acid diffusion, and improved lithography performance. Although the PAG of betaine structure has an acid diffusion suppressing ability and advantages like reduced outgassing, it still suffers from a low solubility in organic solvent and tends to form defects.

As the PAG which has a high solubility in organic solvent and causes less defect development, there are known compounds containing an anion having an acid generating site of imide acid or methide acid structure. Patent Documents 6 to 9 describe PAGs of imide or methide acid type. However, the RAGS described therein allow for noticeable acid diffusion, and their lithography performance is unsatisfactory to the current requirement to form resist patterns at high resolution.

CITATION LIST

Patent Document 1: JP-A 2008-281974
Patent Document 2: JP-A 2008-281975
Patent Document 3: JP 4554665 (U.S. Pat. No. 8,227,183)
Patent Document 4: JP-A 2007-145797
Patent Document 5: JP-A 2011-016746
Patent Document 6: JP-A 2010-008912
Patent Document 7: JP-A 2006-084660
Patent Document 8: JP-A 2006-084530
Patent Document 9: JP-A 2006-330098 (U.S. Pat. No. 7,875,746)
Non-Patent Document 1: Journal of Photopolymer Science and Technology, Vol. 17, No. 4, p587 (2004)

Disclosure of the Invention

The photoacid generator (PAG) produces an acid which must satisfy many requirements including a sufficient acid strength to cleave acid labile groups in a resist material, high sensitivity, stability in the resist material during shelf storage, adequately controlled diffusion in the resist material, low volatility, minimal foreign matter left after development and resist removal, and good degradability in that it is decomposed away after the expiration of its role in lithography without imposing a load to the environment. In the case of ArF immersion lithography, minimal dissolution in water is also desirable. None of prior art PAGs satisfy these requirements.

An object of the invention is to provide a photoacid generator which is fully compatible with resist components, controlled in acid diffusion, and minimized in outgassing which causes contamination of the exposure tool; a chemically amplified resist composition comprising the photoacid generator, which forms a pattern with advantages including sensitivity, MEF, DOF, and minimal defects, when processed by photolithography using high-energy radiation such as ArF excimer laser, EB or EUV as the light source; and a patterning process using the resist composition.

The inventors have found that the above and other objects are attained by a photoacid generator in the form of a sulfonium salt having a specific structure, and a resist composition comprising the photoacid generator is a quite effective resist material for precise micropatterning.

In one aspect, the invention provides a sulfonium salt having the formula (1).

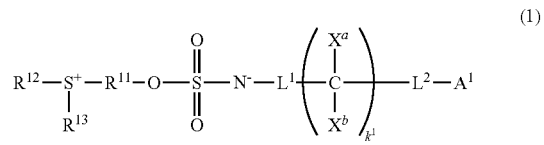

Herein $R^{11}$ is a straight, branched or cyclic $C_1$-$C_{30}$ divalent hydrocarbon group which may contain a heteroatom. $R^{12}$ and $R^{13}$ are each independently a straight, branched or cyclic $C_1$-$C_{20}$ monovalent hydrocarbon group which may contain a heteroatom, any two or more of $R^{11}$, $R^{12}$ and $R^{13}$ may bond together to form a ring with the sulfur atom to which they are attached, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond. $A^1$ is hydrogen, halogen or a straight, branched or cyclic $C_1$-$C_{20}$ monovalent hydrocarbon group which may contain a heteroatom, $X^b$ and $X^b$ are each independently hydrogen, fluorine or trifluoromethyl, at least one of $X^a$ and $X^b$ is fluorine or trifluoromethyl, and $k^1$ is an integer of 1 to 4.

Preferably, $L^1$ is a sulfonyl bond. More preferably, $L^2$ is a single bond and $A^1$ is hydrogen, fluorine or trifluoromethyl.

A photoacid generator comprising the sulfonium salt defined above is also provided.

In another aspect, the invention provides a chemically amplified resist composition comprising the photoacid generator defined above.

In a preferred embodiment, the resist composition further comprises a polymer comprising recurring units having the formula (2) and recurring units having the formula (3) as base resin.

Herein $R^A$ is hydrogen, fluorine, methyl or trifluoromethyl, $Z^A$ is a single bond, phenylene group, naphthylene group or —C(=O)—O—$Z^1$—, $Z^1$ is a straight, branched or cyclic $C_1$-$C_{10}$ alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultana ring and carboxylic anhydride.

The resist composition may further comprise a second photoacid generator other than the photoacid generator defined above. Preferably, the second photoacid generator has the formula (4) or (5).

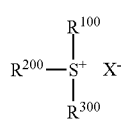

(4)

Herein $R^{100}$, $R^{200}$ and $R^{300}$ are each independently a straight, branched or cyclic $C_1$-$C_{20}$ monovalent hydrocarbon group which may contain a heteroatom, any two or more of $R^{100}$, $R^{200}$ and $R^{300}$ may bond together to form a ring with the sulfur atom to which they are attached, $X^-$ is an anion selected from the formulae (4A) to (4D):

(4A)

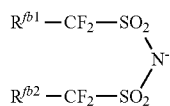

(4B)

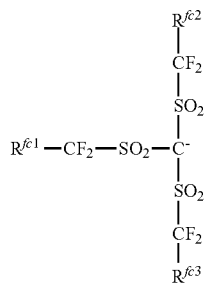

(4C)

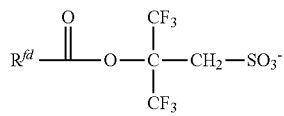

(4D)

wherein $R^{fa}$, $R^{fb1}$, $R^{fb2}$, $R^{fc1}$ $R^{fc2}$ and $R^{fc3}$ are each independently fluorine or a straight, branched or cyclic $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a straight, branched or cyclic $C_1$-$C_{40}$ monovalent hydrocarbon group which may contain a heteroatom.

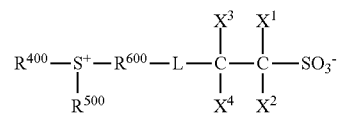

(5)

Herein $R^{400}$ and $R^{500}$ are each independently a straight, branched or cyclic $C_1$-$C_{30}$ monovalent hydrocarbon group which may contain a heteroatom, $R^{600}$ is a straight, branched or cyclic $C_1$-$C_{30}$ divalent hydrocarbon group which may contain a heteroatom, any two or more of $R^{400}$, $R^{500}$ and $R^{600}$ may bond together to form a ring with the sulfur atom to which they are attached, L is a single bond or a straight, branched or cyclic $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl.

The resist composition may further comprise a compound having the formula (6) or (7).

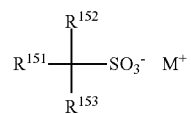

(6)

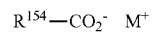

(7)

Herein $R^{151}$, $R^{152}$ and $R^{153}$ are each independently hydrogen, halogen exclusive of fluorine, or a straight, branched or cyclic $C_1$-$C_{40}$ monovalent hydrocarbon group which may contain a heteroatom, any two or more of $R^{151}$, $R^{152}$ and $R^{153}$ may bond together to form a ring with the carbon atom to which they are attached, $R^{154}$ is a straight, branched or cyclic $C_1$-$C_{40}$ monovalent hydrocarbon group which may contain a heteroatom, and $M^+$ is an onium cation.

The resist composition may further comprise a quencher, and a surfactant which is insoluble or substantially insoluble in water and soluble in alkaline developer, and/or a surfactant which is insoluble or substantially insoluble in water and alkaline developer.

In a further aspect, the invention provides a pattern forming process comprising the steps of applying the resist composition defined above onto a substrate, prebaking to form a resist film, exposing a selected region of the resist film to KrF excimer laser. ArF excimer laser, EB or EUV, baking, and developing the exposed resist film in a developer.

In one embodiment, the developing step uses an alkaline aqueous solution as the developer, thereby forming a positive pattern in which an exposed region of the resist film is dissolved away and an unexposed region of the resist film is not dissolved.

In another embodiment, the developing step uses an organic solvent as the developer, thereby forming a negative pattern in which an unexposed region of the resist film is dissolved away and an exposed region of the resist film is not dissolved.

Typically, the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

The exposure step may be carried out by immersion lithography while a liquid having a refractive index of at least 1.0 is held between the resist film and a projection lens. In this embodiment, the process may further comprise the step of coating a protective film on the resist film prior to the exposure step, wherein immersion lithography is carried out while the liquid is held between the protective film and the projection lens.

Advantageous Effects of Invention

The inventive sulfonium salt is fully compatible with resist components and produces less outgassing. When processed by lithography, a chemically amplified resist composition comprising the sulfonium salt forms a pattern with a high sensitivity, improved MEF, improved DOF, and minimal defects.

DESCRIPTION OF THE PREFERRED EMBODIMENTS

Figure 1A:
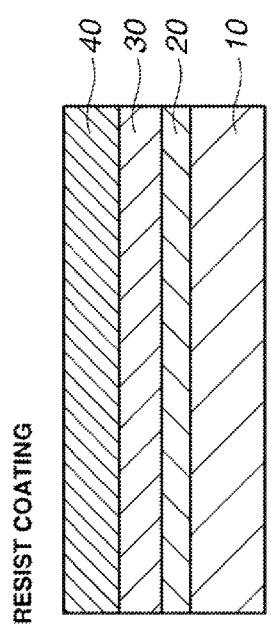
FIGS. 1A, 1B and 1C show in cross-sectional view a patterning process according one embodiment of the invention, FIG. 1A showing a resist film disposed on a substrate, FIG. 1B showing the resist film during exposure, and FIG. 1C showing the resist film during organic solvent development.

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond; Me stands for methyl, Ac for acetyl, and Ph for phenyl. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.
EB: electron beam
UV: ultraviolet
EUV: extreme ultraviolet
PAG: photoacid generator
PEB: post-exposure bake
MEF: mask error factor
MEEF: mask error enhancement factor
DOF: depth of focus The term "high-energy radiation" is intended to encompass KrF excimer laser, ArF excimer laser, EB, and EUV.

Sulfonium Salt

The invention provides a sulfonium salt having the formula (1).

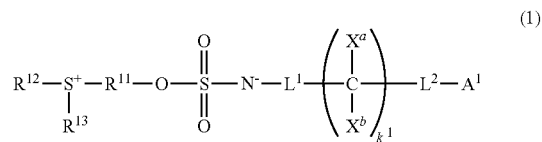

In formula (1), $R^{11}$ is a straight, branched or cyclic $C_1$-$C_{30}$ divalent hydrocarbon group which may contain a heteroatom. Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic hydrocarbon groups such as cyclopentanediyl, cyclohexanediyl, norbornanediyl, and adamantanediyl and unsaturated cyclic hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen Intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical. Preferred are phenylene, naphthylene, and substituted forms thereof in which one or more or even all hydrogen atoms are replaced by functional radicals such as alkyl, alkoxy, acyl and amino.

$R^{12}$ and $R^{13}$ are each independently a straight, branched or cyclic $C_1$-$C_{20}$ monovalent hydrocarbon group which may contain a heteroatom. Suitable monovalent hydrocarbon groups include alkyl, alkenyl, oxoalkyl, aryl, aralkyl, and aryloxoalkyl groups. Specifically, suitable alkyl groups include methyl, ethyl, propyl, isopropyl, n-butyl, s-butyl, t-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Suitable alkenyl groups include vinyl, allyl, propenyl, butenyl, hexenyl and cyclohexenyl. Suitable oxoalkyl groups include 2-oxocyclopentyl, 2-oxocyclohexyl, 2-oxopropyl, 2-oxoethyl, 2-cyclopentyl-2-oxoethyl, 2-cyclohexyl-2-oxoethyl, and 2-(4-methylcyclohexyl)-2-oxoethyl. Suitable aryl groups include phenyl, naphthyl and thienyl; alkoxyphenyl groups such as 4-hydroxyphenyl, 4-methoxyphenyl, 3-methoxyphenyl, 2-methoxyphenyl, 4-ethoxyphenyl, 4-t-butoxyphenyl, 3-t-butoxyphenyl; alkylphenyl groups such as 2-methylphenyl, 3-methylphenyl, 4-methylphenyl 4-ethylphenyl, 4-t-butylphenyl, 4-n-butylphenyl, and 2,4-dimethylphenyl; alkylnaphthyl groups such as methylnaphthyl and ethylnaphthyl; alkoxynaphthyl groups such as methoxynaphthyl, ethoxynaphthyl, n-propoxynaphthyl and n-butoxynaphthyl; dialkylnaphthyl groups such as dimethylnaphthyl and diethylnaphthyl; and dialkoxynaphthyl groups such as dimethoxynaphthyl and diethoxynaphthyl. Suitable aralkyl groups include benzyl, 1-phenylethyl and 2-phenylethyl. Suitable aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl.

Any two or more of $R^{11}$, $R^{12}$ and $R^{13}$ may bond together to form a ring with the sulfur atom to which they are attached. Examples of the ring structure thus formed include structures of the formulae shown below, and substituted forms of these is structures in which at least one hydrogen or carbon atom is replaced by a heteroatom-containing radical, methyl, ethyl, isopropyl, s-butyl, t-butyl, methoxy, t-butoxy, 2-methoxyethoxy, acetyl or the like. Notably, exemplary heteroatoms are oxygen, nitrogen and sulfur.

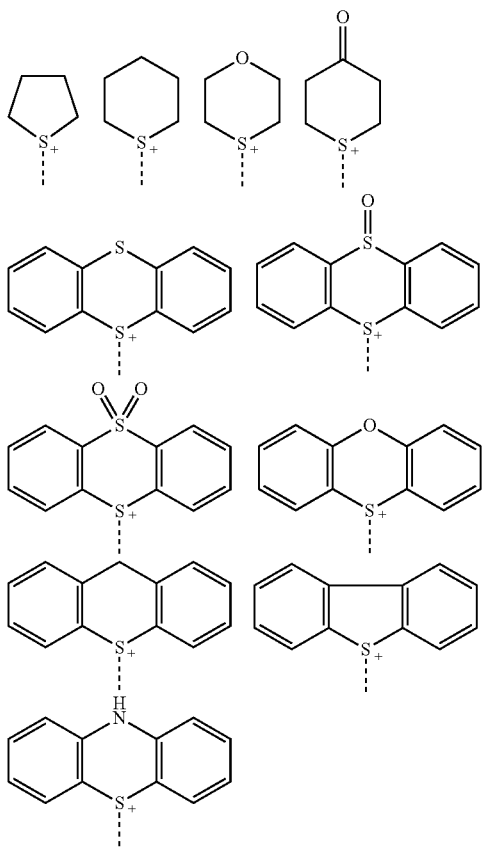

In formula (1), $L^1$ is a carbonyl bond (—CO—), sulfonyl bond (—SO$_2$—) or sulfinyl bond (—S(=O)—). Of these, carbonyl and sulfonyl bonds are preferred because of ease of synthesis and availability of starting reactant. A sulfonyl bond is most preferred when the acidity of the acid generated after exposure is taken into account.

In formula (1), $L^2$ is a single bond, ether bond (—O—), carbonyl bond, ester bond (—C$_2$—), amide bond (—C(=O) NR$^{20}$—), sulfide bond, sulfinyl bond, sulfonyl bond, sulfonic acid ester bond (—SO$_3$—), sulfinamide bond, sulfonamide bond (—SO$_2$NR$^{20}$—), carbamate bond or carbonate bond. Inter alia, a single bond, ether bond, ester bond, amide bond, sulfonic acid ester bond, and sulfonamide bond are preferred, with a single bond, ether bond, ester bond and amide bond being more preferred. Herein $R^{20}$ is hydrogen or a straight, branched or cyclic $C_1$-$C_{20}$ monovalent hydrocarbon group which may contain a heteroatom. Suitable monovalent hydrocarbon groups include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo [5.2.1.0$^{2.6}$]decanyl, adamantyl and adamantylmethyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

In formula (1), $A^1$ is hydrogen, halogen or a straight, branched or cyclic $C_1$-$C_{20}$ monovalent hydrocarbon group which may contain a heteroatom. Suitable monovalent hydrocarbon groups include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo [5.2.1.0$^{2.6}$]decanyl, adamantyl and adamantylmethyl. Also included are the foregoing groups in which at least one hydrogen atom is substituted by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

In formula (1), $X^a$ and $X^b$ are each independently hydrogen, fluorine or trifluoromethyl, with the proviso that at least one of $X^a$ and $X^b$ is fluorine or trifluoromethyl. Preferably both $X^a$ and $X^b$ are fluorine. The subscript $k^1$ is an integer of 1 to 4.

Of the sulfonium salts having formula (1), those wherein $L^1$ is a sulfonyl bond are preferred. That is, sulfonium salts having the following formula are preferred.

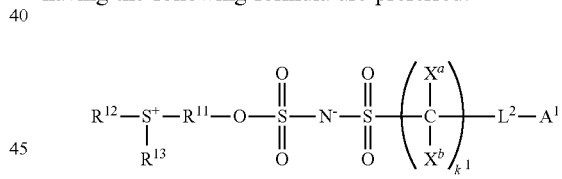

Herein $R^{11}$, $R^{12}$, $R^{13}$, $X^a$, $X^b$, $A^1$, $L^2$, and $k^1$ are as defined above. When $k^1$ is 2, 3 or 4, it is preferred that at least one fluorine atom or trifluoromethyl group be attached to α-carbon relative to the sulfonyl bond.

Because of easy and inexpensive synthesis, sulfonium salts of the above formula wherein $L^2$ is a single bond and $A^1$ is hydrogen, fluorine or trifluoromethyl are more preferred. That is, sulfonium salts of the following formula are more preferred.

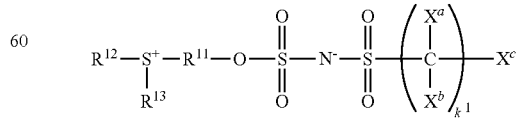

Herein $R^{11}$, $R^{12}$, $R^{13}$, $X^a$, $X^b$, and $k^1$ are as defined above, and $X^c$ is hydrogen, fluorine or trifluoromethyl. Notably, at least one of $X^a$, $X^b$, and $X^c$ is fluorine or trifluoromethyl.

When $k^1$ is 2, 3 or 4, it is preferred that at least one fluorine atom or trifluoromethyl group be attached to α-carbon relative to the sulfonyl bond. It is more preferred that $X^a$, $X^b$, and $X^c$ be fluorine. It is most preferred from the standpoint of availability of starting reactants that $k^1$ be 1 or 4, that is, trifluoromethyl or nonafluorobutyl be bonded to the sulfonyl group. If $k^1$ is equal to or more than 5, lithography performance may be degraded by an increase of acid diffusion.

Exemplary structures of the sulfonium salt having formula (1) are shown below, but not limited thereto.

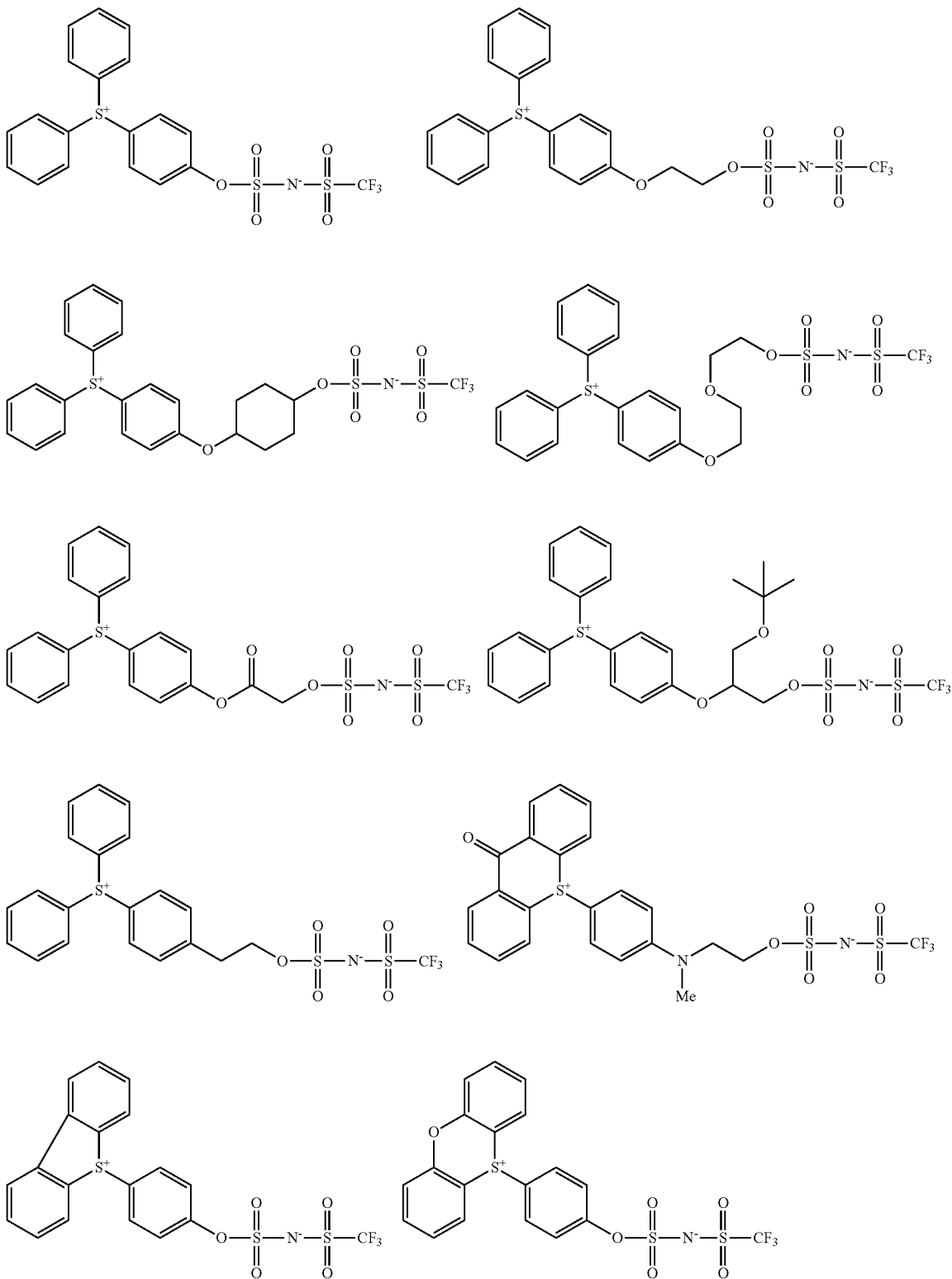

-continued
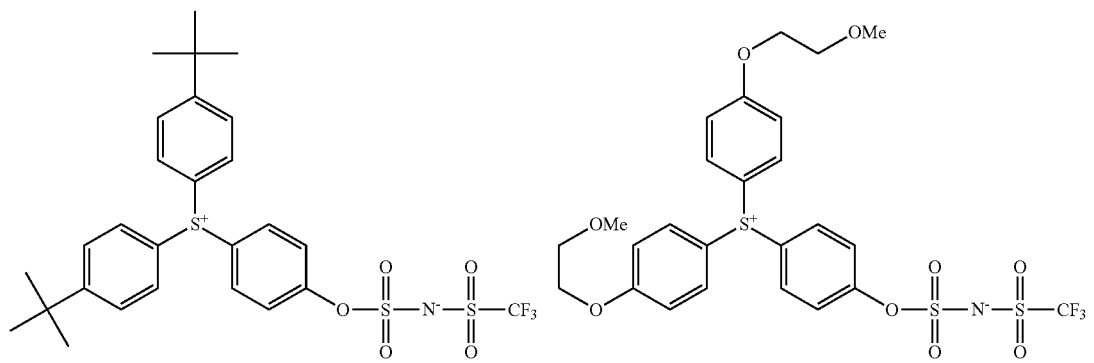
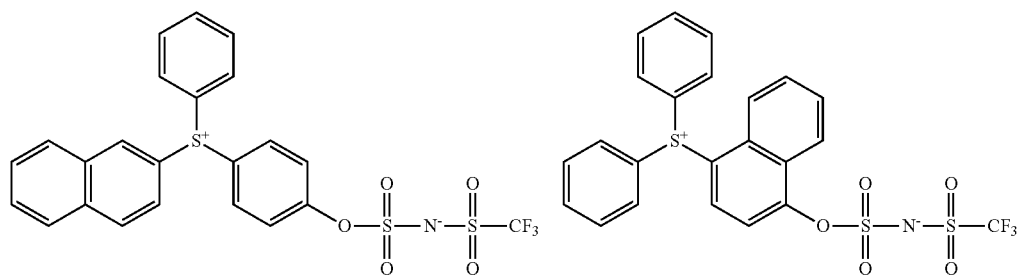
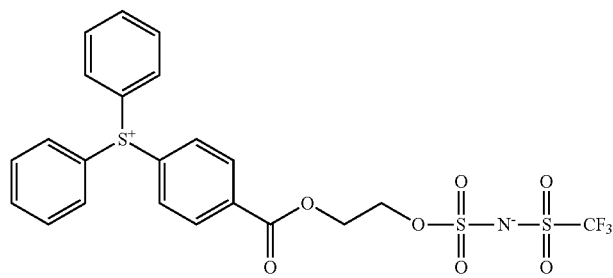
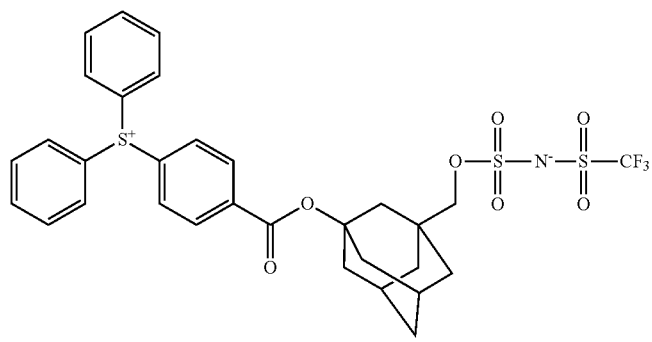
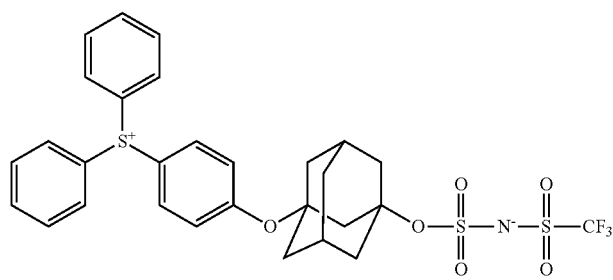

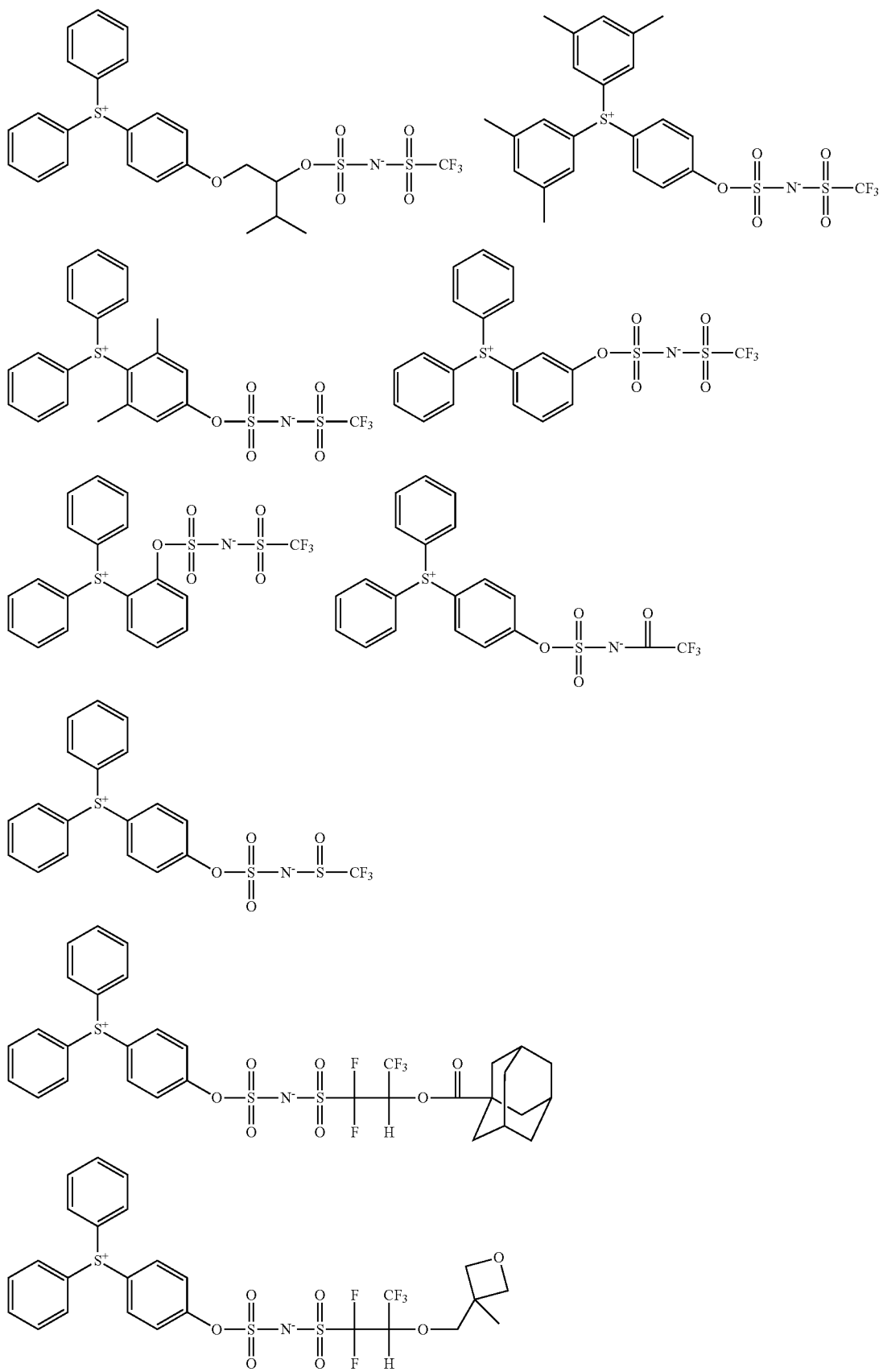

-continued
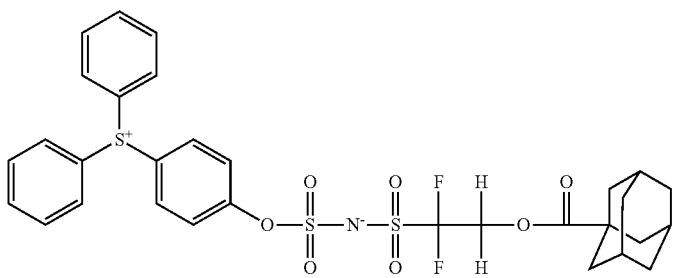
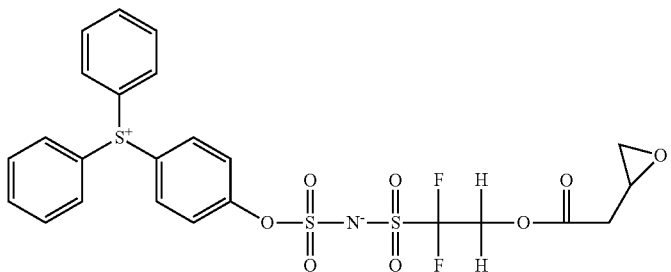
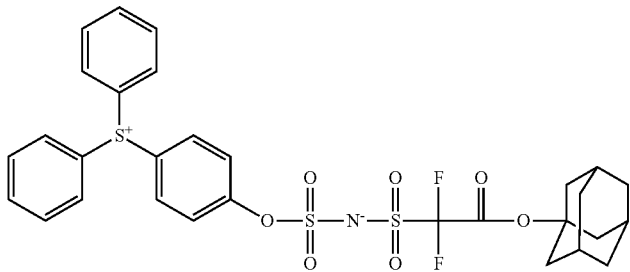
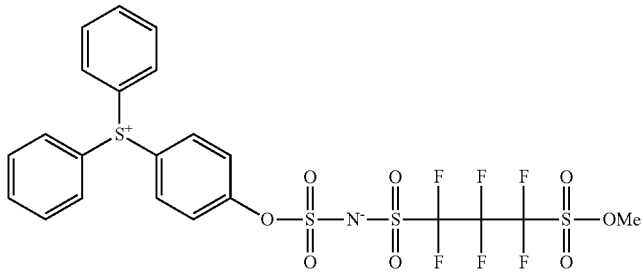
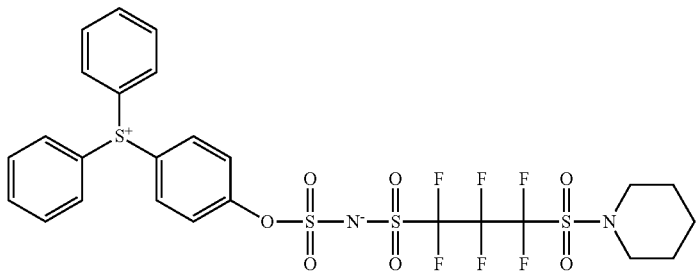
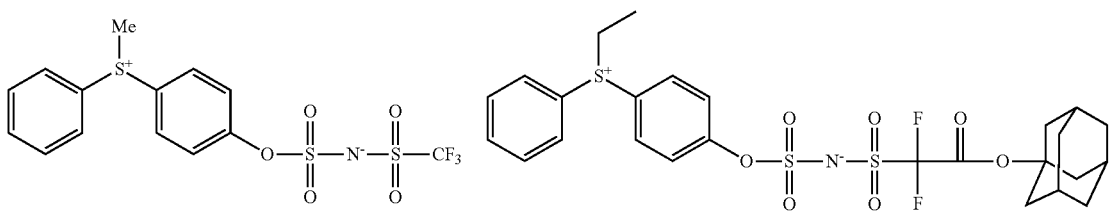

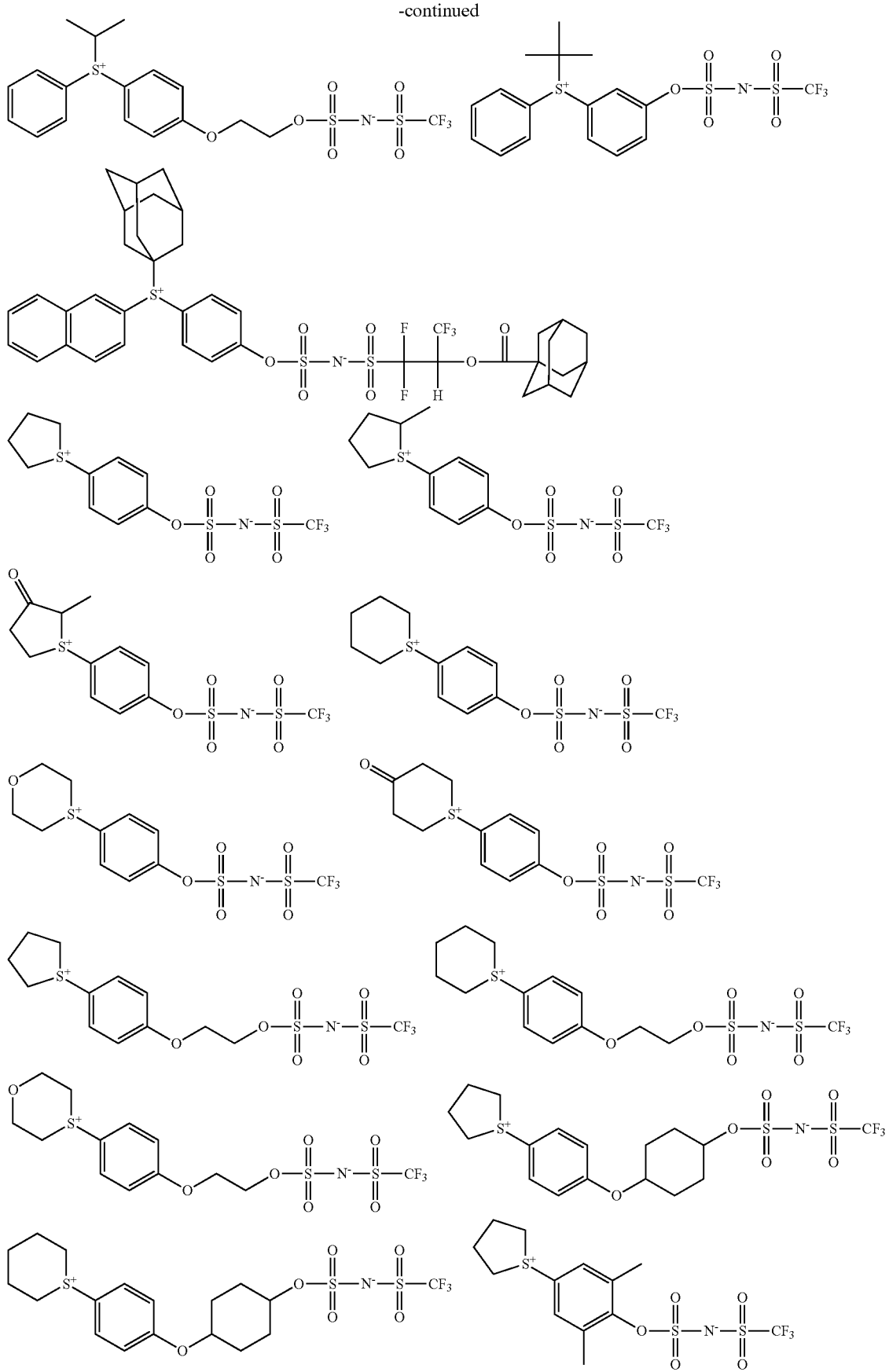

-continued
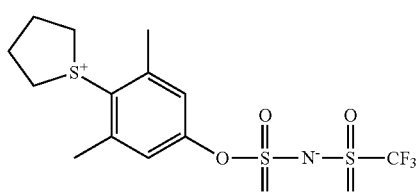
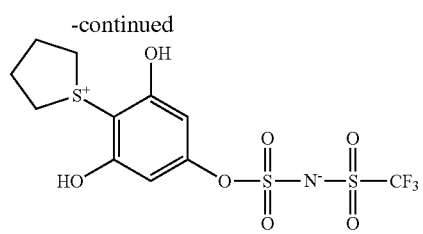
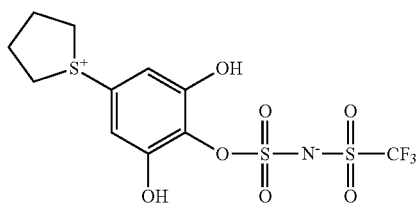
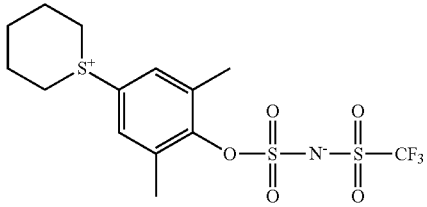
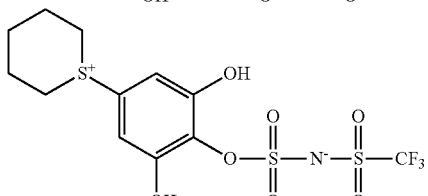
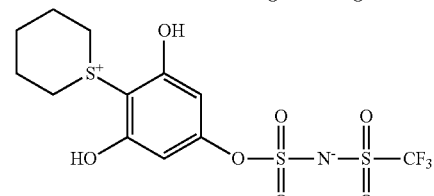
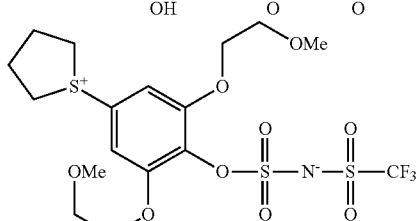
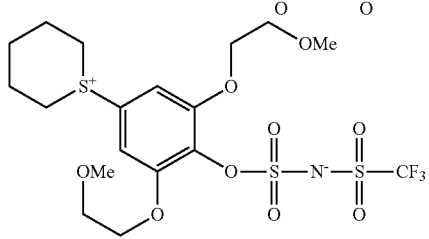
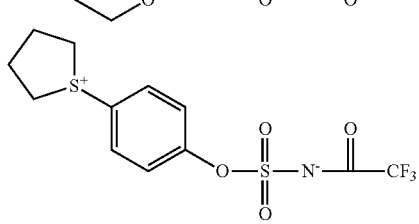
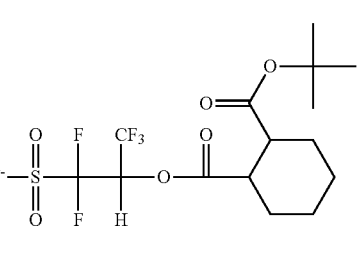
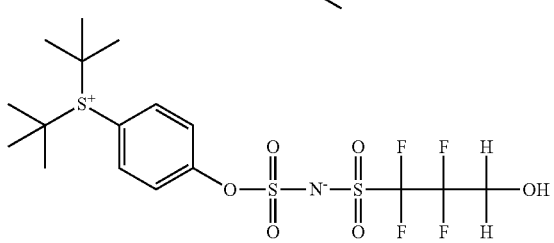
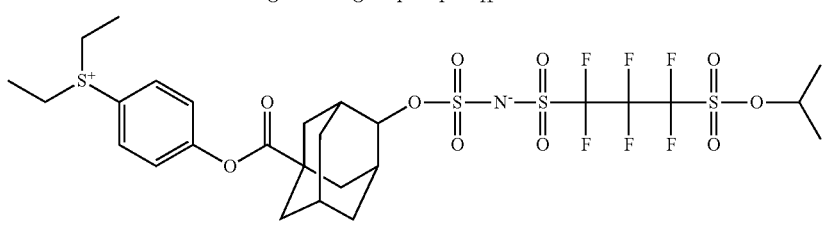

-continued
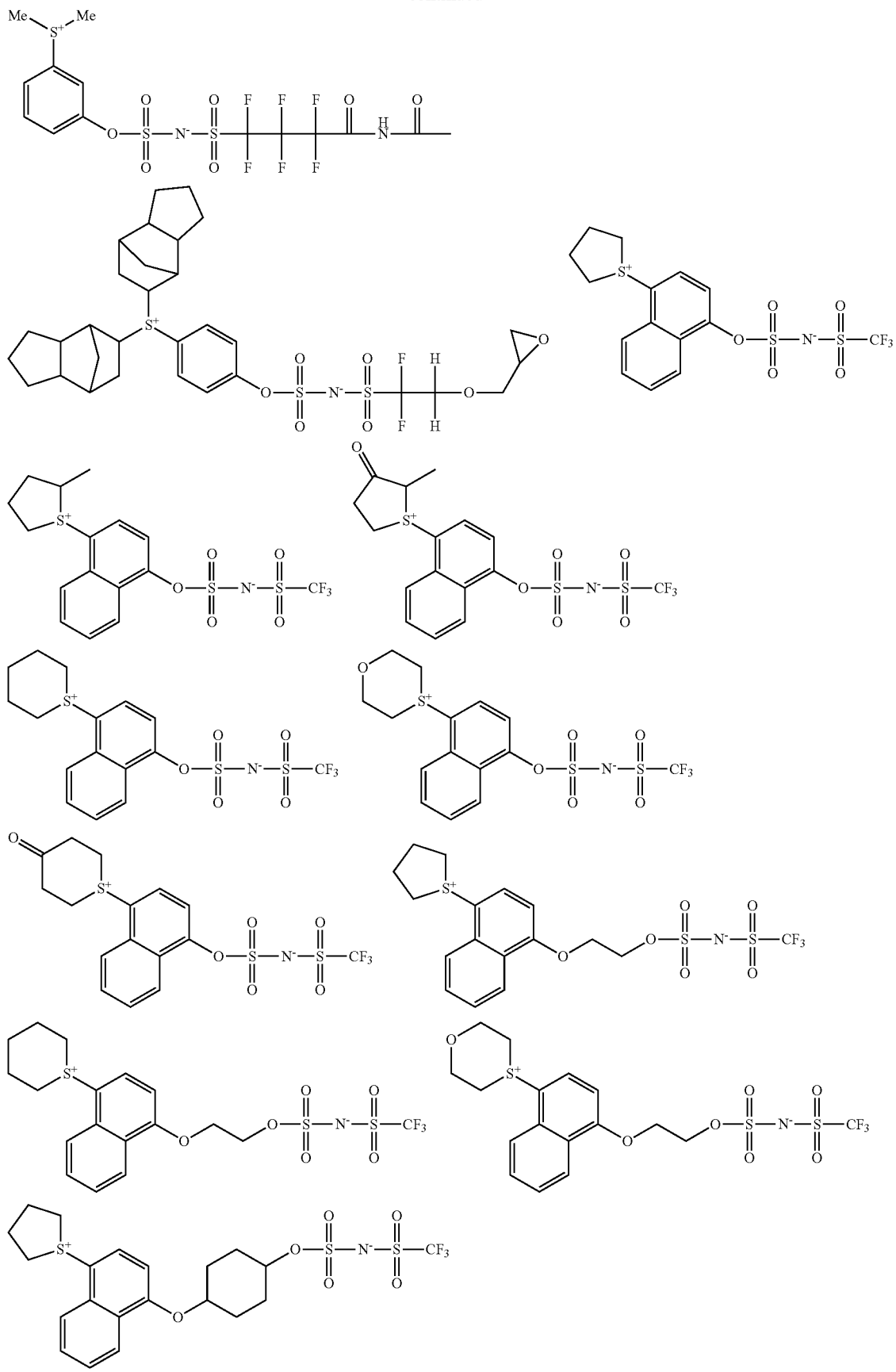

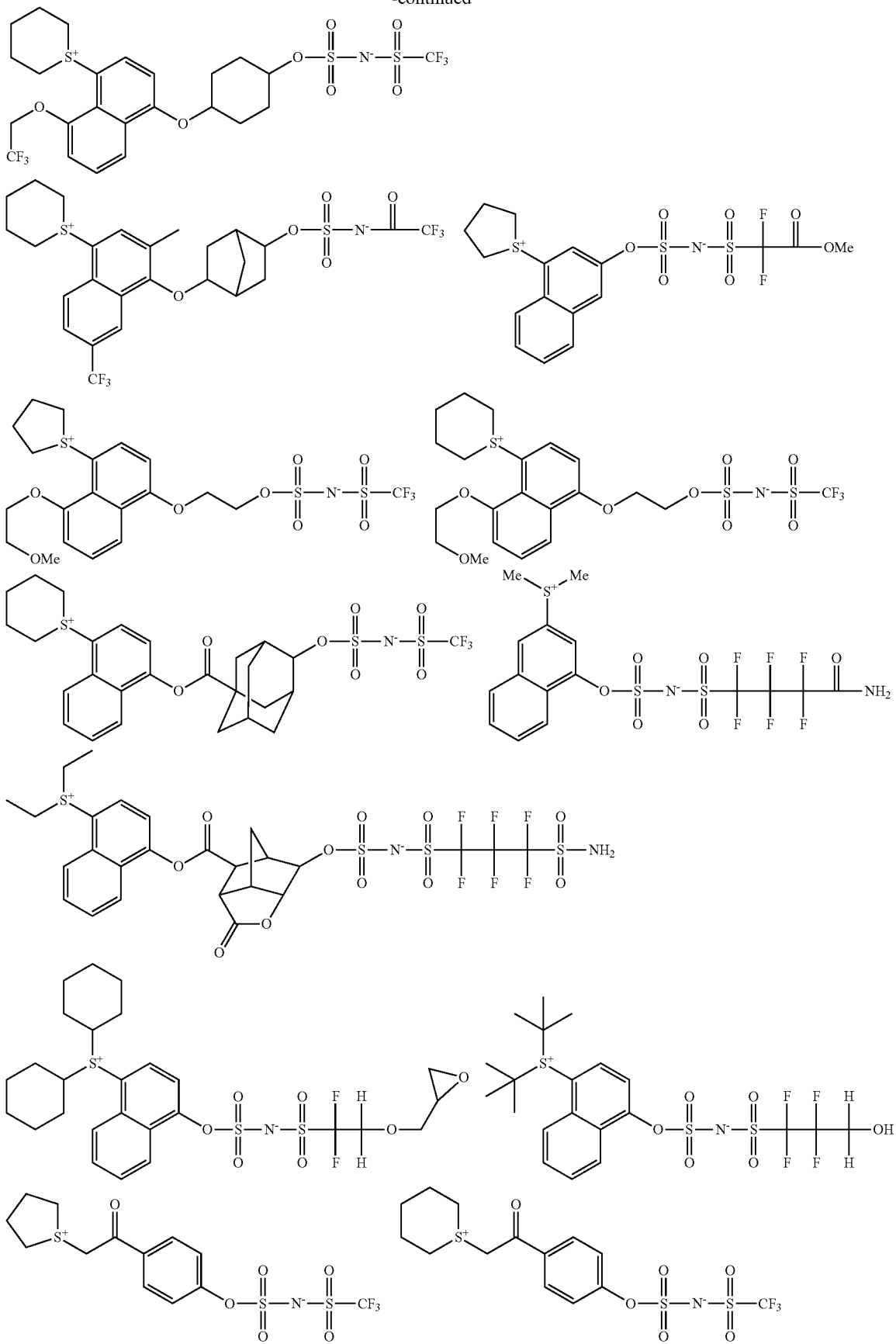

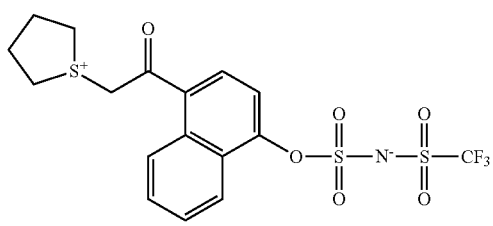
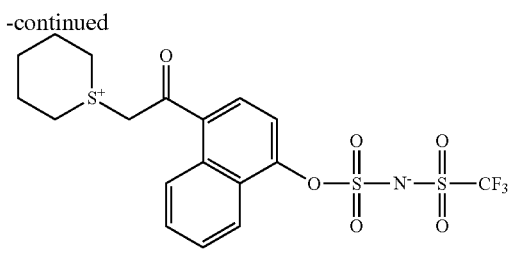
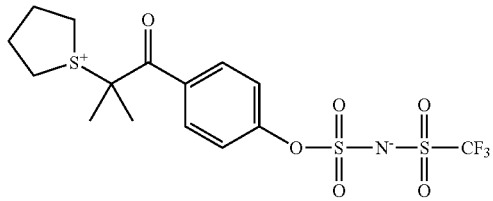
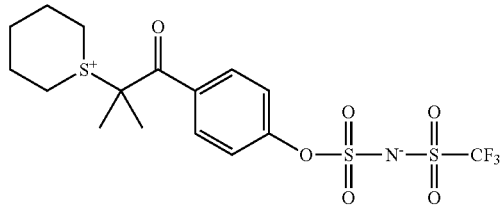
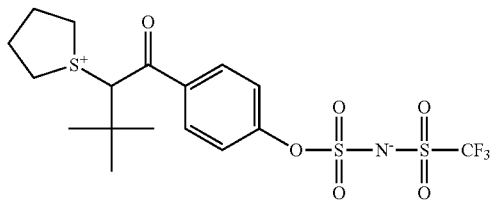
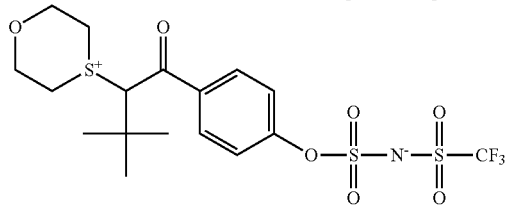
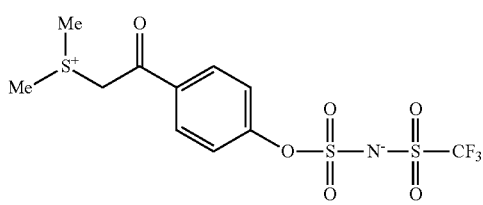
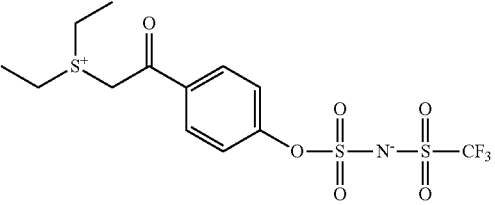
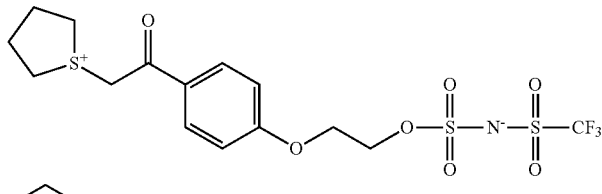
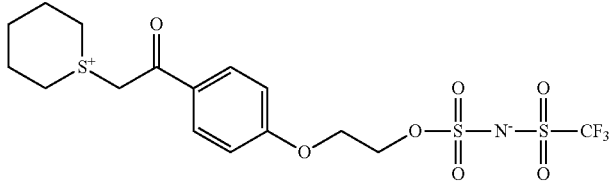
The inventive sulfonium salt may be synthesized according to the following Scheme 1, for example, although the synthesis route is not limited thereto.
Scheme 1
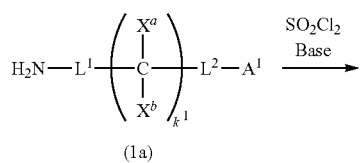
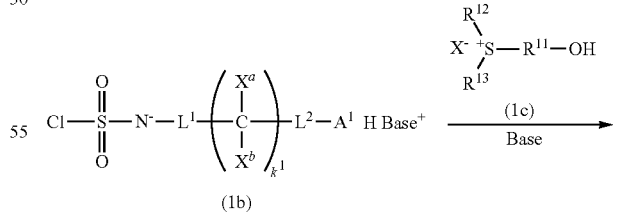
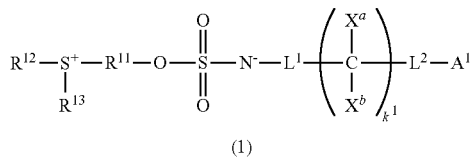

Herein $R^{11}$, $R^{12}$, $R^{13}$, $L^1$, $L^2$, $A^1$, $X^a$, $X^b$, and $k^1$ are as defined above, and $X^-$ is an anion.

First, amide compound (1a) is reacted with sulfuryl chloride under basic conditions to synthesize a sulfonyl chloride derivative (1b) having imide acid structure. At this point, the sulfonyl chloride derivative (1b) may be isolated or passed as such in one-pot to subsequent reaction without isolation.

Examples of the base which can be used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogencarbonate; metals such as sodium; metal hydrides such as sodium hydride; metal alkoxides such as sodium methoxide and potassium t-butoxide; organometallic compounds such as butyl lithium and ethylmagnesium bromide; and metal amides such as lithium diisopropylamide, which may be used alone or in admixture.

An appropriate amount of the base used is 0.5 to 10 moles, more preferably 1.0 to 4.0 moles per mole of amide compound (1a). An appropriate amount of sulfuryl chloride used is 0.5 to 3.0 moles, more preferably 0.8 to 1.5 moles per mole of amide compound (1a). Outside the range, a less amount of the base or sulfuryl chloride may be insufficient to promote reaction whereas an excessive amount may induce side reactions and increase the reactant cost.

A solvent may be used for the reaction. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; aprotic polar solvents such as N,N-dimethylformamide, N,N-dimethylacetamide and dimethyl sulfoxide, which may be used alone or in admixture.

The reaction may be carried out preferably at a temperature in the range from −70° C. to approximately the boiling point of a particular solvent used. While an appropriate reaction temperature may be selected in accordance with other reaction conditions, a temperature the range from 0° C. to approximately the boiling point of a particular solvent used is especially preferred.

Subsequently, sulfonyl chloride derivative (1b) is reacted with a hydroxy-containing sulfonium salt (1c) under basic conditions to form a desired sulfonium salt of betaine type (1).

Examples of the base which can be used herein include amines such as ammonia, triethylamine, pyridine, lutidine, collidine, and N,N-dimethylaniline; hydroxides such as sodium hydroxide, potassium hydroxide, and tetramethylammonium. hydroxide; carbonates such as potassium carbonate and sodium hydrogencarbonate; metals such as sodium; metal hydrides such as sodium hydride; metal alkoxides such as sodium methoxide and potassium t-butoxide; organometallic compounds such as butyl lithium and ethylmagnesium bromide; and metal amides such as lithium diisopropylamide, which may be used alone or in admixture.

An appropriate amount of the base used is 0.8 to 10 moles, more preferably 1.0 to 3.0 moles per mole of sulfonyl chloride derivative (1b). An appropriate amount of the hydroxy-containing sulfonium salt (1c) used is 0.3 to 5.0 moles, more preferably 0.5 to 1.5 moles per mole of sulfonyl chloride derivative (1b). Outside the range, a less amount of the base or hydroxy-containing sulfonium salt (1c) may be insufficient to promote reaction whereas an excessive amount may induce side reactions and increase the reactant cost.

A solvent may be used for the reaction. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether; ketones such as acetone and 2-butanone; esters such as ethyl acetate and butyl acetate; nitriles such as acetonitrile; aprotic polar solvents such as N,N-dimethylformamide, N,N-dimethylacetamide and dimethyl sulfoxide, which may be used alone or in admixture.

The reaction may be carried out preferably at a temperature in the range from —70° C. to approximately the boiling point of a particular solvent used. While an appropriate reaction temperature may be selected in accordance with other reaction conditions, a temperature in the range from 0° C. to approximately the boiling point of a particular solvent used is especially preferred. As alluded to previously, the reaction course from amide compound (1a) to betaine type sulfonium salt (1) may be carried out in one pot.

Alternatively, the inventive sulfonium salt may be synthesized according to the following Scheme 2.

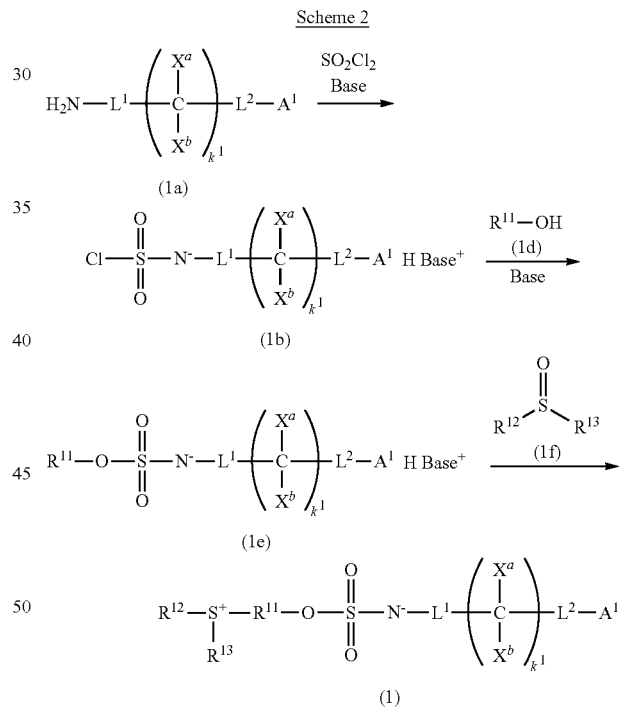

Herein $R^{11}$, $R^{12}$, $R^{13}$, $L^1$, $L^2$, $A^1$, $X^a$, $X^b$, and $k^1$ are as defined above.

After sulfonyl chloride (1b) is prepared according to Scheme 1, it is reacted with an alcohol (1d) under basic conditions according to Scheme 2 to synthesize an imide acid onium salt (1e). This is followed by addition reaction to a sulfoxide (1f) under acidic conditions to synthesize a desired sulfonium salt of betaine type (1).

The addition reaction to sulfoxide (1f) may be carried out as follows. Reference is first made to case (i) wherein $R^{11}$ is a nucleophilic group such as phenyl or naphthyl. The onium salt (1e) is combined with sulfoxide (1f) under acidic conditions, whereby addition reaction takes place. Suitable acids used herein include mineral acids such as hydrochloric acid and sulfuric acid, organic acids such as methanesulfonic acid and toluenesulfonic acid, and aprotic Lewis acids such as trimethylsilyl chloride and titanium tetrachloride.

Although the reaction takes place even in a solventless system, a solvent may be used for the reaction. Suitable solvents include hydrocarbons such as toluene, xylene, hexane and heptane; chlorinated solvents such as methylene chloride, chloroform, and dichloroethane; ethers such as diethyl ether, tetrahydrofuran and dibutyl ether: esters such as ethyl acetate and butyl acetate; nitriles such as acetonitrile; aprotic polar solvents such as N,N-dimethylformamide and N,N-dimethylacetamide: and alcohols such as methanol, ethanol and propanol, which may be used alone or in admixture.

The reaction may be carried out preferably at a temperature in the range from —70° C. to approximately the boiling point of a particular solvent used. While an appropriate reaction temperature may be selected in accordance with other reaction conditions, a temperature in the range from 0° C. to approximately the boiling point of a particular solvent used is preferred, and a temperature from 0° C. to room temperature is especially preferred. At too low temperatures, the reaction may not take place to a certain extent whereas too high temperatures may cause side reactions and a blunt selectivity of a reaction site.

Next, in case (ii) wherein $R^{11}$ is a substituent group having a α-hydrogen-containing carbonyl or sulfonyl group as partial structure, the onium salt (1e) may be converted into an enol or enolate form under basic conditions, before it is reacted with sulfoxide (1f) to form sulfonium salt (1). The reaction intermediate may be once isolated in silyl enol ether form or the like.

PAG

The sulfonium salt having formula (1) functions advantageously as photoacid generator. In the resist composition comprising the photoacid generator, the sulfonium salt generates a corresponding imide acid upon light exposure. The imide acid exhibits a pKa value of about —7.0 to —2.0. In particular, it exhibits a pKa value of about —7.0 to —4.0, i.e., a very high acidity when $L^1$ in formula (1) is a sulfonyl bond. The acidity of this order is considerably strong as compared with the α,α-difluorosulfonic acid generated by conventional PAGs used in ArF resist materials. For example, the PAG having 2-acyloxy-1,1,3,3,3-pentafluoro-propane-1-sulfonic acid, described in Patent Documents 4 and 5, generates an acid having a pKa value of about —3.0, whereas the PAG of the invention generates an imide acid having an acidity which is approximately equal to or about 10,000 times higher than the indicated value. That is, the resist composition comprising the inventive sulfonium salt as PAG has a higher sensitivity, leading to an improvement in throughput of the processing system. For the same reason, it is unlikely that the resist composition is reduced in sensitivity when the content of an acid diffusion regulator or quencher is increased. This means that the resist composition may more widely vary in formulation. As a result, a resist composition having a good balance of lithography properties including sensitivity, MEF, and DOF is available. It is noted that the pKa value is computed using ACD/ChemSketch of Advanced Chemistry Development Inc. (ACD/Labs).

As compared with resist compositions comprising PAGs capable of generating imide acid as described in Patent Documents 6 to 9, the resist composition comprising the inventive sulfonium salt has controlled acid diffusion and improved lithography properties including MEF and DOF. The mechanism is discussed below. The inventive PAG is characterized by the betaine structure, that is, a structure having both cation and anion moieties in one molecule. There is a possibility that when the PAG of betaine structure generates an acid, it becomes an apparently giant compound by forming a salt compound between molecules or with another PAG if added concurrently. As a result, presumably acid diffusion is suppressed, and lithography performance is improved. Also in formation of a negative pattern via organic solvent development, the solubility of the acid-generated region is substantially reduced by the above-mentioned mechanism, which suggests that dissolution contrast is improved, and lithography performance is improved.

Further, the inventive sulfonium salt is fully compatible with other components, which ensures to form a pattern with a minimal number of defects. As compared with a PAG of betaine structure having 2-acyloxy-1,1,3,3,3-pentafluoro-propane-1-sulfonic acid as described in Patent Document 5, the inventive sulfonium salt is fully compatible. This is because the inventive photoacid generator utilizes an imide acid (which generally tends to be more compatible than sulfonic acid) as acid-generating site, has an asymmetric structure with respect to the nitrogen atom serving as the imide acid-generating site, and contains more hydrocarbon groups.

Furthermore, the inventive sulfonium salt has the advantage of minimal outgassing after exposure and hence a least possibility to contaminate the exposure tool. In the EB or EUV lithography requiring exposure in vacuum (or reduced pressure), if PAGs as described in Patent Documents 6 to 9 are used, the acid generated upon exposure will volatilize off, failing to form a pattern of satisfactory profile. Such volatile generated acid and decomposed products of sulfonium cation (e.g., sulfides such as diphenyl sulfide) become outgases, which can cause damages to the expensive exposure tool. Since the inventive sulfonium salt has a photoacid generating site (sulfonium cation moiety) and an anion moiety within a common molecule, a sulfide which is useless and volatile is not generated after acid generation, and rather the sulfide moiety is retained as a part of the generated acid skeleton. The generation of volatile components is minimized.

Resist Composition

A further embodiment of the invention is a resist composition comprising (A) the photoacid generator in the form of the sulfonium salt having formula (1) as an essential component, (B) a base resin, and (C) an organic solvent. The composition may further comprise:

(D) a photoacid generator other than the sulfonium salt having formula (1) (also referred to as second photoacid generator), (E) a quencher, (F) a surfactant which is insoluble or substantially insoluble in water and soluble in alkaline developer, and/or a surfactant which is insoluble or substantially insoluble in water and alkaline developer (also referred to as hydrophobic resin), and (G) another component(s). Components (D), (E), (F), and (G) are optional, that is, may be added if necessary.

In the resist composition, an appropriate amount of the PAG as component (A) is 0.1 to 40 parts by weight, more preferably 0.5 to 20 parts by weight per 100 parts by weight of the base resin (B). As long as the amount is equal to or more than the lower limit, the component exerts a full function of photoacid generator. As long as the amount is equal to or less than the upper limit, there are no performance degradations including a drop of sensitivity, solubility shortage, and foreign particles.

Component (B)

The base resin used herein is preferably a polymer comprising recurring units having the formula (2) and recurring units having the formula (3).

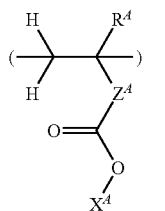
(2)

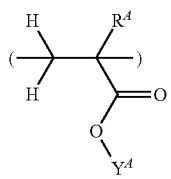
(3)

In formulae (2) and (3), $R^A$ is hydrogen, fluorine, methyl or trifluoromethyl. $Z^A$ is a single bond, phenylene group, naphthylene group or —C(=O)—O—$Z^1$—, wherein $V^1$ is a straight, branched or cyclic $C_1$-$C_{10}$ group which may contain a hydroxyl radical, ether bond, ester bond or lactone ring, or phenylene group or naphthylene group. $X^Z$ is an acid labile group. $Y^A$ is hydrogen or a polar group having at least one structure selected from among hydroxyl, cyano, carbonyl, carboxyl, ether bond, ester bond, sulfonic acid ester bond, carbonate bond, lactone ring, sultone ring and carboxylic anhydride.

Examples of the structure having formula (2) wherein $Z^A$ is a variant are shown below. Notably, $R^A$ and $X^A$ are as defined above.

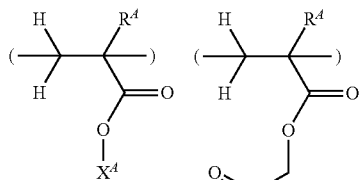

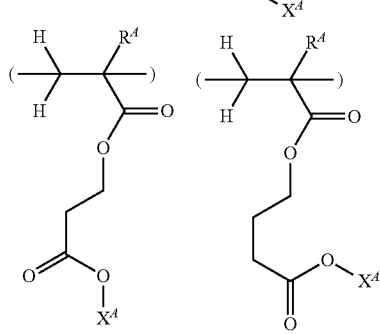

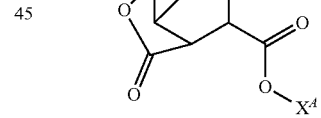

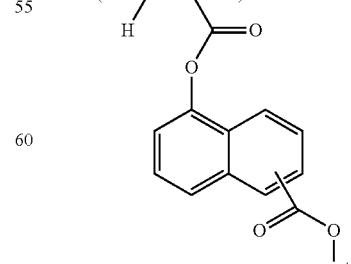

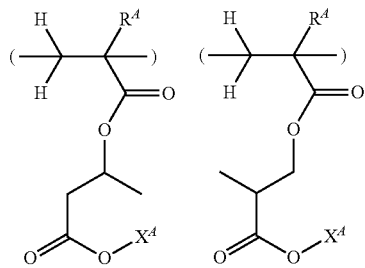

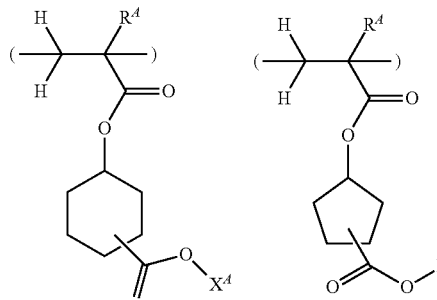

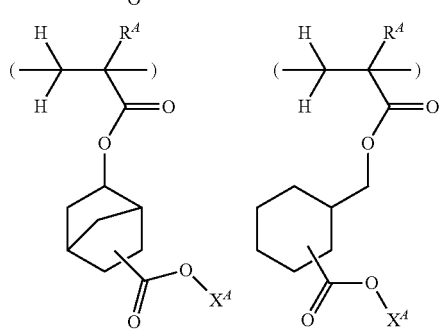

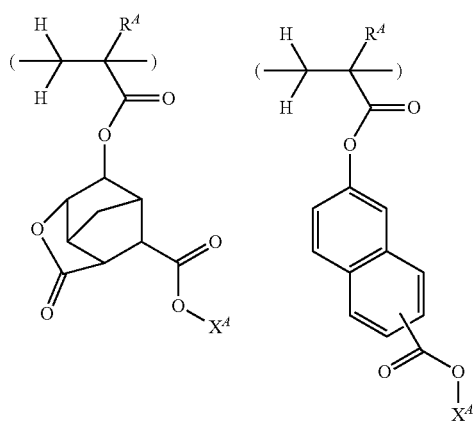

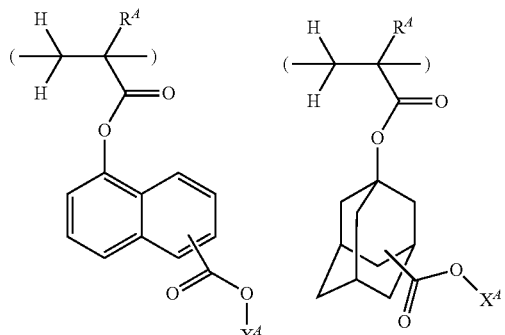

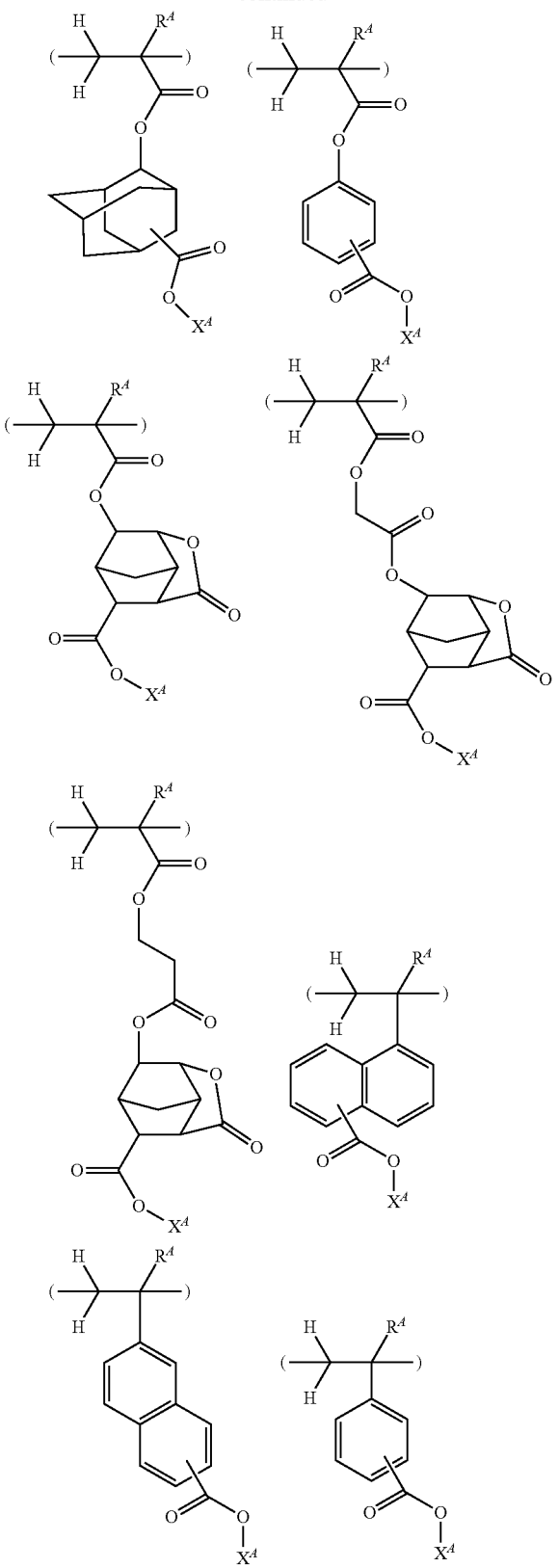

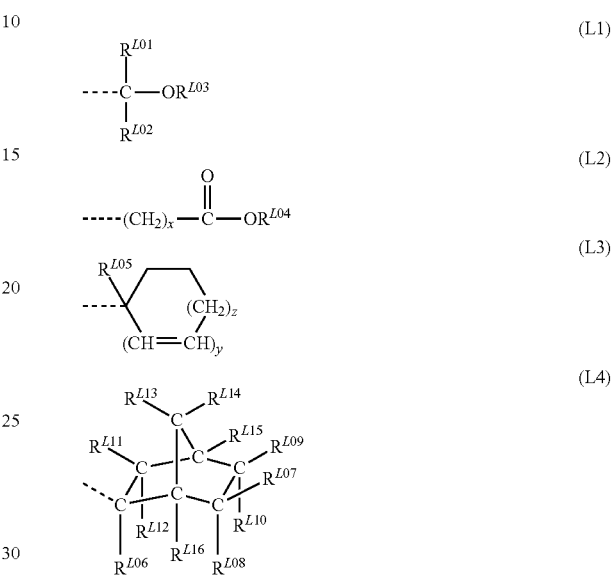

Under the action of acid, a polymer comprising recurring units of formula (2) is decomposed to generate carboxylic acid, turning to be an alkali soluble polymer.

The acid labile group represented by $X^A$ may be selected from a variety of such groups. Examples of the acid labile group include groups of the following formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

In formula (L1), $R^{L01}$ and $L^{L02}$ each are hydrogen or a straight, branched or cyclic alkyl group of 1 to 18 carbon atoms, preferably 1 to 10 carbon atoms. Exemplary alkyl groups Include methyl, ethyl, propyl, isopropyl, n-butyl, s-butyl, t-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a heteroatom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like, or in which a heteroatom such as oxygen intervenes between carbon atoms. Suitable alkyl groups are as exemplified above for $R^{L01}$ and $R^{L02}$. Illustrative examples of the substituted alkyl groups are shown below.

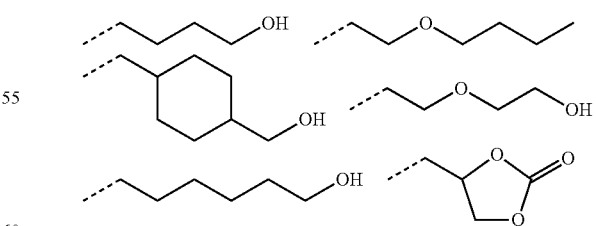

A pair of $R^{L01}$ and $R^{L02}$, $R^{L01}$, or $R^{L03}$, or $R^{L02}$ and $R^{L03}$ may bond together to form a ring with the carbon and oxygen atoms to which they are attached. Ring-forming participants of $R^{L01}$, $R^{L02}$ and $R^{L03}$ represent a straight or branched alkylene group of 1 to 18 carbon atoms, preferably 1 to 10 carbon atoms.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are t-butyl, t-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-t-butylsilyl. Exemplary oxoalkyl groups are 3-oxocyclohexyl, 4-methyl-2-oxooxan-4-yl, and 5-methyl-2-oxooxolan-5-yl. Letter x is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, s-butyl, t-butyl, t-pentyl, n-pentyl, n-hexyl, cyclopentyl, and cyclohexyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl, and substituted forms of such groups in which some hydrogen atoms are substituted by hydroxyl, alkoxy, carboxyl, alkoxycarbonyl, oxo, amino, alkylamino, cyano, mercapto. alkylthio, sulfo or other groups. Letter y is equal to 0 or 1, z is an integer of 0 to 3, and 2y+z is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$, $R^{L07}$ to $R^{L16}$ independently represent hydrogen or $C_1$-$C_{15}$ monovalent hydrocarbon groups. Exemplary hydrocarbon groups are straight, branched or cyclic alkyl groups such as methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Ring-forming participants of $R^{L07}$ to $R^{L16}$ represent a divalent $C_1$-$C_{15}$ hydrocarbon group, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

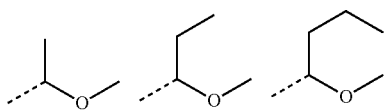

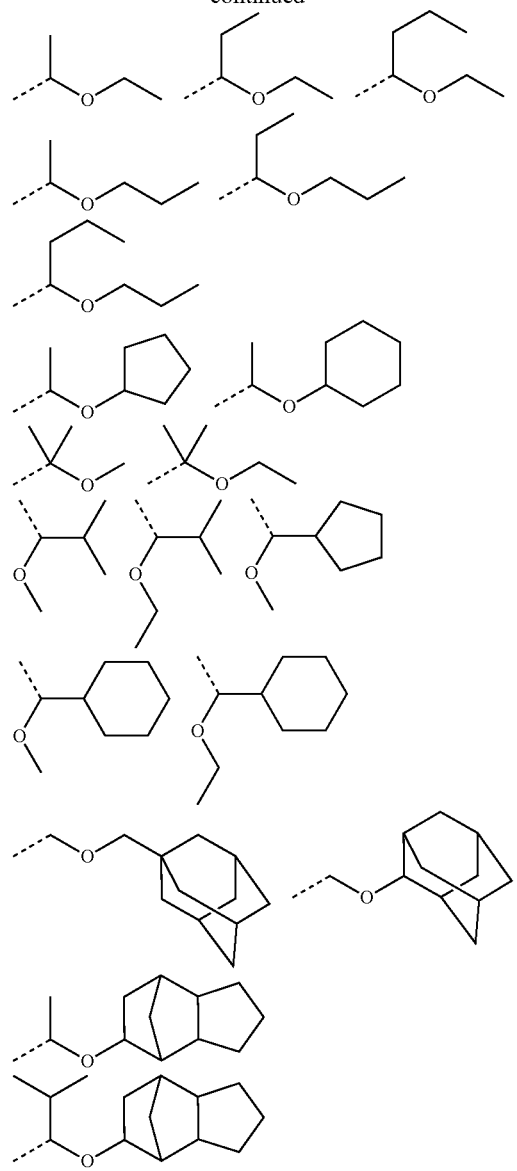

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, t-butoxycarbonylmethyl, t-pentyloxycarbonyl, t-pentyloxycarbonylmethyl, 1,1-diethylpropyloxycarbonyl, 1,1-diethylpropyloxycarbonylmethyl, 1-ethyicyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile groups of formula (L3) include 1-methylcyclopentyl. 1-ethylcyclopentyl, 1-n-propyloycyclopentyl, 1-isopropylcyclopentyl, 1-n-butylcyclopentyl, 1-s-butylcyclopentyl, 1-cyclohexylcyclopentyl, 1-(4-methoxy-n-butyl)cyolopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups having formula (L4), groups having the following formulas (L4-1) to (L4-4) are preferred.

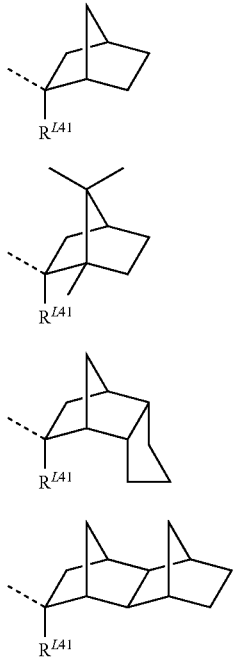

(L4-1)

(L4-2)

(L4-3)

(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, s-butyl, t-butyl, t-pentyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When $X^A$ is an acid labile group of formula (L4), a plurality of stereoisomers may be contained.

For example, the formula (L4-3) represents one or a mixture of two selected from groups having the following formulas (L4-3-1) and (L4-3-2).

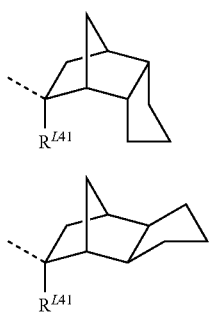

(L4-3-1)

(L4-3-2)

Similarly, the formula (L4-4) represents one or a mixture of two or more selected from groups having the following formulas (L4-4-1) to (L4-4-4).

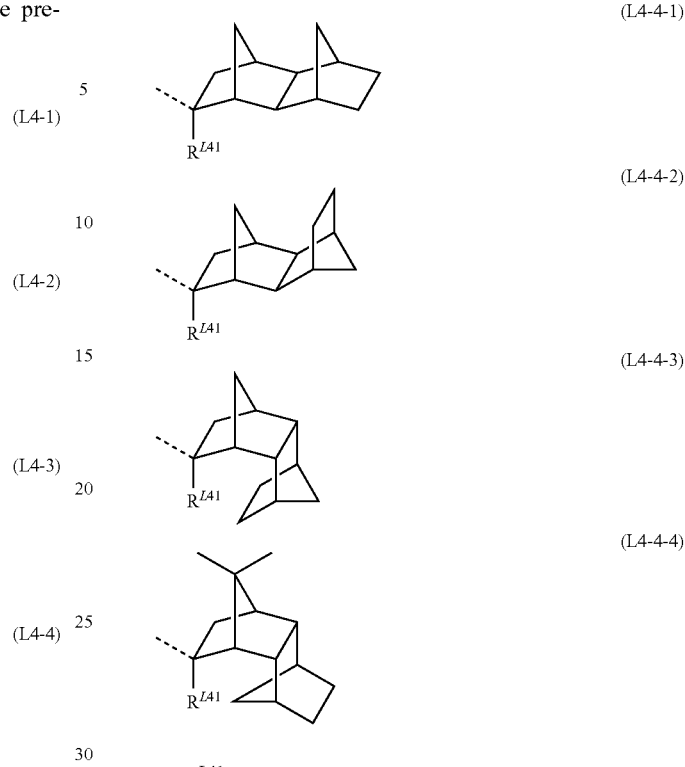

(L4-4-1)

(L4-4-2)

(L4-4-3)

(L4-4-4)

Herein $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

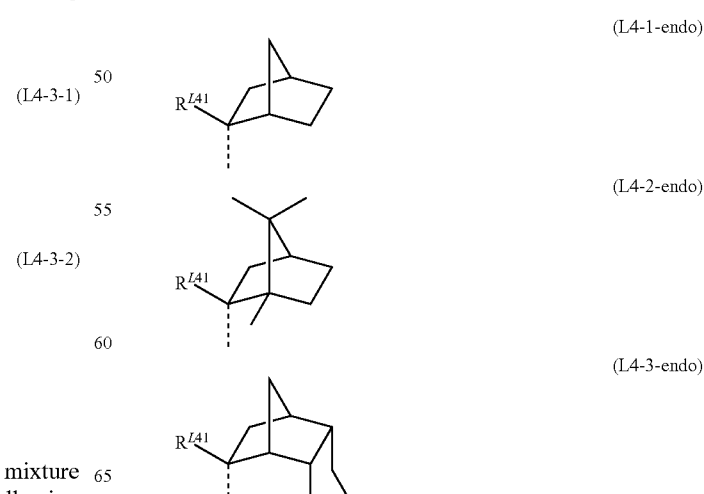

(L4-1-endo)

(L4-2-endo)

(L4-3-endo)

-continued

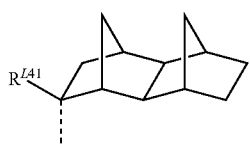
(L4-4-endo)

Herein $R^{L41}$ is as defined above.

Illustrative examples of the acid labile group of formula (L4) are given below, but not limited thereto.

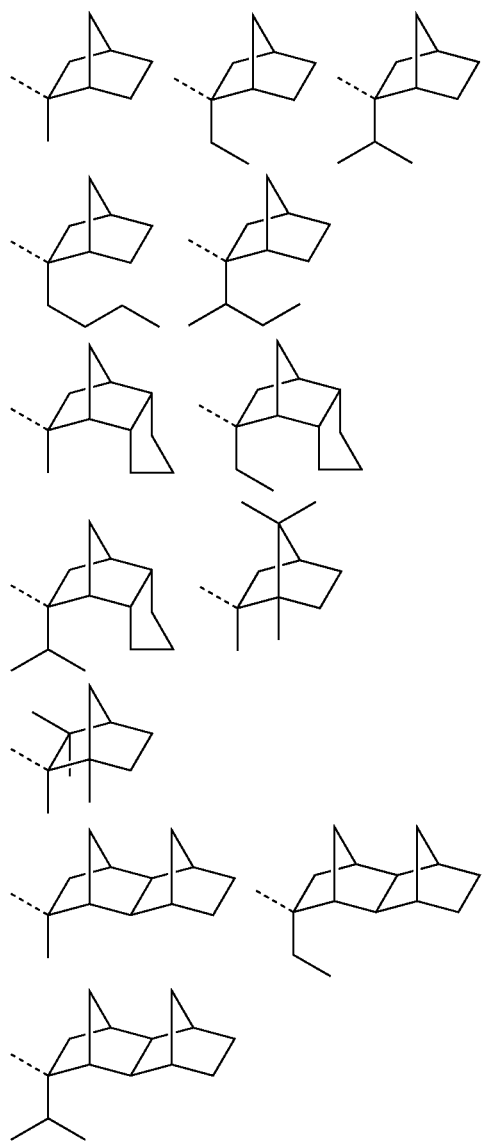

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups, represented by $X^A$, are as exemplified for $R^{L04}$.

Illustrative examples of the recurring units of formula (2) are given below, but not limited thereto. Herein $R^A$ is as defined above.

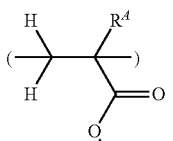
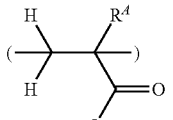
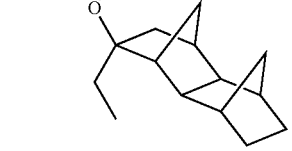
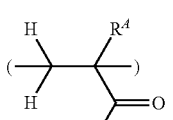
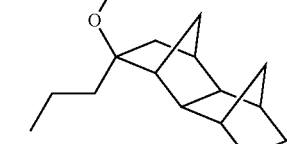
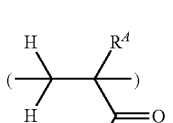
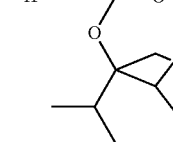
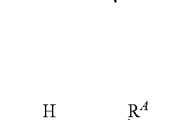
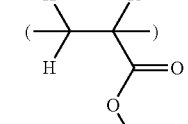
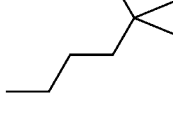
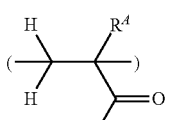
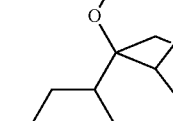

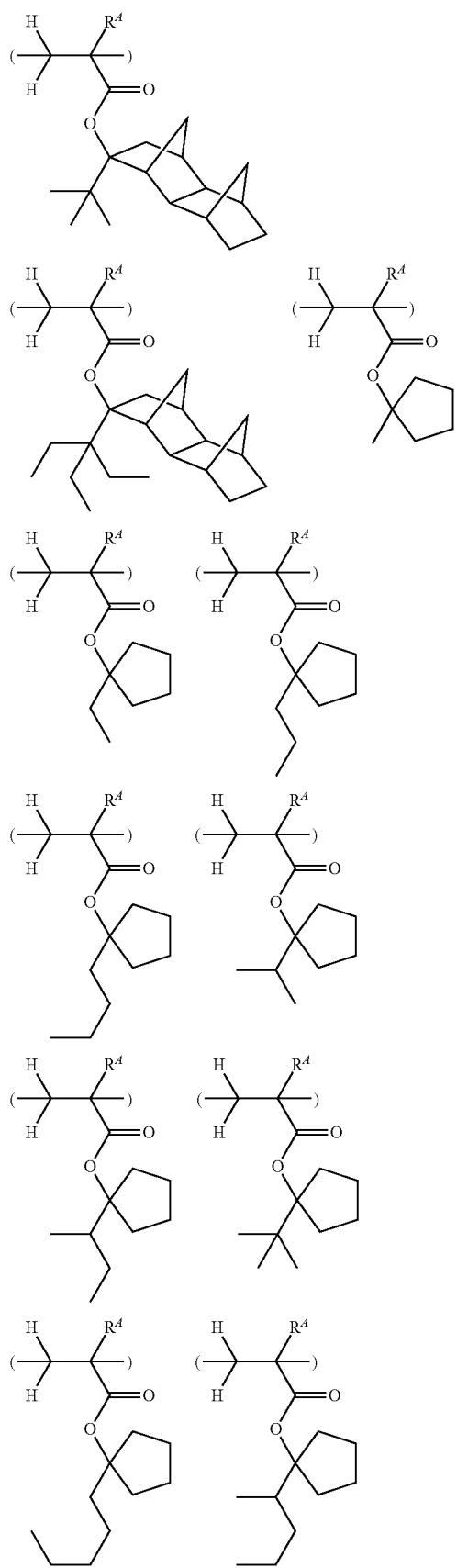
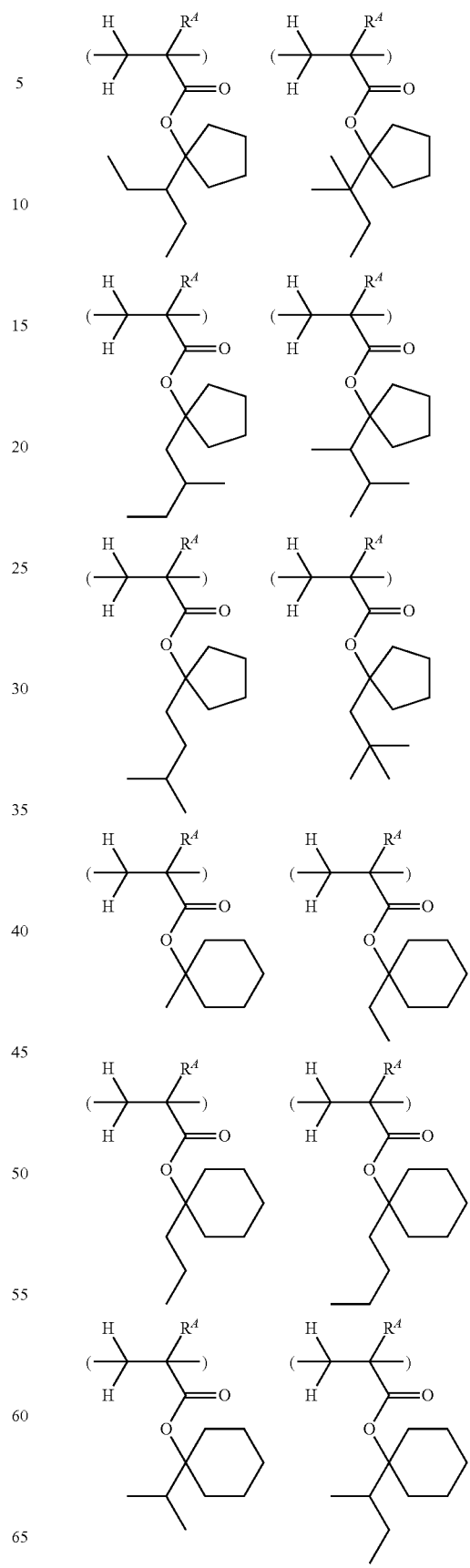

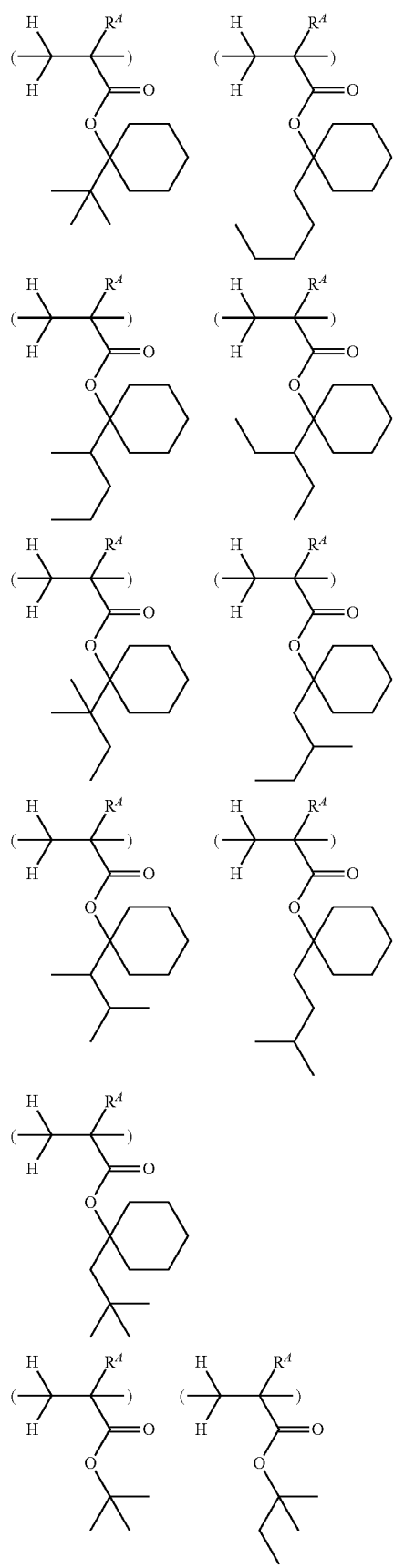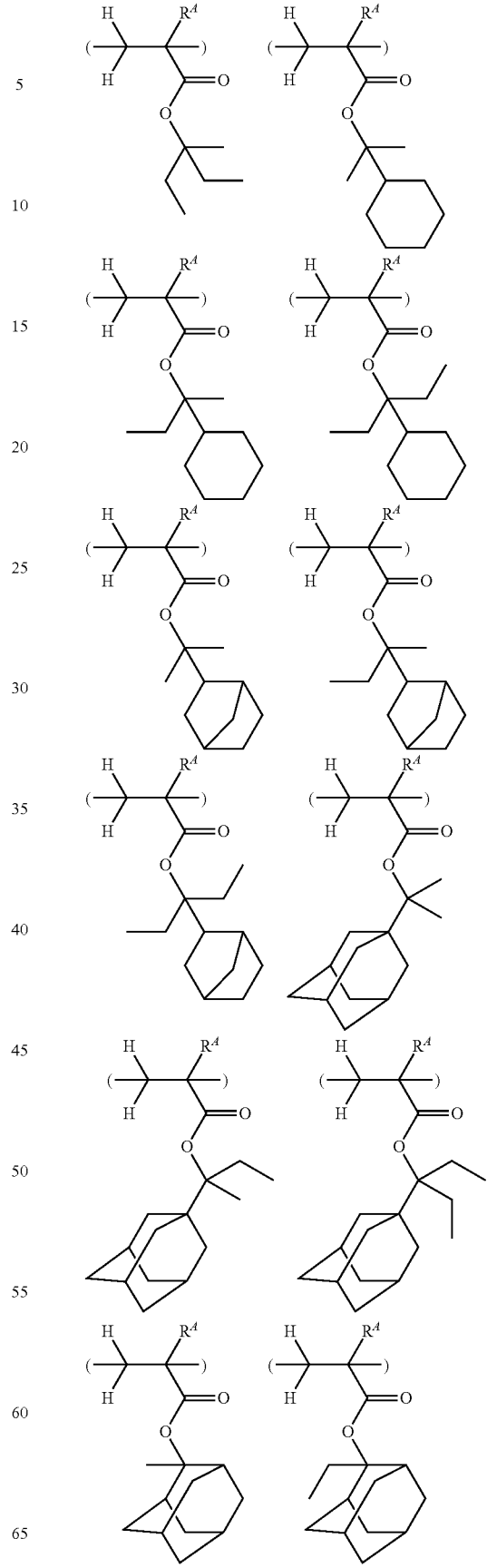

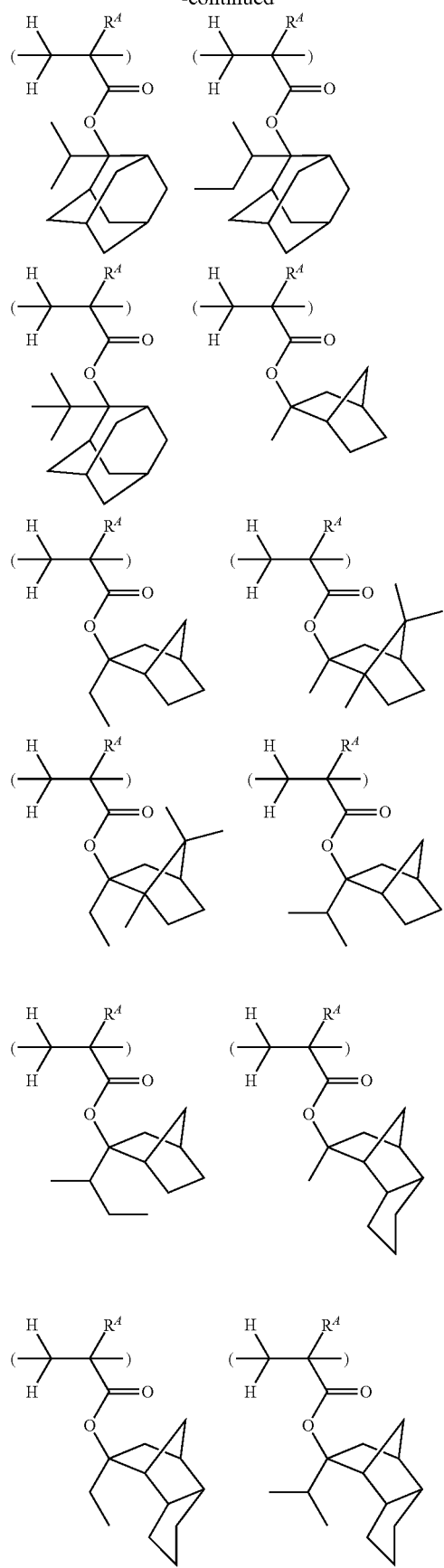
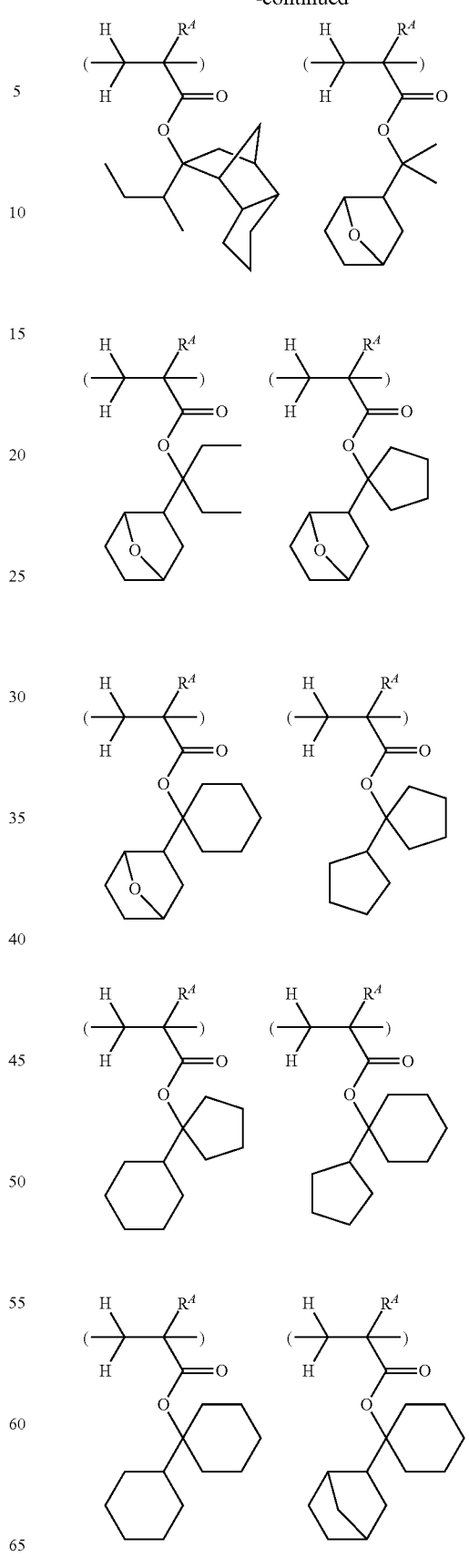

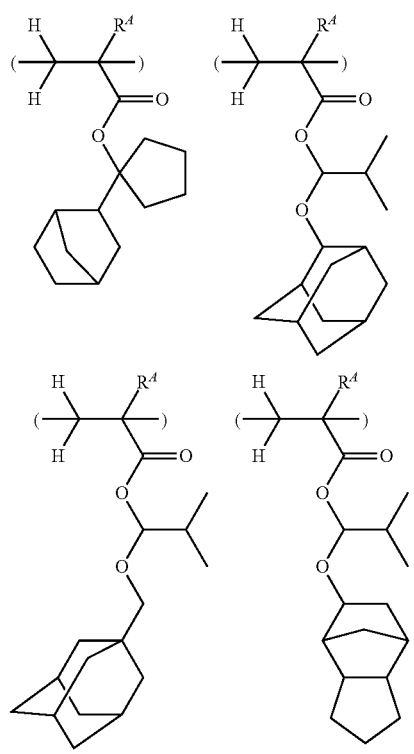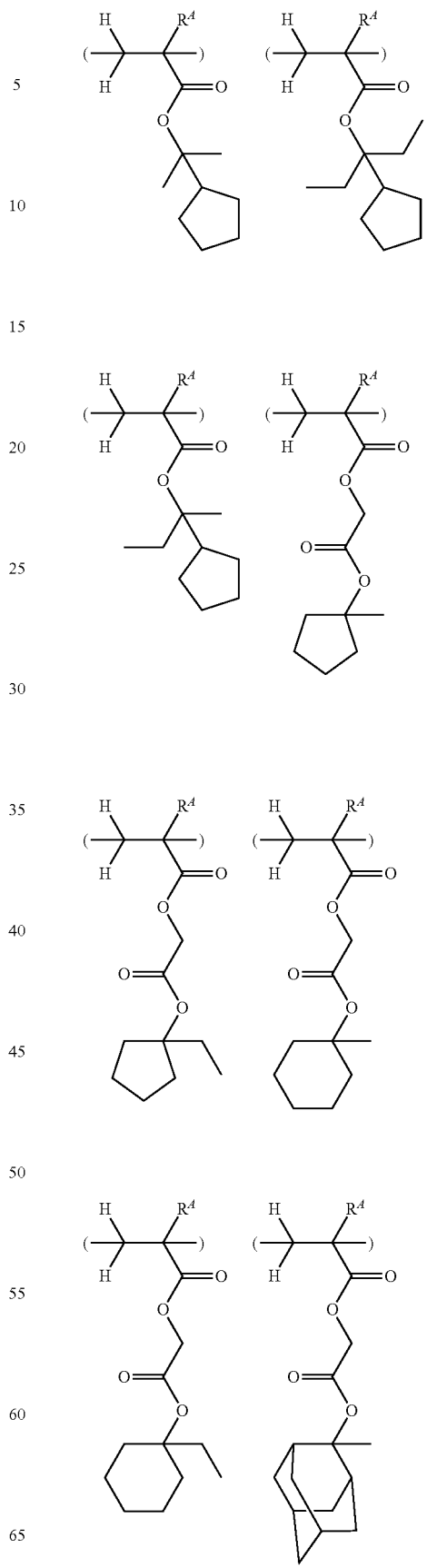

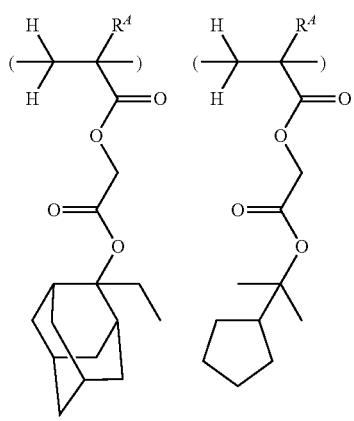
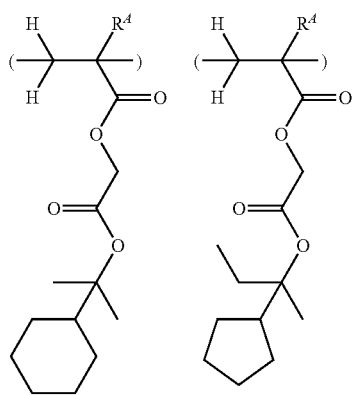
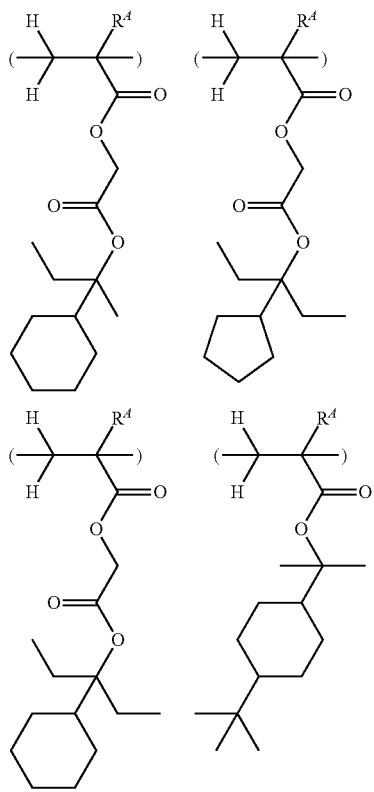
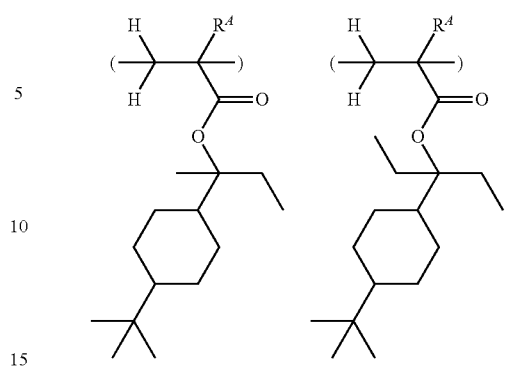
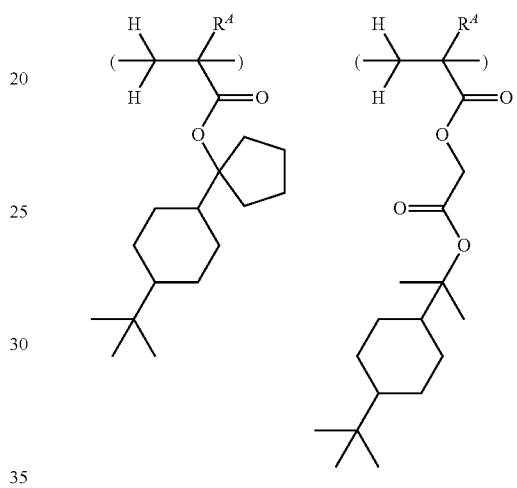
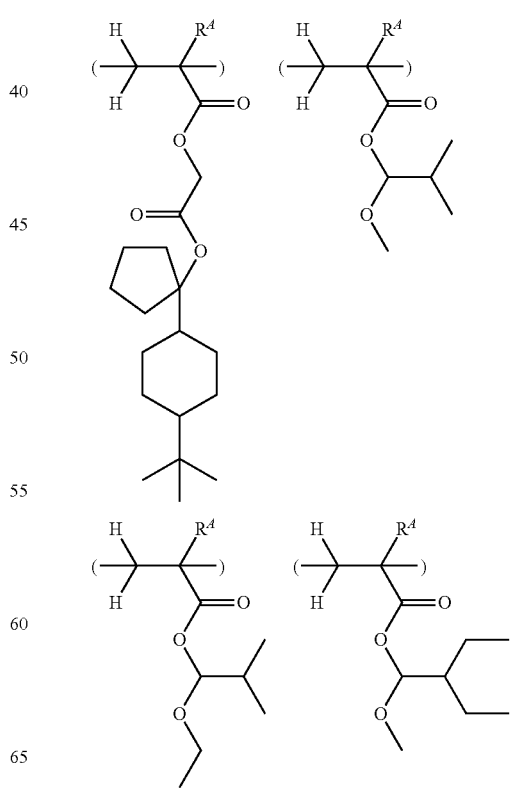

-continued

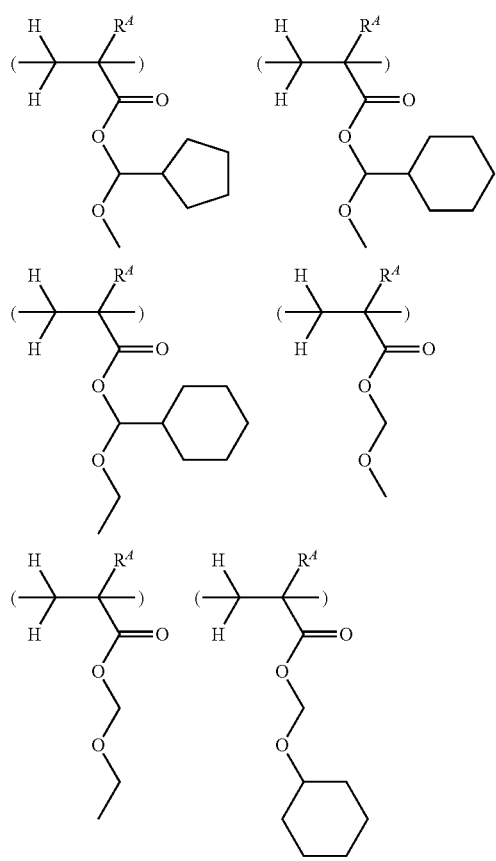

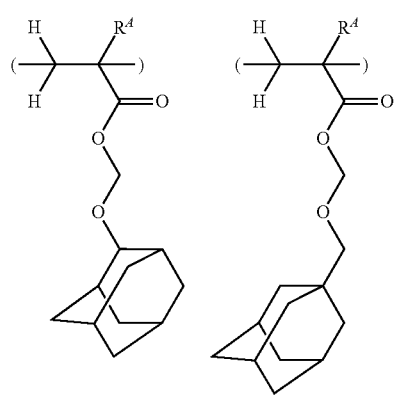

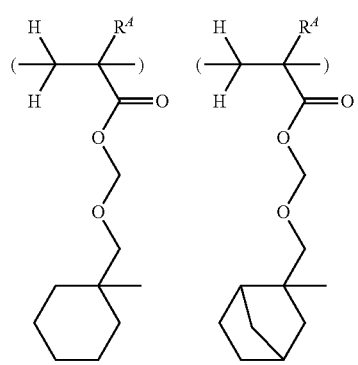

-continued

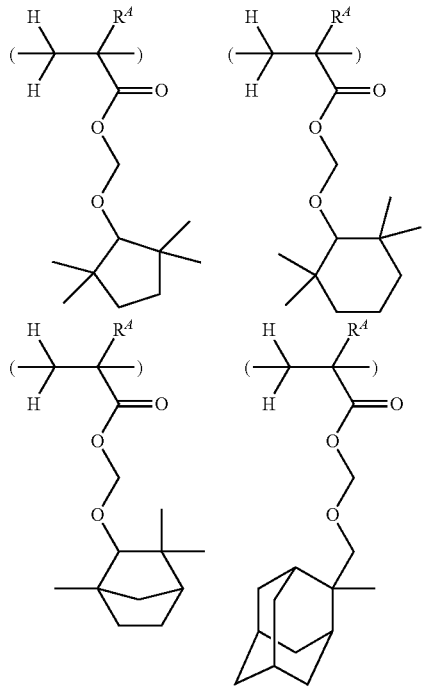

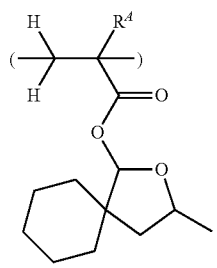

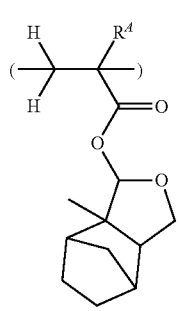

While the foregoing examples correspond to those units wherein $Z^A$ is a single bond, $Z^A$ which is other than a single bond may be combined with similar acid labile groups. Examples of units wherein $Z^A$ is other than a single bond are substantially the same as illustrated above.

In formula (3), $R^A$ is as defined above, and $Y^A$ is hydrogen, or a polar group having one or more structures selected from among hydroxyl, cyano, carbonyl, carboxyl, ether bond, ester bond, sulfonic acid ester bond, carbonate bond, lactone ring, sultone ring, and carboxylic anhydride.

Illustrative, non-limiting examples of the recurring units having formula (3) are shown below. Herein $R^A$ is as defined above.

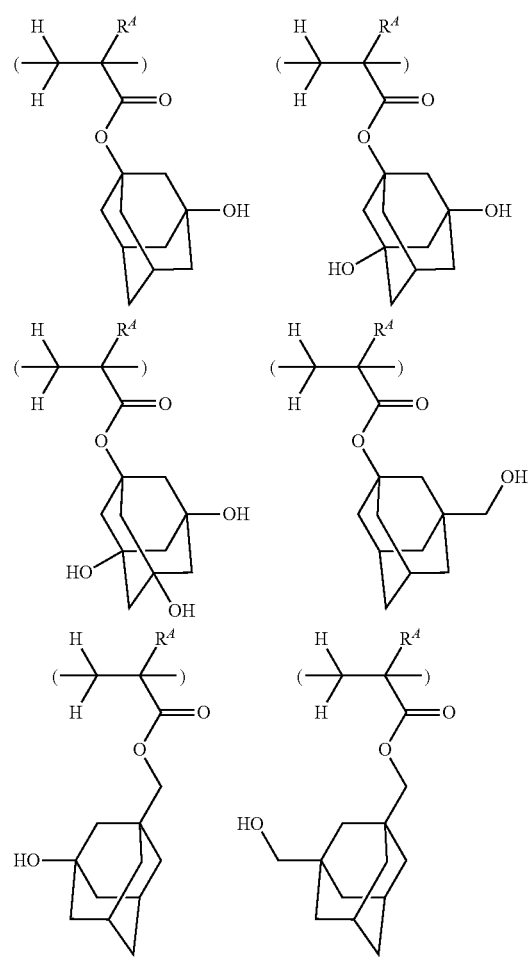
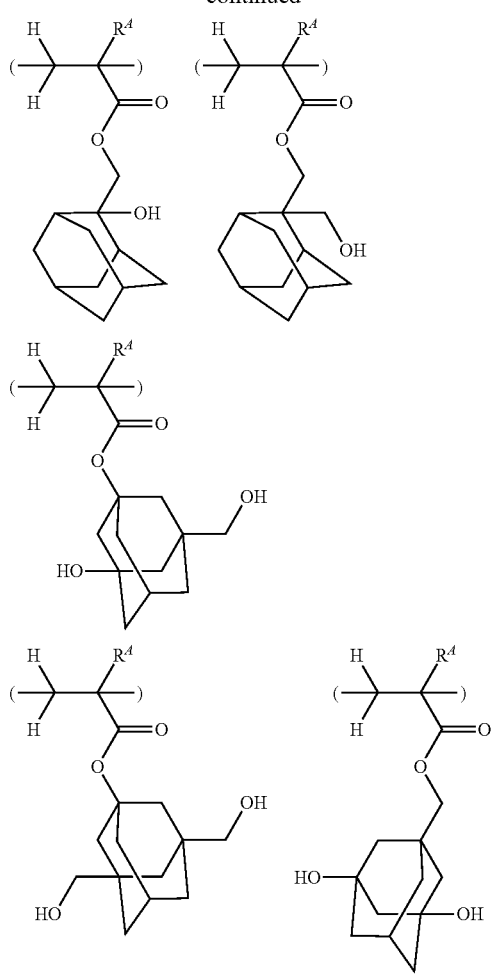
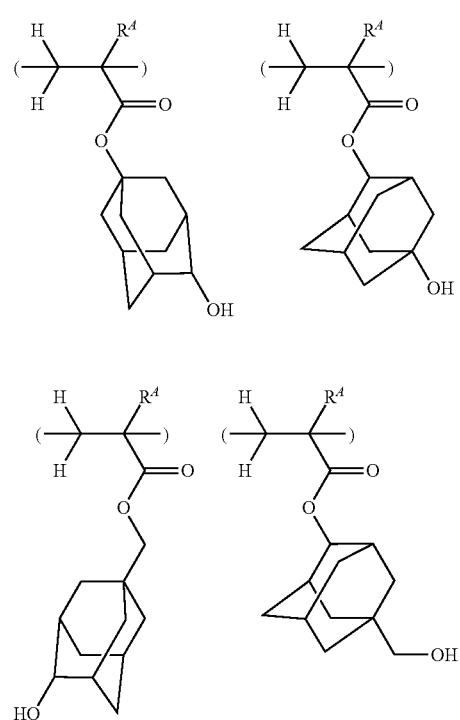
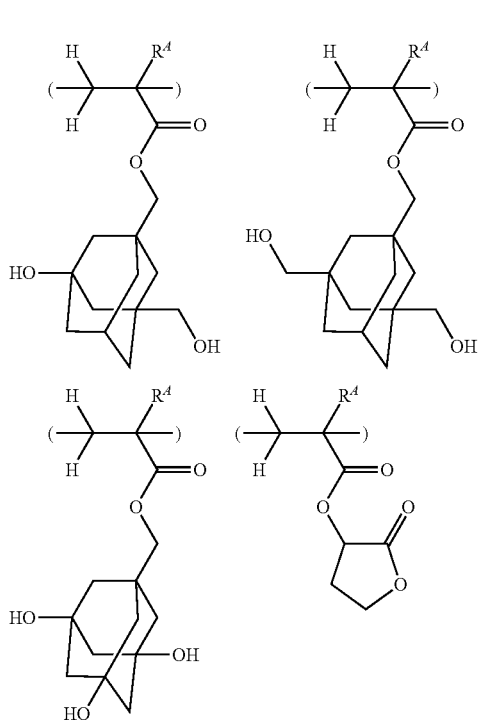

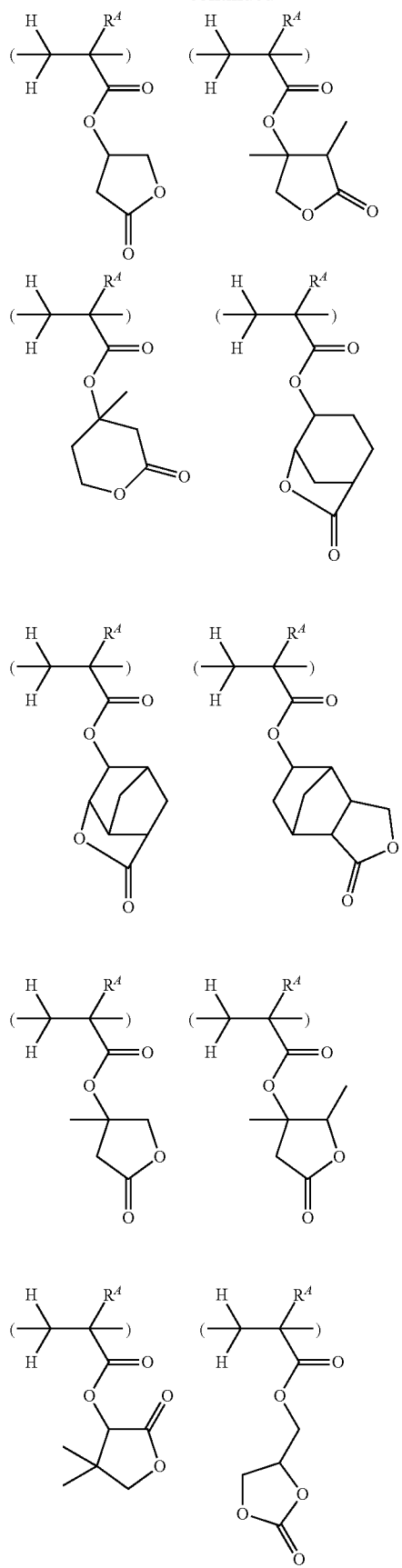
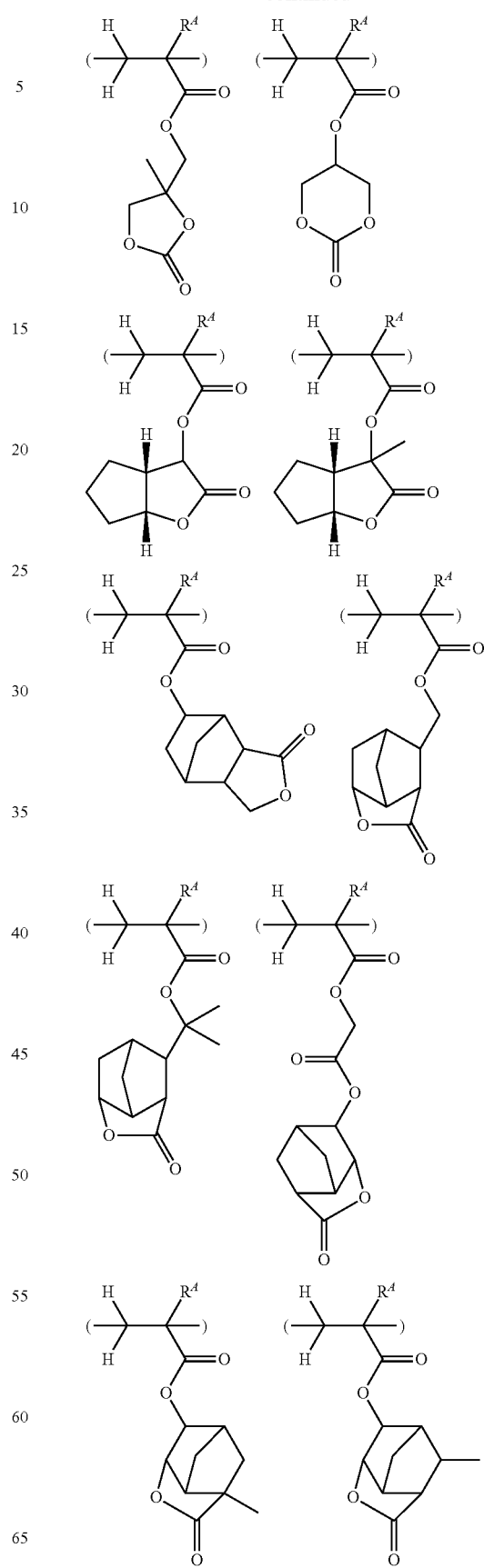

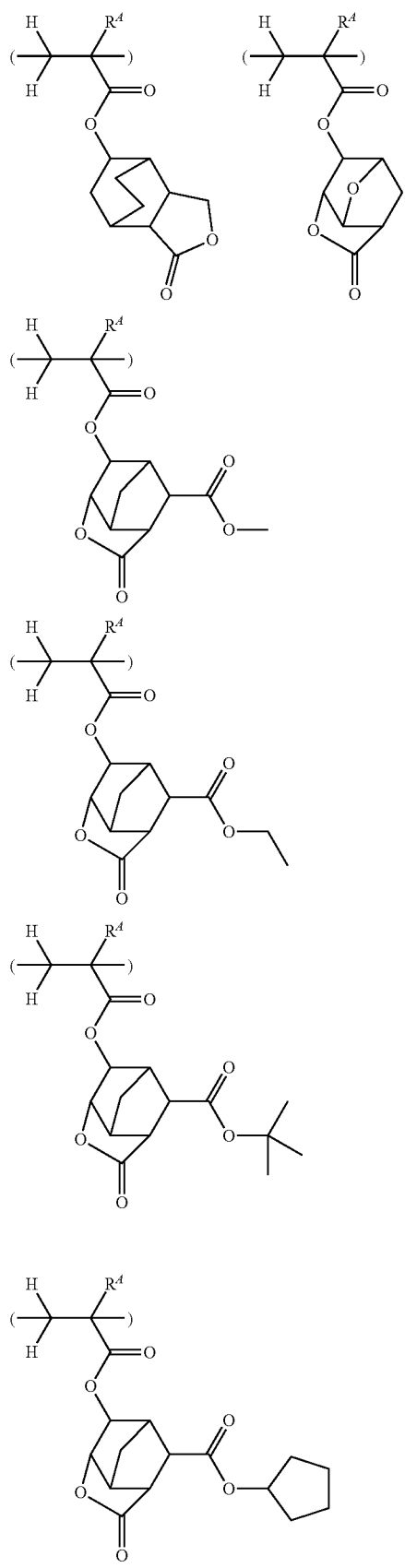
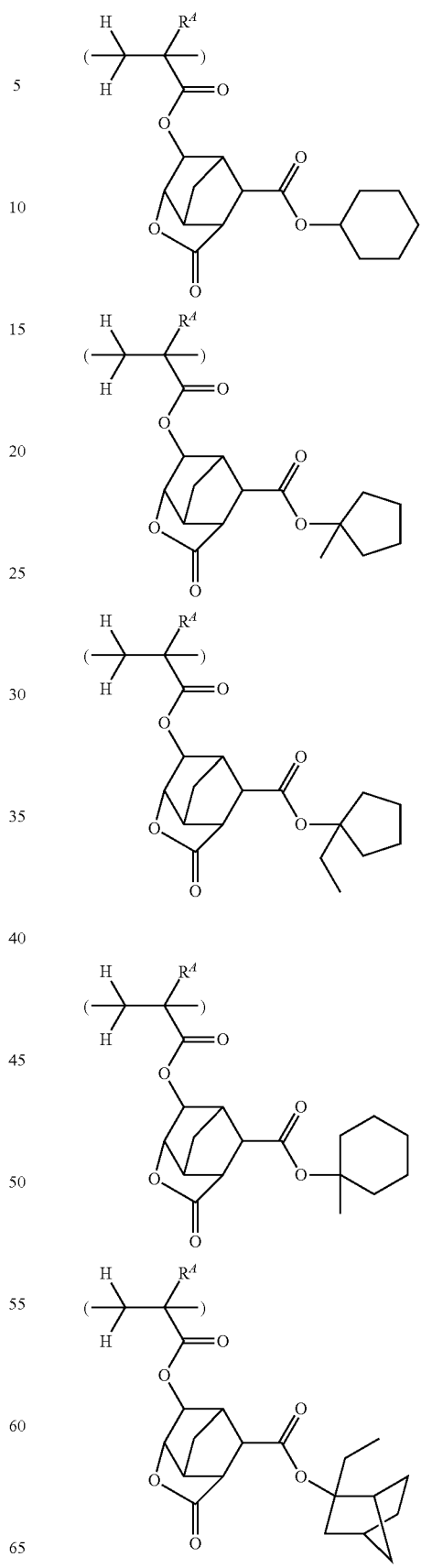

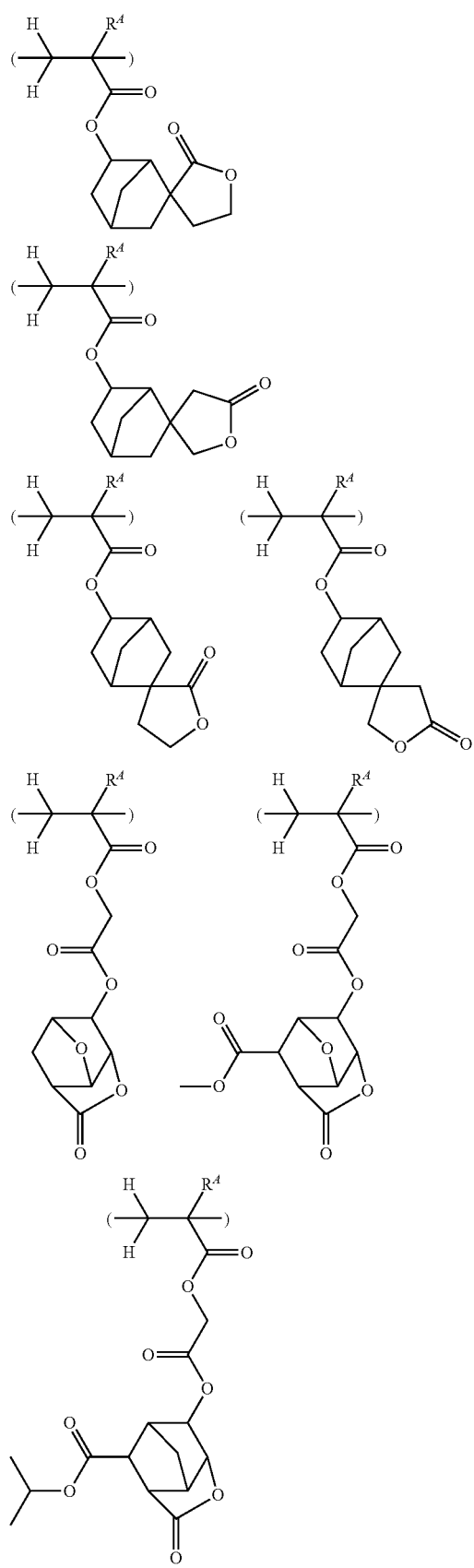
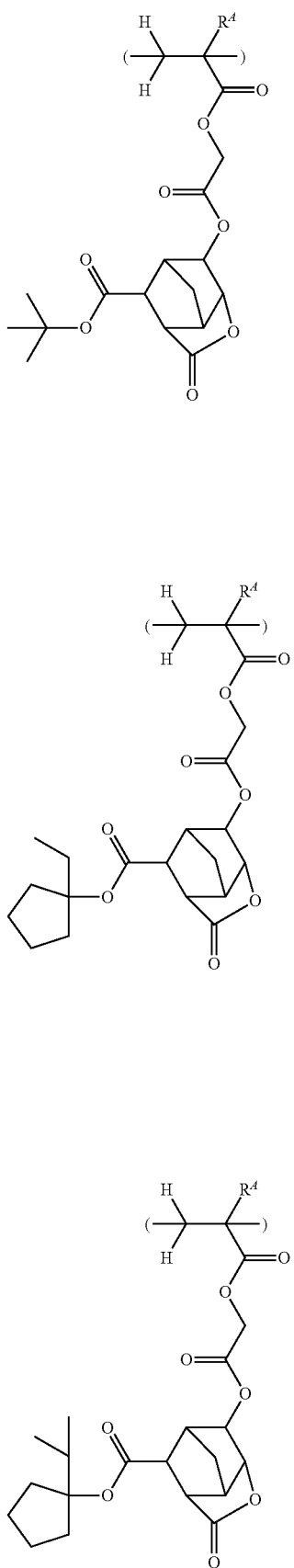

-continued
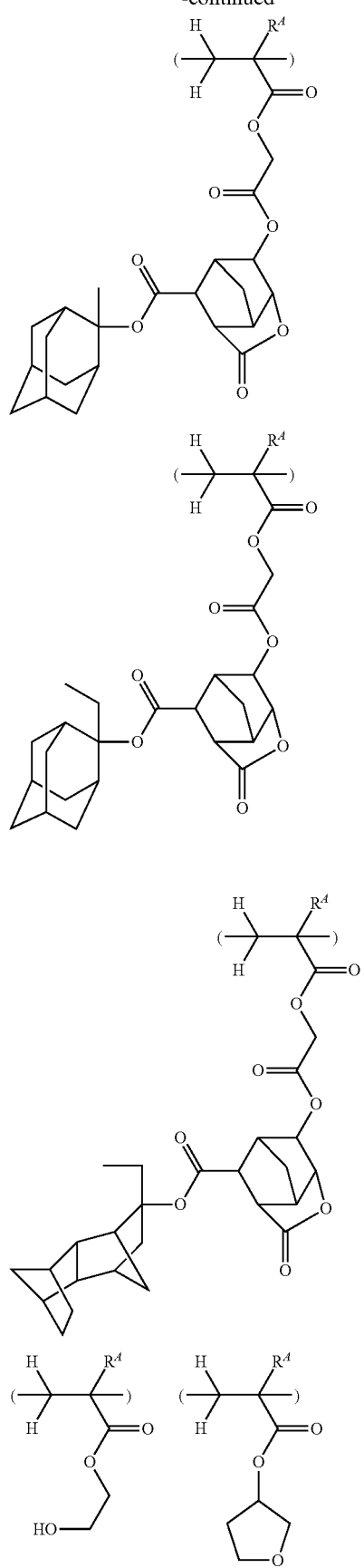
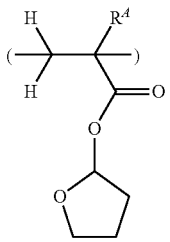
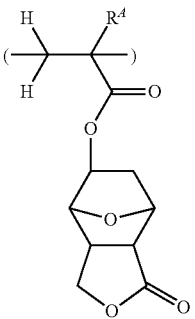
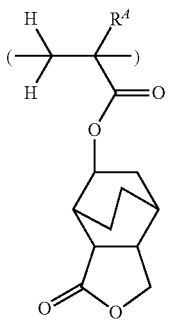
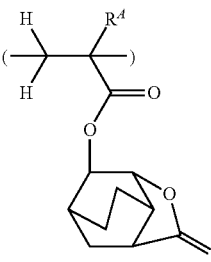
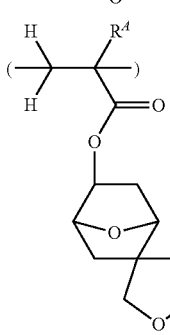
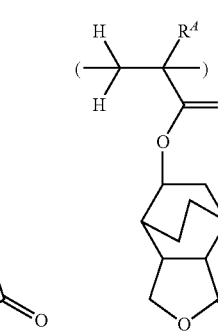
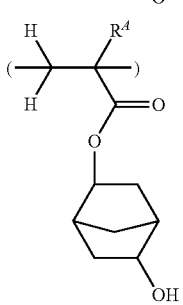
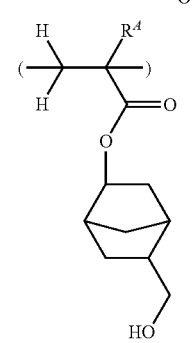
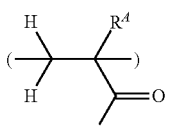
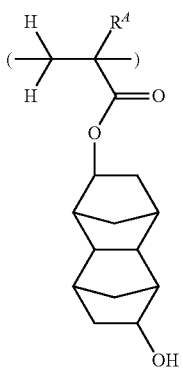
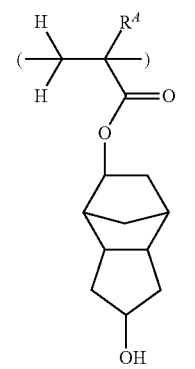

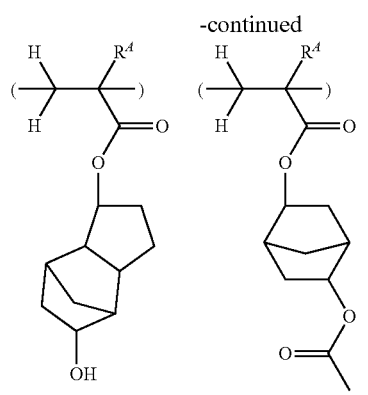
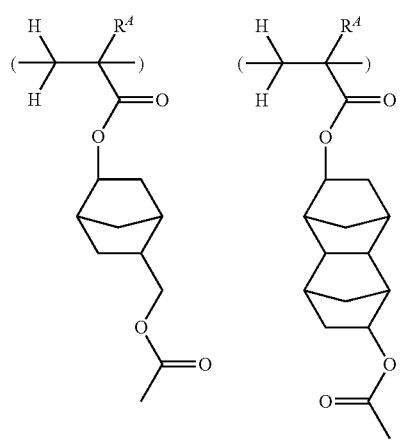
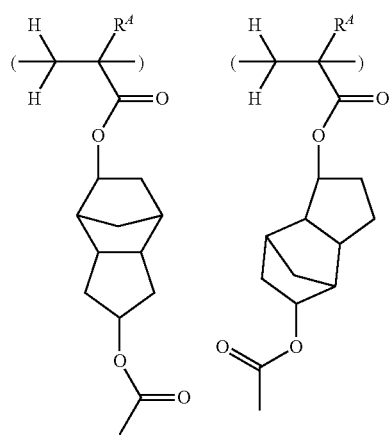
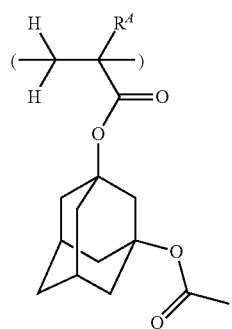
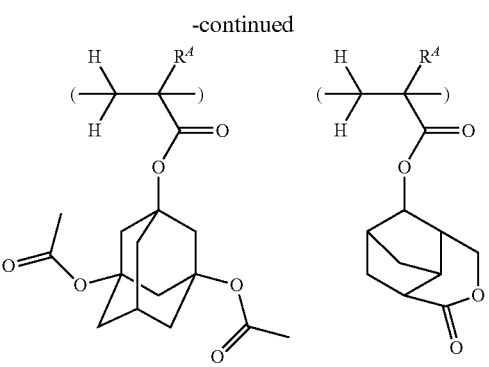
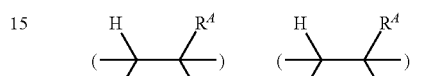
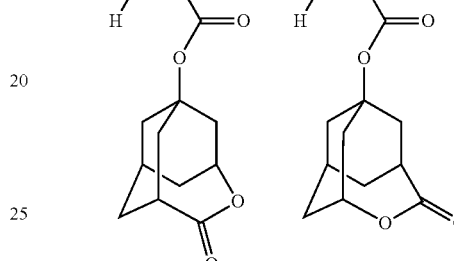
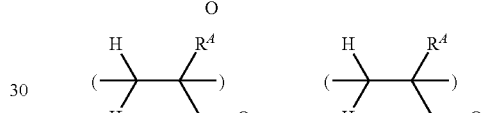
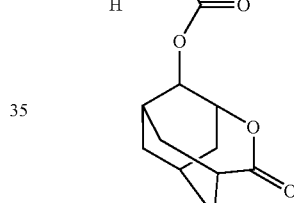
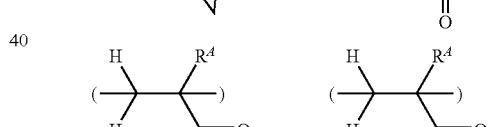
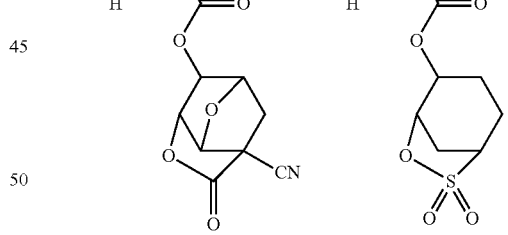
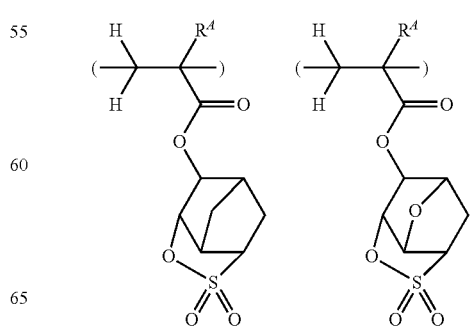

67
-continued
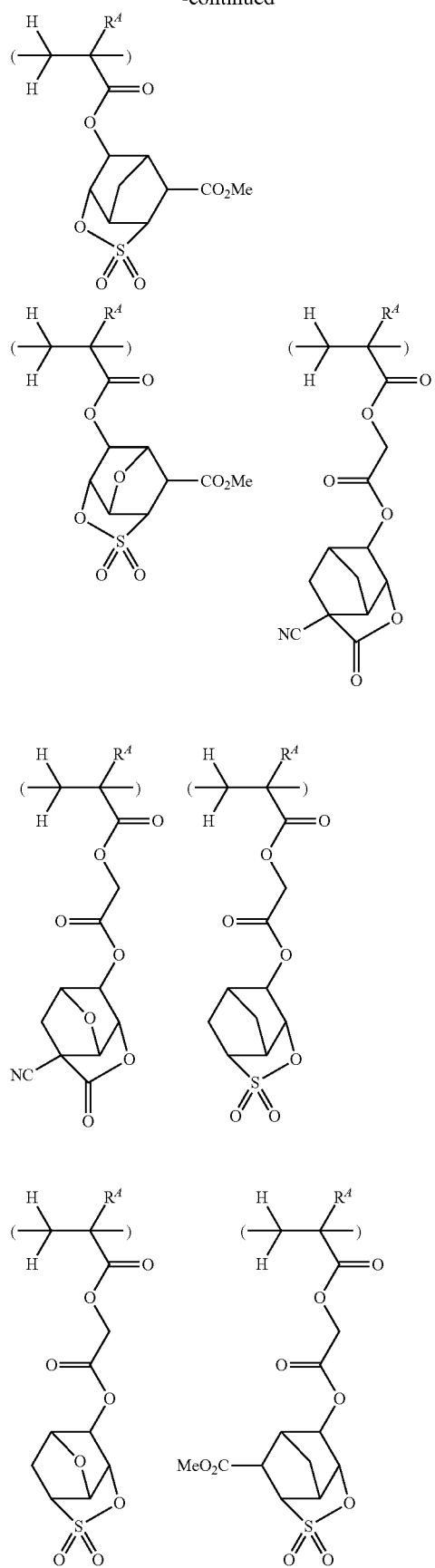
68
-continued
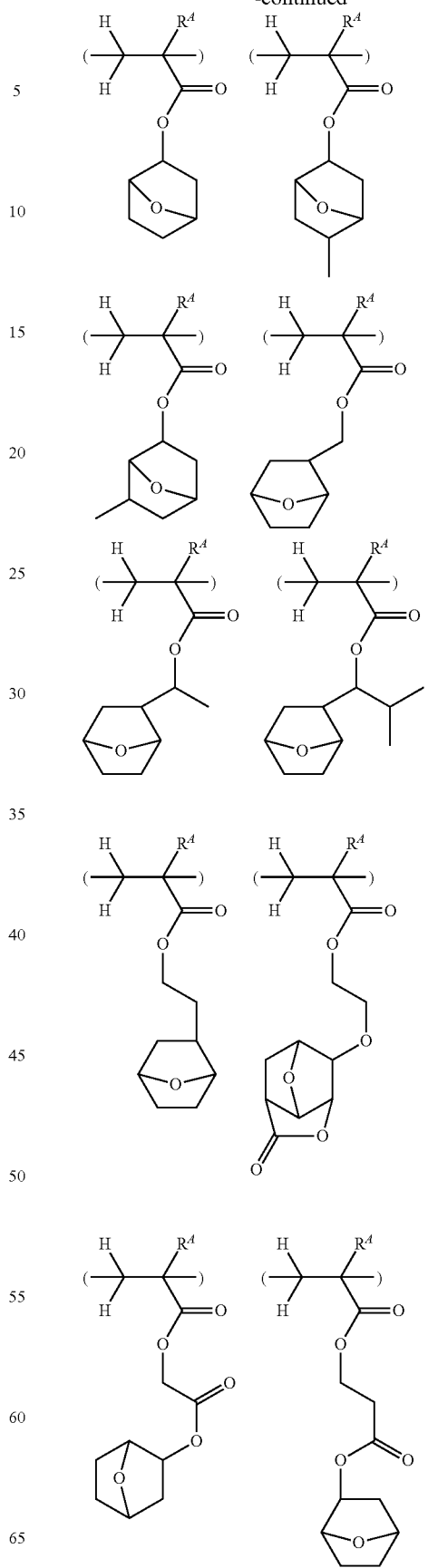

69
-continued
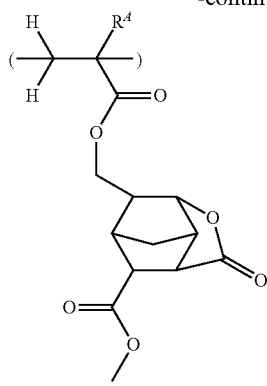
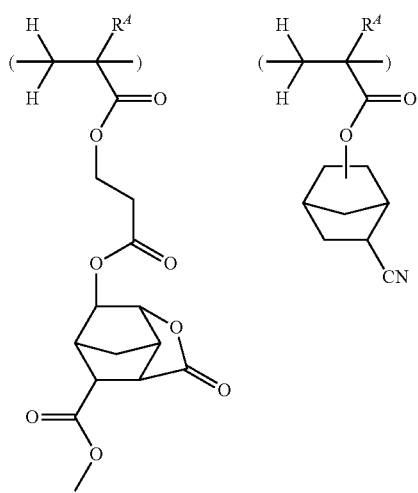
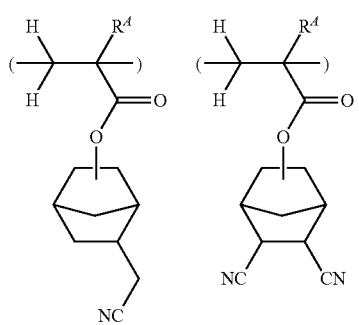
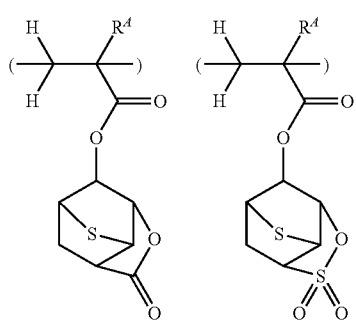
70
-continued
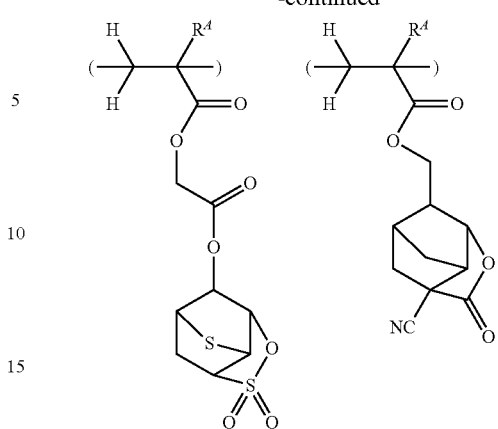
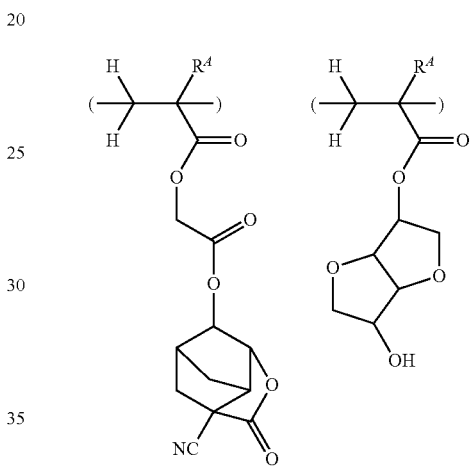
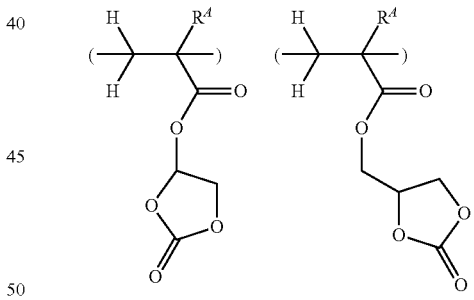
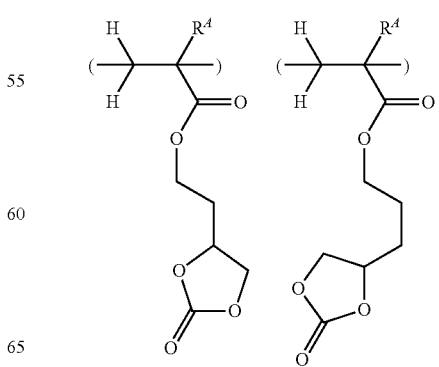

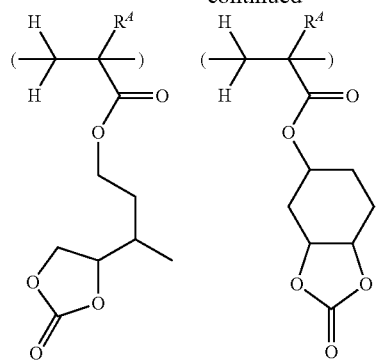
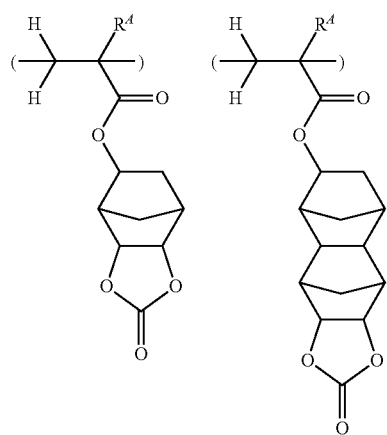
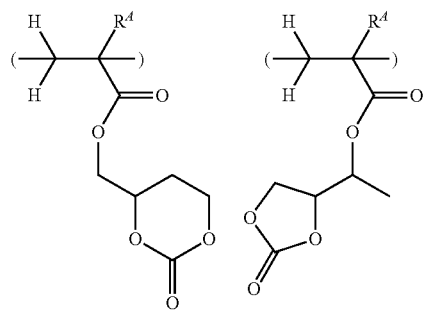
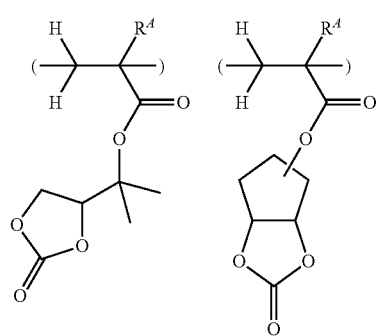
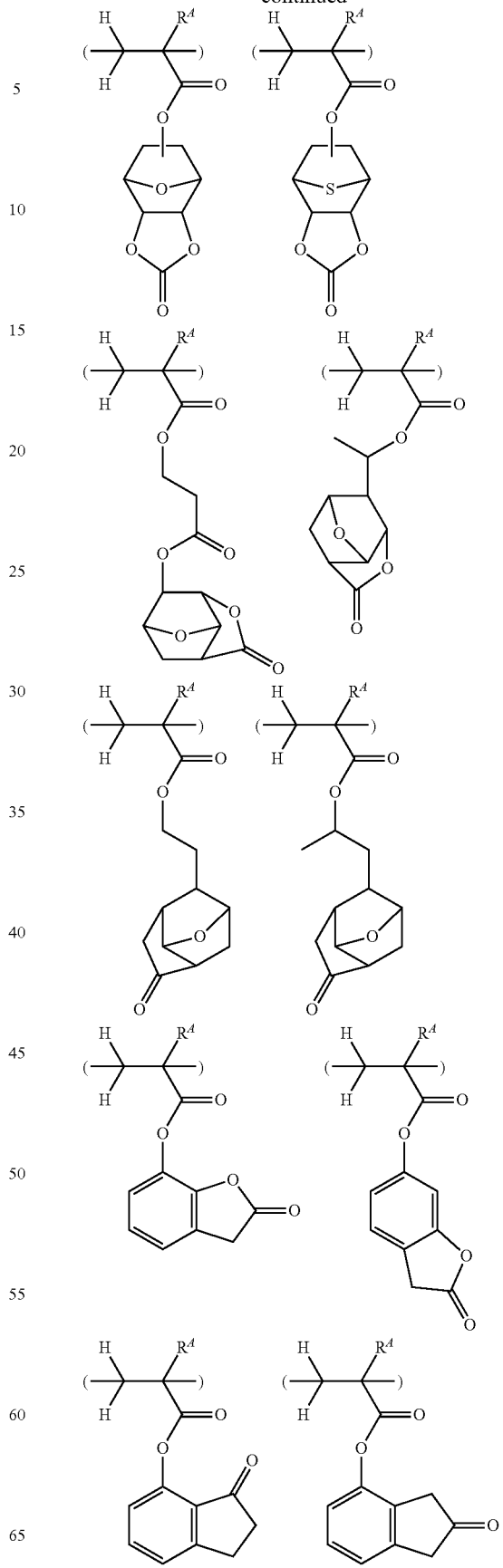

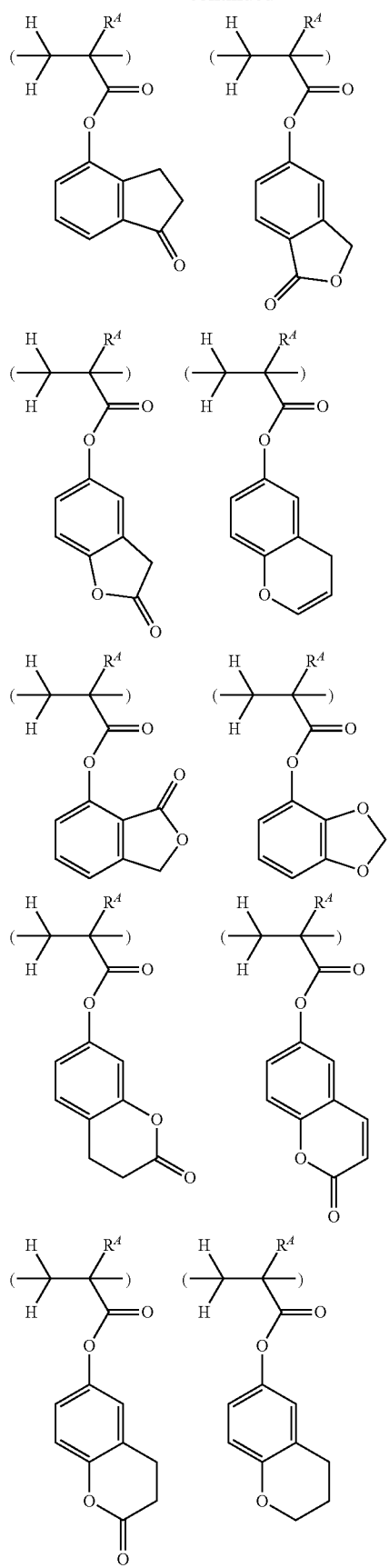
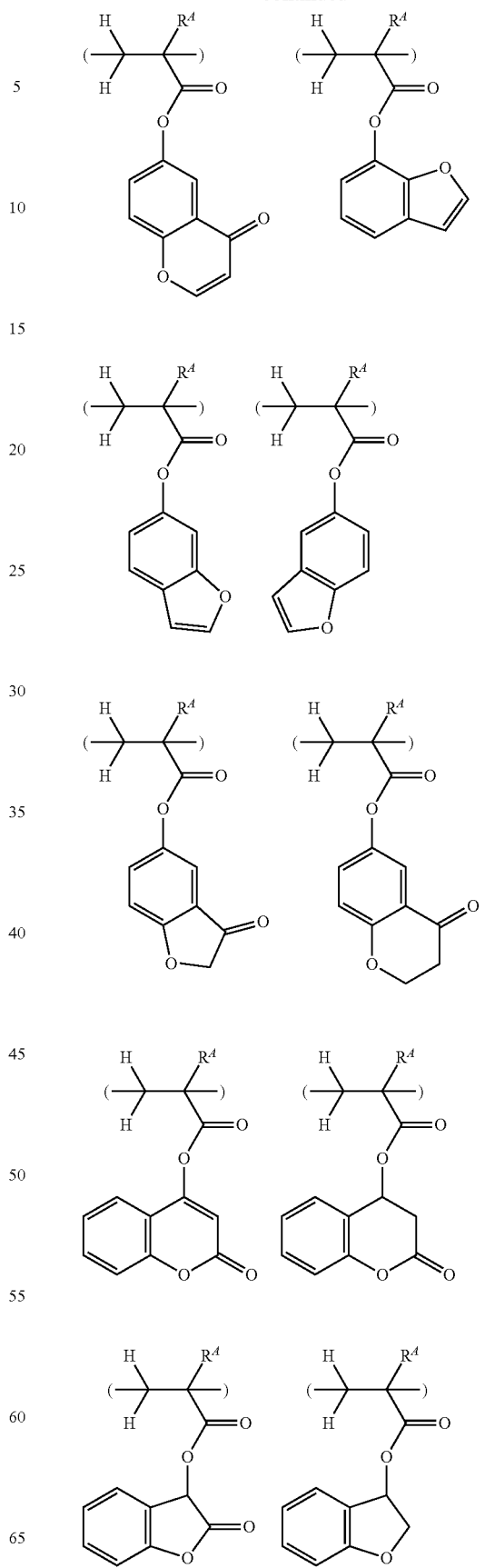

-continued
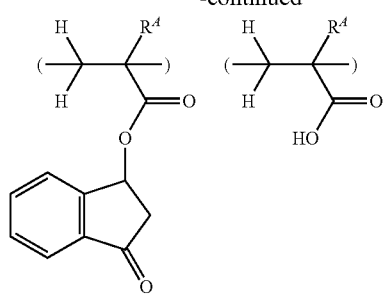
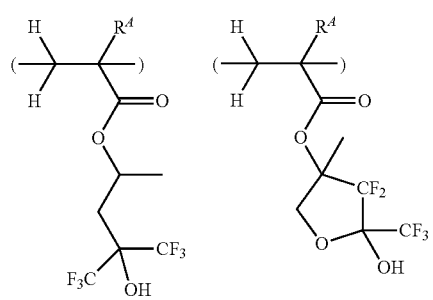
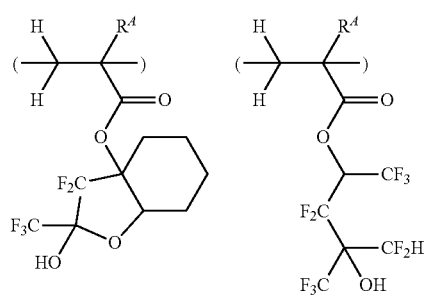
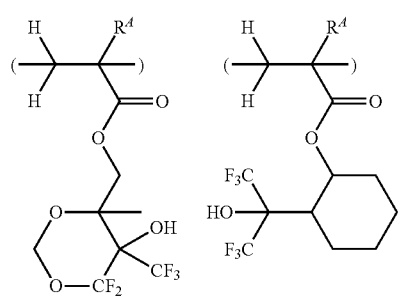
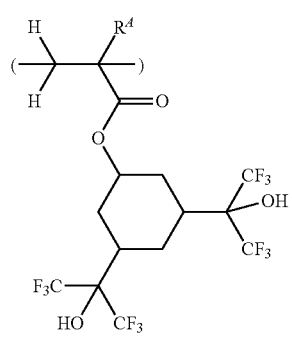
-continued
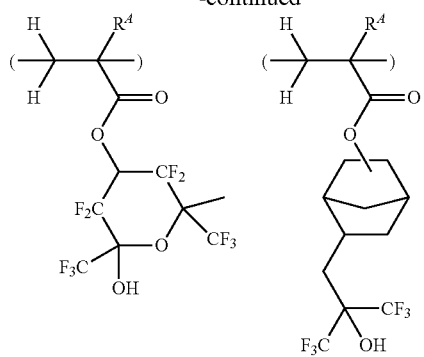
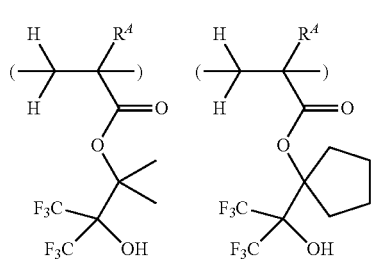
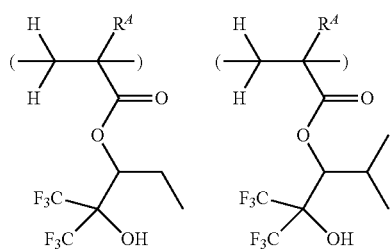
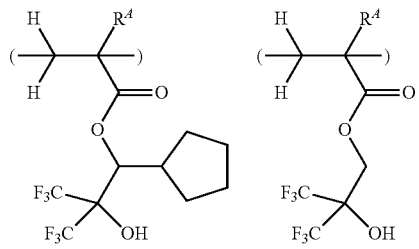
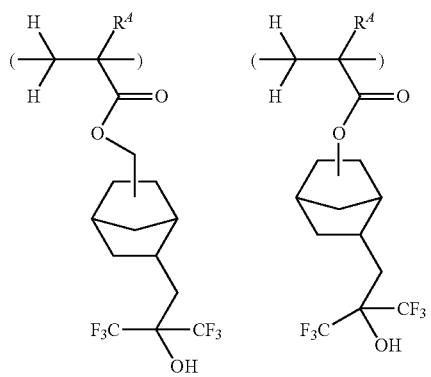

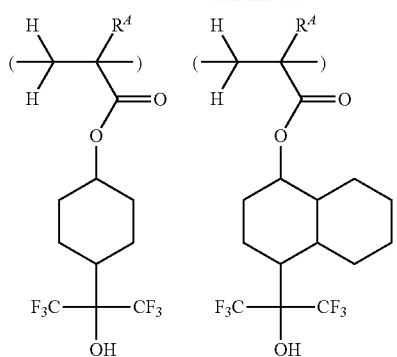
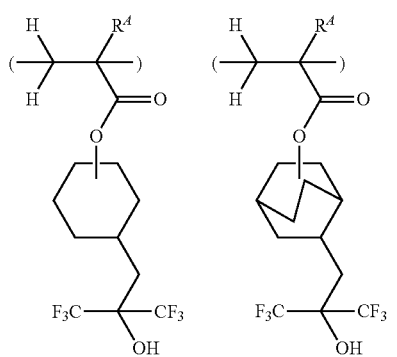
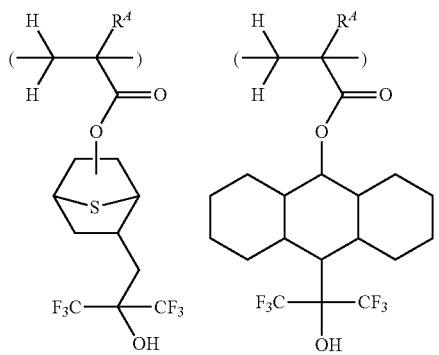
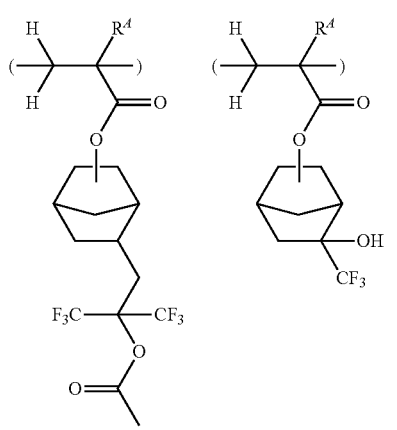
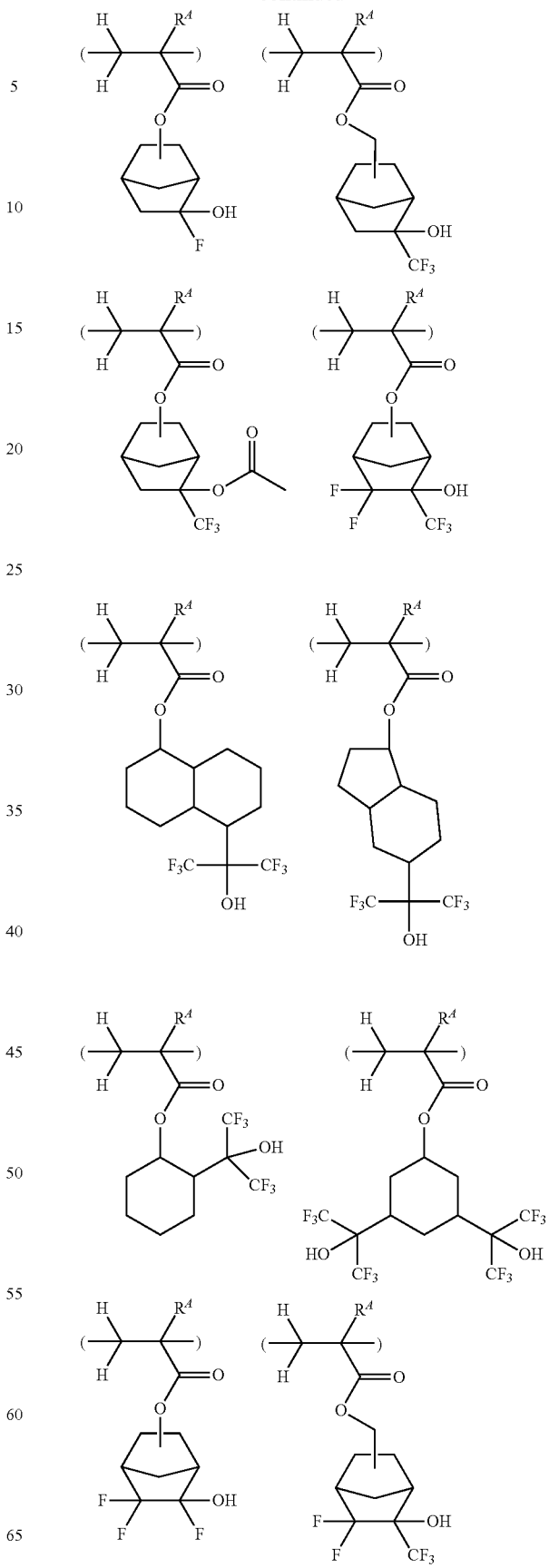

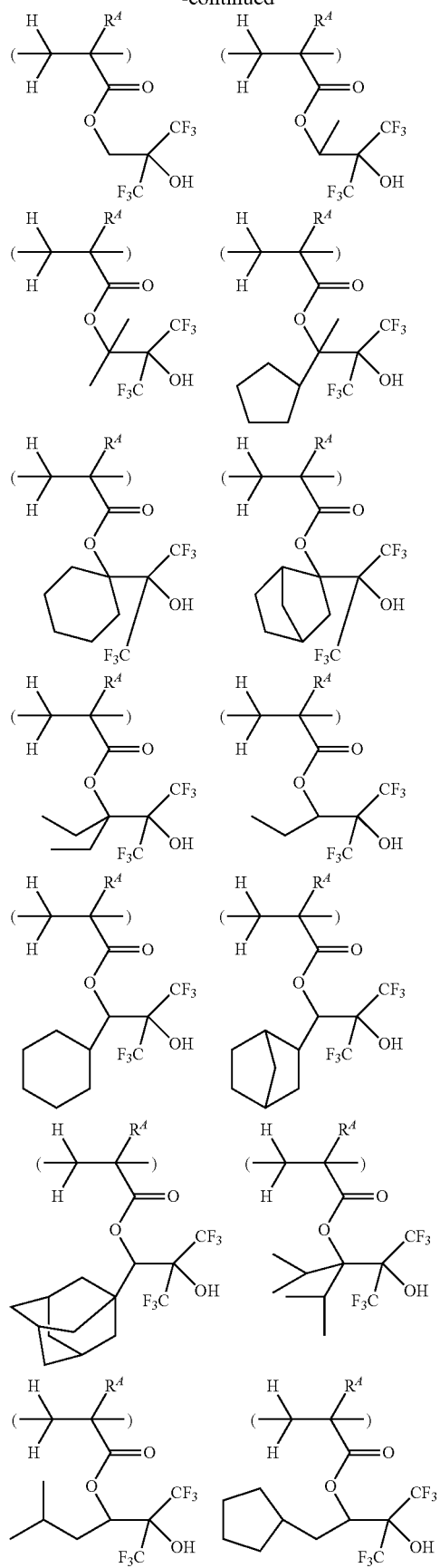
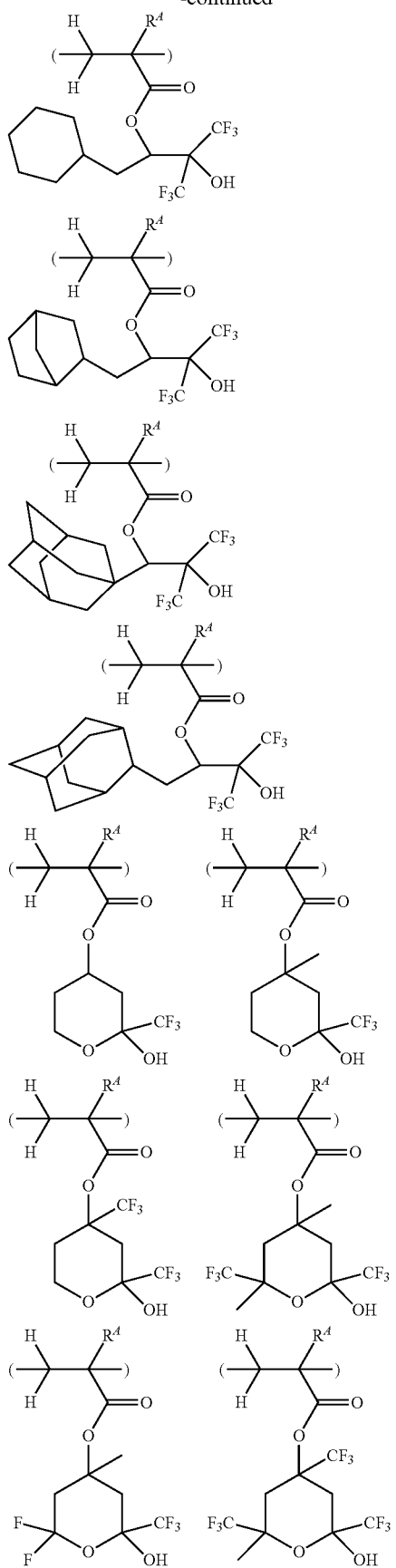

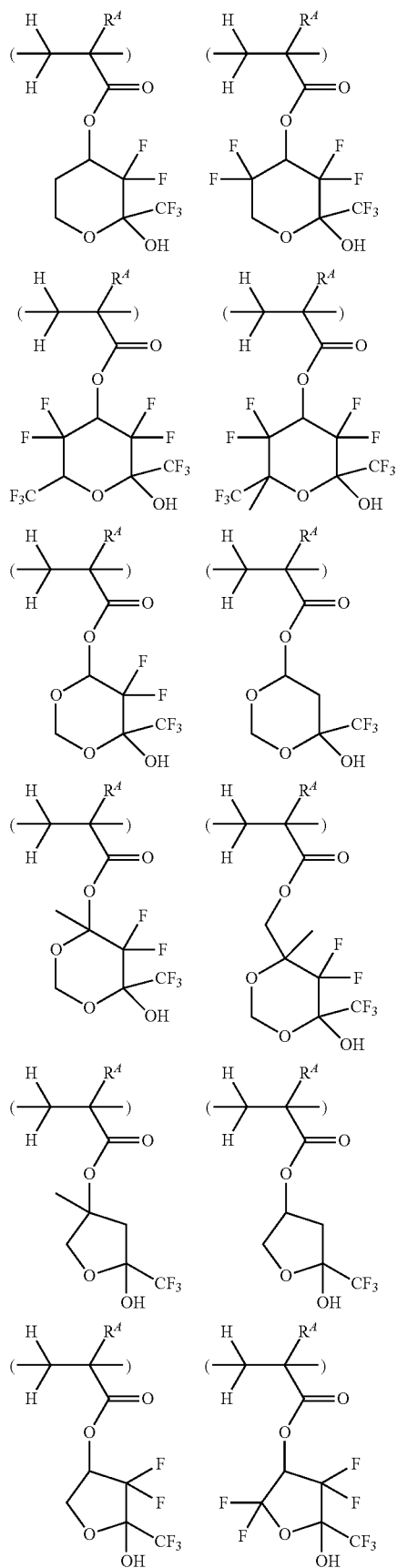
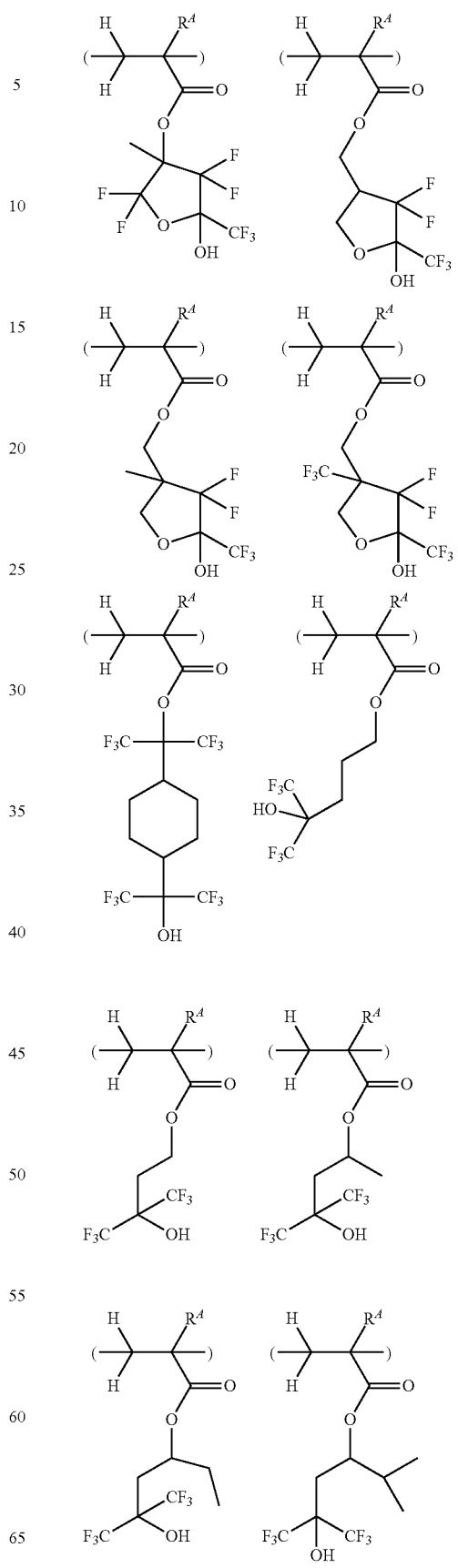

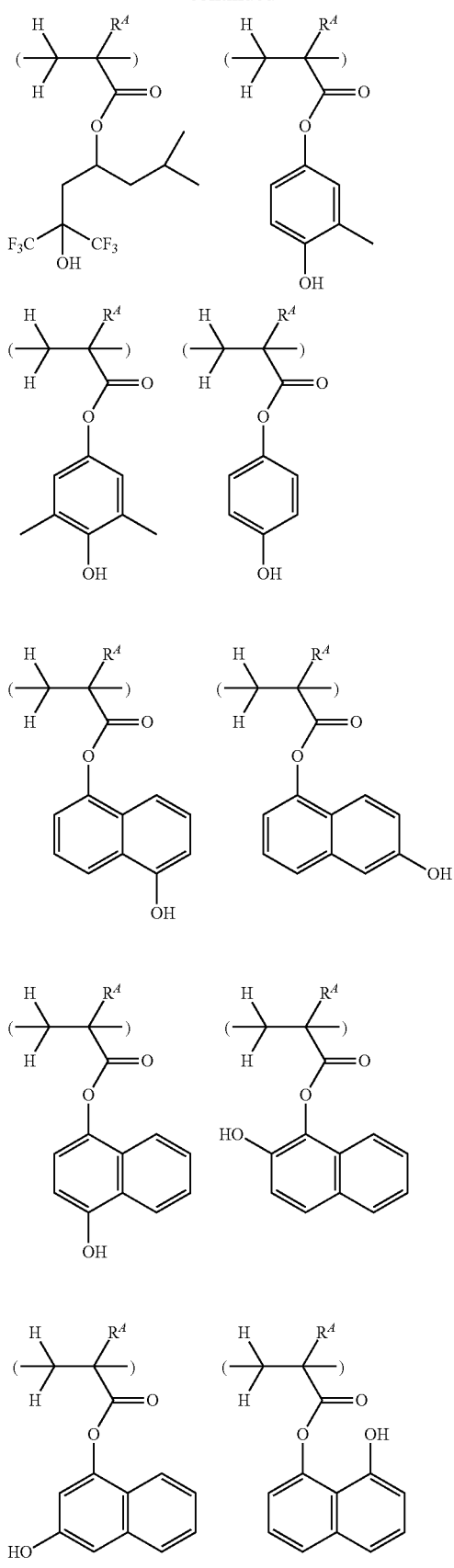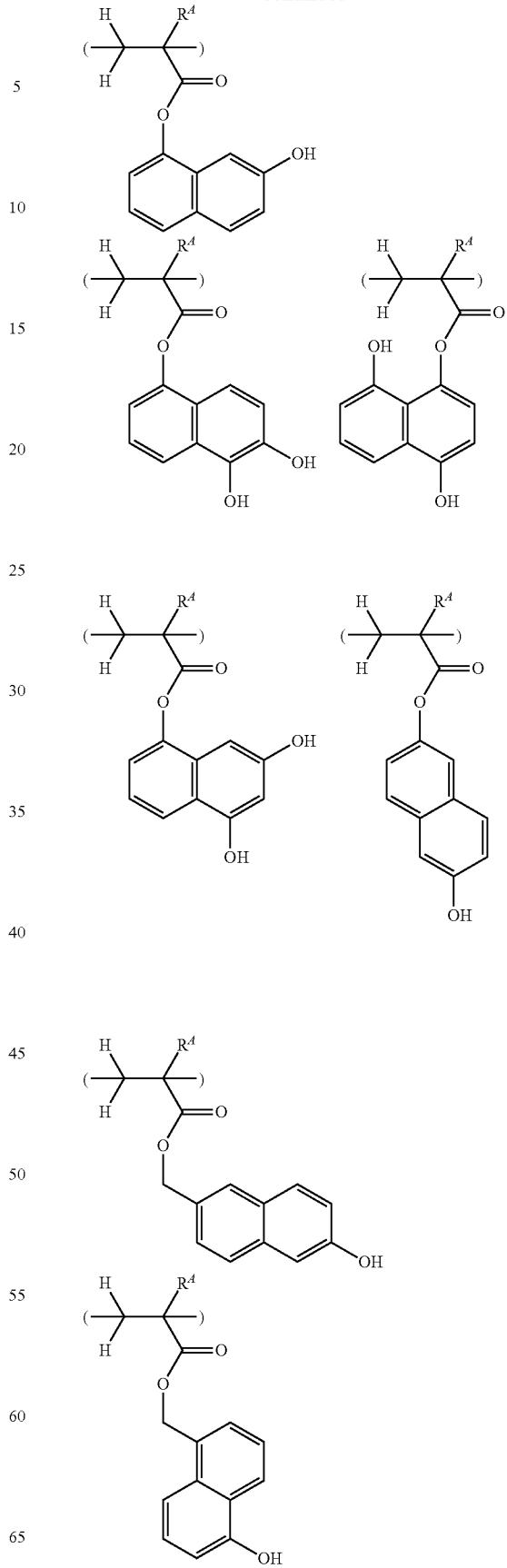

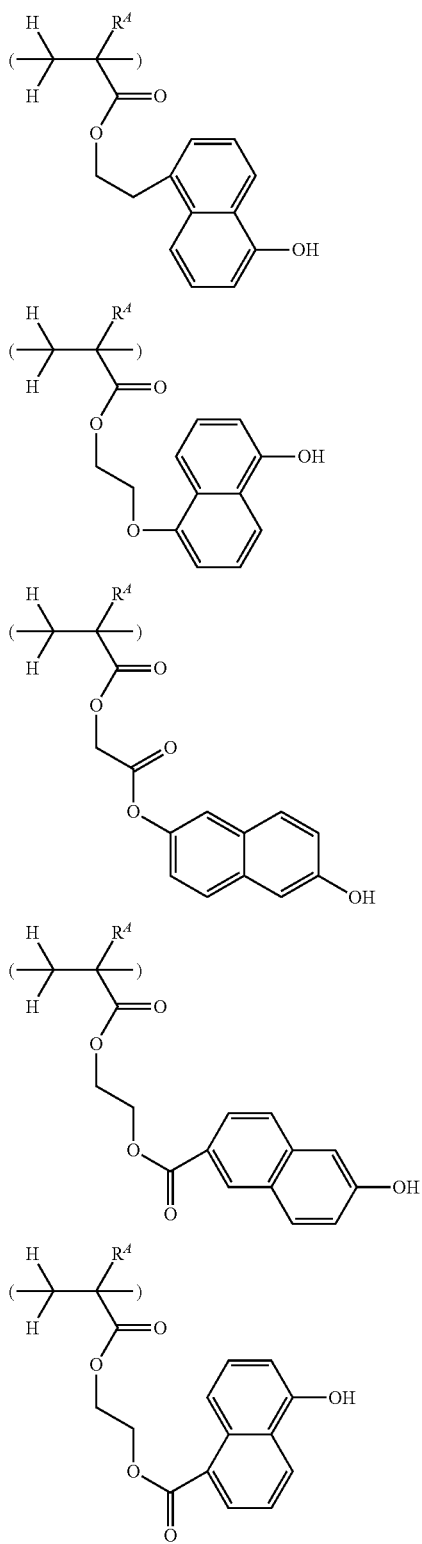

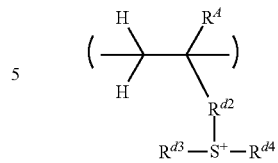

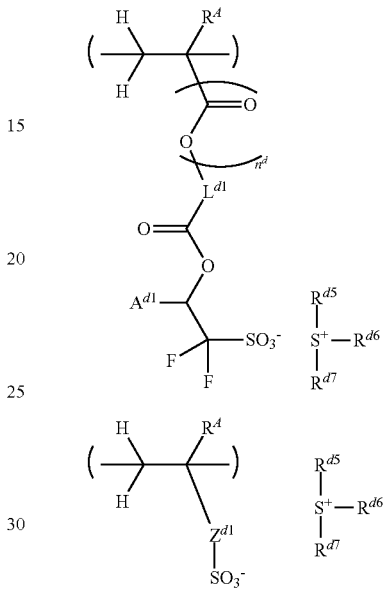

Of the recurring units having formula (3), those units having a lactone ring as the polar group are most preferred.

In addition to the recurring units having formulae (2) and (3), the polymer as base resin (B) may further comprise recurring units having the formula (d1), (d2) or (d3).

In formulae (d1) to (d3), $R^A$ is as defined and exemplified above. $R^{d2}$ is a single bond, phenylene group, —O—$R^{d1}$— or —C(=O)—$Y^{d1}$—$R^{d1}$— wherein $Y^{d1}$ is oxygen or NH, and $R^{d1}$ is a straight, branched or cyclic $C_1$-$C_{20}$ alkylene group, straight, branched or cyclic $C_2$-$C_{20}$ alkenylene group, or phenylene group, which may contain a heteroatom. $R^{d3}$, $R^{d4}$, $R^{d5}$, $R^{d6}$ and $R^{d7}$ are each independently a straight, branched or cyclic $C_1$-$C_{20}$ monovalent hydrocarbon group which may contain a heteroatom. Any two or more of $R^{d2}$, $R^{d3}$ and $R^{d4}$ may bond together to form a ring with the sulfur atom to which they are attached, and any two or more of $R^{d5}$, $R^{d5}$, and $R^{d7}$ may bond together to form a ring with the sulfur atom to which they are attached. $Xd^-$ is a non-nucleophilic counter ion. $A^{d1}$ is hydrogen or trifluoromethyl. $L^{d1}$ is a single bond or a straight, branched or cyclic $C_1$-$C_{20}$ divalent hydrocarbon group which may contain a heteroatom. The subscript $n^d$ is 0 or 1, and $n^d$ is 0 when $L^{d1}$ is a single bond. $Z^{d1}$ is a single bond, methylene, ethylene, phenylene, fluorophenylene, —O—$R^{d1}$—, or —C(=O)—$Y^{d1}$—$R^{d1}$—.

Examples of the non-nucleophilic counter ion represented by $Xd^-$ in formula (d1) include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imides such as bis(trifluoromethylsulfonyl)imide, bis(perfluoroethylsulfonyl)imide, and bis(perfluorobutylsulfonyl)imide; and methides such as tris(trifluoromethylsulfonyl)methide and tris(perfluoroethylsulfonyl)methide.

Other non-nucleophilic counter ions include anions having the formulae (d4) and (d5).

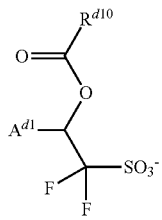
(d4)

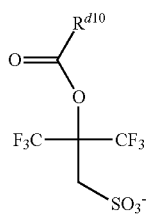
(d5)

In formulae (d4) and (d5), $A^{d1}$ is as defined above, and $R^{d10}$ is a straight, branched or cyclic $C_1$-$C_{20}$ monovalent hydrocarbon group which may contain a heteroatom.

The anion moiety of formula (d4) is exemplified by those structures illustrated in JP-A 2010-113209 and JP-A 2007-145797. The anion moiety of formula (d5) is exemplified by those structures illustrated in JP-A 2010-215608.

The anion moiety in formula (d2) wherein $A^{d1}$ is hydrogen is exemplified by those structures illustrated in JP-A 2010-116550. The anion moiety in formula (d2) wherein $A^{d1}$ is trifluoromethyl is exemplified by those structures illustrated in JP-A 2010-077404.

Illustrative examples of the sulfonium cation in formulae (d2) and (d3) are shown below, but not limited thereto.

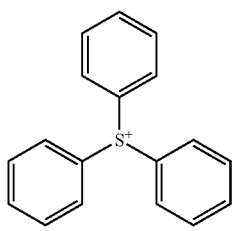

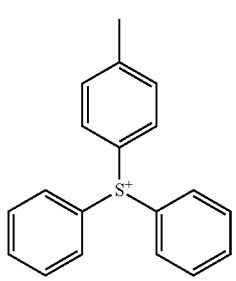

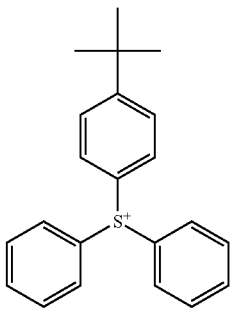

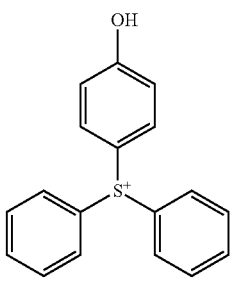

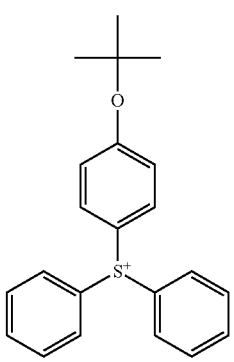

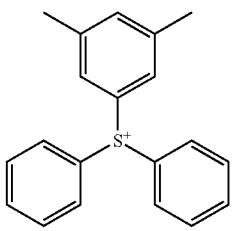

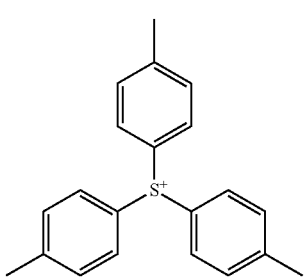

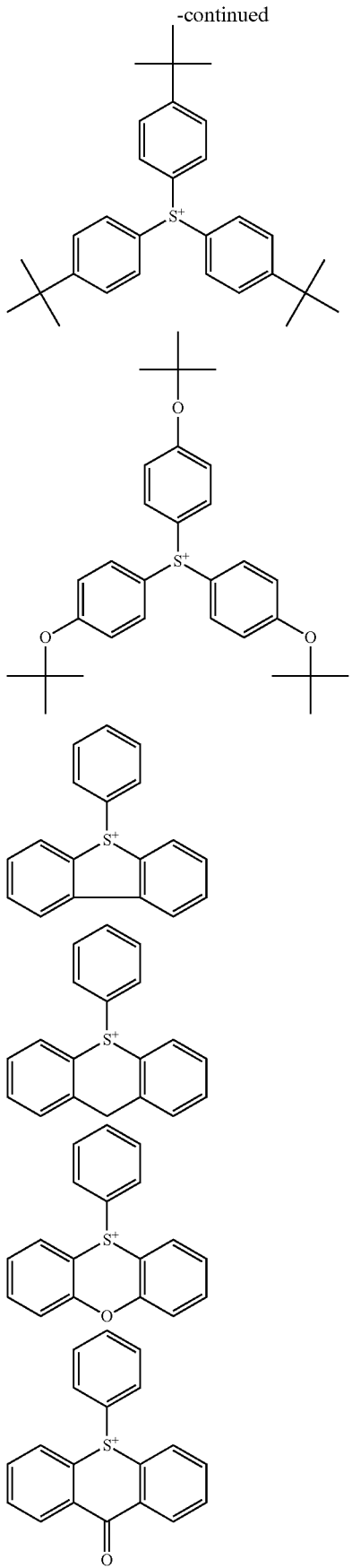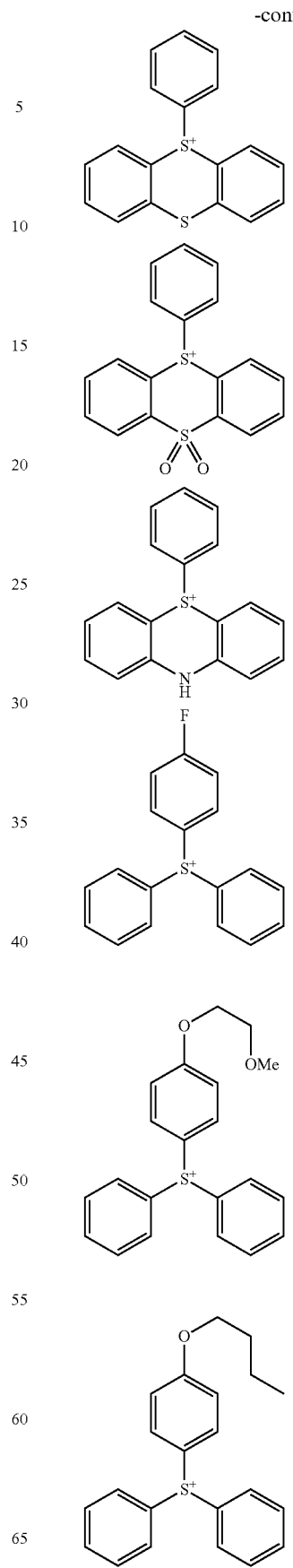

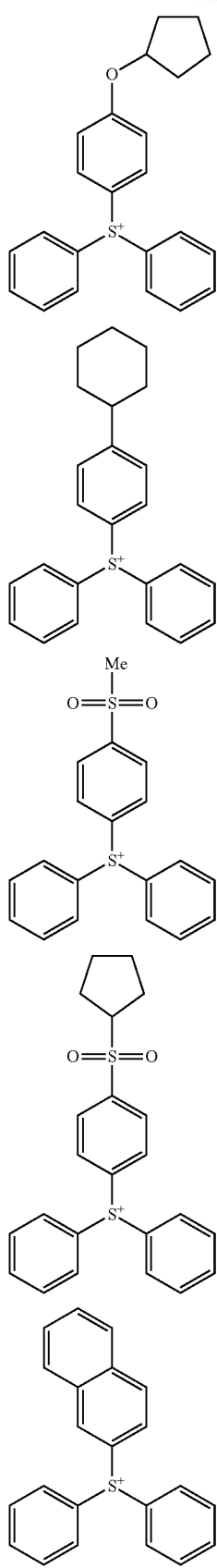
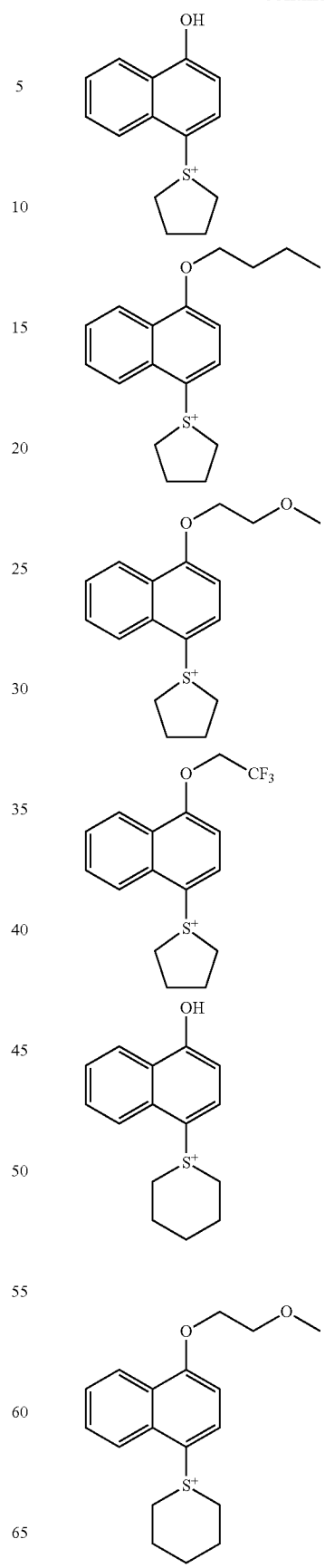

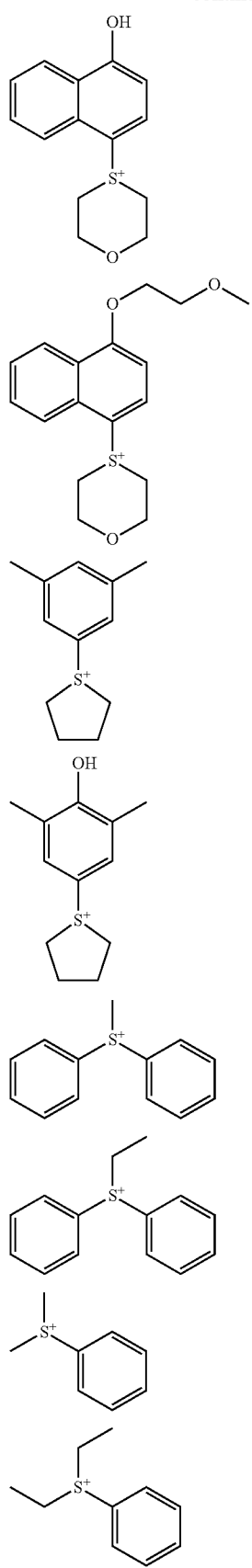
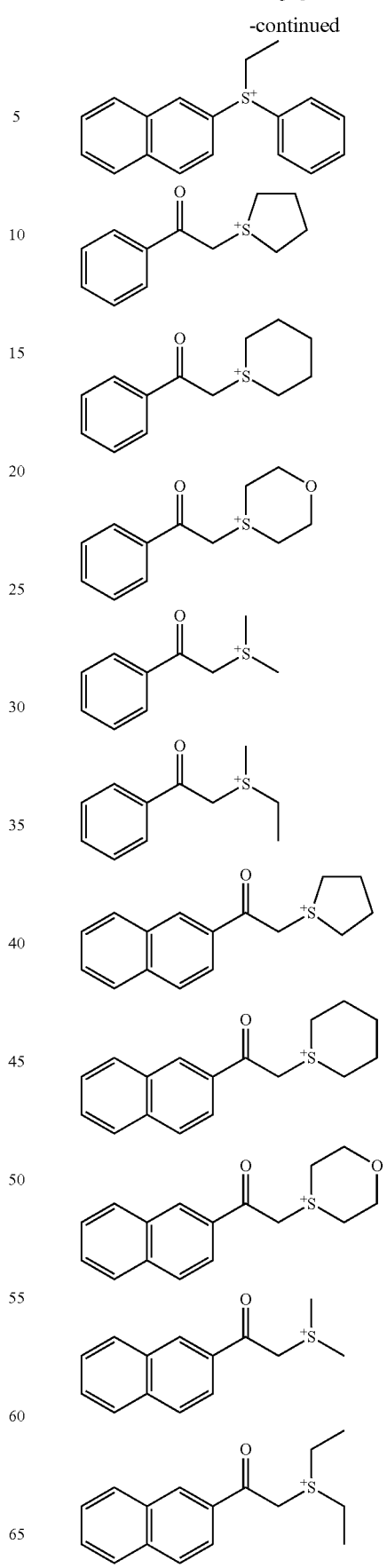

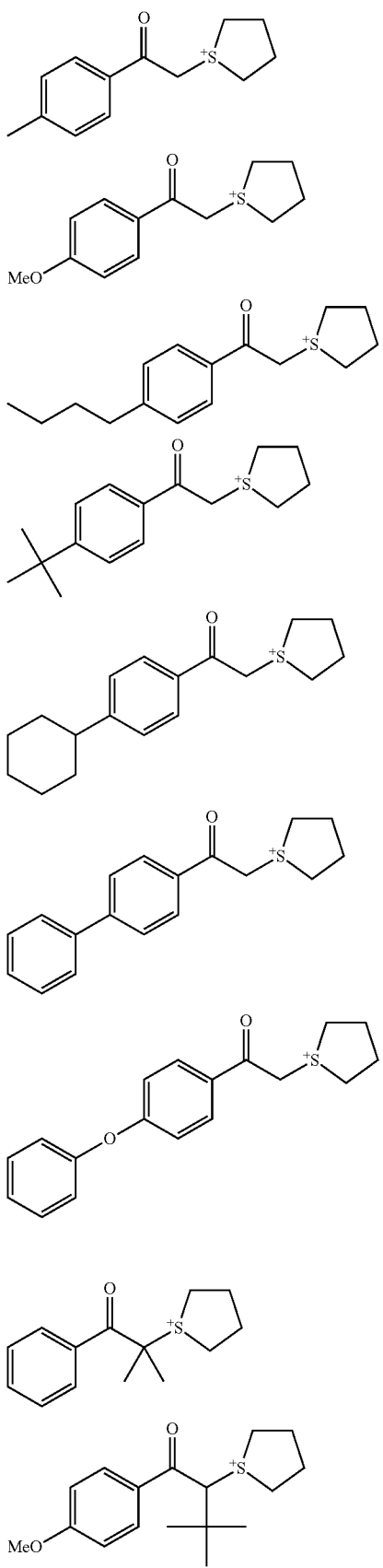

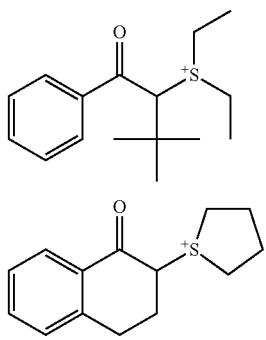

The base resin (B) may have further copolymerized therein recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Inter alia, recurring units having the formula (e1) are preferred.

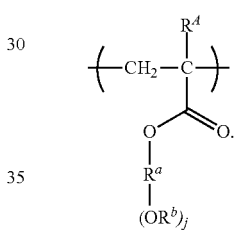

(e1)

In formula (e1), $R^A$ is as defined above, $R^a$ is a straight, branched or cyclic $C_1$-$C_{30}$ di- to pentavalent hydrocarbon group which may contain a heteroatom, $R^b$ is an acid labile group, and j is an integer of 1 to 4.

Examples of the recurring unit of formula (e1) are shown below, but not limited thereto. Herein $R^A$ and $R^b$ are as defined above.

97
-continued
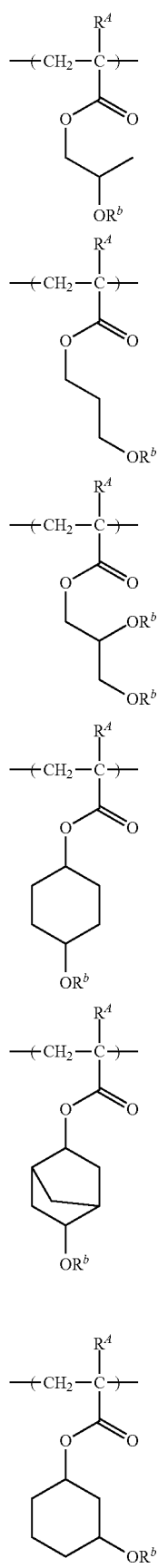
98
-continued
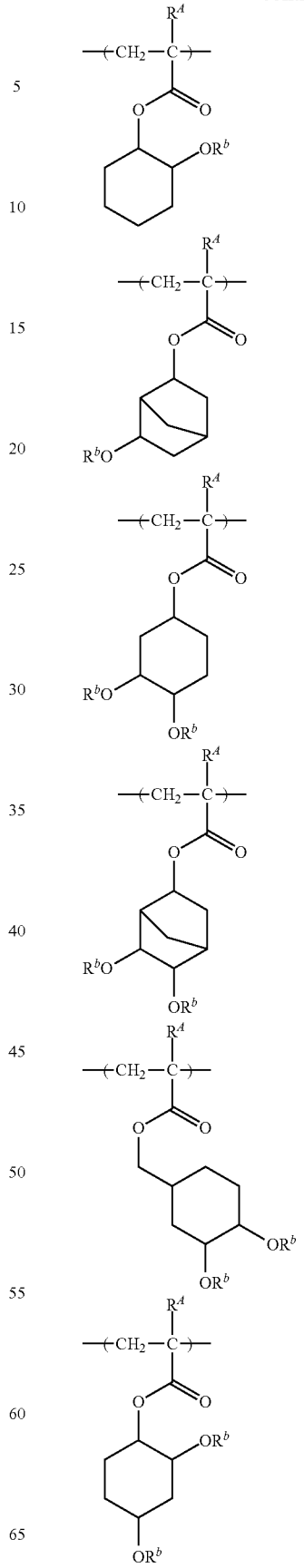

99
-continued
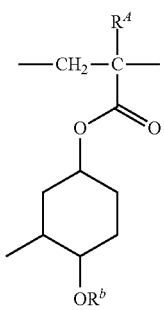
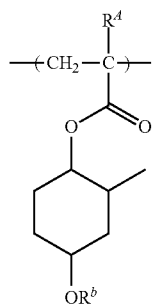
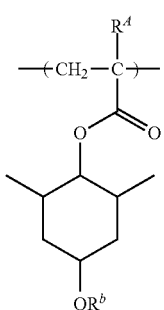
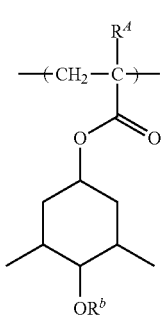
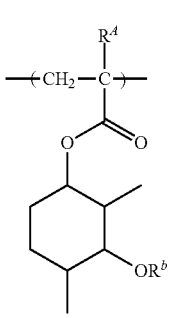
100
-continued
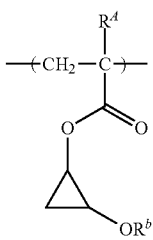
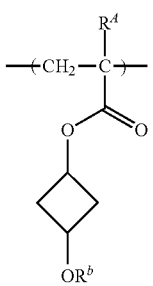
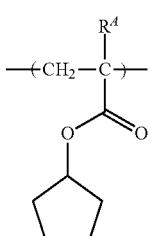
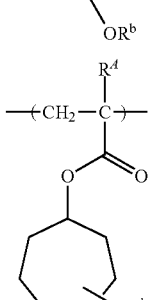
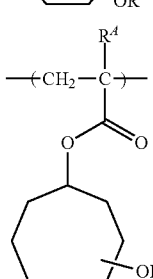
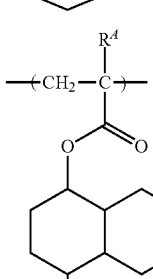

101
-continued
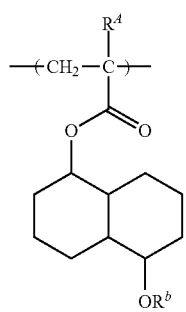
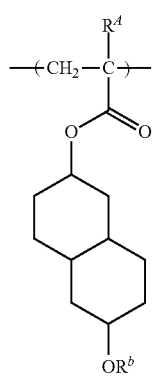
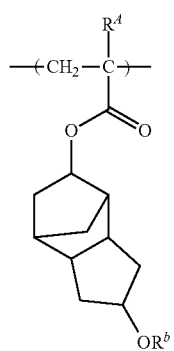
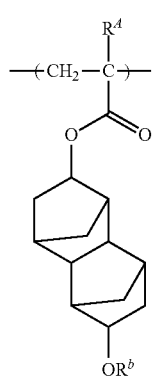
102
-continued
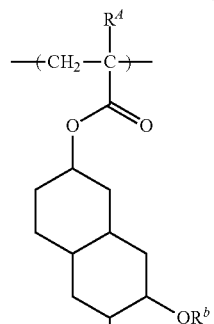
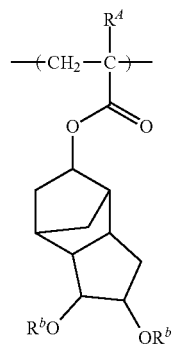
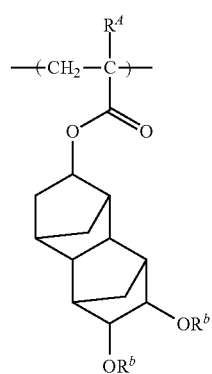
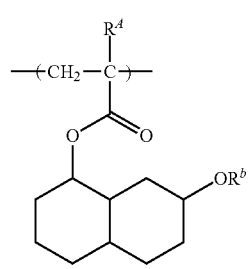
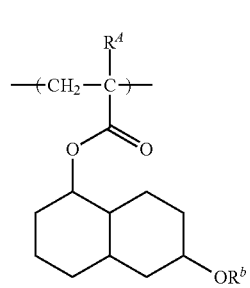

103
-continued
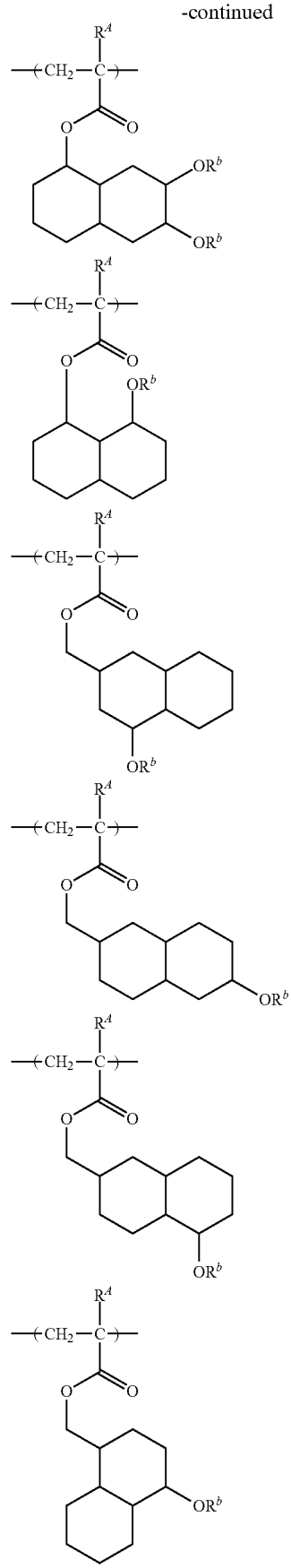
104
-continued
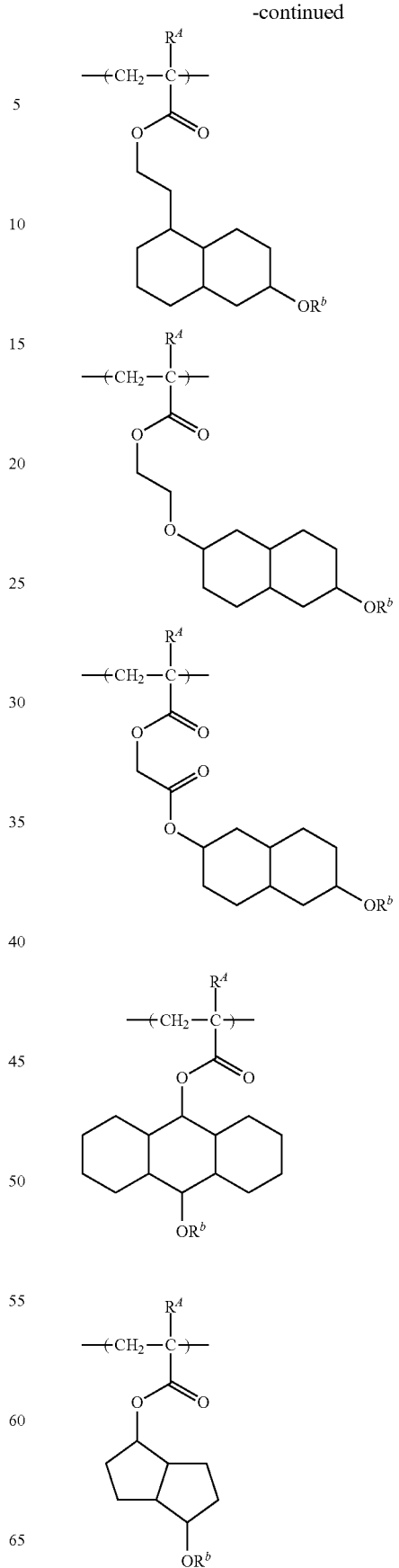

105
-continued
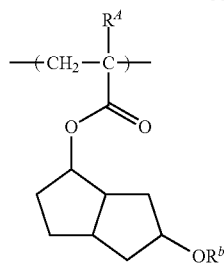
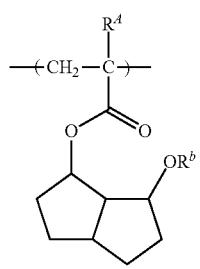
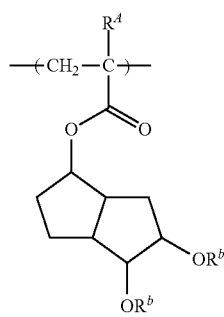
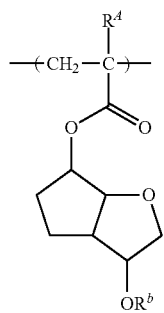
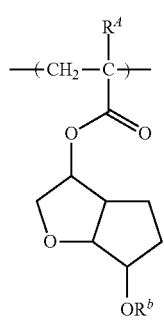
106
-continued
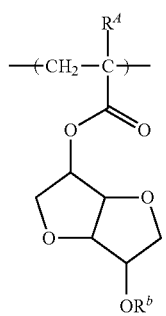
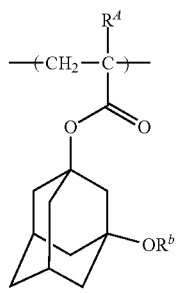
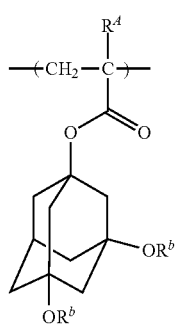
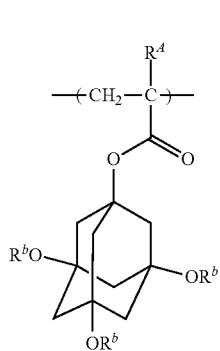
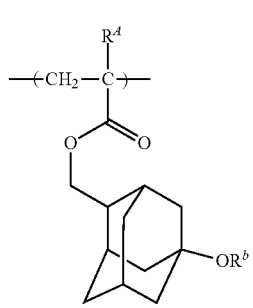

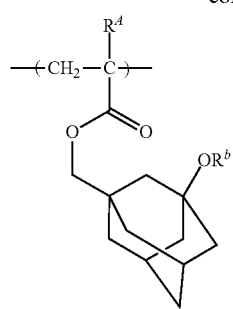
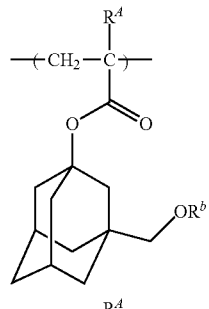
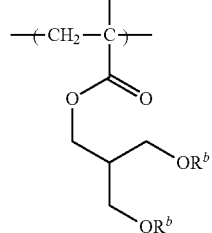
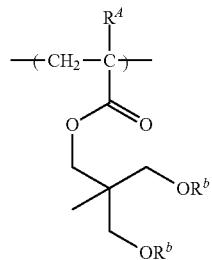
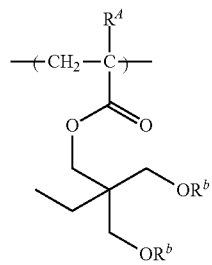
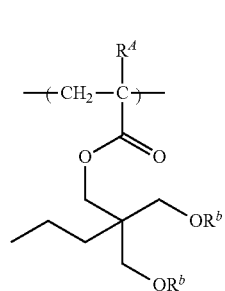
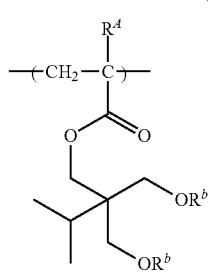
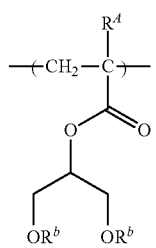
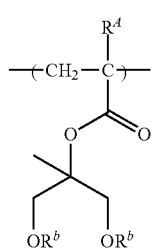
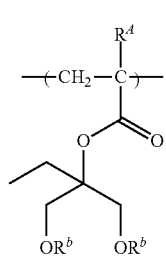
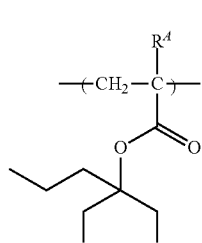
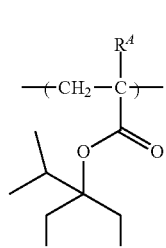

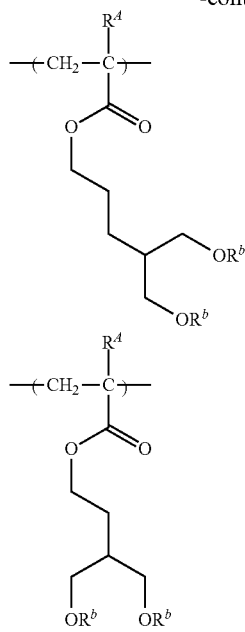

The structure of the acid labile group $R^b$ in formula (e1) is not particularly limited as long as it is deprotected to generate a hydroxyl group under the action of acid. Typical acid labile groups are groups of acetal or ketal structure and alkoxycarbonyl groups, with their examples being shown below.

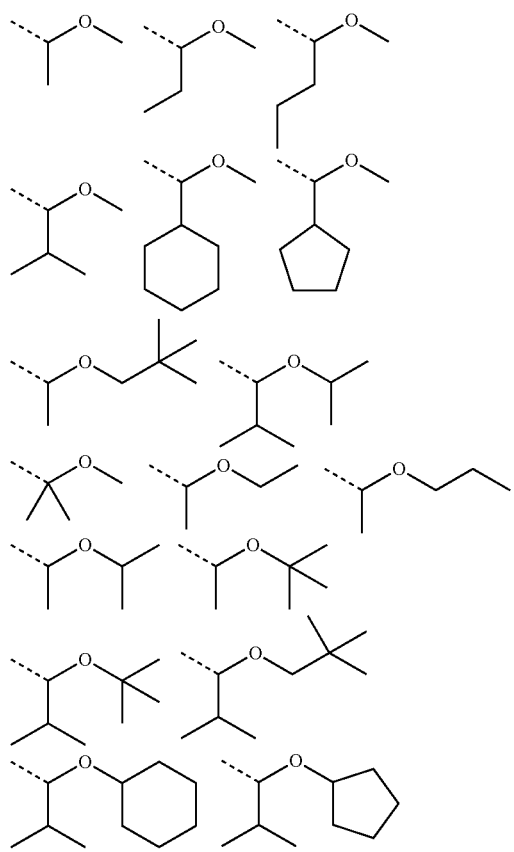

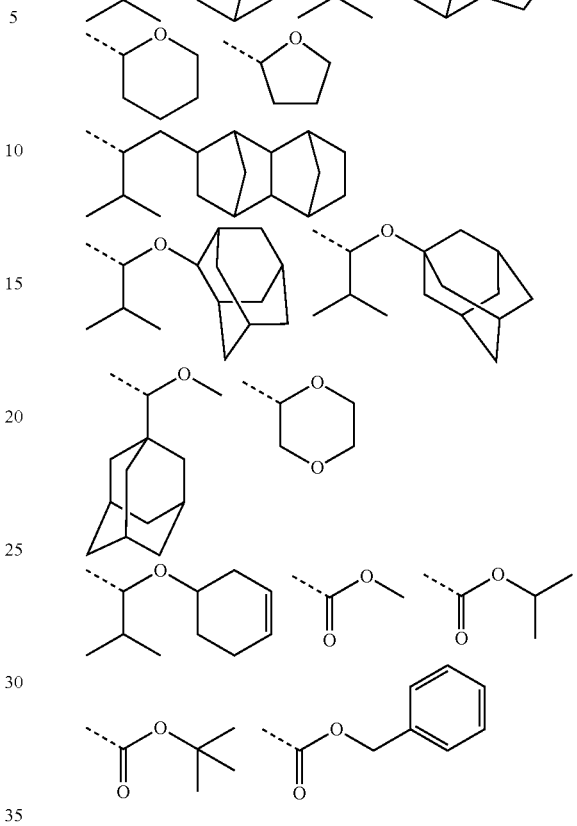

Of the acid labile group $R^b$, preferred are alkoxymethyl groups having the formula (e2)

wherein $R^c$ is a straight, branched or cyclic $C_1$-$C_{20}$ monovalent hydrocarbon group such as alkyl.

Examples of the id labile group of formula (e2) are shown below, but not limited thereto.

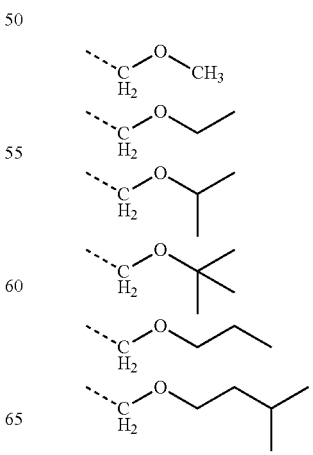

111
-continued
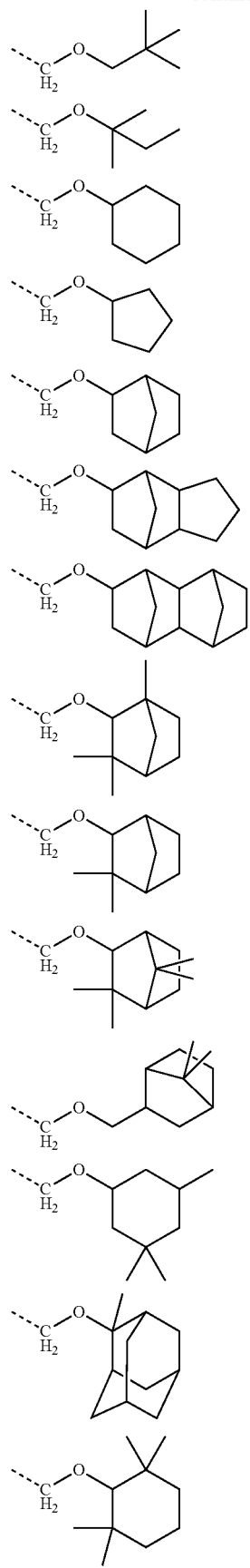
112
-continued
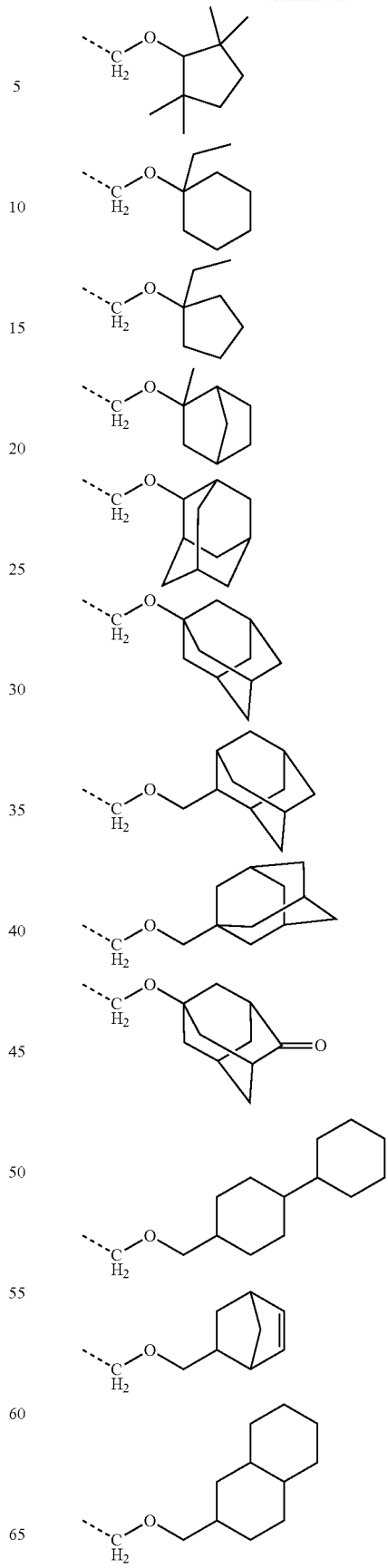

113
-continued
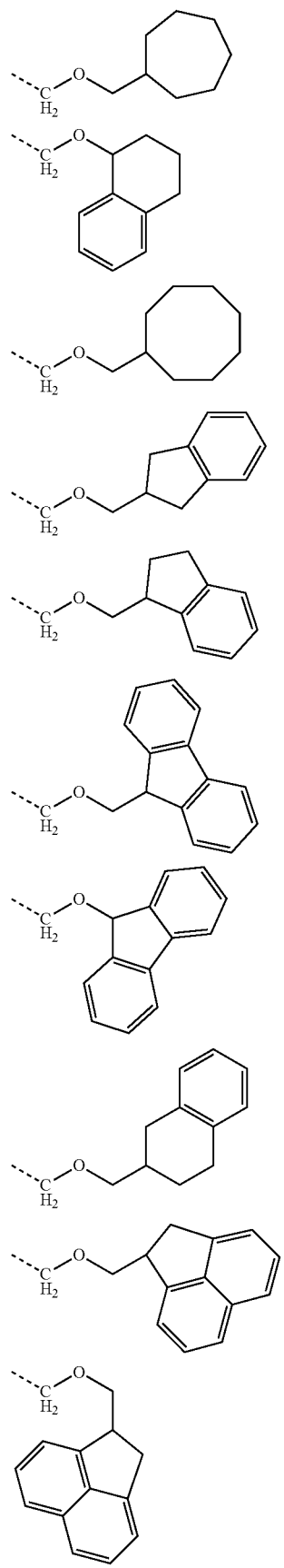
114
-continued
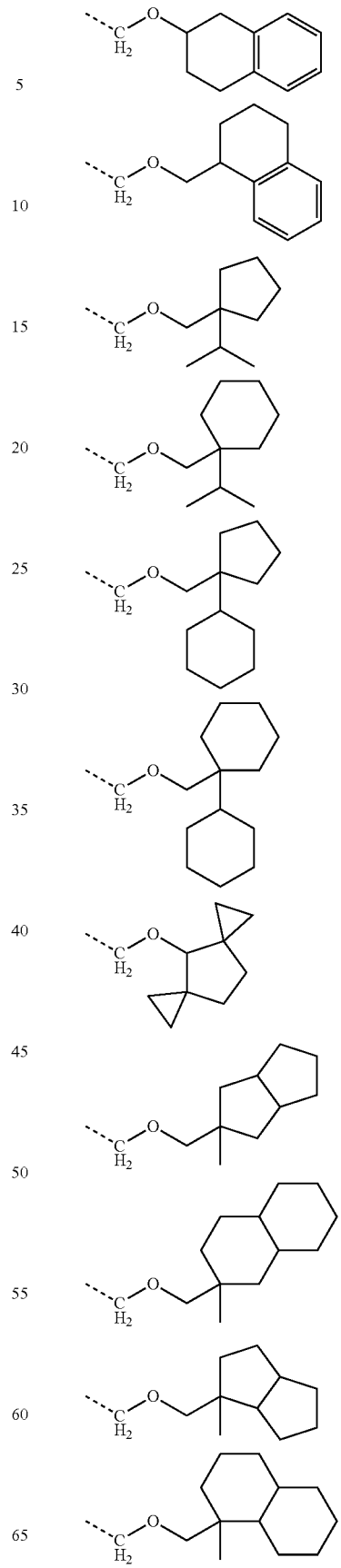

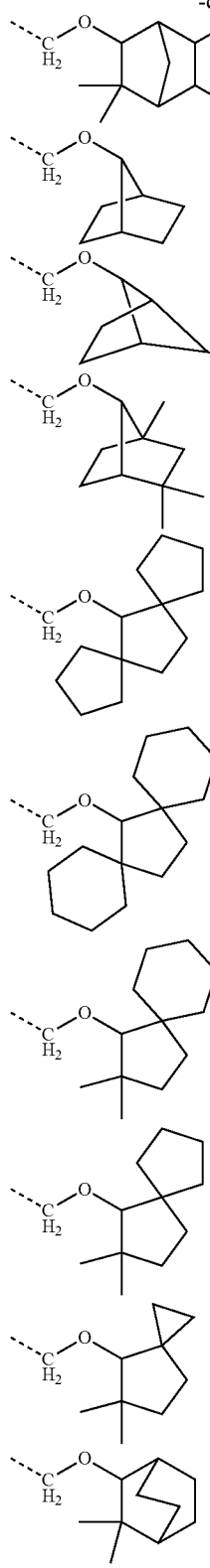
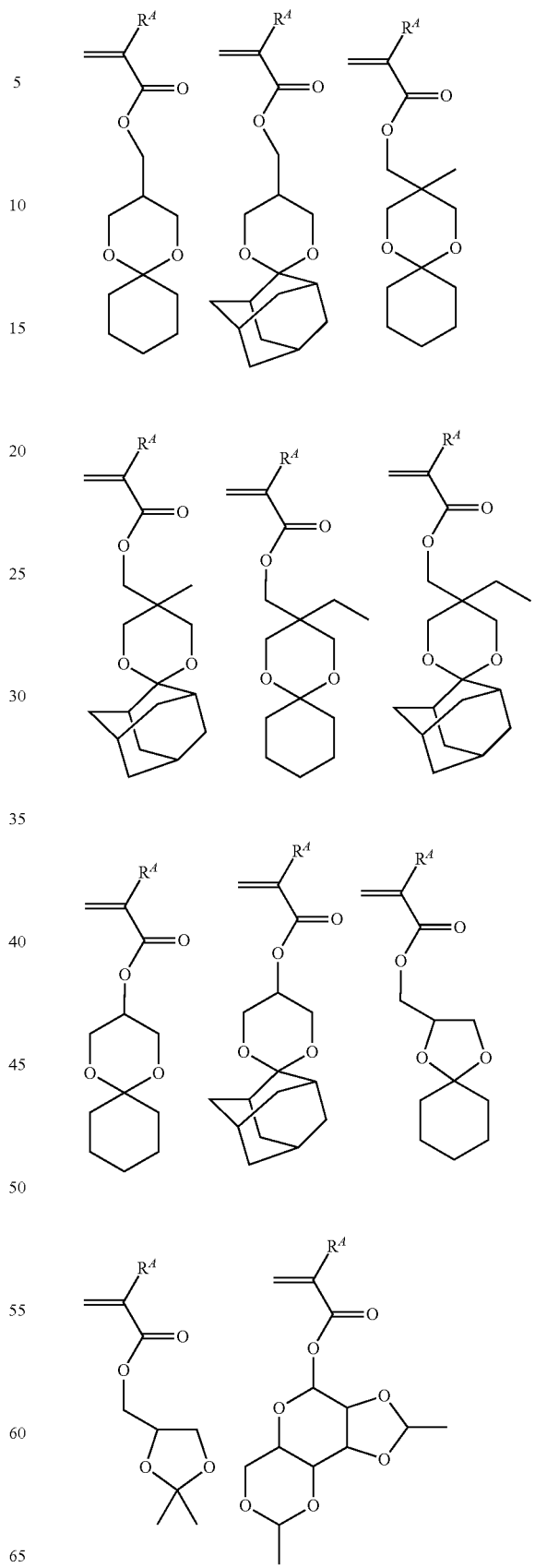
Besides the aforementioned structures, a monomer having a plurality of hydroxyl groups which are acetal-protected with one ketone compound as shown below is also exemplary of the monomer providing the recurring unit having formula (e1). Herein $R^A$ is as defined above.

117
-continued
118
-continued
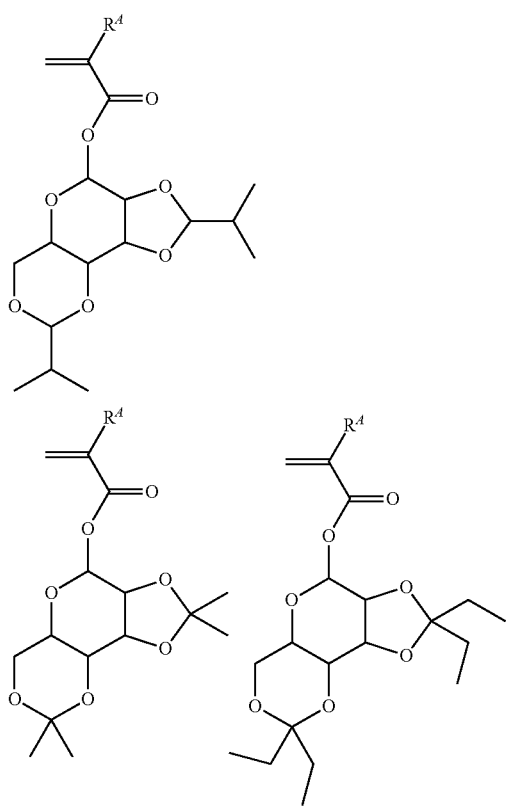
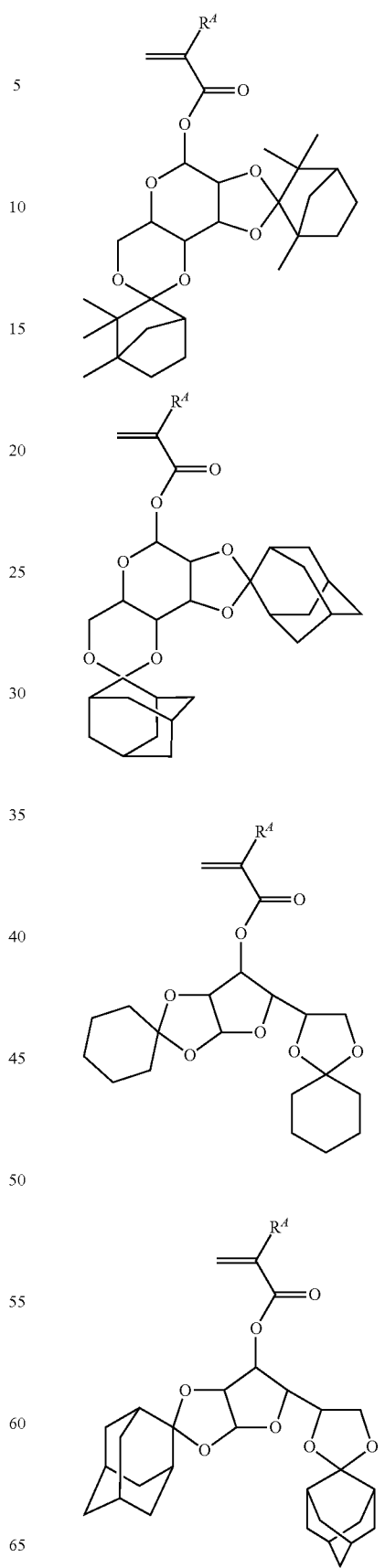

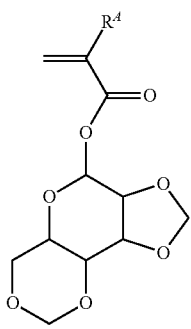

In addition to the foregoing units, the base resin (B) may further comprise recurring units having an oxetane ring or oxirane ring. Copolymerization of oxetane or oxirane ring-containing units ensures that the resist film is crosslinked in the exposed region. The exposed region of resist film is thus improved in retention and etch resistance.

Examples of the monomer providing the recurring unit having an oxetane ring or oxirane ring are shown below, but not limited thereto. Herein $R^A$ is as defined above.

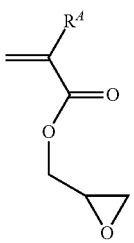

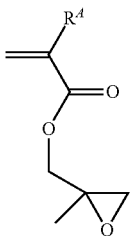

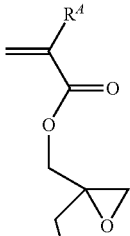

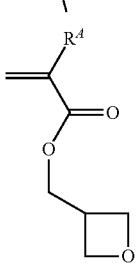

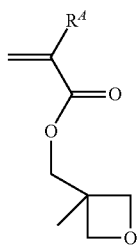

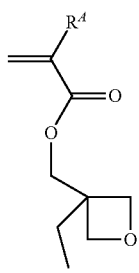

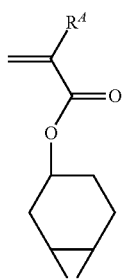

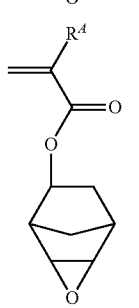

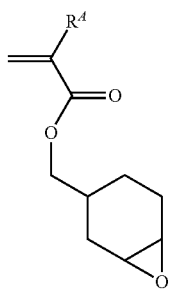

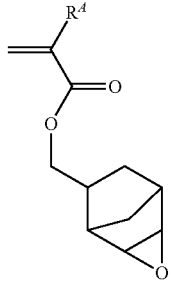

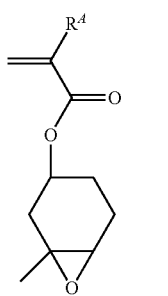
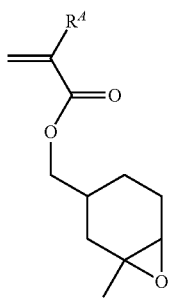
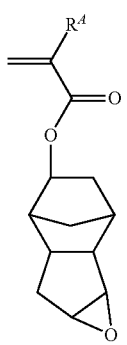
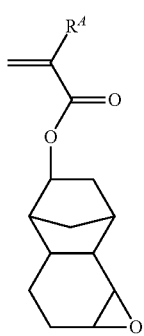
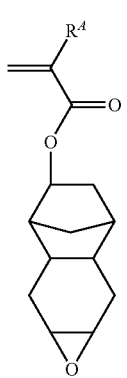
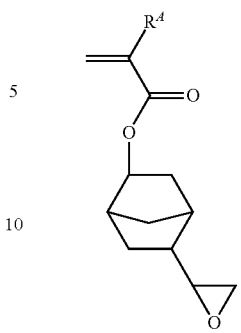
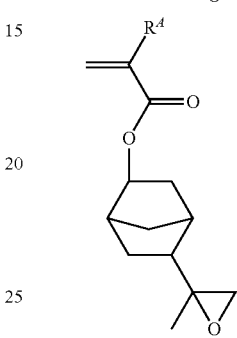
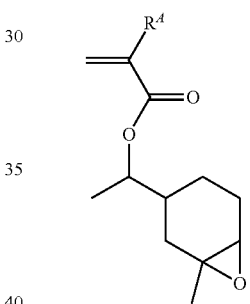
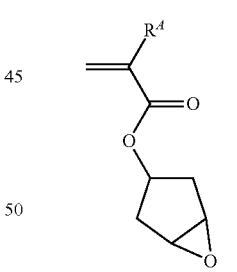
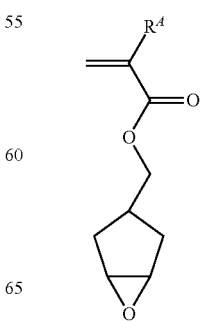

123
-continued
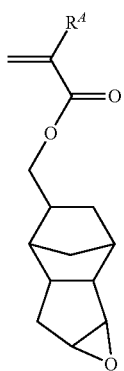
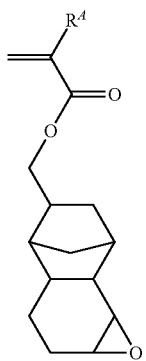
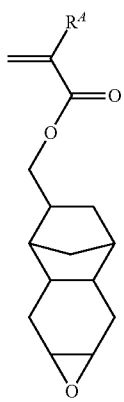
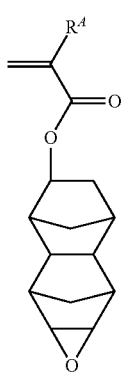
124
-continued
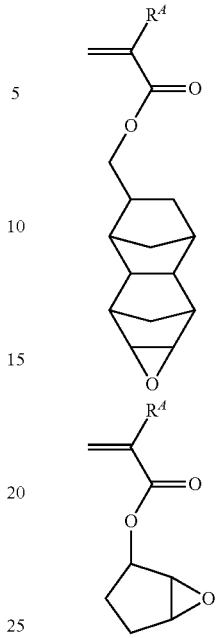
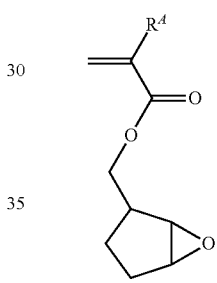
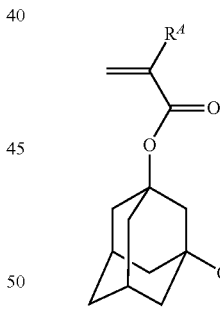
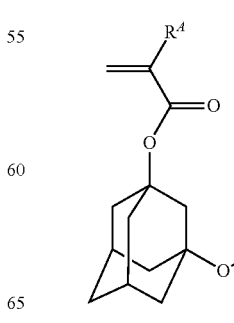
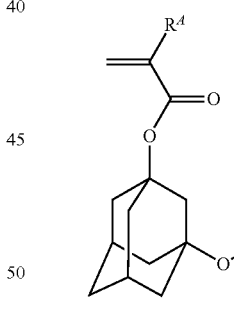

125
-continued
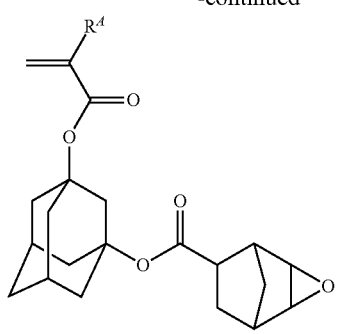
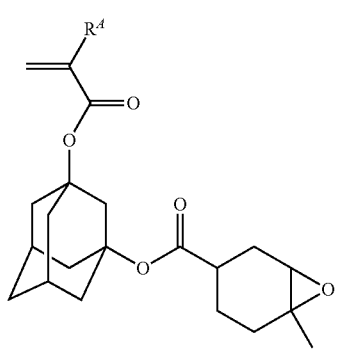
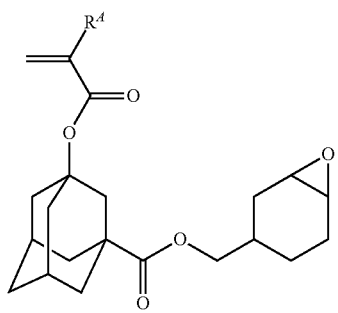
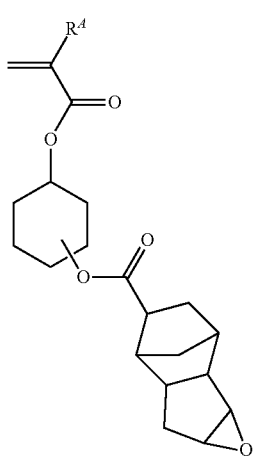
126
-continued
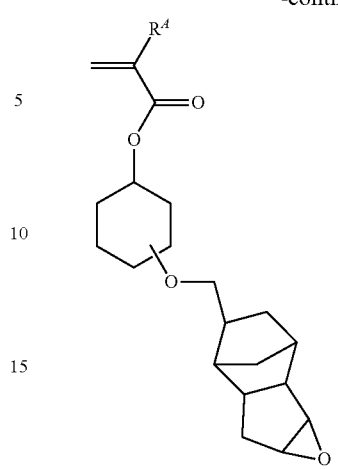
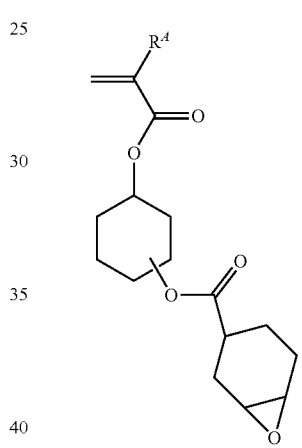
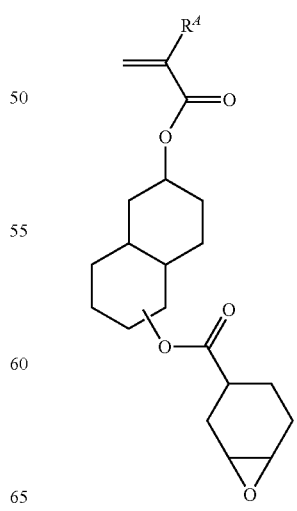

127
-continued
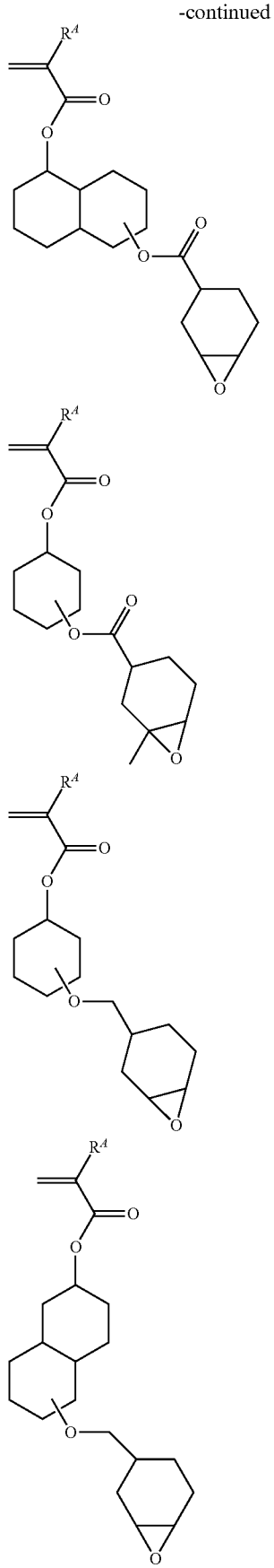
128
-continued
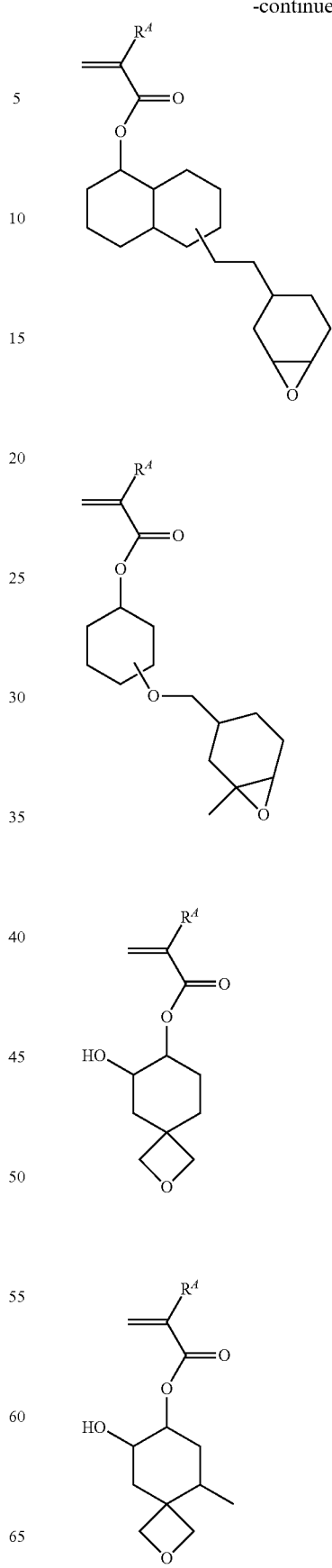

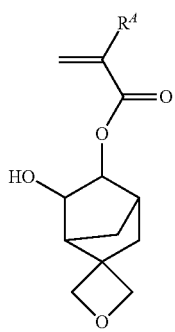

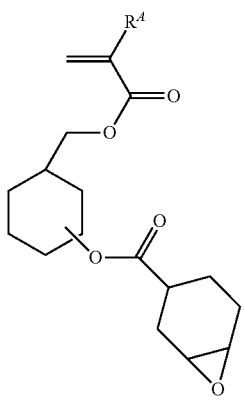

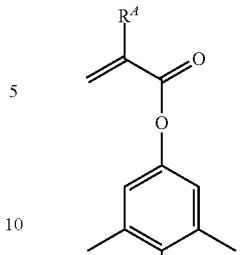

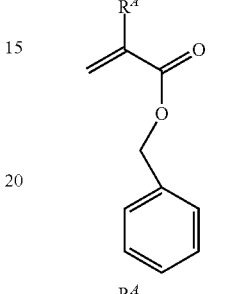

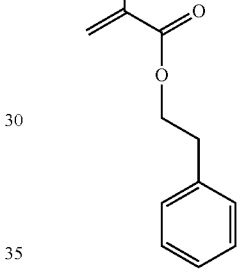

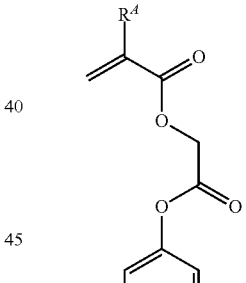

In addition to the foregoing unite, the base ruin (B) may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo [6.2.1.1$^{3,6}$. 0$^{2,7}$] dodecene derivatives, unsaturated acid anhydrides such as itaconic anhydride, and other monomers. Also, hydrogenated ROMP polymers as described in. JP-A 2003-066612 may be used.

The other monomers are exemplified below, but not limited thereto.

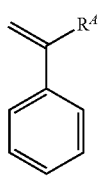

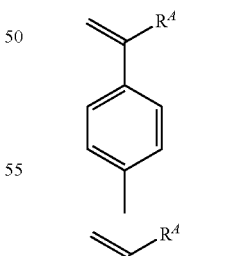

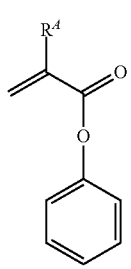

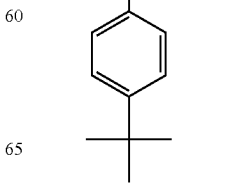

131
-continued
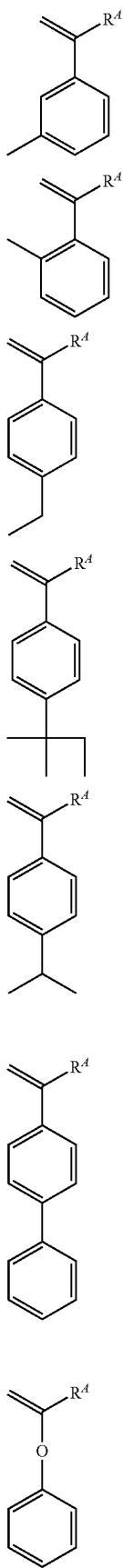
132
-continued
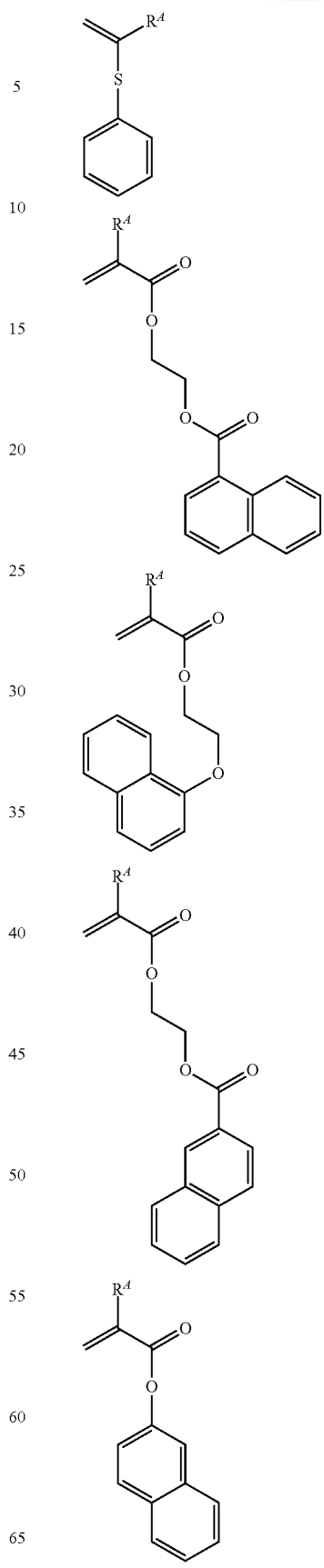

133
-continued
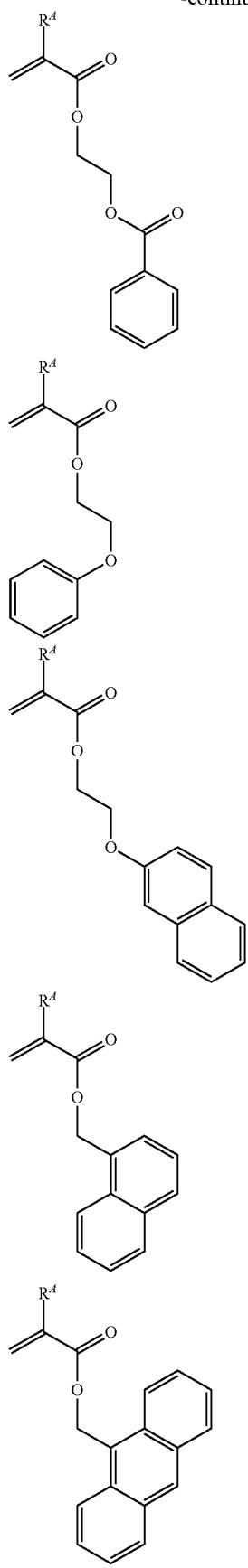
134
-continued
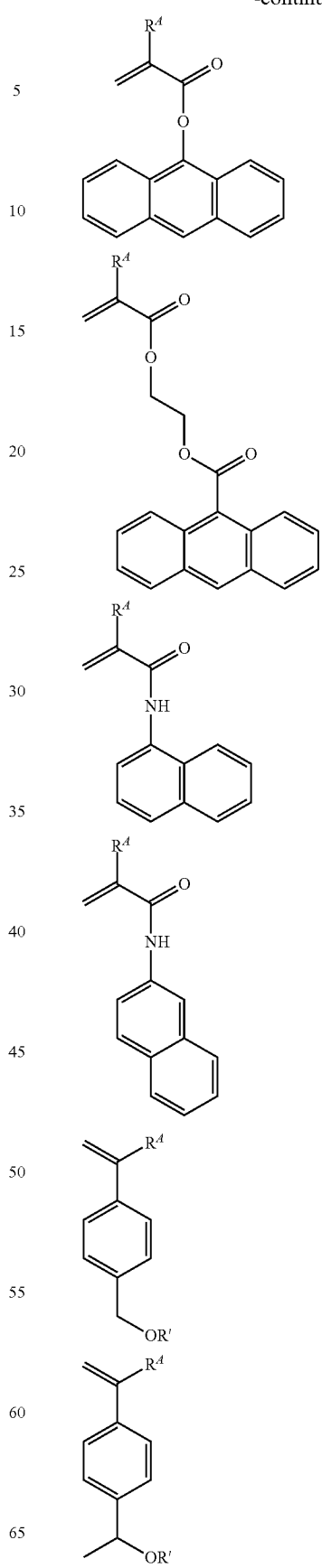

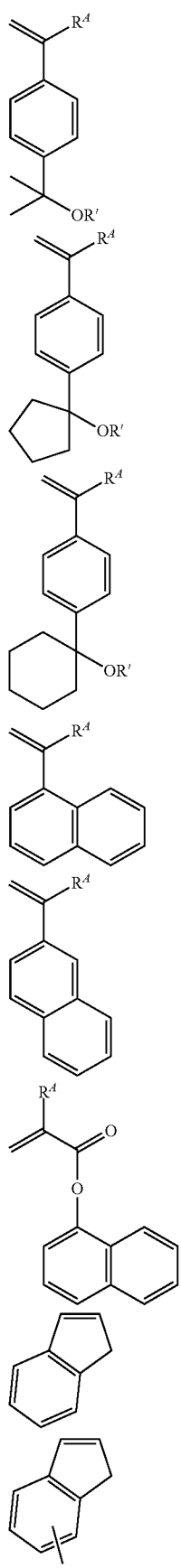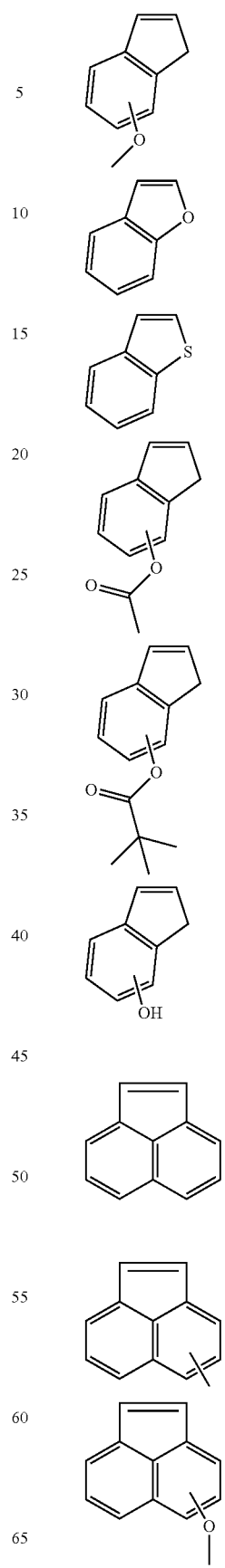

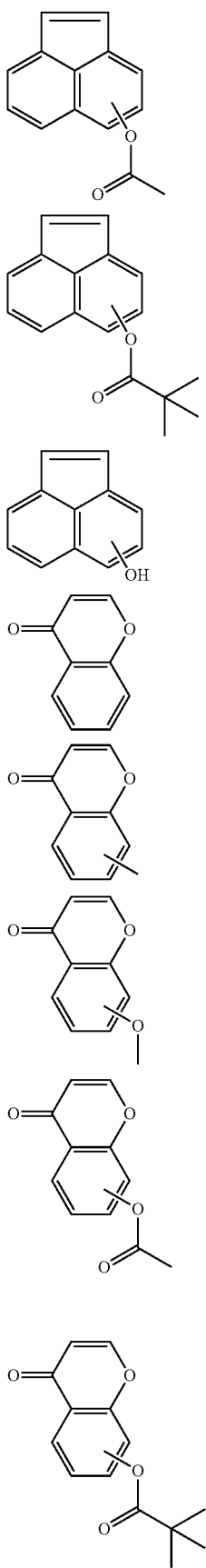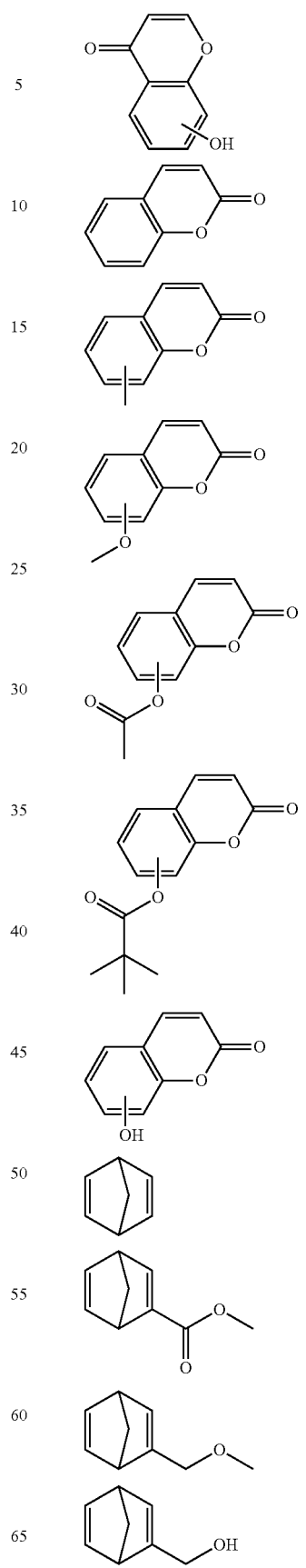

-continued

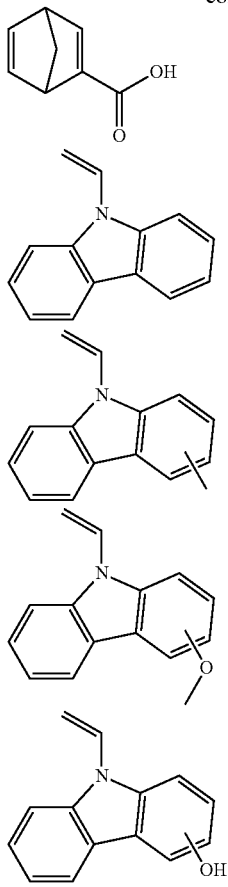

Herein $R^4$ is as defined above and $R^1$ is $C_1$-$C_{10}$ alkyl.

The base resin (B) has a weight average molecular weight (Mw) of preferably 1,000 to 500,000, more preferably 3,000 to 15,000, as measured by gel permeation chromatography (GPC) versus polystyrene standards using tetrahydrofuran solvent. As long as Mw is equal to or more than the lower limit, no film thickness loss occurs during organic solvent development. As long as Mw is equal to or less than the upper limit, the resin is fully soluble in an organic solvent and no footing phenomenon occurs after pattern formation.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base resin (B) should preferably have a narrow dispersity (Mw/Mn) of 1.0 to 2.0, especially 1,0 to 1.6 in order to formulate a resist composition suited for fine size pattern formation.

The method of synthesizing the polymer or base resin (B) is, for example, by dissolving one or more unsaturated bond-bearing monomers in an organic solvent, adding a radical initiator, and effecting heat polymerization. Examples of the organic solvent which can be used for polymerization include toluene, benzene, tetrahydrofuran, diethyl ether, dioxane, cyclohexane, cyclopentane, cyclohexanone, cyclopentanone, methyl ethyl ketone, and γ-butyrolactone. Examples of the polymerization initiator used herein include 2,2'-azobisisobutyronitrile (AIBN), 2,2'-azobis(2,4-dimethyl-valeronitrile), dimethyl 2,2-azobis(2-methylpropionate), benzoyl peroxide, and lauroyl peroxide. Preferably the reaction temperature is in a range of 50 to 80° C. and the reaction time is 2 to 100 hours, more preferably 5 to 20 hours. The acid labile group that has been incorporated in the monomer may be kept as such, or polymerization may be followed by protection or partial protection.

It is acceptable to use a blend of two or more polymers which differ in compositional ratio, molecular weight or dispersity as the base resin (B).

In a further embodiment, the base resin may be blended with a polymer of the conventional type wherein the exposed region is dissolved on alkaline development such as (meth)acrylate polymer, polynorbornene, cycloolefin-maleic anhydride copolymer, or ring-opening metathesis polymerization (ROMP) polymer. Also, the base resin may be blended with a (meth)acrylate polymer, polynorbornene, or cycloolefin-maleic anhydride copolymer having an acid labile group-substituted hydroxyl group wherein the exposed region is not dissolved by alkaline development, but a negative pattern is formed by organic solvent development.

While the base resin (B) comprises recurring units derived from monomers, the molar fractions of respective units preferably fall in the following range (mol %), but are not limited thereto:

(I) 1 to 80 mol %, more preferably 5 to 70 mol %, even more preferably 10 to 60 mol % of constituent units of at least one type having formula (2), (II) 20 to 99 mol %, more preferably 30 to 95 mol %, even more preferably 40 to 90 mol % of constituent units of at least one type having formula (3), and optionally, (III) 0 to 30 mol %, more preferably 0 to 20 mol %, and even more preferably 0 to 10 mol %, of constituent units of at least one type having formula (d1), (d2) or (d3), and optionally, (IV) 0 to 80 mol %, more preferably to 70 mol %, and even more preferably 0 to 50 mol % of constituent units of at least one type having formula (e1) or derived from another monomer(s).

Component (C)

The resist composition may comprise (C) an organic solvent. The organic solvent used herein is not particularly limited as long as the base resin. PAG, acid diffusion regulator (or quencher) and other additives are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof because the PAG is most soluble therein.

An appropriate amount of the organic solvent (C) used 50 to 10,000 parts, more preferably 100 to 8,000 parts by weight per 100 parts by weight of the base resin (B).

Component (D)

The resist composition may further comprise (D) a photoacid generator other than the sulfonium salt having formula (1), which is referred to as second photoacid generator. The second photoacid generator preferably has the formula (4) or (5).

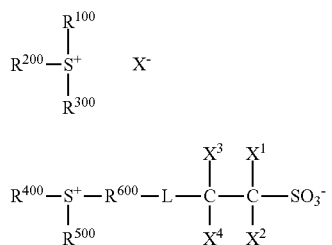

In formula (4), $R^{100}$, $R^{200}$ and $R^{300}$ are each independently a straight, branched or cyclic $C_1$-$C_{20}$ monovalent hydrocarbon group which may contain a heteroatom, any two or more of $R^{100}$, $R^{200}$ and $R^{300}$ may bond together to form a ring with the sulfur atom to which they are attached. Examples of the sulfonium cation are the same as exemplified above for the sulfonium cation.

In formula (4). $X^-$ is an anion selected from the formulae (4A) to (4D).

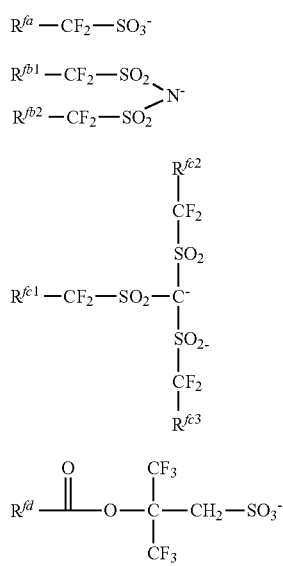

In formula (4A), $R^{fa}$ is fluorine or a straight, branched or cyclic $C_1$-$C_{40}$ monovalent hydrocarbon group which may contain a heteroatom.

Of the anions of formula (4A), a structure having formula (4A') is preferred.

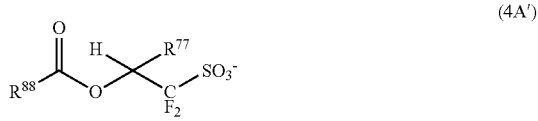

In formula (4A'), $R^{77}$ is hydrogen or trifluoromethyl, preferably trifluoromethyl. $R^{88}$ is a straight, branched or cyclic $C_1$-$C_{38}$ monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation. Suitable monovalent hydrocarbon groups include methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, icosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxapropyl, 4-oxo-1-adamantyl, and 3-oxocyclohexyl. Also included are the foregoing groups in which at least one hydrogen is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical.

With respect to the synthesis of the sulfonium salt having an anion of formula (4A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (4A) are shown below, but not limited thereto.

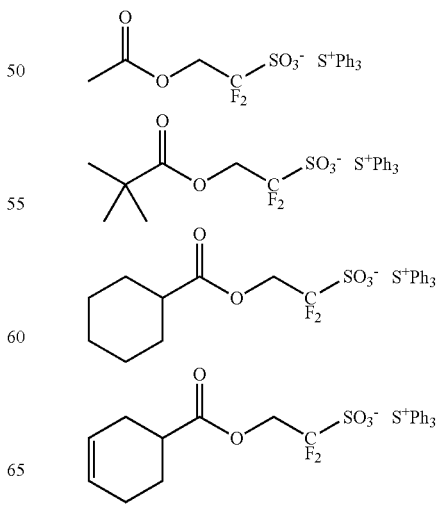

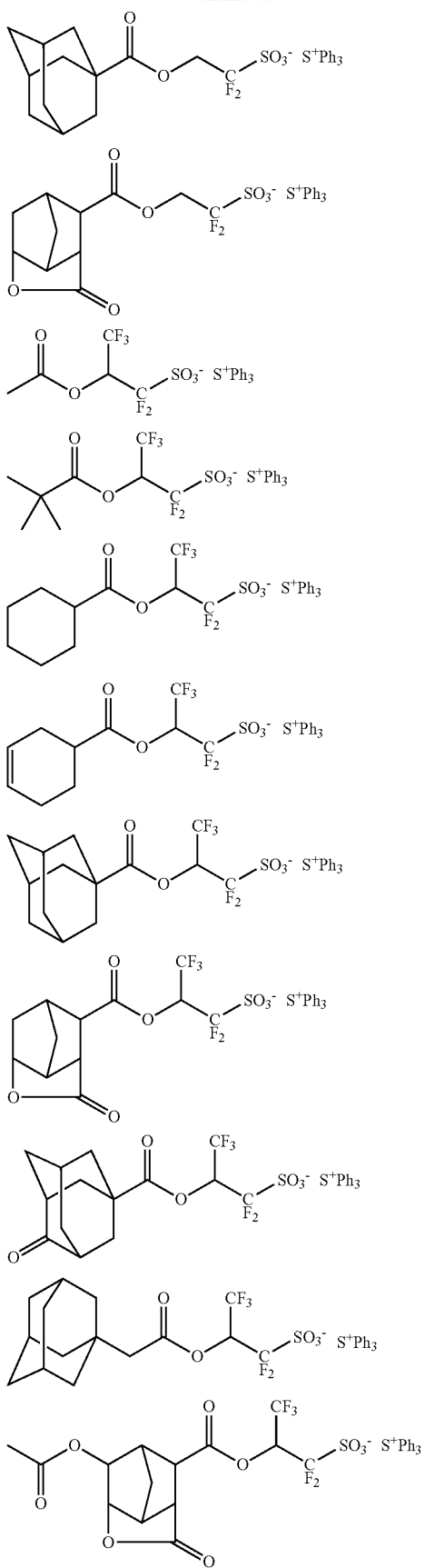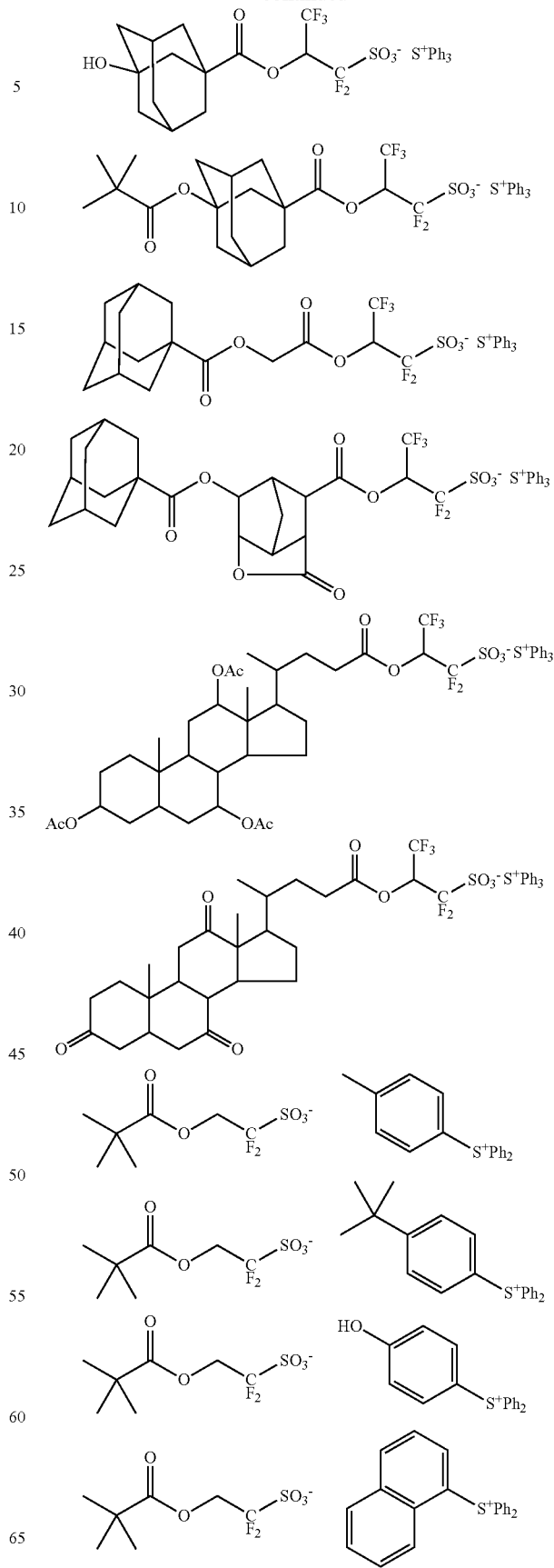

-continued
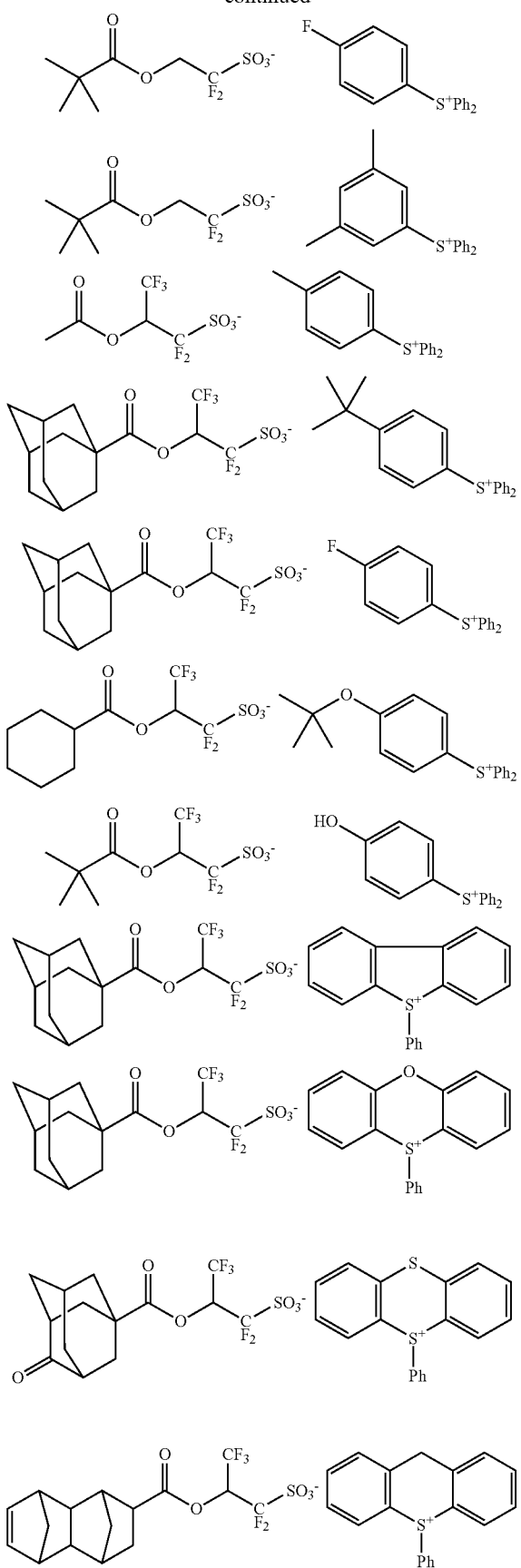
-continued
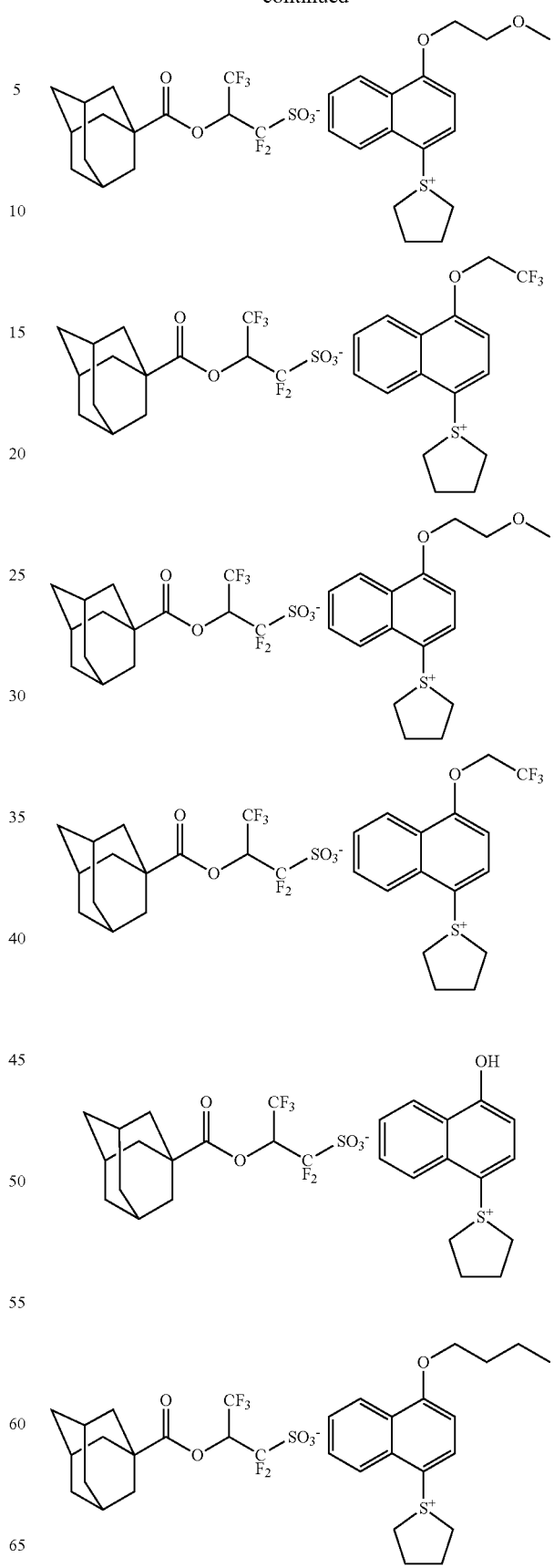

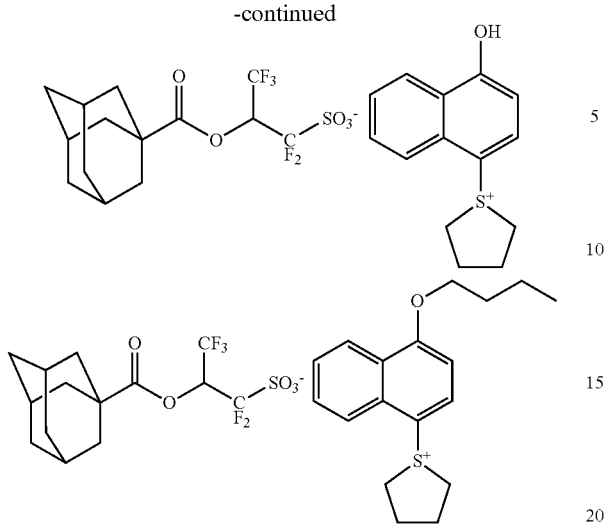

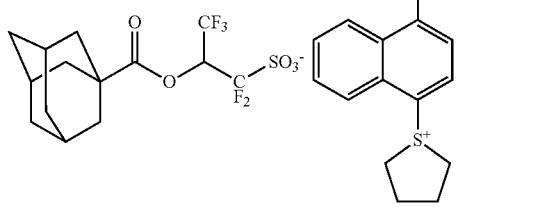

In formula (4B), $R^{fb1}$ and $R^{fb2}$ are each independently fluorine or a straight, branched or cyclic $C_1$-$C_{40}$ monovalent hydrocarbon group which may contain a heteroatom. Suitable monovalent hydrocarbon groups are as exemplified above for $R^{88}$. Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group forming a ring structure.

In formula (4C), $R^{fc1}$, $R^{fc2}$ and $R^{fc3}$ are each independently fluorine or a straight, branched or cyclic $C_1$-$C_{40}$ monovalent hydrocarbon group which may contain a heteroatom. Suitable monovalent hydrocarbon groups are as exemplified above for $R^{88}$. Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the the linkage (—$CF_2$—$SO_2$—$C^-$—$SO_2$—$CF_2$—) to which they are attached, and preferably the pair is a fluorinated ethylene or fluorinated propylene group forming a ring structure.

In formula (4D), $R^{fd}$ is a straight, branched or cyclic $C_1$-$C_{40}$ monovalent hydrocarbon group which may contain a heteroatom. Suitable monovalent hydrocarbon groups are as exemplified above for $R^{88}$.

With respect to the synthesis of the sulfonium salt having an anion of formula (4D), reference is made to JP-A 2010-215608 and JP-A 2014-133723.

Examples of the sulfonium salt having an anion of formula (4D) are shown below, but not limited thereto.

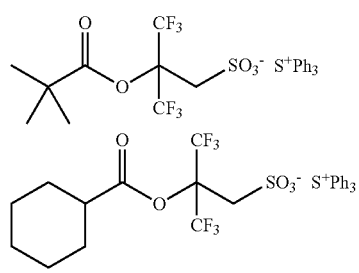

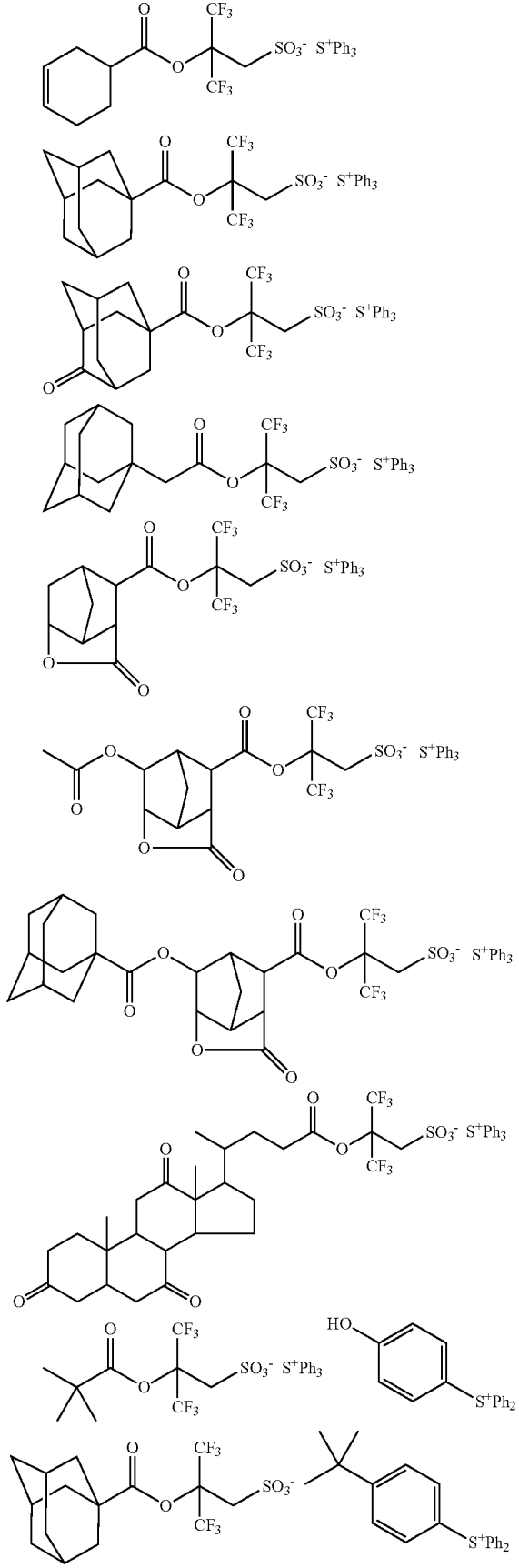

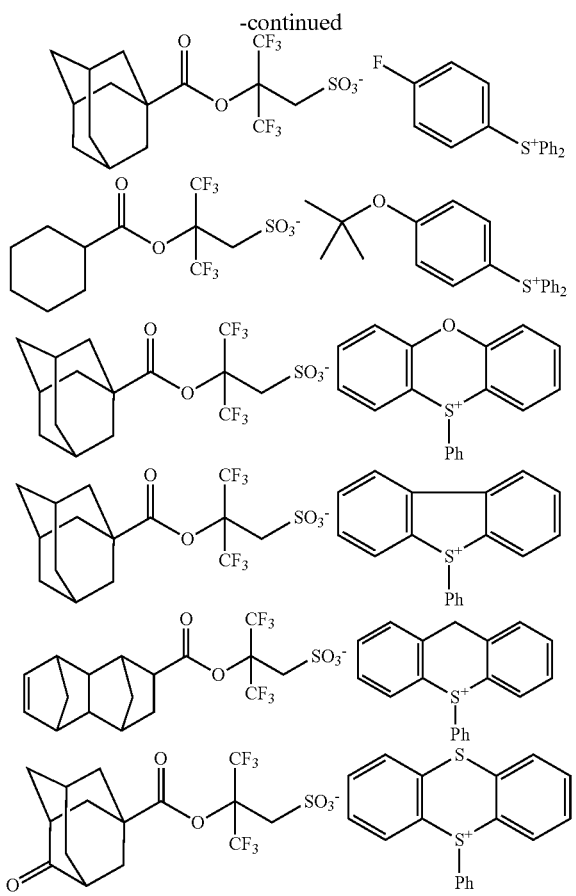

The compound having the anion of formula (4D) has a sufficient acid strength to cleave acid labile groups in the resist polymer because it is free of fluorine at α-position of sulfo group, but has two trifluoromethyl groups at β-position. Thus the compound is a useful PAG.

In formula (5), $R^{400}$ and $R^{500}$ are each independently a straight, branched or cyclic $C_1$-$C_{30}$ monovalent hydrocarbon group which may contain a heteroatom. $R^{600}$ is a straight, branched or cyclic $C_1$-$C_{30}$ divalent hydrocarbon group which may contain a heteroatom. Any two or more of $R^{400}$, $R^{500}$ and $R^{600}$ may bond together to form a ring with the sulfur atom to which they are attached. L is a single bond or a straight, branched or cyclic $C_1$-$C_{20}$ divalent hydrocarbon group which may contain a heteroatom. $X^1$, $X^2$, $X^3$ and $X^4$ are each independently hydrogen, fluorine or trifluoromethyl, with the proviso that at least one of $X^1$, $X^2$, $X^3$ and $X^4$ is a substituent group other than hydrogen.

Examples of the monovalent hydrocarbon group are as exemplified above for R.

Suitable divalent hydrocarbon groups include linear alkane diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, heptadecane-1,17-diyl; saturated cyclic divalent hydrocarbon groups such as cyclopentanediyl, cyclohexanediyl, norbornanediyl, and adamantanediyl; and unsaturated cyclic divalent hydrocarbon groups such as phenylene and naphthylene. Also included are the foregoing groups in which at least one hydrogen atom is replaced by an alkyl group such as methyl, ethyl, propyl, n-butyl or t-butyl, or in which at least one hydrogen atom is replaced by a radical containing a heteroatom such as oxygen, sulfur, nitrogen or halogen, or in which a radical containing a heteroatom such as oxygen, sulfur or nitrogen intervenes between carbon atoms, so that the group may contain a hydroxyl radical, cyano radical, carbonyl radical, ether bond, ester bond, sulfonic acid ester bond, carbonate bond, lactone ring, sultone ring, carboxylic acid anhydride or haloalkyl radical. Suitable heteroatoms include oxygen, nitrogen, sulfur and halogen, with oxygen being preferred.

Of the PAGs having formula (5), those having formula (5') are preferred.

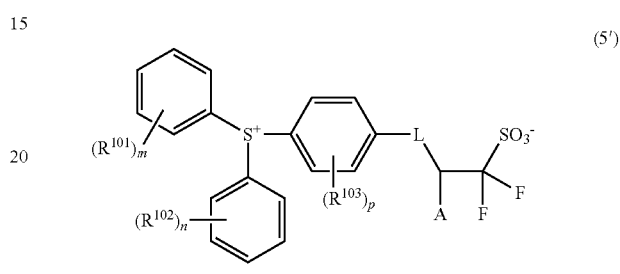

(5')

In formula (5'), L is as defined above. A is hydrogen or trifluoromethyl, preferably trifluoromethyl. $R^{101}$, $R^{102}$ and $R^{103}$ are each independently hydrogen or a straight, branched or cyclic $C_1$-$C_{20}$ monovalent hydrocarbon group which may contain a heteroatom. Suitable monovalent hydrocarbon groups are as exemplified above for $R^{88}$. The subscripts m and n each are an integer of 0 to 5, and p is an integer of 0 to 4.

Examples of the PAG having formula (5) are shown below, but not limited thereto. Herein, A is as defined above.

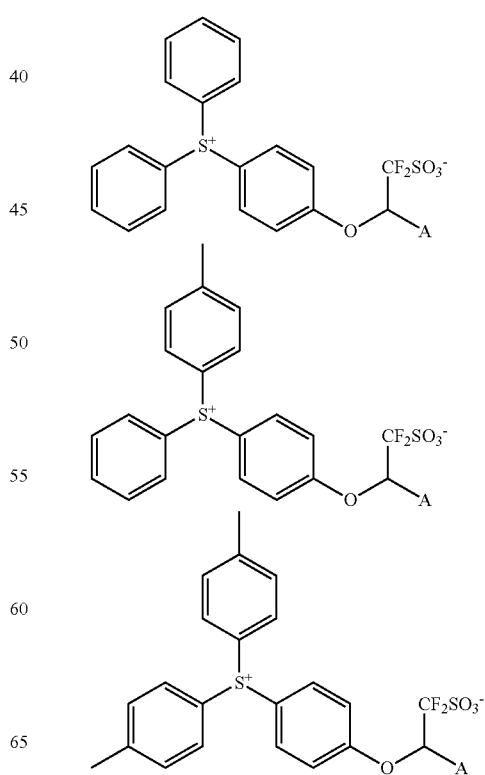

151
-continued
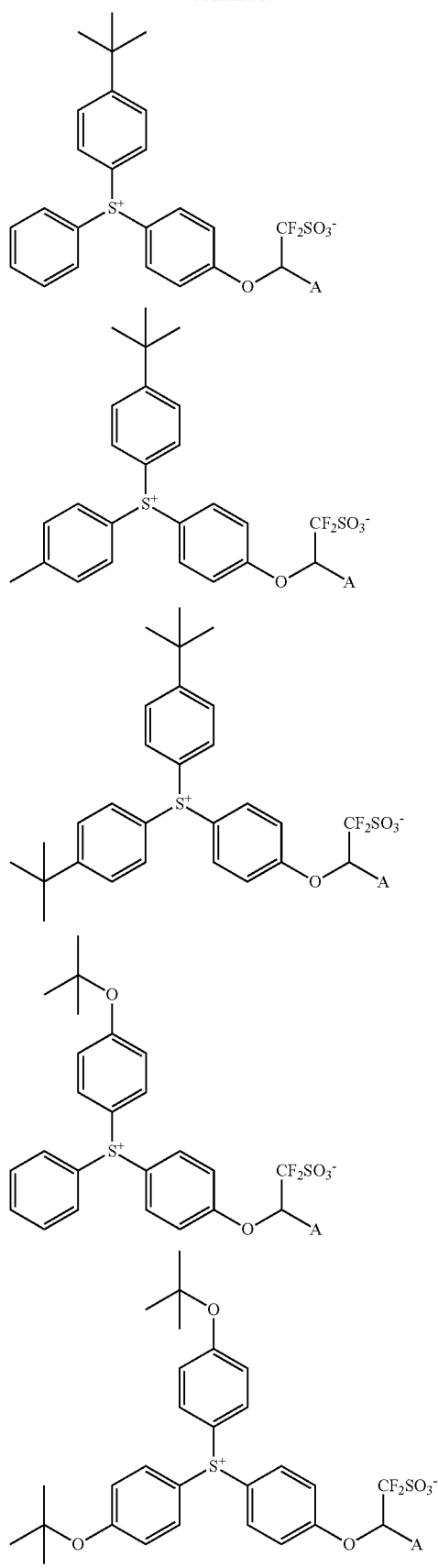
152
-continued
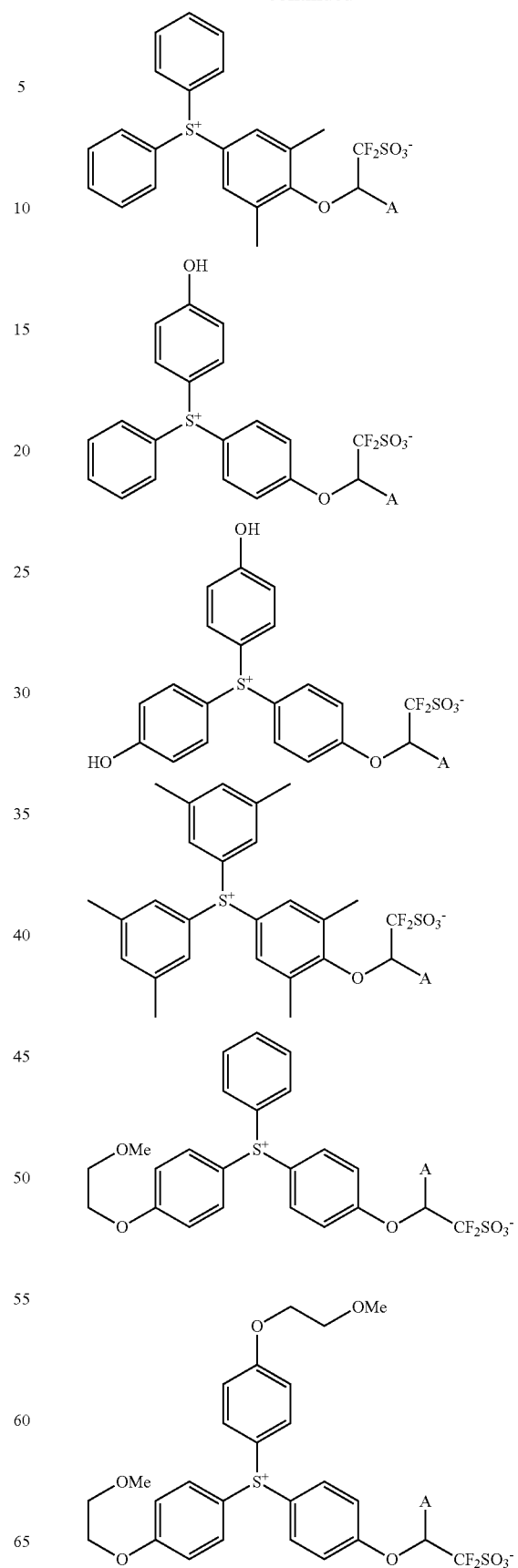

153
-continued
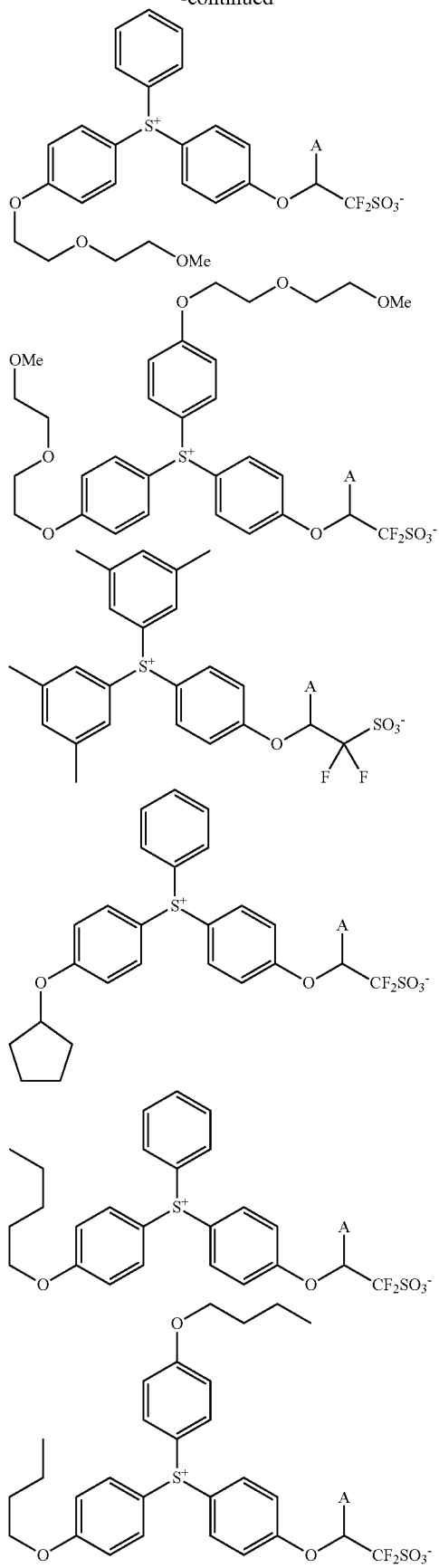
154
-continued
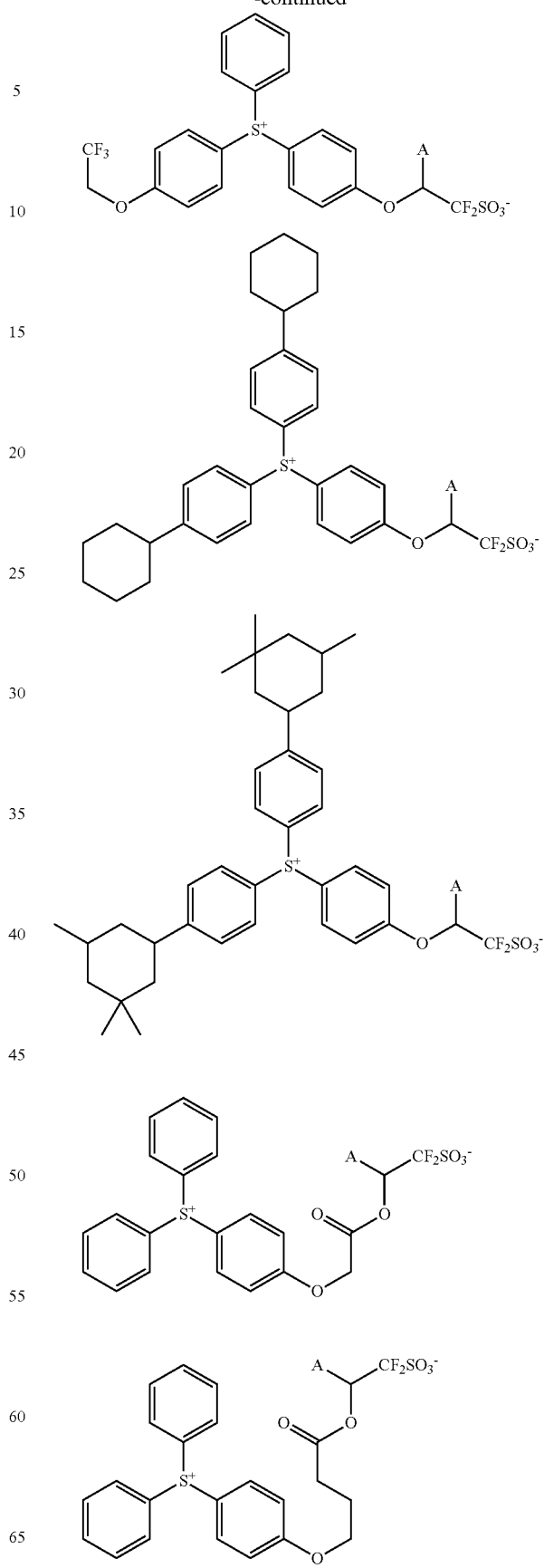

-continued

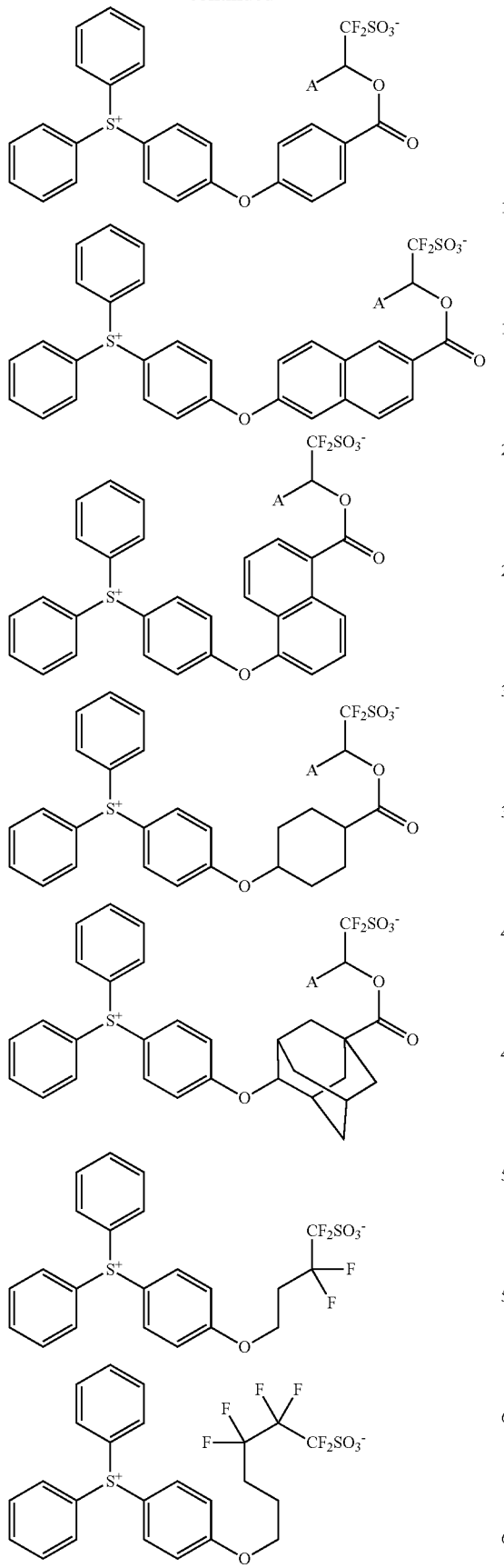

-continued

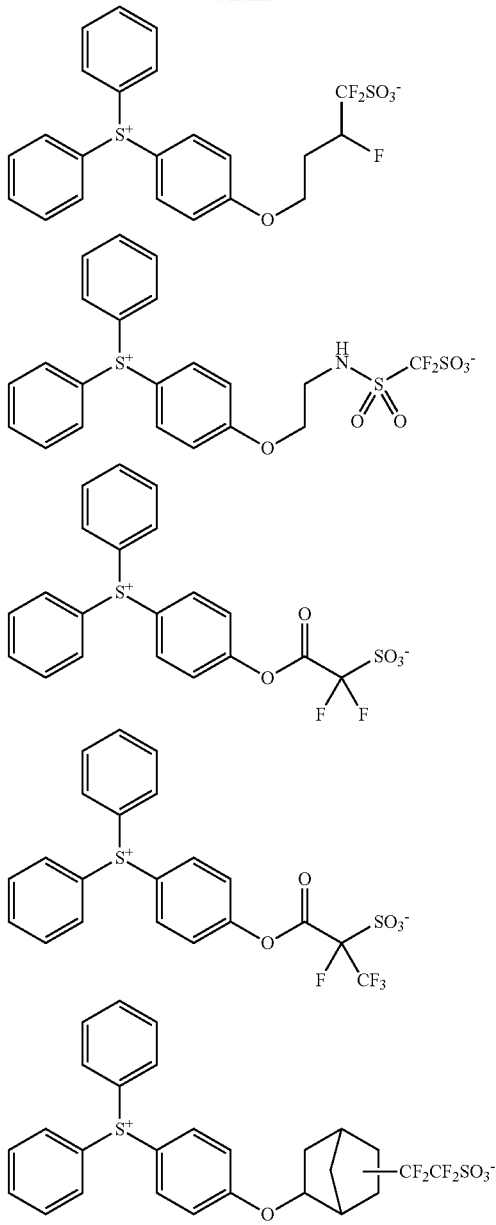

Of the foregoing second PAGs, those compounds having an anion of formula (4A') or (4D) are especially preferred because of reduced acid diffusion and high solubility in resist solvent, and those compounds having an anion of formula (5') are especially preferred because of minimized acid diffusion.

An appropriate amount of the PAG (D) added is 0 to 40 parts by weight per 100 parts by weight of the base resin (B). An amount in the range ensures good resolution and leaves no foreign particles after resist development or during separation.

Component (E)

The resist composition may further comprise (E) a quencher. As used herein, the "quencher" refers to a compound capable of suppressing the rate of diffusion when the acid generated by the PAG diffuses within the resist film. Suitable quenchers include primary, secondary and tertiary amine compounds, specifically amine compounds having a hydroxyl, ether, ester, lactone, cyano or sulfonate group, as described in JP-A 2008-111103, paragraphs [0146] to [0164] (U.S. Pat. No. 7,537,880), and compounds having primary or secondary amine protected as a carbamate group, as described in JP 3790649.

Also an onium salt of sulfonic acid which is not fluorinated at α-position or carboxylic acid as represented by the formula (6) or (7) is useful as the quencher.

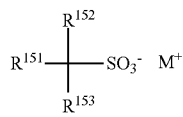

(6)

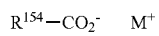

(7)

Herein $R^{151}$, $R^{152}$ and $R^{153}$ are each independently hydrogen, halogen exclusive of fluorine, or a straight, branched or cyclic $C_1$-$C_{40}$ monovalent hydrocarbon group which may contain a heteroatom, any two or More of $R^{151}$, $R^{152}$ and $R^{153}$ may bond together to form a ring with the carbon atom to which they are attached. $R^{154}$ is a straight, branched or cyclic $C_1$-$C_{40}$ monovalent hydrocarbon group which may contain a heteroatom. $M^+$ is an onium cation.

The onium salt of sulfonic acid which is not fluorinated at α-position is described in U.S. Pat. No. 8,795,942 (JP-A 2008-158339). The PAGs capable of generating sulfonic acid which is not fluorinated at α-position are exemplified in JP-A 2010-155824, paragraphs [0019] to [0036] and JP-A 2010-215608, paragraphs [0047] to [0082]. The onium salts of carboxylic acid are described in JP 3991462.

The anion in formula (6) or (7) is a conjugated base of weak acid. As used herein, the weak acid indicates an acidity insufficient to deprotect an acid labile group from an acid labile group-containing unit in the base resin. The onium salt having formula (6) or (7) functions as a quencher when used in combination with an onium salt type photoacid generator having a conjugated base of a strong acid, typically a sulfonic acid which is fluorinated at α-position as the counter anion.

In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

In particular, since sulfonium salts and iodonium salts of an α-position non-fluorinated sulfonic acid and a carboxylic acid are photo-decomposable, those portions receiving a high light intensity are reduced in quenching capability and increased in the concentration of an α-position fluorinated sulfonic acid, imide acid, or methide acid. This enables to form a pattern having an improved contrast in exposed area, further improved DOF and satisfactory dimensional control.

If a photoacid generator capable of generating a strong acid is an onium salt, an exchange from the strong acid generated upon exposure to high-energy radiation to a weak is acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In case the acid labile group is an acetal group which is very sensitive to acid, the acid for eliminating the protective group need not necessarily be an a-fluorinated sulfonic acid, imide acid or methide acid. Sometimes, deprotection reaction may take place even with α-position non-fluorinated sulfonic acid. In this case, since an onium salt of sulfonic acid cannot be used as the quencher, an onium salt of carboxylic acid is preferably used alone as the quencher.

Of the onium salts of α-position non-fluorinated sulfonic acid and carboxylic acid, sulfonium salts of sulfonic acid having the following formula (Z1) and sulfonium salts of carboxylic acid having the following formula (Z2) are preferred.

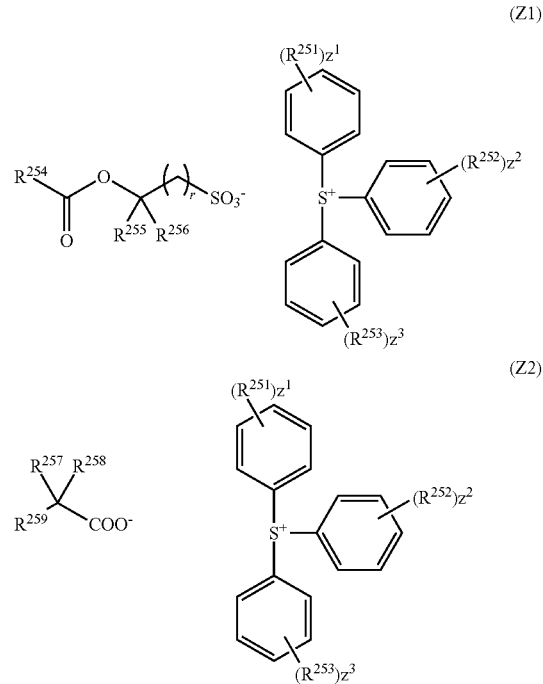

Herein $R^{251}$, $R^{252}$ and $R^{253}$ are each independently a straight, branched or cyclic $C_1$-$C_{20}$ monovalent hydrocarbon group which may contain a heteroatom, any two or more of $R^{251}$, $R^{252}$ and $R^{253}$ may bond together to form a ring with the atom to which they are attached and intervening atoms. $R^{254}$ is a straight, branched or cyclic $C_1$-$C_{40}$ monovalent hydrocarbon group which may contain a heteroatom. $R^{255}$ and $R^{256}$ are each independently hydrogen or trifluoromethyl. $R^{255}$ and $R^{258}$ are each independently hydrogen, fluorine or trifluoromethyl. $R^{259}$ is hydrogen, hydroxyl, a straight, branched or cyclic $C_1$-$C_{35}$ monovalent hydrocarbon group which may contain a heteroatom, or optionally substituted $C_6$-$C_{30}$ aryl group. The subscript r is an integer of 1 to 3, $z^1$, $z^2$ and $z^3$ are each independently an integer of 0 to 5.

Illustrative, non-limiting examples of the onium salts of α-position non-fluorinated sulfonic acid and carboxylic acid are given below.

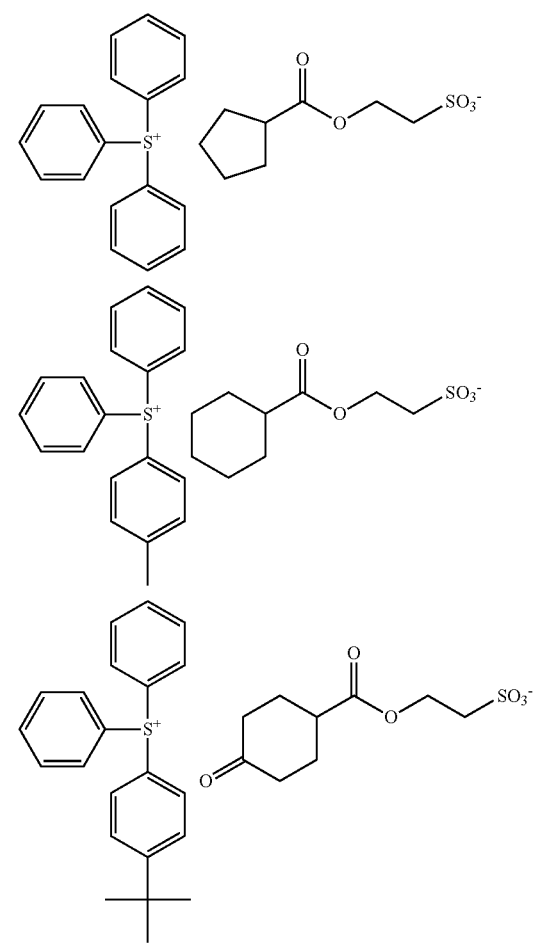
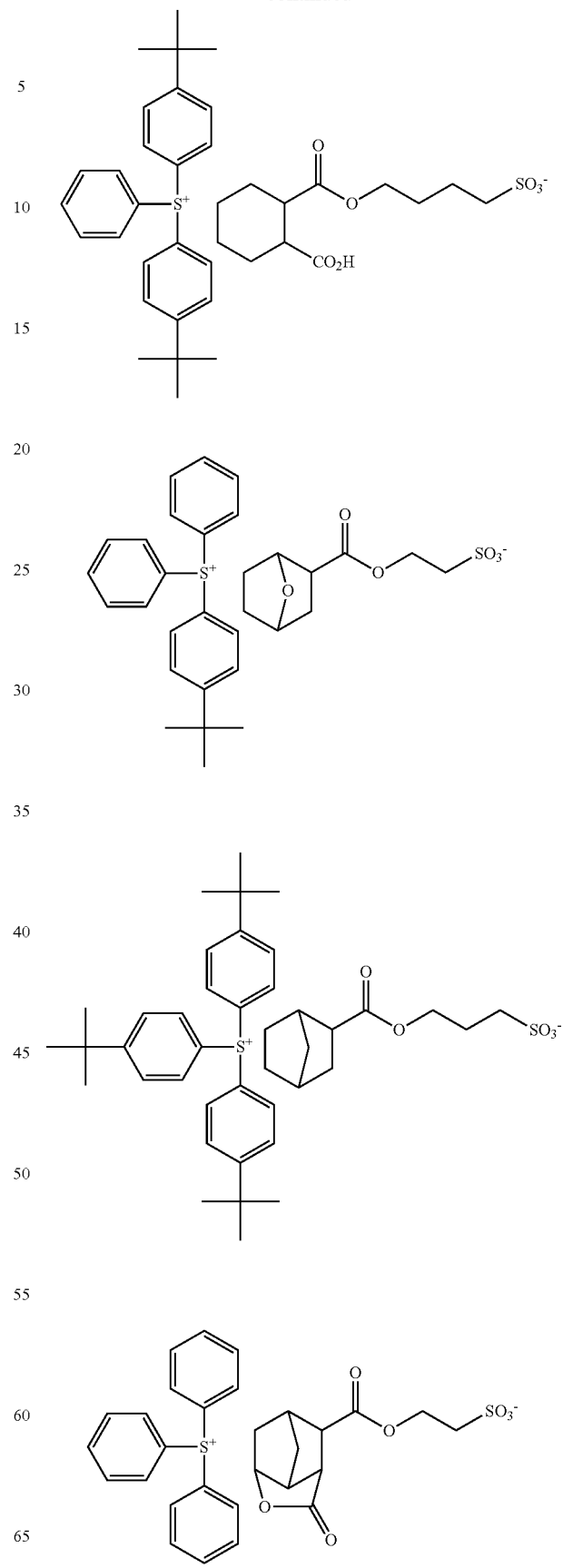

161
-continued
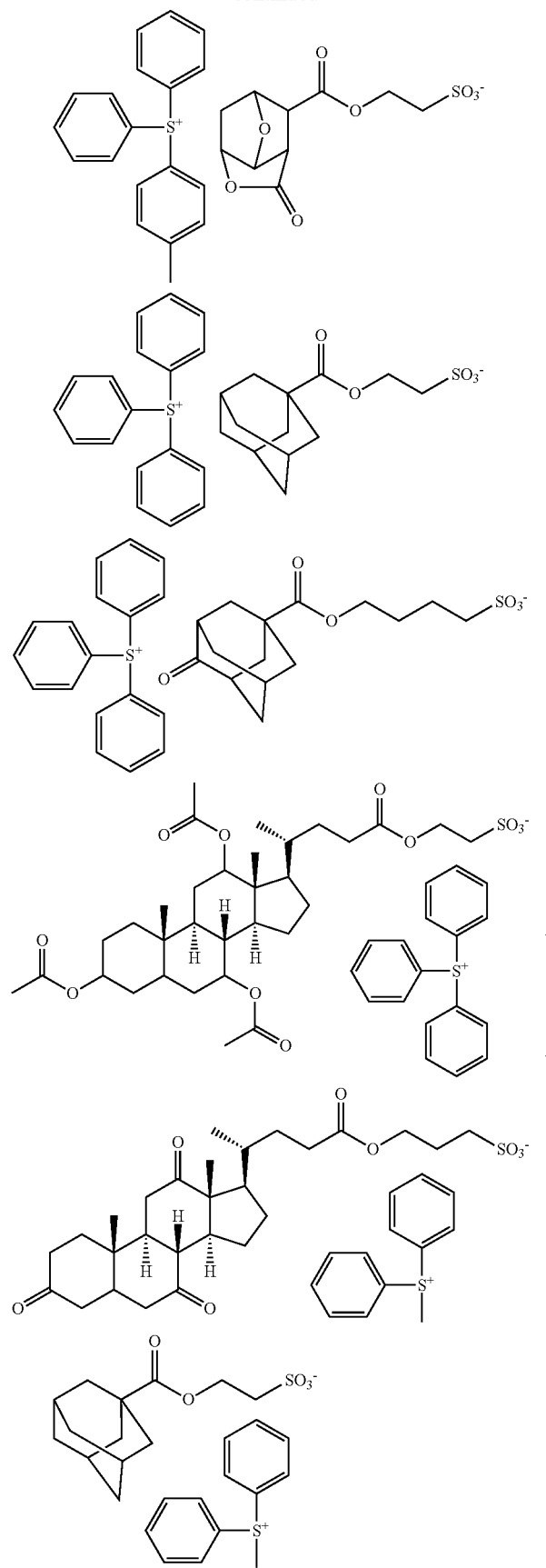
162
-continued
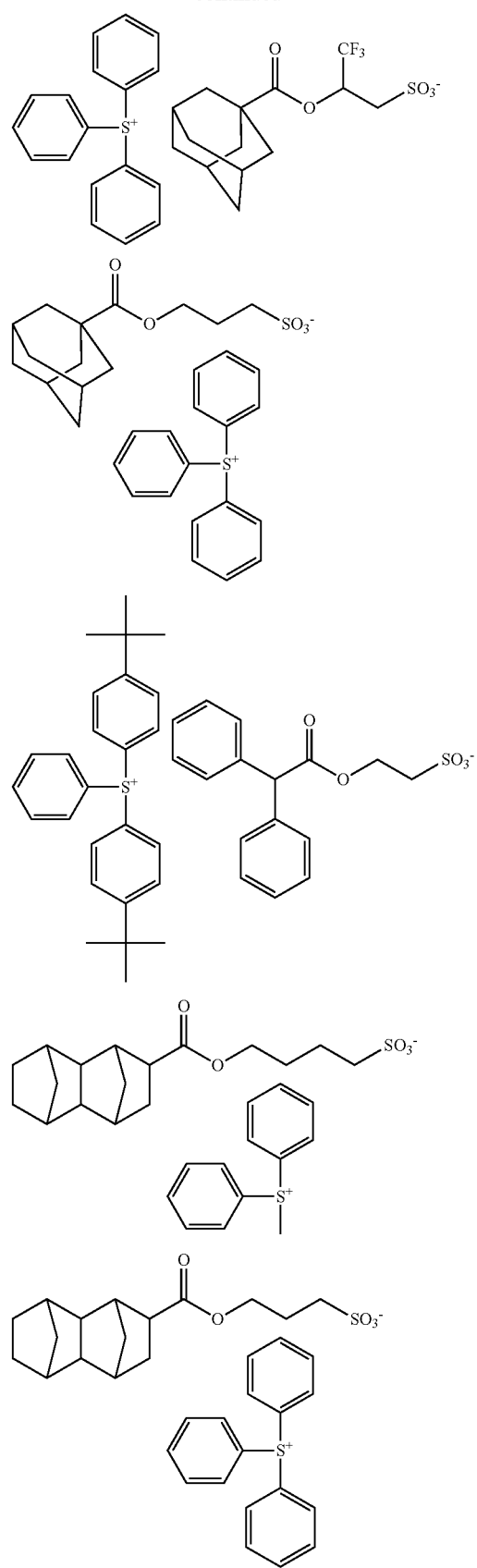

163
-continued
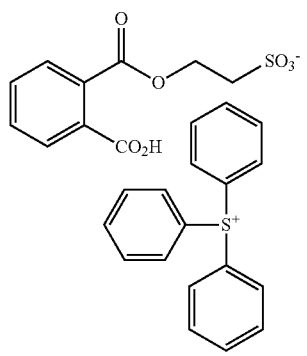
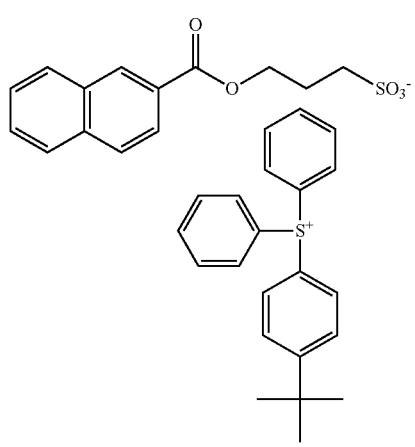
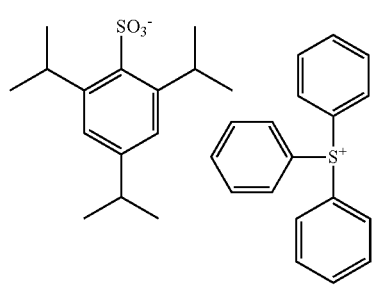
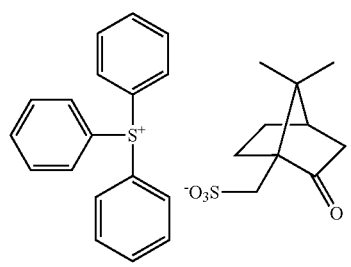
164
-continued
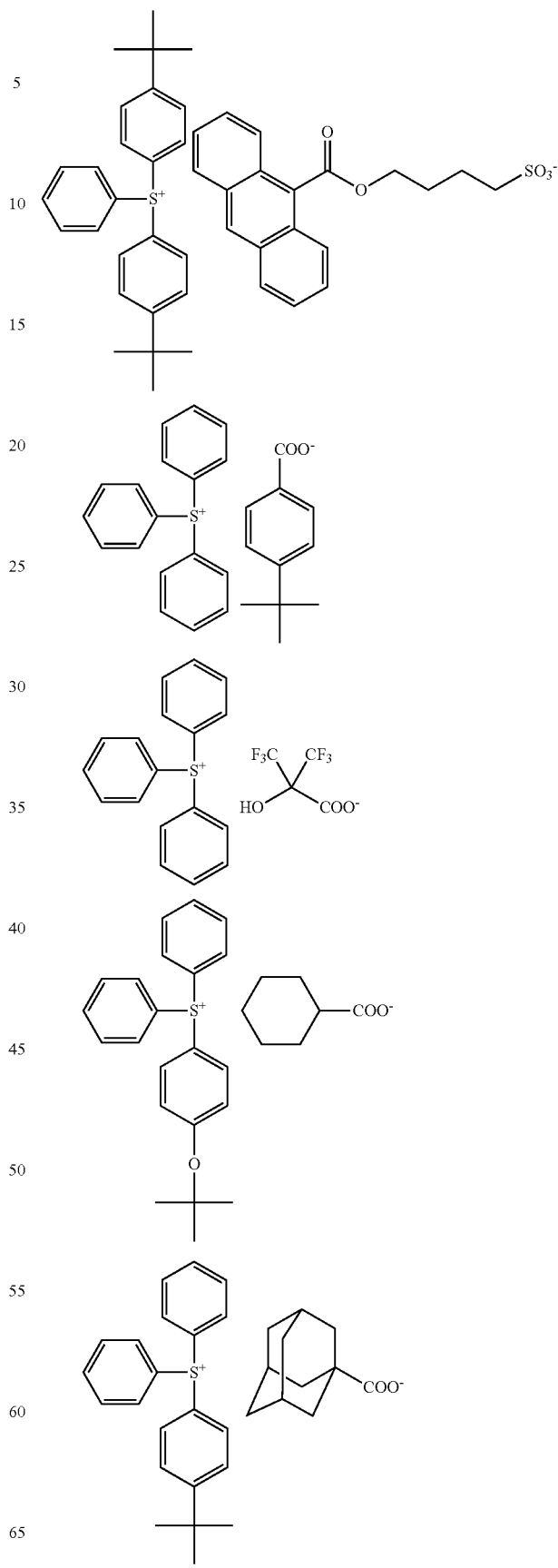

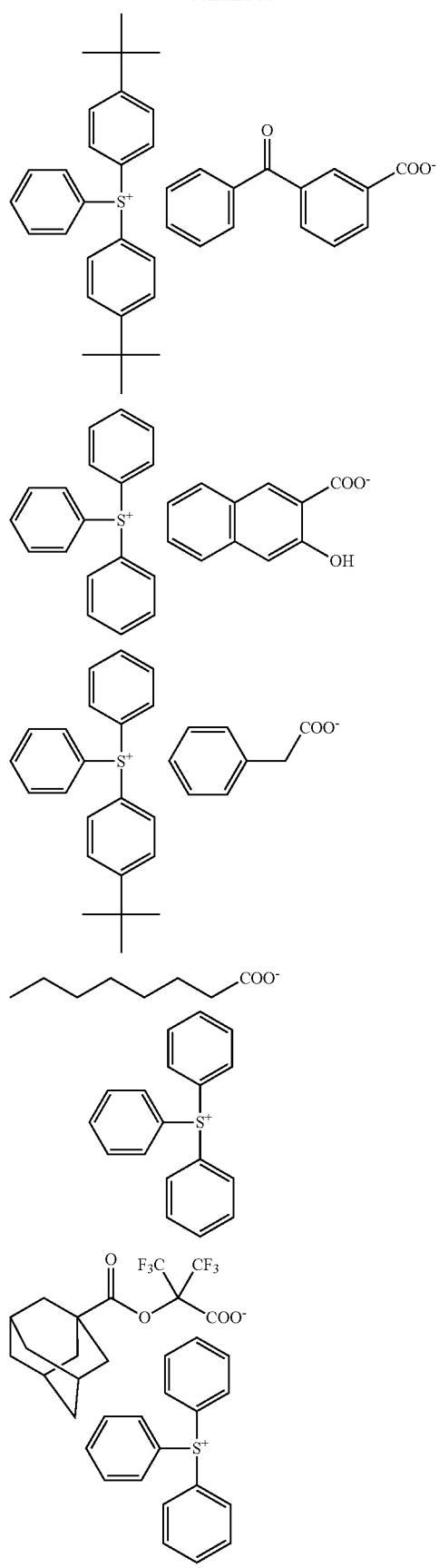
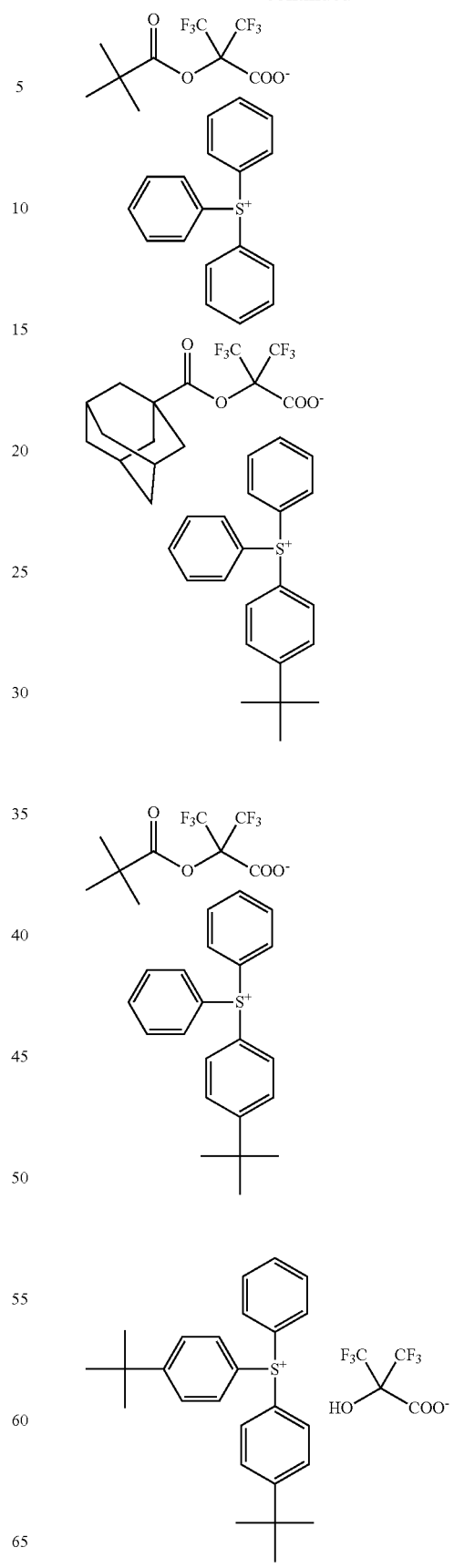

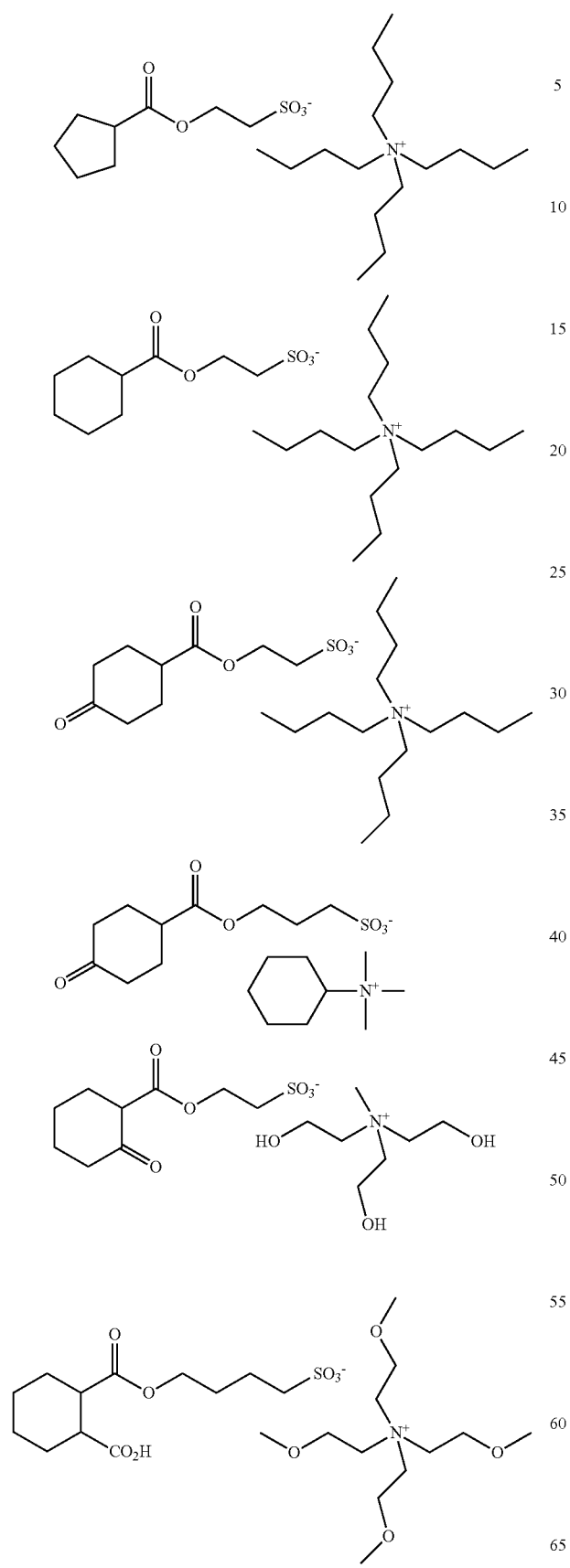
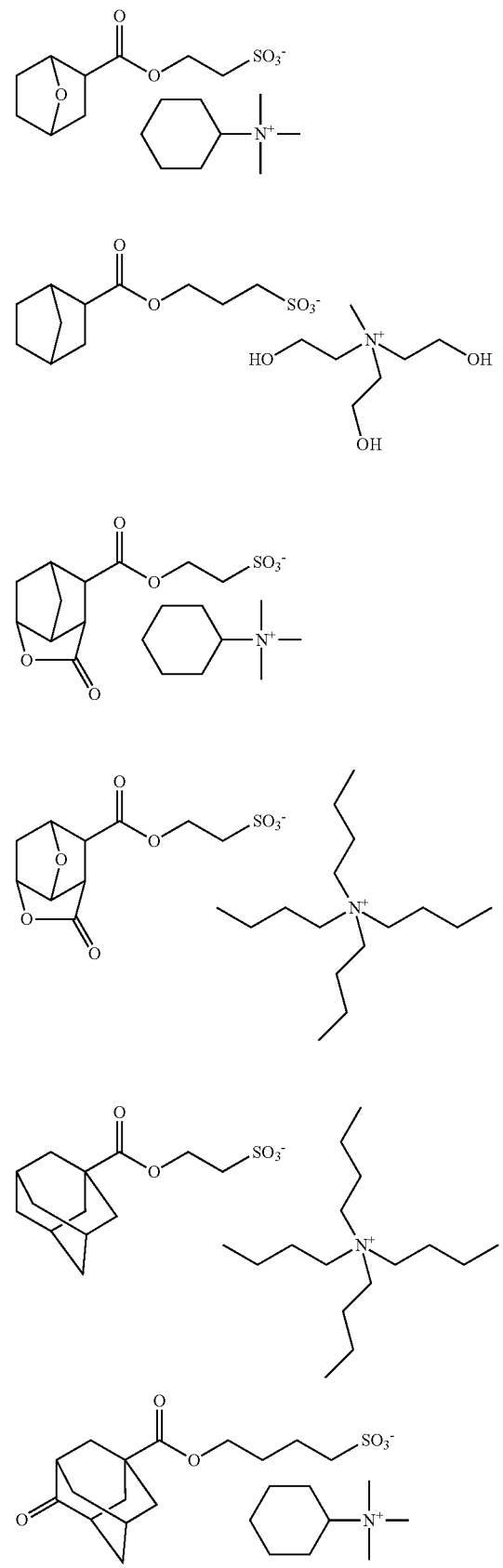

169
-continued
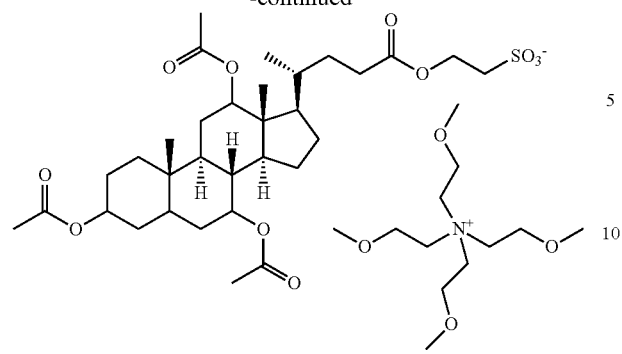
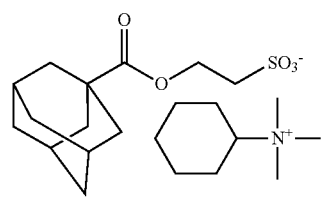
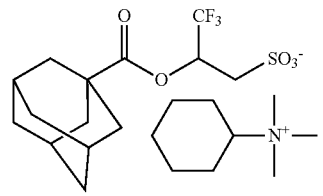
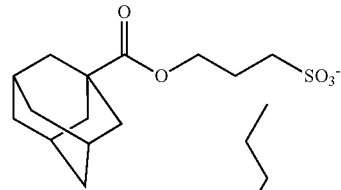
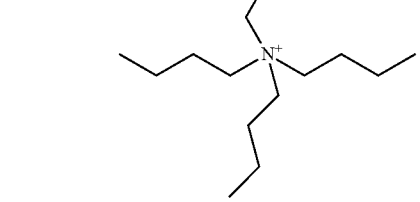
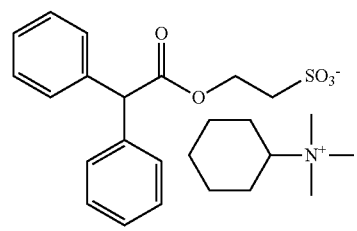
170
-continued
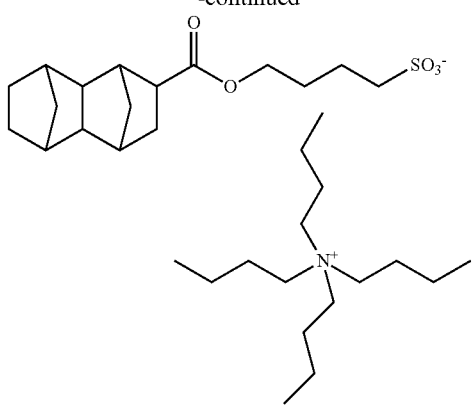
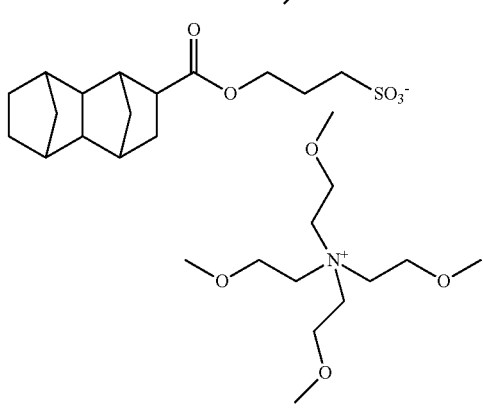
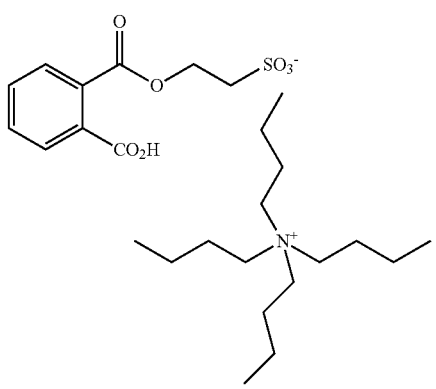
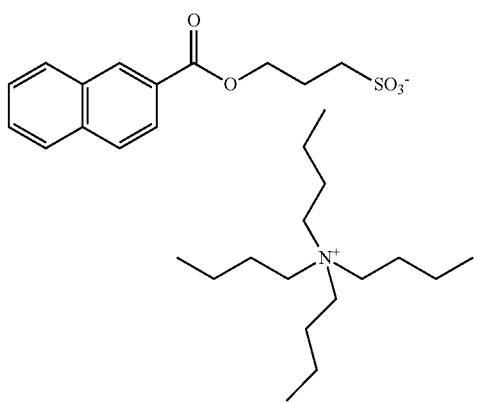

171
-continued
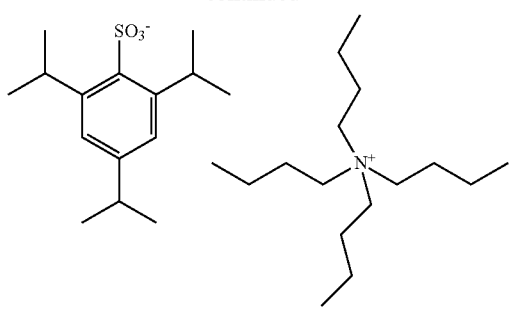
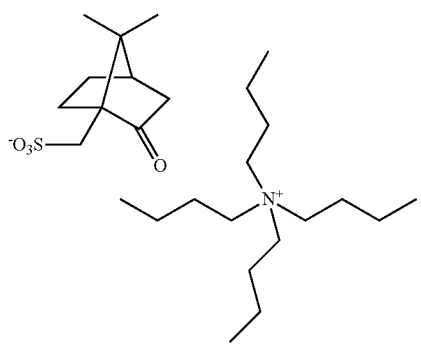
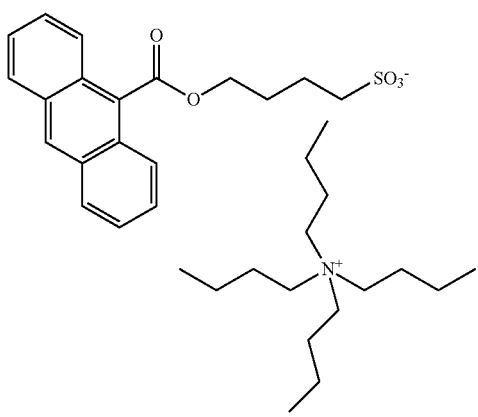
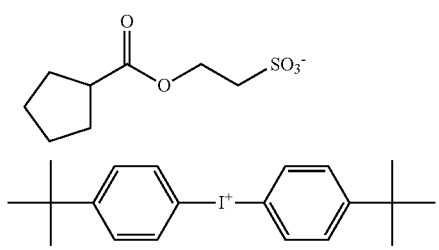
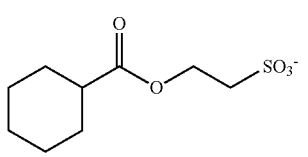
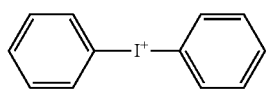
172
-continued
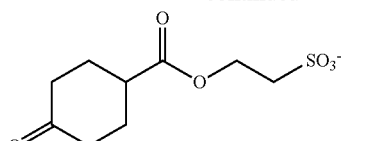
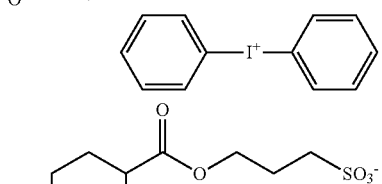
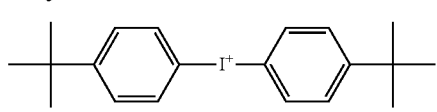
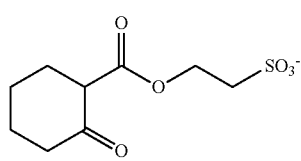
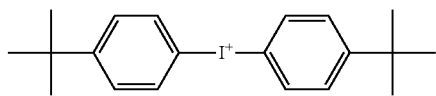
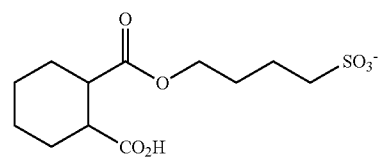
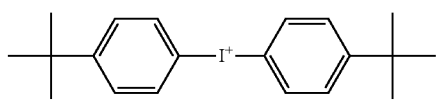
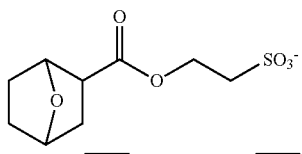
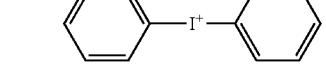
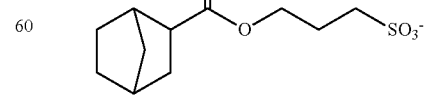
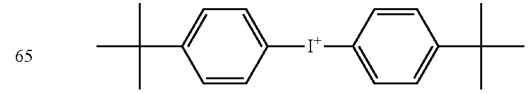

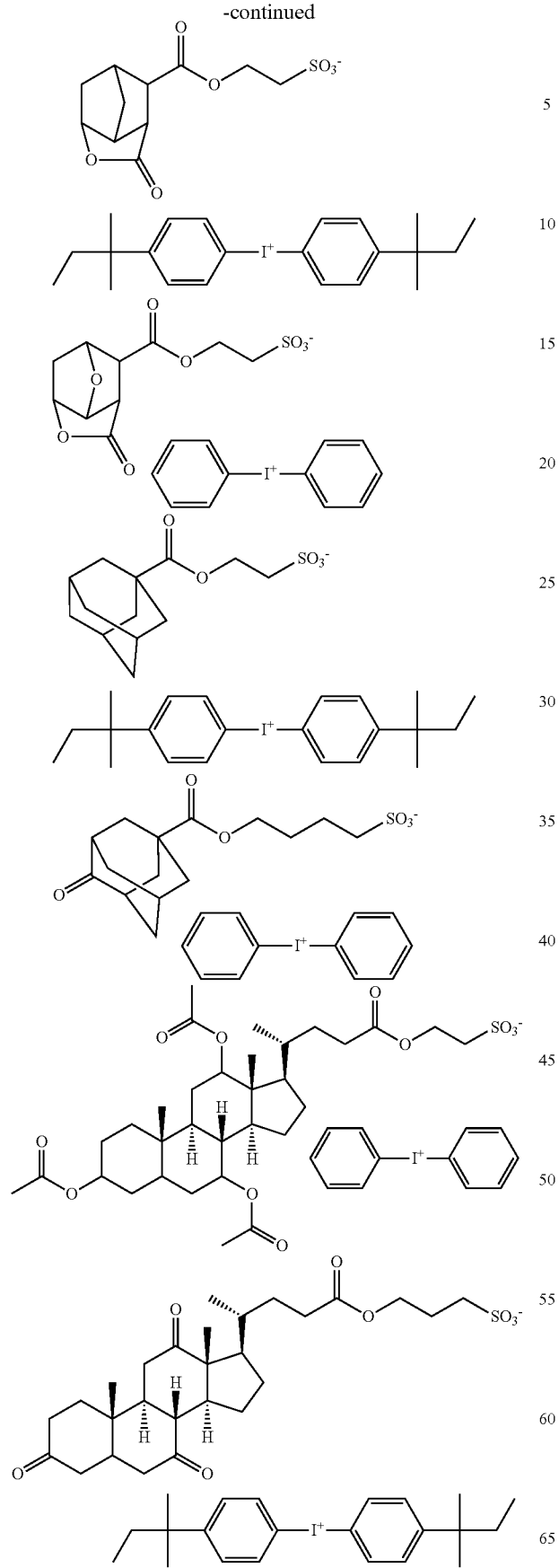
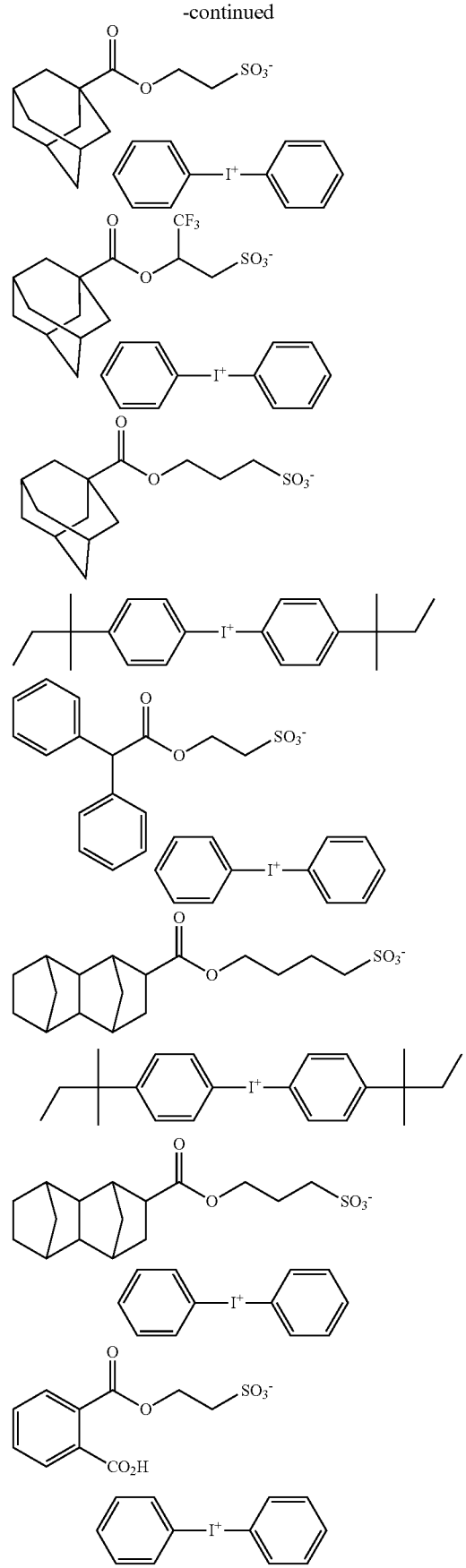

175
-continued
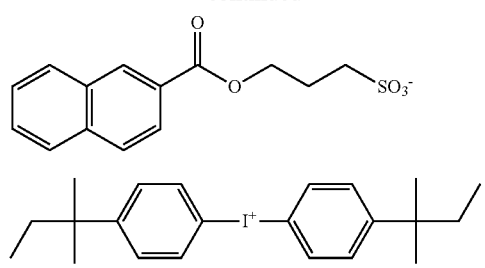
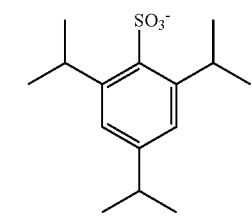
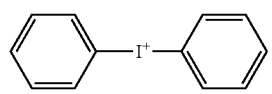
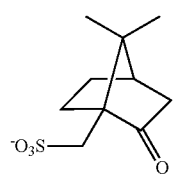
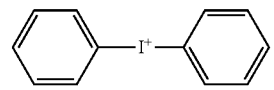
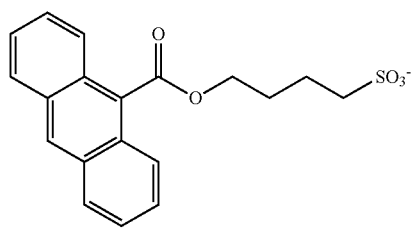
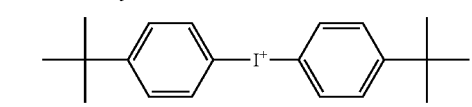
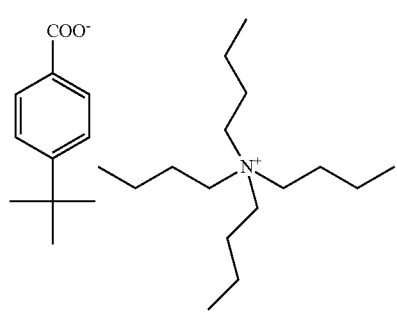
176
-continued
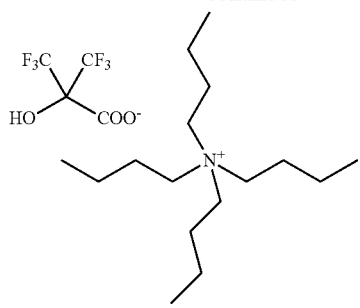
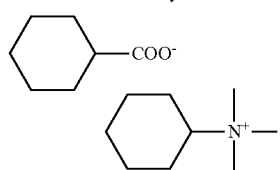
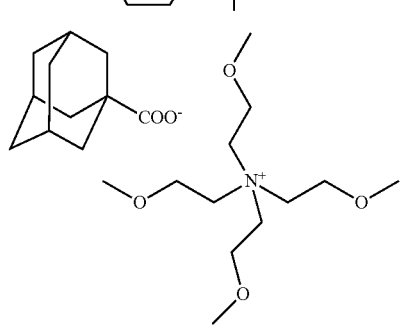
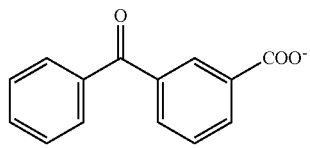
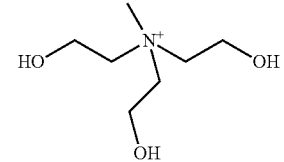
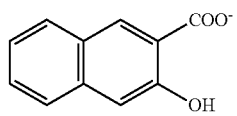
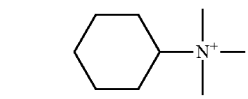
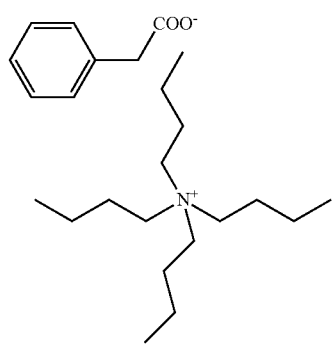

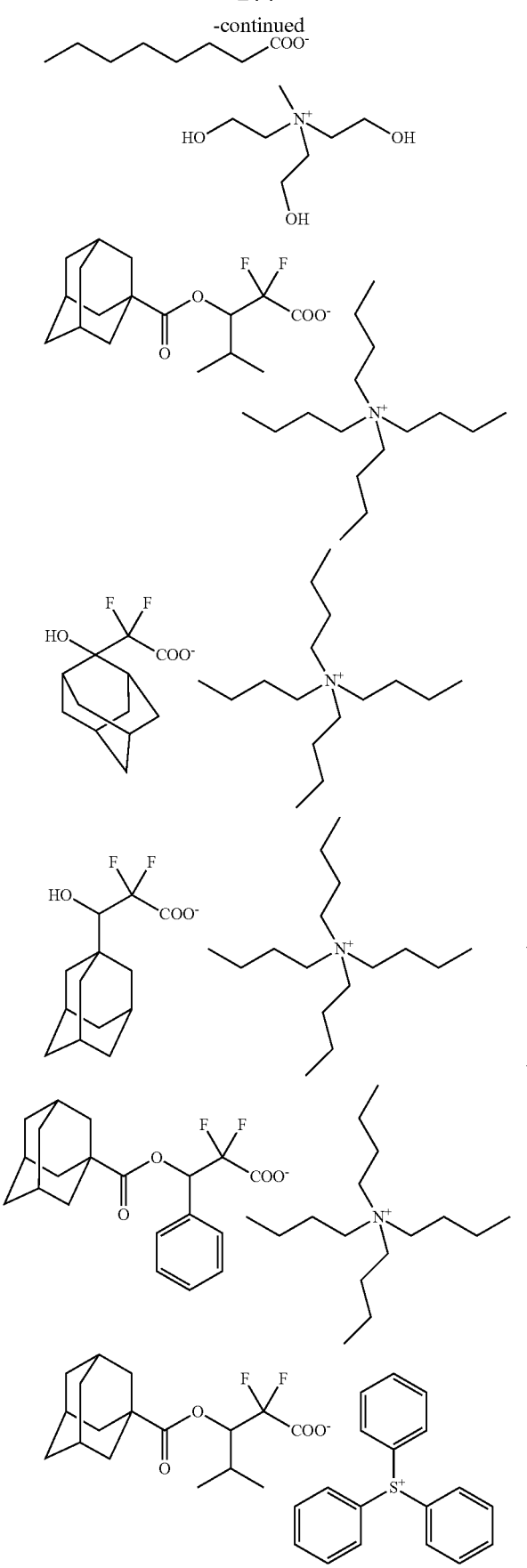
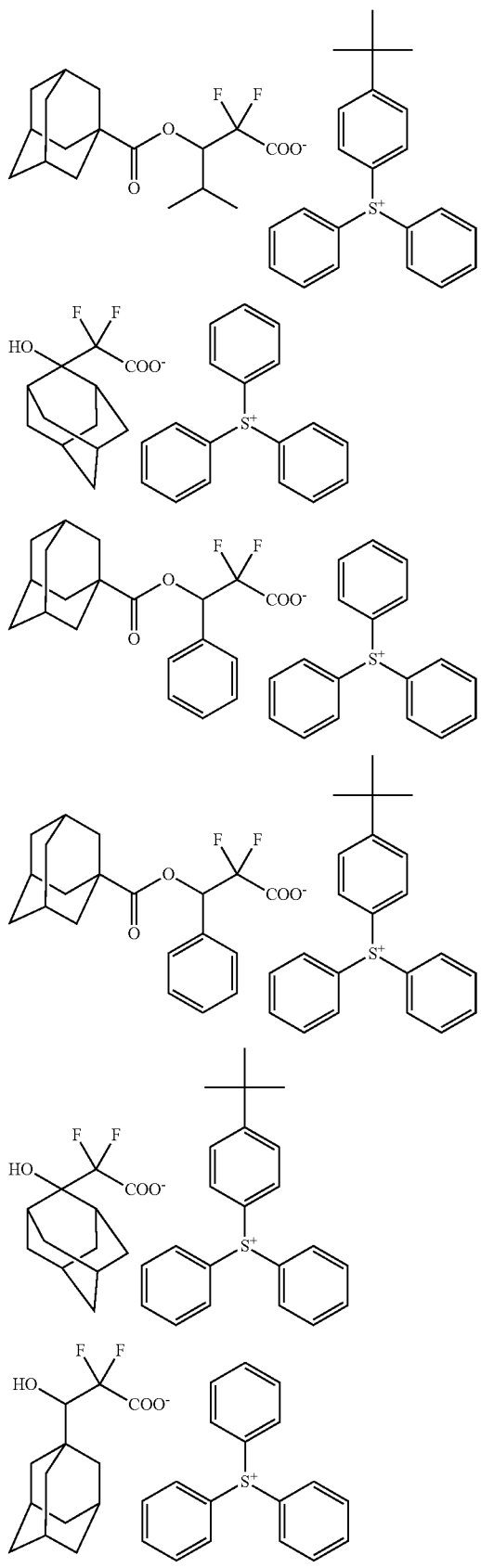

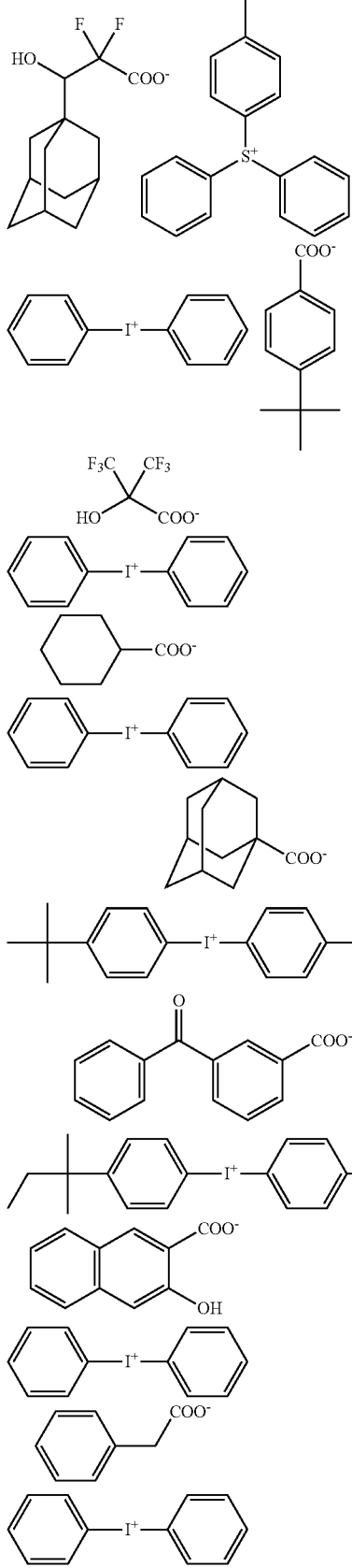

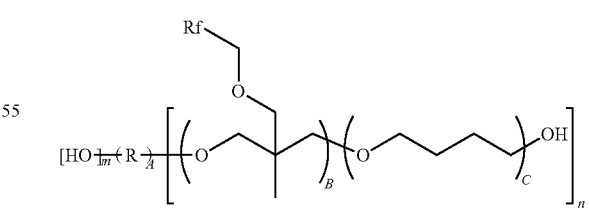

Also an onium salt having a nitrogen-containing substituent group may be used as the quencher. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and 2012-046501, for example.

The quencher (E) may be used alone or in admixture of two or more. An appropriate amount of the quencher is 0 to 50 parts, preferably 0.001 to 50 parts, more preferably 0.01 to 20 parts by weight, per 100 parts by weight of the base resin (B). The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

Component (F)

The resist composition may further comprise (F) a surfactant which is insoluble or substantially insoluble in water and soluble in alkaline developer, and/or a surfactant which is insoluble or substantially insoluble in water and alkaline developer (hydrophobic resin). For the surfactant (F) which can be added to the resist composition, reference should be made to those compounds described in JP-A 2010-215608 and JP-A 2011-016746.

While many examples of the surfactant which is insoluble or substantially insoluble in water and alkaline developer are described in the patent documents cited herein, preferred examples are FC-4430, Surflone® S-381, Surfynol® E1004, KH-20 and KH-30, which may be used alone or in admixture. Partially fluorinated oxetane ring-opened polymers having the formula (surf-1) are also useful.

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

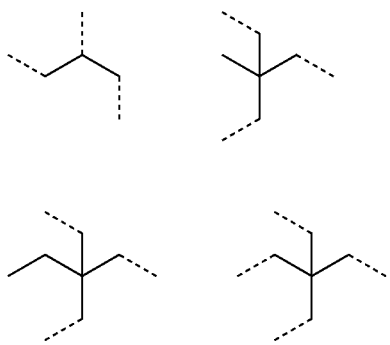

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R. is an integer of 2 to 4. A is equal to 1, B is an integer of 2 to 25, and C is an integer of 0 to 10. Preferably, B is an integer of 4 to 20, and C is 0 or 1. Note that the formula (surf-1) does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage.

Suitable polymeric surfactants are shown below.

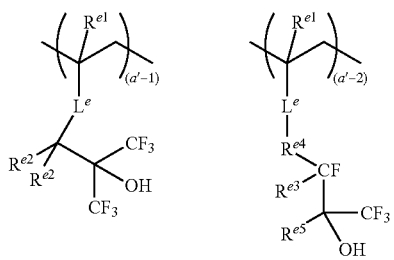

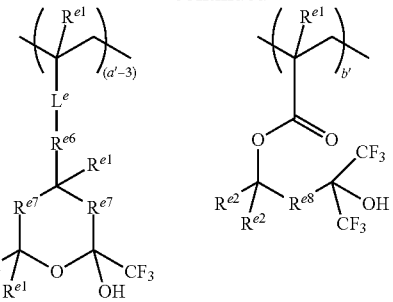

-continued

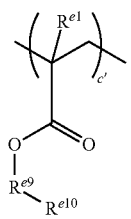

Herein $R^{e1}$ is each independently hydrogen, fluorine, methyl or trifluoromethyl. $R^{e2}$ is each independently hydrogen or a straight, branched or cyclic $C_1$-$C_{20}$ alkyl or fluoroalkyl group, or two $R^{e2}$ in a common monomer may bond together to form a ring with the carbon atom to which they are attached, and in this event, they together represent a straight, branched or cyclic $C_2$-$C_{20}$ alkylene or fluoroalkylene group. $R^{e3}$ is fluorine or hydrogen, or $R^{e3}$ may bond with $R^{e4}$ to form a non-aromatic ring of 3 to 10 carbon atoms in total with the carbon atom to which they are attached. $R^{e4}$ is a straight, branched or cyclic $C_1$-$C_6$ alkylene group in which at least one hydrogen atom may be substituted by a fluorine atom. $R^{e5}$ is a straight or branched $C_1$-$C_{10}$ alkyl group in which at least one hydrogen atom is substituted by a fluorine atom. Alternatively, $R^{e4}$ and $R^{e5}$ may bond together to form a non-aromatic ring with the carbon atoms to which they are attached. In this event, $R^{e4}$, $R^{e5}$ and the carbon atoms to which they are attached together represent a trivalent organic group of 3 to 12 carbon atoms in total. $R^{e6}$ a single bond or a $C_1$-$C_4$ alkylene. $R^{e7}$ is each independently a single bond, —O—, or —$CR^{e1}R^{e1}$—. $R^{e8}$ is a straight $C_1$-$C_4$ or branched $C_3$-$C_4$ alkylene group, or may bond with $R^{e2}$ within a common unit to form a $C_3$-$C_6$ non-aromatic ring with the carbon atom to which they are attached. $R^{e9}$ is a $C_1$-$C_{30}$ divalent hydrocarbon group which may contain a heteroatom. $R^{e10}$ is a linear perfluoroalkyl group of 3 to 6 carbon atoms, typically 3H-perfluoropropyl, 4H-perfluorobutyl, 5H-perfluoropentyl or 6H-perfluorohexyl. $L^e$ is each independently —C(=O)—O—, —O—, or —C(=O)—$R^{e11}$—C(=O)—O—. $R^{e11}$ is a straight, branched or cyclic $C_1$-$C_{10}$ alkylene group. The subscripts are in the range: $0 \leq (a'-1) \leq 1$, $0 \leq (a'-2) \leq 1$, $0 \leq (a'-3) \leq 1$, $0 \leq b' \leq 1$, $0 \leq c' \leq 1$, and $0 < (a'-1)+(a'-2)+(a'-3)+b'+c' \leq 1$.

Examples of these units are shown below. Herein $R^{e1}$ is as defined above.

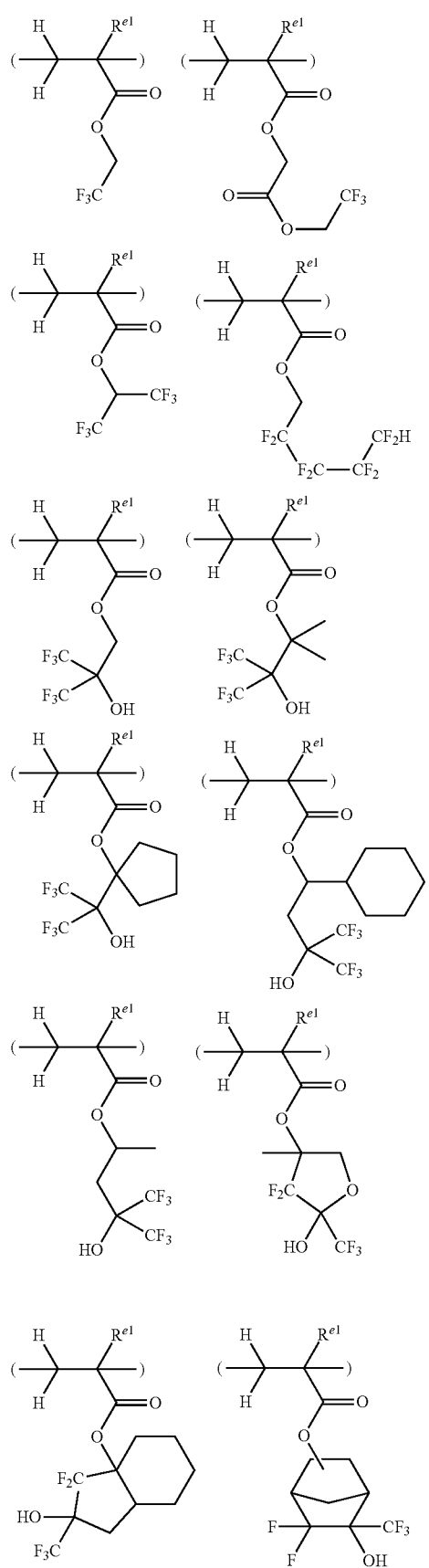
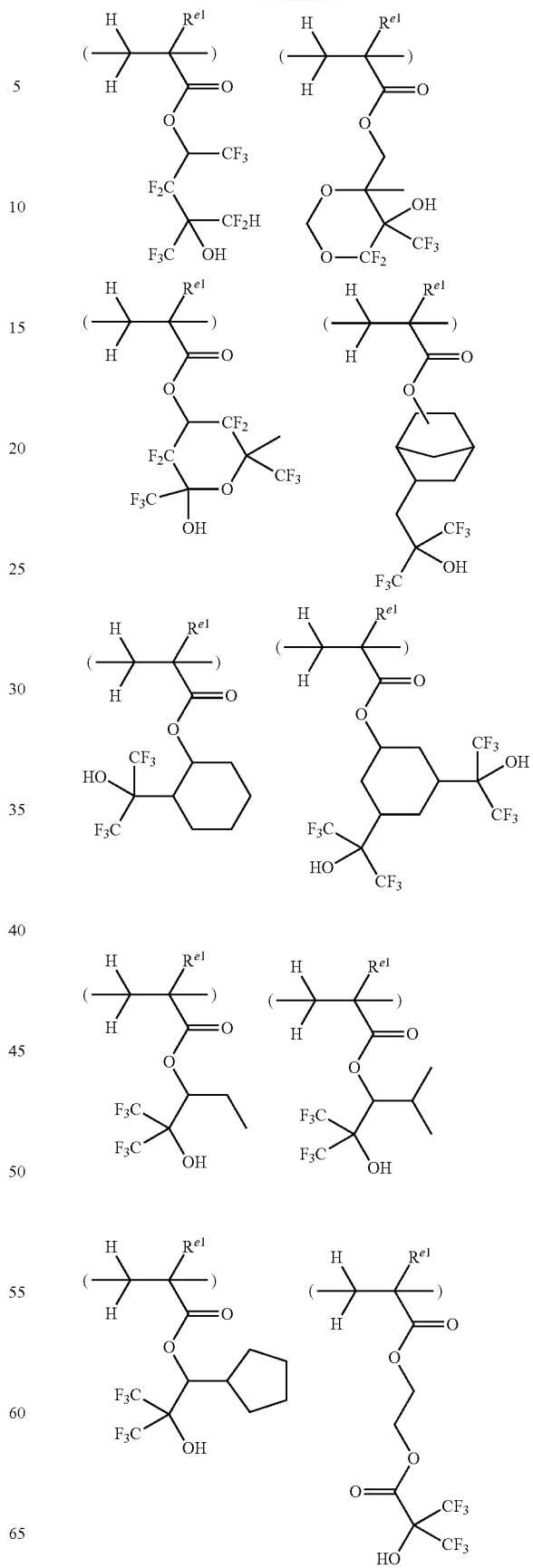

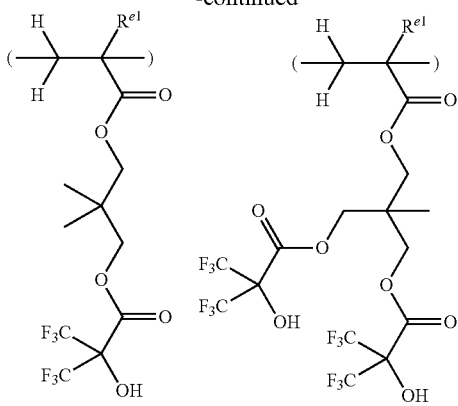

For the surfactant which is insoluble or substantially insoluble in water and soluble in alkaline developer, reference may be made to JP-A 2008-122932, 2009-098638, 2009-191151, 2009-192784, 2009-276363, 2010-107695, 2010-134012, 2010-250105, and 2011-042789.

The polymeric surfactant has a Mw of preferably 1,000 to 50,000, more preferably 2,000 to 20,000 as measured by GPC versus polystyrene standards. A surfactant with a Mw within the range may be effective for surface modification and cause no development defects. An appropriate amount of component (F) is 0 to 20 parts, preferably 0.001 to 20 parts, and more preferably 0.01 to 10 parts by weight per 100 parts by weight of the base resin (B).

Other Components (G)

To the resist composition, a compound which is decomposed with an acid to generate another acid (acid amplifier compound), an organic acid derivative, a fluorinated alcohol, or a compound having a Mw of up to 3,000 which changes its solubility in alkaline developer under the action of an acid (dissolution inhibitor) may be added. For the acid amplifier compound, reference should be made to JP-A 2009-269953 and 2010-215608. In the resist composition, an appropriate amount of the acid amplifier compound is 0 to 5 parts, and especially 0 to 3 parts by weight per 100 parts by weight of the base resin (B). Excessive amounts of the acid amplifier compound make diffusion control difficult, leading to degradation of resolution and pattern profile. With respect to the organic acid derivative, fluorinated alcohol, and dissolution inhibitor, reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of applying the resist composition onto a substrate, prebaking to form a resist film, exposing a selected region of the resist film to high-energy radiation, PEB and developing the resist film in a developer to form a resist pattern. Several steps may be added if necessary, The process of forming a positive resist pattern using an alkaline aqueous solution as the developer may be carried out with reference to U.S. Pat. No. 8,647,808 (JP-A 2011-231312, paragraphs [0138] to [0146]).

The process of forming a negative resist pattern using an organic solvent as the developer is described with reference to FIG. 1. First, the resist composition is coated on a substrate to form a resist film thereon. Specifically, a resist film 40 of a resist composition is formed on a processable layer 20 disposed on a substrate 10 directly or via an intermediate intervening layer 30 as shown in FIG. 1A. The resist film preferably has a thickness of 10 to 1,000 nm and more preferably 20 to 500 nm. Prior to exposure, the resist film is heated or prebaked, preferably at a temperature of 60 to 180° C., especially 70 to 150° C. for a time of 10 to 600 seconds, especially 15 to 300 seconds.

The substrate 10 used herein is generally a silicon substrate. The processable layer (or target film) 20 used herein includes $SiO_2$, SiN, SiON, SiOC, p-Si, α-Si, TiN, WSi, BPSG, SOG, Cr, CrO, CrON, MoSi, low dielectric film, and etch stopper film. The intermediate intervening layer 30 includes hard masks of $SiO_2$, SiN, SiON or p-Si, an undercoat in the form of carbon film, a silicon-containing intermediate film, and an organic antireflective coating.

Figure 1B:
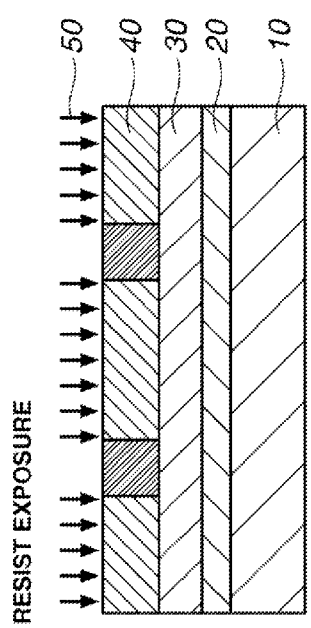

Next comes exposure depicted at 50 in FIG. 1B. In the exposure step, a photomask may be used if necessary. For the exposure, preference is given to high-energy radiation having a wavelength of 140 to 250 nm, EUV having a wavelength of 13.5 nm, and EB, and especially ArF excimer laser radiation of 193 nm. The exposure may be done either in a dry atmosphere such as air or nitrogen stream or by immersion lithography.

The immersion lithography uses deionized water or liquids having a refractive index of at least 1 and highly transparent to the exposure wavelength such as alkanes as the immersion solvent. In the immersion lithography, the resist film as prebaked is exposed to light through a projection lens while the liquid, typically water is introduced between the resist film and the projection lens. Since this allows lenses to be designed to a NA of 1.0 or higher, formation of finer feature size patterns is possible. The immersion lithography is important for the ArF lithography to survive to the 45-nm node. In the case of immersion lithography, deionized water rinsing for post-soaking) may be carried out after exposure for removing water droplets left on the resist film, or a protective film may be applied onto the resist film after pre-baking for preventing any leach-out from the resist film and improving water slip on the film surface.

The resist protective film used in the immersion lithography is preferably formed from a solution of a polymer which is soluble in the developer, in a solvent selected from alcohols of at least 4 carbon atoms, ethers of 8 to 12 carbon atoms, and mixtures thereof. The protective film-forming composition used herein may be based on a polymer comprising recurring units derived from a monomer having a 1,1,1,3,3,3-hexafluoro-2-propanol residue, for example. While the protective film must dissolve in the organic solvent developer, the polymer comprising recurring units having a 1,1,1,3,3,3-hexafluoro-2-propanol residue dissolves in organic solvent developers. In particular, protective film-forming materials having 1,1,1,3,3,3-hexafluoro-2-propanol residues as described in JP-A 2007-025634, JP-A 2008-003569, JP-A 2008-081716 and JP-A 2008-111089 readily dissolve in organic solvent developers.

In the protective film-forming composition, an amine compound or amine salt may be added, or a polymer comprising recurring units containing an amino group or ammonium salt may be used. This component is effective for controlling diffusion of the acid generated in the exposed region of the photoresist film to the unexposed region for thereby preventing any hole opening failure. Useful protective film materials having an amine compound added thereto are described in JP-A 2008-003569, and useful polymers comprising recurring units having an amino group or amine salt are described in JP-A 2007-316448. The amine compound or amine salt may be selected from the compounds enumerated above as quencher (E). An appropriate amount of the amine compound or amine salt added is preferably 0.01 to 10 parts, more preferably 0.02 to Is 8 parts by weight per 100 parts by weight of the base polymer.

After formation of the resist film, deionized water rinsing (or post-soaking) may be carried out for extracting the acid generator and the like from the film surface or washing away particles, or after exposure, rinsing (or post-soaking) may be carried out for removing water droplets left on the resist film. If the acid evaporating from the exposed region during PEB deposits on the unexposed region to deprotect the protective group on the surface of the unexposed region, there is a possibility that the surface s edges of holes or lines of a hole or line-and-space pattern after development are bridged. Particularly in the case of negative development, regions surrounding the holes receive light so that acid is generated therein. There is a possibility that the holes are not opened if the acid outside the holes evaporates and deposits inside the holes during PES. Provision of a protective film is effective for preventing evaporation of acid and for avoiding any hole opening failure. A protective film having an amine compound or amine salt added thereto is more effective for preventing acid evaporation. On the other hand, a protective film to which an acid compound such as a carboxyl or sulfo group is added or which is based on a polymer having copolymerized therein monomeric units containing a carboxyl or sulfa group is undesirable because of a potential hole opening failure.

With respect to the recurring units having a 1,1,1,3,3,3-hexafluoro-2-propanol residue, those monomers having a —C(CF$_3$) (OH) group, i.e., a carbon atom having CF$_3$ and OH radicals bonded thereto are preferably selected among the exemplary monomers listed for the polymeric surfactant. The amino group-containing compound may be selected from the exemplary amine compounds described in JP-A 2008-111103, paragraphs [0146] to [0164]. As the amine salt-containing compound, salts of the foregoing amine compounds with carboxylic acid or sulfonic acid may be used.

The solvent in the protective film-forming composition is preferably selected from alcohols of at least 4 carbon atoms, ethers of 8 to 12 carbon atoms, and mixtures thereof. Suitable alcohols of at least 4 carbon atoms include 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether solvents of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether.

Exposure is preferably performed in an exposure dose of about 1 to 200 mJ/cm$^2$, more preferably about 10 to 100 mJ/cm$^2$. This is followed by baking (PEB) on a hot plate at 60 to 150° C. for 1 to 5 minutes, preferably at 84 to 140° C. for 1 to 3 minutes.

Figure 1C:
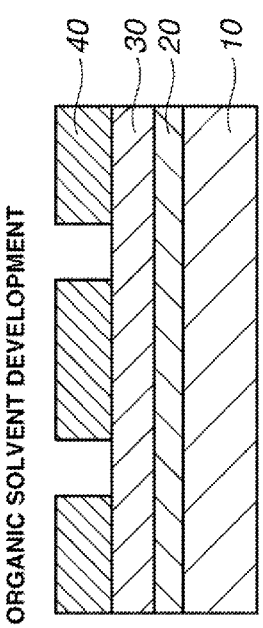

Thereafter the exposed resist film is developed in an organic solvent base developer for 0.1 to 3 minutes, preferably 0.5 to 2 minutes by any conventional techniques such as dip, puddle and spray techniques. In this way, the unexposed region of resist film was dissolved away, leaving a negative resist pattern 40 on the substrate 10 as shown in FIG. 1C.

The developer used herein is based on an organic solvent which is preferably selected from among ketones such as 2-octanone, 2-nonanone, 2-heptanone, 3-heptanone, 4-heptanone, 2-hexanone, 3-hexanone, diisobutyl ketone, methylcyclohexanone, acetophenone, and methylacetophenone, and esters such as propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

These solvents may be used alone or in admixture of two or more. The organic solvent or solvents are preferably present in a total amount of at least 60% by weight of the developer. More preferably the organic solvent(s) accounts for 80 to 100% by weight of the developer. A surfactant may be added to the developer while it may be selected from the same list of compounds as exemplified for the surfactant to be added to the resist composition. The surfactant is preferably added in an amount of 0 to 5%, more preferably 0 to 3% by weight of the developer.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2, 3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, coterie, cyclohexene, methylcyclohexene, dimethylcyclohexene, cycloheptene, and cyclooctene. Suitable alkynes of 6 to 12 carbon atoms include hexyne, heptyne, and octyne. The solvents may be used alone or in admixture. Besides the foregoing solvents, aromatic solvents may be used, for example, toluene, xylene, ethylbenzene, isopropylbenzene, t-butylbenzene and mesitylene.

While rinsing is effective for mitigating collapse and defect formation in the resist pattern, rinsing is not essential. If the rinsing step is omitted, the amount of solvent used in the process may be reduced.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

In another embodiment, the hole pattern printed as the reversal pattern may be shrunk by the RELACS method. A shrink agent is coated on the hole pattern and baked. During bake, the acid catalyst diffuses from the resist layer to promote crosslinking of the shrink agent on the resist surface so that the shrink agent is attached to side walls of the ho pattern. The baking is preferably at a temperature of 70 to 180° C., more preferably 80 to 170° C. for a time of 10 to 300 seconds. Then the extra shrink agent is removed, and the hole pattern is reduced.

EXAMPLE

Synthesis Examples, Examples and Comparative Examples are given below by way of illustration and not by way of limitation. The abbreviation "pbw" is parts by weight. For all polymers, Mw and Mn are determined by GPC versus polystyrene standards using tetrahydrofuran solvent. MEK stands for methyl ethyl ketone, MIBK for methyl isobutyl ketone. Analytic instruments are as shown below.

IR: NICOLET 6700 by Thermo Fisher Scientific Inc.
$^1$H-NMR: ECA-500 by JEOL Ltd.
$^{19}$F-NMR: ECA-500 by JEOL Ltd.
LC-MS: Agilent 6130 by Agilent Technologies
1) Synthesis of PAG Synthesis Example 1

Synthesis of PAG-1
PAG-1 was synthesized according to the following scheme.

Under ice cooling, a solution of 2.98 g of trifluoromethanesulfonamide and 6.33 g of pyridine in 5 g of acetonitrile was added dropwise to a mixture of 2.70 g of sulfuryl chloride and 5 g of acetonitrile. The reaction solution was stirred at room temperature for 1 hour for aging. Under ice cooling, a solution of 9.01 g of diphenyl(p-hydroxyphenyl)sulfonium p-toluenesulfate and 0.49 g of N,N-dimethylaminopyridine in 10 g of acetonitrile was added dropwise to the reaction solution. The reaction solution was heated at 80-100° C. in an oil bath for 4 days for aging. The solution was allowed to cool down to 50° C. Thereafter, 4.88 g of meso-erythritol, 3.16 g of pyridine, and 5 g of acetonitrile were added to the solution, which was stirred at 80° C. for 3 hours. Water, 20 g, was added to the solution, acetonitrile was removed by vacuum concentration, and the concentrate was extracted with 120 g of methylene chloride. The organic layer was washed twice with 20 g of deionized water, twice with 20 g of 1 wt % hydrochloric acid, and three times with 20 g of deionized water, and concentrated under reduced pressure. Steps of adding 50 g of diisopropyl ether to the concentrate, stirring, and removing a supernatant were repeated three times. The residue was dissolved in 150 g of MIBK. Then 20 g of methanol and 50 g of deionized water were added to the solution, which was stirred. The organic layer was taken out, and further washed twice with 50 g of deionized water and once with a mixture of 50 g deionized water and 20 g methanol. After vacuum concentration, 50 g of isopropyl ether was added to the concentrate. During stirring, a white solid precipitated. The solid was filtered and dried in vacuum, obtaining 400 g of the target compound, PAG-1 (yield 40%). Analytic results by IR, $^1$H-NMR, $^{19}$F-NMR and LC-MS are shown below.

IR (D-ATR): ν=3093, 3066, 1585, 1486, 1449, 1361, 1328, 1191, 1160, 1140, 1055, 1009, 1000, 862, 847, 793, 758, 727, 710, 687, 651, 636, 629, 606, 564 cm$^{-1}$ $^1$H-NMR (500 MHz, DMSO-d$_6$): δ=7.63 (2H, m), 7.75-7.57 (10H, m), 7.91 (2H, m) ppm $^{19}$F-NMR (500 MHz, DMSO-d$_6$): δ-79.0 (3F, s) ppm LC-MS: [M+H]$^+$=489.9 (corresponding to $C_{19}H_{15}F_3NO_5S_3$+H$^+$)

Synthesis Example 2

Synthesis of PAG-2
PAG-2 was synthesized according to the following scheme.

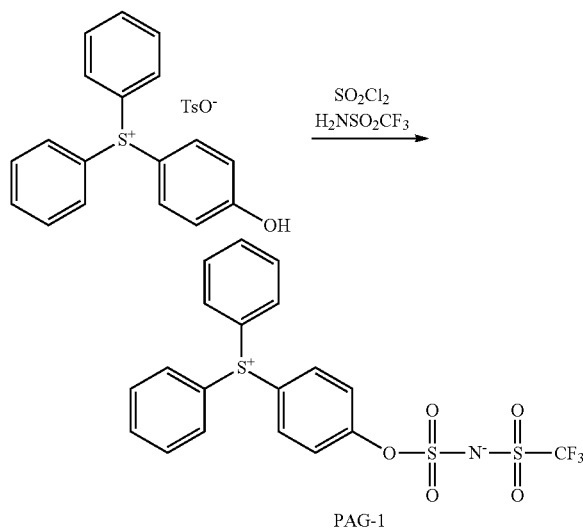

PAG-1

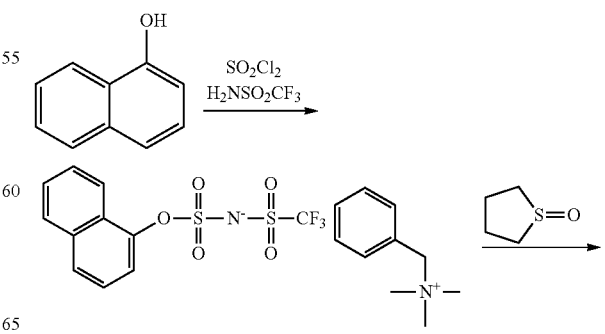

Intermediate A

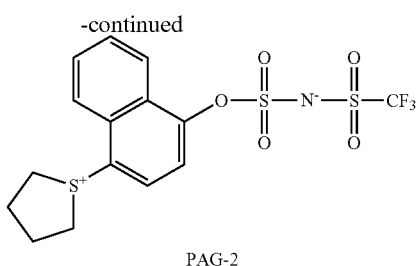

PAG-2

Synthesis Example 2-1

Synthesis of Intermediate A

Under ice cooling, a solution of 2.98 g of trifluoromethanesuifonamide and 6.01 g of pyridine in 10 g of acetonitrile was added dropwise to a mixture of 2.70 g of sulfuryl chloride and 10 g of acetonitrile. The reaction solution was stirred under ice cooling for 5 minutes and at room temperature for 1 hour. Under ice cooling, a solution of 4.33 g of 1-naphthol and 0.12 g of N,N-dimethylaminopyridine in 20 g of acetonitrile was added dropwise to the reaction solution. The solution was stirred at 70° C. for 5 days for aging. Methanol, 5 g, was added to the reaction solution, which was aged at 70° C. for 24 hours. Acetonitrile was removed by vacuum concentration, and 80 g of MIBK was added to the concentrate, which was washed three times with 40 g of water. To the organic layer, 4.09 g of benzyltrimethylammonium chloride and 40 g of water were added, followed by stirring for 1 hour. The organic layer was washed once with 40 g of 10 wt % benzyltrimethylammonium chloride aqueous solution, and five times with 40 g of water, followed by vacuum concentration to remove the solvent. Steps of adding 70 g of dilsopropyl ether to the concentrate, stirring for 5 minutes, and removing a supernatant were repeated seven times. Subsequent vacuum concentration gave 5.98 g of an oily matter, Intermediate A (yield 59%). Analytic results by $^1$H-NMR and $^{19}$F-NMR are shown below.

$^1$H-NMR (500 MHz, DMSO-d$_6$): δ3.00 (9H, s), 4.49 (2H, s), 7.48-7.68 (9H, m), 7.82 (1H, d), 7.95 (1H, m), 8.21 (1H, m) ppm $^{19}$F-NMR (500 MHz, DMSO-d$_6$): δ=−79.0 (3F, s) ppm

Synthesis Example 2-2

Synthesis of PAG-2

Under ice cooling, 1.12 g of tetramethylene sulfoxide was added dropwise to a mixture of 5.00 g of Intermediate A and 10 g of Eaton reagent (phosphorus pentoxide/methanesulfonic acid solution, weight ratio 1/10). The solution was stirred under ice cooling for 4 hours and at room temperature for 15 hours for aging. Water, 30 g, was added to the solution to quench the reaction. The mixture was held stationary, during which it separated into two layers. The supernatant was removed. This was followed by steps of adding 20 g of diisopropyl ether to the lower layer, stirring, and removing a supernatant. The residue was dissolved in 60 g of dichloromethane and washed four times with 30 g of water, followed by vacuum concentration to remove the solvent. The concentrate was added dropwise to 60 g of diisopropyl ether, a supernatant was removed, dichloromethane was added in divided portions until a solid precipitated. The solid precipitate was filtered and dried in vacuum, obtaining 1.60 g of the target compound, PAG-2 (yield 36%). Analytic results by IR, $^1$H-NMR, $^1$F-NMR and LC-MS are shown below.

IR (D-ATR): υ=3106, 3018, 2959, 1621, 1594, 1566, 1506, 1459, 1422, 1373, 1352, 1328, 1264, 1228, 1192, 1181, 1169, 1155, 1146, 1132, 1068, 1048, 942, 881, 835, 803, 773, 762, 701, 651, 633, 602, 590, 571 cm$^{-1}$ $^1$H-NMR (500 MHz, DMSO-d$_6$): δ2.33 (2H, m), 2.44 (2H, m), 3.87 (2H, m), 4.07 (2H, m), 7.79 (1H, d), 7.84 (1H, m), 7.91 (1H, m), 8.26 (1H, d), 8.38 (1H, t) ppm $^{19}$F-NMR (500 MHz, DMSO-d$_6$): δ=−79.0 (3F, s) ppm LC-MS: [M+H]$^+$=442.0 (corresponding to $C_{15}H_{14}F_3NO_5S_3$+H$^+$)

Synthesis Example 3

Synthesis of PAG-3

PAG-3 was synthesized according to the following scheme.

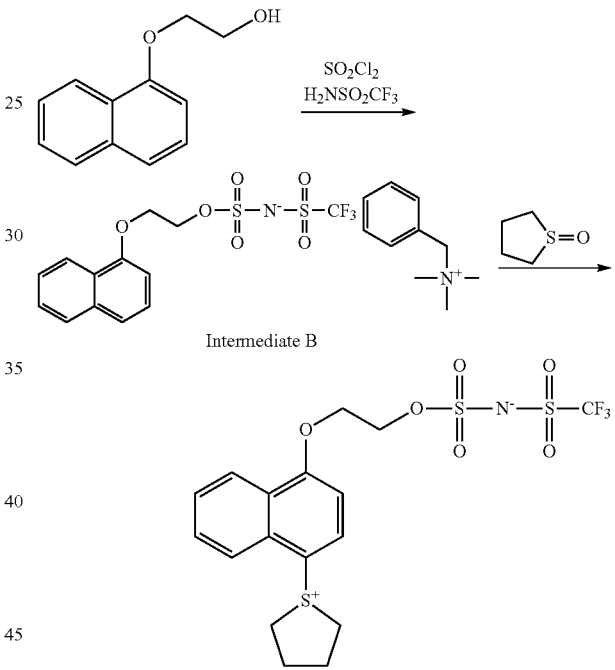

PAG-3

Synthesis Example 3-1

Synthesis of Intermediate B

Under ice cooling, a solution of 3.58 g of trifluoromethanesulfonamide and 6.01 g of pyridine in 10 g of acetonitrile was added dropwise to a mixture of 3.24 g of sulfuryl chloride and 10 g of acetonitrile. The reaction solution was stirred at room temperature for 1.5 hours. Under ice cooling, a solution of 4.43 g of 2-naphthoxyethanol and 0.12 g of N,N-dimethylaminopyridine in 10 g of acetonitrile was added dropwise to the reaction solution. The solution was stirred at 50° C. for 20 hours and at 80° C. for 4 hours for aging. The reaction solution was quenched by adding 5 g of methanol. To the solution were added 80 g of MIBK, 40 g of water, and 1 g of pyridine. An organic layer was taken out and washed twice with 40 g of water. To the organic layer, 4.46 g of benzyltrimethylammonium chloride and 40 g of water were added, followed by stirring for 30 minutes. The organic layer was taken out, washed twice with a mixture of 40 g water and 3 g methanol, and twice with 40 g of water, followed by vacuum concentration to remove the solvent. The concentrate was diluted with 5 g of dichloroethane. Steps of adding 60 g of diisopropyl ether to the concentrate, stirring for 5 minutes, and removing a supernatant were repeated four times. Subsequent vacuum concentration gave 10.31 g of an oily matter, Inteiuediate B (yield 90%). Analytic results by IR, $^1$H-NMR and $^{19}$F-NMR are shown below.

IR (D-ATR): υ=3054, 2961, 1595, 1581, 1.509, 1488, 1477, 1457, 1397, 1338, 1270, 1227, 1191, 1163, 1141, 1107, 1070, 1036, 930, 890, 797, 777, 727, 703, 607, 569 cm$^{-1}$ $^1$H-NMR (00 MHz, DMSO-d$_6$): δ=3.00 (9H, s), 4.37 (2H, m), 4.45 (2H, m), 4.49 (2H, s), 6.96 (1H, d), 7.40 (1H, t), 7.46-7.56 (8H, m), 7.85 (1H, m), 8.21 (1H, m) ppm $^{19}$F-NMR (500 MHz, DMSO-d$_6$): δ=−78.8 (3F, s) ppm Synthesis Example 3-2

Synthesis of PAG-3

Under ice cooling, 0.60 g of tetramethylene sulfoxide was added dropwise to a mixture of 3.00 g of Intermediate B and 6 g of Eaton reagent. The solution was stirred under ice cooling for 4 hours and at room temperature for 16 hours for aging. Water, 15 g, was added to the solution to quench the reaction. A solid precipitate was filtered and washed with 20 g of water and then with 20 g of diisoproyl ether. The solid was dissolved in 2 g of dimethyl sulfoxide, which was poured into a mixture of 20 mL acetone and 20 mL water for crystallization. The solid was filtered and dried in vacuum, obtaining 1.42 g of the target compound, PAG-3 (yield 55%). Analytic results by IR, $^1$H-NMR, $^{19}$F-NMR and LC-MS are shown below.

IR (D-ATR): υ=3099, 2960, 1623, 1592, 1573, 1509, 1464, 1427, 1377, 1330, 1320, 1280, 1270, 1254, 1224, 1179, 1135, 1101, 1065, 1043, 1022, 933, 889, 835, 813, 761, 729, 634, 613, 590, 569 cm$^{-1}$ $^1$H-NMR (500 MHz, DMSO-d$_6$): δ2.32 (2H, m), 2.43 (2H, m), 3.79 (2H, m), 4.04 (2H, m), 4.48 (2H, m), 4.54 (2H, m), 7.23 (1H, d), 7.74 (1H, t), 786 (1H, m), 8.11 (1H, d), 8.32 (1H, d), 8.42 (1H, d) ppm $^{19}$F-NMR (500 MHz, DMSO-d$_6$): δ=−78.8 (3F, s) ppm LC-MS: [M+H]$^+$=486.0 (corresponding to C$_{17}$H$_{18}$F$_3$NO$_6$S$_3$+H$^+$)

Synthesis Example 4

Synthesis of PAG-4

PAG-4 was synthesized according to the following scheme.

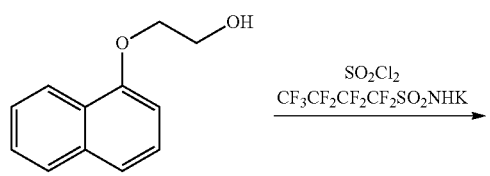

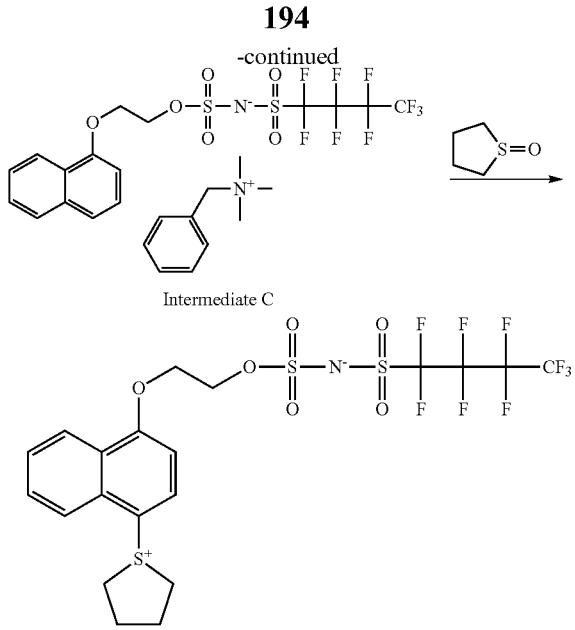

Synthesis Example 4-1

Synthesis of Intermediate C

A mixture of 2.02 g of sulfuryl chloride and 20 g of acetonitrile was ice cooled, 5.06 g of potassium nonafluorobutanesulfonamide was added thereto, and 2.73 g of pyridine was added dropwise under ice cooling. The solution was stirred at room temperature for 1 hour. A mixture of 14.04 g of a 720 g/mol solution of 2-naphthoxyethanol in methylene chloride and 0.18 g of N,N-dimethylaminopyridine was added dropwise to the solution at room temperature. The solution was stirred at 50° C. for 19 hours for aging. The reaction solution was quenched by adding 30 g of water. To the solution were added 50 g of MIBK and 20 g of water. An organic layer was taken out and washed with 30 g of water. To the organic layer, 2.79 g of benzyltrimethylammonium chloride and 30 g of water were added, followed by stirring for 30 minutes. The organic layer was taken out and washed twice with 30 g of water, followed by vacuum concentration to remove the solvent. Steps of adding 50 g of diisopropyl ether to the concentrate, stirring for 5 minutes, and removing a supernatant were repeated three times. Subsequent vacuum concentration gave 8.35 g of an oily matter, Intermediate C (yield 78%). Analytic results by $^1$H-NMR and $^{19}$F-NMR are shown below.

$^1$H-NMR (500 MHz, DMSO-d$_6$) δ=3.00 (9H, s), 4.37 (2H, m), 4.46 2H, m), 4.49 (2H, s), 6.96 (1H, d), 7.40 (1H, t), 7.46-7.56 (8H, m), 7.86 (1H, d), 8.20 (1H, d) ppm $^{19}$F-NMR (500 MHz, DMSO-d$_6$): δ=−81.8 (3F, m), −114.2 (2F, m), −122.5 (2F, m), −127.1 (2F, m) ppm Synthesis Example 4-2

Synthesis of PAG-4

Under ice cooling, 0.64 g of tetramethylene sulfoxide was added dropwise to a mixture of 4.00 g of Intermediate C and 8 g of Eaton reagent. The solution was stirred under ice cooling for 4 hours and at room temperature for 18 hours for aging. The reaction solution was quenched by adding 15 g of water and 6.4 g of 29 wt % aqueous ammonia. To the solution was added 30 g of methylene chloride. A solid precipitate was filtered and washed with 20 g of water and then with 20 g of diisopropyl ether. The solid was dissolved in 2 g of dimethyl sulfoxide, which was poured into 50 mL of water for crystallization. The solid was filtered and washed in sequence with 20 g of water, 20 g of diisopropyl ether, and 20 g of methylene chloride. Subsequent vacuum drying gave 2.90 g of the target compound, PAG-4 (yield 75%). Analytic results by IR, $^1$H-NMR, $^{19}$F-NMR and LC-MS are shown below.

IR (D-ATR): ν=3427, 3092, 2962, 1589, 1571, 1510, 1463, 1448, 1429, 1373, 1347, 1324, 1273, 1252, 1213, 1191, 1169, 1135, 1089, 1075, 1045, 1030, 1009, 950, 920, 881, 856, 837, 795, 786, 765, 750, 733, 716, 696, 644, 615, 587 m$^{-1}$ $^1$H-NMR (500 MHz, DMSO-d$_6$):
δ=2.31 (2H, m), 2.43 (2H, m), 3.79 (2H, m), 4.04 (2H, m), 4.50 (2H, m), 7.73 (1H, m), 7.87 (1H, m), 8.12 (1H, d), 8.32 (1H, d), 8.41 (1H, d) ppm $^{19}$F-NMR (500 MHz, DMSO-d$_6$): δ=−81.8 (3F, m), −114.2 (2F, m), −122.5 (2F, m), −127.1 (2F, m) ppm LC-MS: [M+H]$^+$=636.0 (corresponding to C$_{20}$H$_{18}$F$_9$NO$_6$S$_3$+H$^+$)

Synthesis Example 5

Synthesis of PAG-5

PAG-5 was synthesized according to the following scheme.

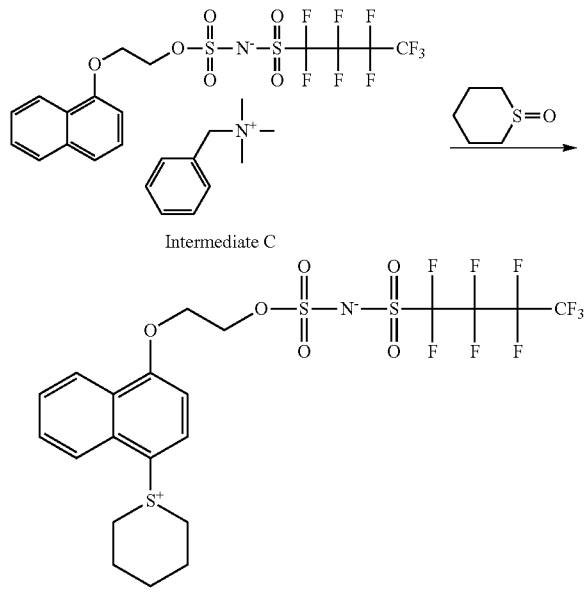

Under ice cooling, 0.62 g of pentamethylene sulfoxide was added dropwise to a mixture of 2.15 g of Intermediate C and 8.6 g of Eaton reagent. The solution was stirred at room temperature for 18 hours for aging. The reaction solution was quenched by adding 30 g of water. To the solution was added 30 g of MIBK. A solid precipitate was filtered, followed by addition of 5 g of methanol, stirring and further addition of 50 g of water. A solid precipitate was collected by filtration, and dissolved in 25 g of dimethyl sulfoxide, which was poured into 60 g of water for crystallization. The solid was filtered, washed with 20 g of diiso-propyl ether and dried in vacuum, obtaining 0.76 g of the target compound, PAG-5 (yield 38%). Analytic results by IR, $^1$H-NMR, $^{19}$F-NMR and LC-MS are shown below.

IR (D-ATR): ν=3109, 3015, 2953, 2871, 1591, 1572, 1511, 1451, 1434, 1386, 1377, 1334, 1318, 1275, 1232, 1201. 1165, 1137, 1094, 1042, 1028, 1009, 969, 949, 915, 878, 820, 798, 786, 769, 733, 696, 607, 585, 575, 560 cm$^{-1}$ $^1$H-NMR (500 MHz, DMSO-d$_6$): δ1.71 (1H, m), 1.84 (1H, m), 1.99 (2H, m), 2.33 (2H, m), 3.84 (4H, m), 4.54 (4H, m), 7.37 (1H, d), 7.72 (1H, m), 7.84 (1H, m), 8.36 (1H, d), 8.41 (1H, d), 8.51 (1H, d) ppm $^{19}$F-NMR (500 MHz, DMSO-d$_6$): δ=81.8 (3F, m), −114.2 (2F, m), −122.5 (2F, m), −127.1 (2F, m) ppm LC-MS: [M+H]$^+$=650.0 (corresponding to C$_{21}$H$_{20}$F$_9$NO$_6$S$_3$+H$^+$)

2) Synthesis of Base Resin

Synthesis Example 6

Synthesis of Polymer P-1

In a flask under nitrogen atmosphere, 22 g of 1-t-butyl-cyclopentyl methacrylate, 17 g of 2-oxotetrahydrofuran-3-yl methacrylate, 0.48 g of dimethyl 2,2'-azobis(2-methylpropionate) (V-601 by Wako Pure Chemical Industries, Ltd.), 0.41 g of 2-mercaptoethanol, and 50 g of MEK were combined to form a monomer/initiator solution. Another flask in nitrogen atmosphere was charged with 23 g of MEK, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of a copolymer (Polymer P-1) in white powder form (yield 90%). On GPC analysis, the copolymer had a Mw of 9,640 and a dispersity Mw/Mn of 1.90.

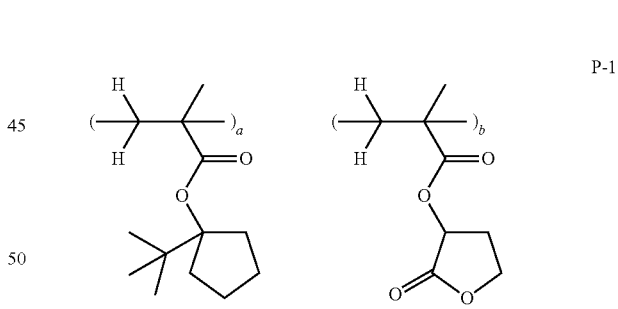

(a = 0.50, b = 0.50)

Synthesis Examples 7 to 12

Synthesis of Polymers P-2 to P-6

Polymers P-2 to P-6 were synthesized by the same procedure as in Synthesis Example 6 aside from changing the type and amount of monomers. Table 1 shows the proportion in molar ratio) of units incorporated in these polymers. The structure of recurring units is shown in Tables 2 and 3.

TABLE 1

| Resin | Unit 1 (molar ratio) | Unit 2 (molar ratio) | Unit 3 (molar ratio) | Unit 4 (molar ratio) |
|---|---|---|---|---|
| P-1 | A-1 (0.50) | B-1 (0.50) | — | — |
| P-2 | A-1 (0.50) | B-2 (0.50) | — | — |
| P-3 | A-1 (0.40) | B-1 (0.45) | B-3 (0.15) | — |
| P-4 | A-2 (0.20) | A-3 (0.30) | B-1 (0.40) | B-4 (0.10) |
| P-5 | A-2 (0.20) | A-3 (0.30) | B-2 (0.40) | B-4 (0.10) |
| P-6 | A-4 (0.50) | B-3 (0.50) | — | — |

TABLE 2

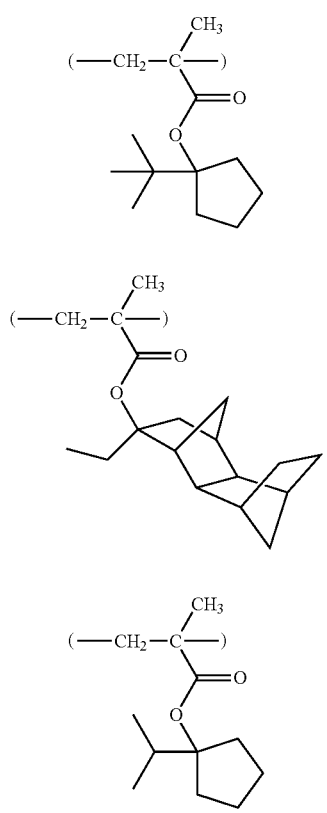
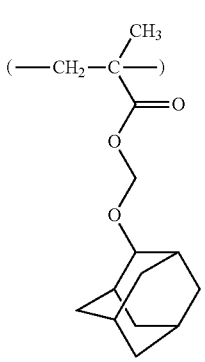 [SMILES: CCC(C)(C)C(=O)OCOC1C2CC3CC(C2)CC1C3]

TABLE 3

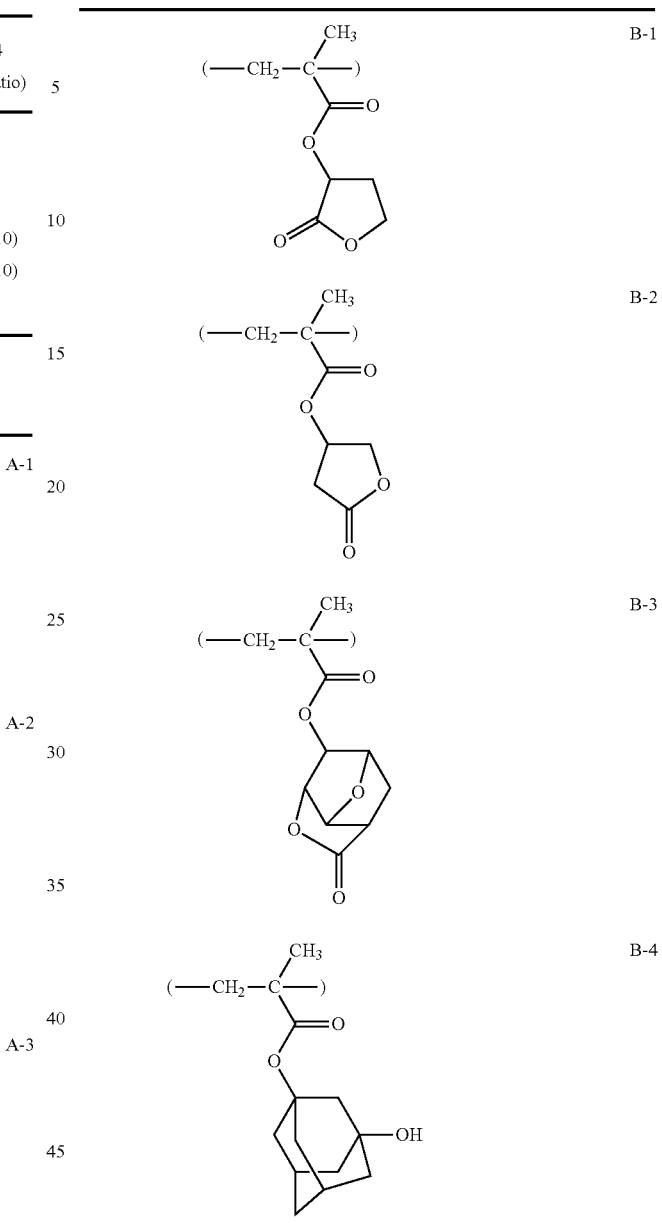

3) Preparation of Resist Composition

Examples 1-1 to 1-9 & Comparative Examples 1-1 to 1-7

Resist compositions in solution form were prepared by dissolving a photoacid generator (Synthesis Examples 1 to 5), base resin (Synthesis Examples 6 to 12), optionally another acid generator (PAG-A to PAG-G), quencher (Q-1), and alkali-soluble surfactant (SF-1) in an organic solvent containing 0.01 wt % of surfactant A, and filtering through a Teflone® filter with a pore size of 0.2 μm. Tables 4 and 5 show the formulation of the resulting resist compositions.

The solvent, quencher (Q-1), other acid generator (PAG-A to PAG-G), alkali-soluble surfactant (SF-1) and surfactant A used herein are identified below.

Quencher (Q-1): 2-(4-morpholinyl)ethyl octadecanoate

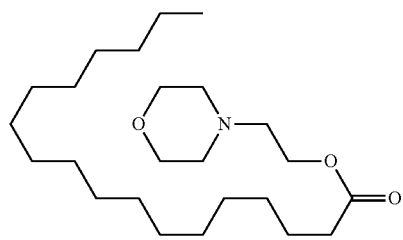
(Q-1)

Solvent:
  PGMEA=propylene glycol monomethyl ether acetate
  GBL=γ-butyrolactone Other Photoacid Generator
PAG-A: triphenylsulfonium bis(trifluoromethanesulfonyl) imide

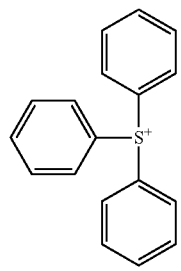
PAG-A

PAG-B: compound described in JP-A 2011-016746, synthesized according to its teaching

PAG-B

PAG-C: compound described in JP-A 2013-167826

PAG-C

PAG-D: compound described in JP-A 2011-022560 (U.S. Pat. No. 9,116,437)

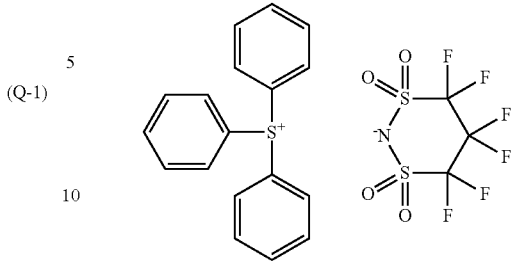
PAG-D

PAG-E: compound described in JP-A 2011-022560

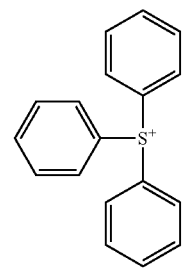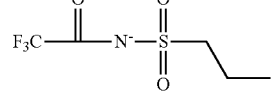
PAG-E

PAG-F: compound described in JP-A 2013-167826

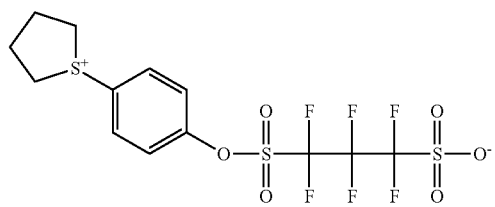
PAG-F

PAG-G: compound described in JP-A 2013-167826

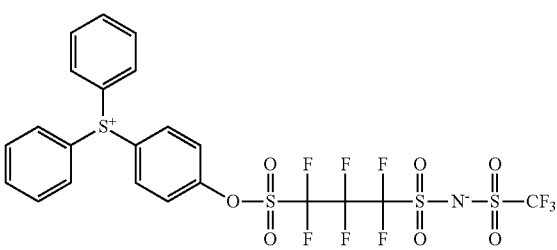
PAG-G

Alka-Soluble Surfactant (SF-1):
  poly(2,2,3,3,4,4,4-heptafluoro-1-isobutyl-1-butyl methacrylate/9-(2,2,2-trifluoro-1-trifluoroethyloxycarbonyl)-4-oxatricyclo-[4.2.1.0$^{3,7}$]nonan-5-on-2-yl methacrylate)
  Mw=7,700
  Mw/Mn=1.82

(SF-1)

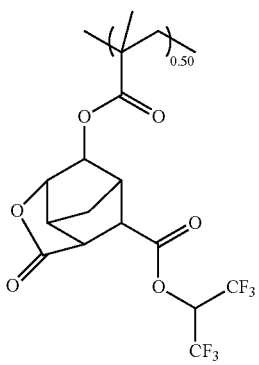

Surfactant A: 3-methyl-3-(2,2,2-trifluoroethoxymethyl)-oxetane/tetrahydrofuran/2,2-dimethyl-1,3-propanediol copolymer (Omnova Solutions, Inc.)

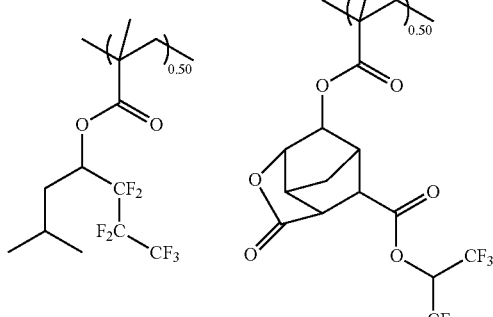

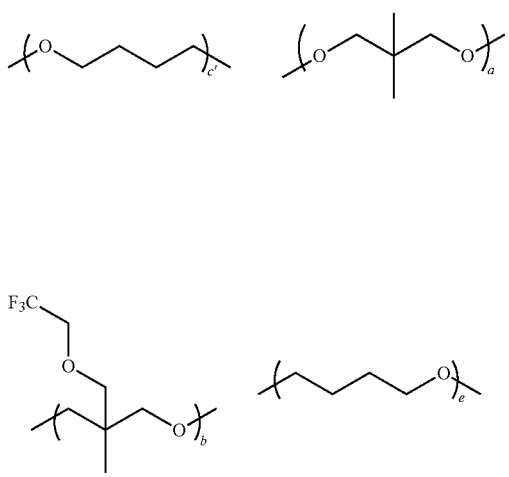

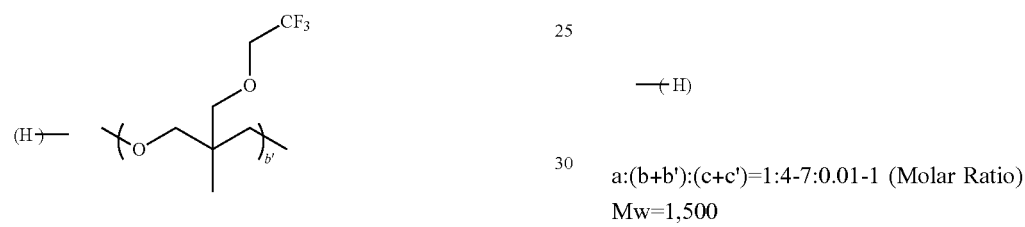

a:(b+b'):(c+c')=1:4-7:0.01-1 (Molar Ratio)
Mw=1,500

TABLE 4

| | | Resist composition | Resin (pbw) | Acid generator (pbw) | Quencher (pbw) | Surfactant (pbw) | Solvent 1 (pbw) | Solvent 2 (pbw) |
|---|---|---|---|---|---|---|---|---|
| Example | 1-1 | R-1 | P-1 (80) | PAG-1 (8.0) | — | SF-1 (3.0) | PGMEA (1,536) | GBL (384) |
| | 1-2 | R-2 | P-1 (80) | PAG-2 (8.5) | — | SF-1 (3.0) | PGMEA (1,344) | GBL (576) |
| | 1-3 | R-3 | P-1 (80) | PAG-3 (8.5) | — | SF-1 (3.0) | PGMEA (1,344) | GBL (576) |
| | 1-4 | R-4 | P-2 (80) | PAG-4 (8.5) | — | SF-1 (3.0) | PGMEA (1,536) | GBL (384) |
| | 1-5 | R-5 | P-3 (80) | PAG-5 (9.0) | — | SF-1 (3.0) | PGMEA (1,536) | GBL (384) |
| | 1-6 | R-6 | P-4 (80) | PAG-5 (9.0) | — | SF-1 (3.0) | PGMEA (1,536) | GBL (384) |
| | 1-7 | R-7 | P-5 (80) | PAG-1 (8.0) | — | SF-1 (3.0) | PGMEA (1,536) | GBL (384) |
| | 1-8 | R-8 | P-6 (80) | PAG-2 (8.5) | Q-1 (1.5) | SF-1 (3.0) | PGMEA (1,536) | GBL (384) |
| | 1-9 | R-9 | P-2 (80) | PAG-1 (8.5) | Q-1 (1.5) | SF-1 (3.0) | PGMEA (1,536) | GBL (384) |

TABLE 5

| | | Resist composition | Resin (pbw) | Acid generator (pbw) | Quencher (pbw) | Surfactant (pbw) | Solvent 1 (pbw) | Solvent 2 (pbw) |
|---|---|---|---|---|---|---|---|---|
| Comparative Example | 1-1 | R-10 | P-2 (80) | PAG-A (8.5) | Q-1 (1.5) | SF-1 (3.0) | PGMEA (1,536) | GBL (384) |
| | 1-2 | R-11 | P-2 (80) | PAG-B (8.5) | Q-1 (1.5) | SF-1 (3.0) | PGMEA (1,536) | GBL (384) |
| | 1-3 | R-12 | P-2 (80) | PAG-C (8.5) | Q-1 (1.5) | SF-1 (3.0) | PGMEA (1,536) | GBL (384) |

TABLE 5-continued

|  | Resist composition | Resin (pbw) | Acid generator (pbw) | Quencher (pbw) | Surfactant (pbw) | Solvent 1 (pbw) | Solvent 2 (pbw) |
|---|---|---|---|---|---|---|---|
| 1-4 | R-13 | P-2 (80) | PAG-D (8.5) | Q-1 (1.5) | SF-1 (3.0) | PGMEA (1,536) | GBL (384) |
| 1-5 | R-14 | P-2 (80) | PAG-E (8.5) | Q-1 (1.5) | SF-1 (3.0) | PGMEA (1,536) | GBL (384) |
| 1-6 | R-15 | P-2 (80) | PAG-F (8.5) | Q-1 (1.5) | SF-1 (3.0) | PGMEA (1,536) | GBL (384) |
| 1-7 | R-16 | P-2 (80) | PAG-G (8.5) | Q-1 (1.5) | SF-1 (3.0) | PGMEA (1,536) | GBL (384) |

4) ArF Lithography Patterning Test #1: Evaluation of Hole Pattern

Examples 2-1 to 2-9 and Comparative Examples 2-1 to 2-7

On a substrate, a spin-on carbon film ODL-50 (Shin-Etsu Chemical Co., Ltd.) having a carbon content of 80 wt % was deposited to a thickness of 200 nm, and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (Inventive R-1 to R-9 or Comparative R-10 to R-16) was spin coated and baked on a hot plate at 100° C. for 60 seconds to form a resist film of 100 nm thick.

Using an ArF excimer laser immersion lithography stepper (NSR-610C by Nikon Corp., NA 1.30, σ0.98/0.78, dipole opening 20 deg., azimuthally polarized illumination, dipole illumination, 6% halftone phase shift mask), the resist film was exposed through a first mask having X-axis direction lines with a pitch of 80 nm and a width of 40 nm (on-wafer size) and then through a second mask having Y-axis direction lines with a pitch of 80 nm and a width of 40 nm (on-wafer size). After exposure, the resist film was baked (PEB) at the temperature shown in Table 6 for 60 seconds and developed. Specifically, butyl acetate was injected from a development nozzle for 3 seconds while the wafer was spun at 30 rpm, which was followed by stationary puddle development for 27 seconds.

[Evaluation of Sensitivity]

The resist pattern thus formed was observed under an electron microscope. The optimum dose (Eop) is a dose (mJ/cm$^2$) which provides a hole pattern having a diameter of 40 nm at a pitch of 80 nm.

[Evaluation of Mask Error Factor (MEF)]

A pattern was formed by exposure in the optimum dose (determined in the sensitivity evaluation) through a mask with the pitch fixed and the line width varied. MEF was calculated from variations of the mask line width and the pattern space width according to the following equation:

MEF=(pattern space width)/(mask line width)−b wherein b is a constant. A value closer to unity (1) indicates better performance.

[Evaluation of Depth-of-Focus (DOF) Margin]

The hole size printed at the optimum dose was measured under TD-SEM (S-9380 by Hitachi Hitechnologies, Ltd.). The margin of DOF capable of forming a resist pattern with a size of 40±5 nm was determined. A larger value indicates a smaller change of pattern size per DOF change and hence, better DOF margin.

The results are shown in Table 6.

TABLE 6

|  |  | Resist composition | PEB temp. (° C.) | Eop (mJ/cm$^2$) | MEF | DOF (nm) |
|---|---|---|---|---|---|---|
| Example | 2-1 | R-1 | 85 | 26 | 2.45 | 100 |
|  | 2-2 | R-2 | 85 | 30 | 2.88 | 120 |
|  | 2-3 | R-3 | 85 | 31 | 2.90 | 90 |
|  | 2-4 | R-4 | 85 | 29 | 2.91 | 105 |
|  | 2-5 | R-5 | 85 | 32 | 2.70 | 100 |
|  | 2-6 | R-6 | 90 | 29 | 2.66 | 95 |
|  | 2-7 | R-7 | 90 | 24 | 2.88 | 100 |
|  | 2-8 | R-8 | 105 | 26 | 2.98 | 110 |
|  | 2-9 | R-9 | 85 | 28 | 2.82 | 105 |
| Comparative Example | 2-1 | R-10 | 85 | 23 | 3.89 | 85 |
|  | 2-2 | R-11 | 85 | 38 | 3.30 | 90 |
|  | 2-3 | R-12 | 85 | 39 | 3.34 | 80 |
|  | 2-4 | R-13 | 85 | 23 | 4.12 | 85 |
|  | 2-5 | R-14 | 85 | 42 | 4.05 | 90 |
|  | 2-6 | R-15 | 85 | 49 | 3.59 | 80 |
|  | 2-7 | R-16 | 85 | 25 | 3.61 | 75 |

It is evident from Table 6 that when the inventive resist composition is processed by lithography and organic solvent development, a hole pattern with a good balance of sensitivity, MEF and DOF is formed.

5) ArF Lithography Patterning Test #2: Evaluation of L/S and Trench Patterns

Examples 3-1 to 3-9 and Comparative Examples 3-1 to 3-7

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 (Shin-Etsu Chemical Co Ltd.) having a silicon content of 43 wt % was deposited thereon to a thickness of 35 nm. On this substrate for trilayer process, each of the resist compositions (Inventive R-1 to R-9 or Comparative R-10 to R-16) was spin coated and baked on a hot plate at 100° C. for 60 seconds to form a resist film of 100 nm thick. Using an ArF excimer laser immersion lithography scanner NSR-610C (Nikon Corp., NA 1.30, σ0.98/0.78, 4/5 annular illumination), pattern exposure was performed through Mask A or B described below.

Mask A is a 6% halftone phase shift mask bearing a line pattern with a pitch of 100 nm and a line width of 50 nm (on-wafer size). After exposure through Mask A, the wafer was baked (PEB) for 60 seconds and developed. Specifically, butyl acetate was injected from a development nozzle for 3 seconds while the wafer was spun at 30 rpm, which was followed by stationary puddle development for 27 seconds. As a result, the unexposed regions which had been masked with Mask A were dissolved in the developer, that is, image reversal took place to form a line-and-space (L/S) pattern with a space width of 50 nm and a pitch of 100 nm.

Mask B is a 6% halftone phase shift mask bearing a line pattern with a pitch of 200 nm and a line width of 45 nm (on-wafer size). After exposure through Mask. B, the wafer was baked (PEB) for 60 seconds and developed. Specifically, butyl acetate was injected from a development nozzle for 3 seconds while the wafer was spun at 30 rpm, which was followed by stationary puddle development for 27 seconds. As a result, the unexposed regions which had been masked with Mask B were dissolved in the developer, that is, image reversal took place to form an isolated space pattern (referred to as "trench pattern", hereinafter) with a space width of 45 nm and a pitch of 200 nm.

[Evaluation of Defect Density]

Further, defects in the pattern as developed were inspected by a flaw detector KLA2800 (KLA-Tencor). A defect density (count/cm$^2$) was computed by dividing the total number of detected defects by a detection area. The pattern formed was an iterated 50-nm 1:1 L/S pattern. The defect inspection conditions included light source UV, inspected pixel size 0.28 μm, and cell-to-cell mode. In this test, the sample was rated good for a defect density of less than 0.05 defect/cm$^2$ and NG for a density of equal to or more than 0.05 defect/cm$^2$.

The results are shown in Table 7.

TABLE 7

| | | Resist composition | PEB temp. (° C.) | Eop (mJ/cm$^2$) | Profile | MEF | DOF (nm) | Defect density |
|---|---|---|---|---|---|---|---|---|
| Example | 3-1 | R-1 | 85 | 27 | Good | 2.38 | 105 | Good |
| | 3-2 | R-2 | 85 | 30 | Good | 2.88 | 110 | Good |
| | 3-3 | R-3 | 85 | 31 | Good | 2.89 | 90 | Good |
| | 3-4 | R-4 | 85 | 29 | Good | 2.93 | 105 | Good |
| | 3-5 | R-5 | 85 | 32 | Good | 2.67 | 100 | Good |
| | 3-6 | R-6 | 90 | 30 | Good | 2.70 | 95 | Good |
| | 3-7 | R-7 | 90 | 24 | Good | 3.02 | 100 | Good |
| | 3-8 | R-8 | 105 | 26 | Good | 2.91 | 110 | Good |
| | 3-9 | R-9 | 85 | 28 | Good | 2.84 | 110 | Good |
| Comparative Example | 3-1 | R-10 | 85 | 24 | NG | 3.91 | 85 | NG |
| | 3-2 | R-11 | 85 | 38 | NG | 3.40 | 90 | NG |
| | 3-3 | R-12 | 85 | 39 | NG | 3.57 | 80 | NG |
| | 3-4 | R-13 | 85 | 23 | NG | 4.12 | 85 | NG |
| | 3-5 | R-14 | 85 | 42 | NG | 4.00 | 90 | NG |
| | 3-6 | R-15 | 85 | 49 | NG | 3.61 | 80 | NG |
| | 3-7 | R-16 | 85 | 25 | NG | 3.70 | 70 | NG |

[Evaluation of Xensitivity]

As an index of sensitivity, the optimum dose (Eop, mJ/cm$^2$) which provided an L/S pattern with a space width of 50 nm and a pitch of 100 nm on exposure through Mask A was determined.

[Evaluation of Pattern Profile]

The profile of a pattern printed at the optimum dose was examined and judged good or not according to the following criterion.

Good: rectangular pattern profile with perpendicular sidewall

NG: tapered pattern profile with largely slanted sidewall, or rounded top profile due to top loss

[Evaluation of MEF]

An L/S pattern was formed by exposure in the optimum dose (determined in the sensitivity evaluation) through Mask A with the pitch fixed and the line width varied. MEF was calculated from variations of the mask line width and the pattern space width according to the following equation:

MEF=(pattern space width)/(mask line width)–b wherein b is a constant. A value closer to unity (1) indicates better performance.

[Evaluation of DOF Margin]

The exposure dose and DOF which ensured to form a trench pattern with a space width of 35 nm on exposure through Mask B were defined as the optimum exposure dose and the optimum DOF, respectively. The depth over which focus was changed that could form a resist pattern with a space width of 35 nm±10% (i.e., 31.5 nm to 38.5 nm) was determined and reported as DOF. A larger value indicates a smaller change of pattern size with a change of DOF and hence, better DOF margin.

As seen from the results of Table 7, the resist compositions within the scope of the invention offer a good balance of sensitivity, MEF and DOF when a negative pattern is formed therefrom via organic solvent development. It is confirmed that a pattern of rectangular profile is formed with minimal defects after development. These data demonstrate that the inventive resist composition is useful in the organic solvent development process.

6) ArF Lithography Patterning Test #3: Evaluation of L/S and Trench Patterns

Examples 4-1 to 4-9 and Comparative Examples 4-1 to 4-7

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 (Shin-Etsu Chemical Co., Ltd.) having a silicon content of 43 wt % was deposited thereon to a thickness of 35 nm. On this substrate for trilayer process, each of the resist compositions (Inventive R-1 to R-9 or Comparative R-10 to R-16) was spin coated and baked on a hot plate at 100° C. for 60 seconds to form a resist film of 100 nm thick. Using an ArF excimer laser immersion lithography is scanner NSR-610C (Nikon Corp., NA 1.30, σ0.98/0.78, 4/5 annular illumination), pattern exposure was performed through Mask C or D described below.

Mask C is a 6% halftone phase shift mask bearing a pattern with a pitch of 100 nm and a space width of 50 nm (on-wafer size). After exposure through Mask C, the wafer was baked (PEB) for 60 seconds and developed. Specifically, 2.38 wt % tetramethylammonium hydroxide aqueous solution was injected from a development nozzle for 3 seconds while the wafer was spun at 30 rpm, which was followed by stationary puddle development for 27 seconds. As a result, the exposed regions were dissolved in the developer, obtaining a line-and-space (L/S) pattern with a space width of 50 nm and a pitch of 100 nm.

Mask D is a 6% halftone phase shift mask bearing a pattern with a pitch of 200 nm and a space width of 45 nm (on-wafer size). After exposure through Mask D, the wafer was baked (PEB) for 60 seconds and developed. Specifically, 2.38 wt % tetramethylammonium hydroxide aqueous solution was injected from a development nozzle for 3 seconds while the wafer was spun at 30 rpm, which was followed by stationary puddle development for 27 seconds. As a result, the exposed regions were dissolved in the developer, obtaining a trench pattern with a space width of 45 nm and a pitch of 200 nm,

[Evaluation of Sensitivity]
As an index of sensitivity, the optimum dose (Eop, mJ/cm$^2$) which provided an L/S pattern with a space width of 50 nm and a pitch of 100 nm on exposure through Mask C was determined.

[Evaluation of Pattern Profile]
The profile of a pattern printed at the optimum dose was examined and judged good or not according to the following criterion.
Good: rectangular pattern profile with perpendicular sidewall
NG: tapered pattern profile with largely slanted sidewall, or rounded top profile due to top loss

[Evaluation of MEF]
An L/S pattern was formed by exposure in the optimum dose (determined in the sensitivity evaluation) through Mask C with the pitch fixed and the line width varied. MEF was calculated from variations of the mask line width and the pattern space width according to the following equation:

MEF =(pattern space width)/(mask line width)−$b$ wherein $b$ is a constant. A value closer to unity (1) indicates better performance.

[Evaluation of DOF Margin]
The exposure dose and DOF which ensured to form a trench pattern with a space width of 45 nm on exposure through Mask D were defined as the optimum exposure dose and the optimum DOF, respectively. The depth over which focus was changed that could form a resist pattern with a space width of 45 nm±10% (i.e., 40.5 nm to 49.5 nm) was determined and reported as DOF. A larger value indicates a smaller change of pattern size with a change of DOF and hence, better DOF margin.

[Evaluation of Defect Density]
Further, defects in the pattern as developed were inspected by a flaw detector KLA2800 (KLA-Tencor). A defect density (count/cm$^2$) was computed by dividing the total number of detected defects by a detection area. The pattern formed was an iterated 50-nm 1:1 L/S pattern. The defect inspection conditions included light source UV, inspected pixel size 0.28 μm, and cell-to-cell mode. In this test, the sample was rated good for a defect density of less than 0.05 defect/cm$^2$ and NG for a density of equal to or more than 0.05 defect/cm$^2$.

The results are shown in Table 8.

TABLE 8

|  |  | Resist composition | PEB temp. (° C.) | Eop (mJ/cm$^2$) | Profile | MEF | DOF (nm) | Defect density |
|---|---|---|---|---|---|---|---|---|
| Example | 4-1 | R-1 | 85 | 29 | Good | 2.56 | 65 | Good |
|  | 4-2 | R-2 | 85 | 31 | Good | 2.98 | 70 | Good |
|  | 4-3 | R-3 | 85 | 34 | Good | 2.77 | 65 | Good |
|  | 4-4 | R-4 | 85 | 30 | Good | 2.75 | 60 | Good |
|  | 4-5 | R-5 | 85 | 33 | Good | 2.59 | 65 | Good |
|  | 4-6 | R-6 | 90 | 30 | Good | 2.66 | 55 | Good |
|  | 4-7 | R-7 | 90 | 25 | Good | 3.11 | 50 | Good |
|  | 4-8 | R-8 | 105 | 28 | Good | 2.95 | 75 | Good |
|  | 4-9 | R-9 | 85 | 28 | Good | 2.74 | 75 | Good |
| Comparative Example | 4-1 | R-10 | 85 | 26 | NG | 4.12 | 25 | NG |
|  | 4-2 | R-11 | 85 | 42 | NG | 4.20 | 25 | NG |
|  | 4-3 | R-12 | 85 | 45 | NG | 4.63 | 30 | NG |
|  | 4-4 | R-13 | 85 | 27 | NG | 4.10 | 30 | NG |
|  | 4-5 | R-14 | 85 | 45 | NG | 3.99 | 25 | NG |
|  | 4-6 | R-15 | 85 | 52 | NG | 3.96 | 35 | NG |
|  | 4-7 | R-16 | 85 | 29 | NG | 3.88 | 25 | NG |

As seen from the results of Table 8, the resist compositions within the scope of the invention offer a good balance of sensitivity and MEF when a positive pattern is formed via alkaline solution development. It is confirmed that an isolated space pattern with an improved DOF margin is formed. It is also confirmed that a pattern of satisfactory profile is formed with minimal defects after development. These data demonstrate that the inventive resist composition is useful in the alkaline solution development process.

While the invention has been illustrated and described in typical embodiments, it is not intended to be limited to the details shown. Any modified embodiments having substantially the same features and achieving substantially the same results as the technical idea disclosed herein are within the spirit and scope of the invention.

Japanese Patent Application No. 2015-107652 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A sulfonium salt having the formula (1):

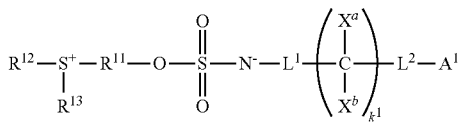
(1)

wherein $R^{11}$ is a straight, branched or cyclic $C_1$-$C_{30}$ divalent hydrocarbon group which may contain a heteroatom, $R^{12}$ and $R^{13}$ are each independently a straight, branched or cyclic $C_1$-$C_{20}$ monovalent hydrocarbon group which may contain a heteroatom, any two or more of $R^{11}$, $R^{12}$ and $R^{13}$ may bond together to form a ring with the sulfur atom to which they are attached, $L^1$ is a carbonyl bond, sulfonyl bond or sulfinyl bond, $L^2$ is a single bond, ether bond, carbonyl bond, ester bond, amide bond, sulfide bond, sulfinyl bond, sulfonyl bond, sulfonic acid ester bond, sulfinamide bond, sulfonamide bond, carbamate bond or carbonate bond, $A^1$ is hydrogen, halogen or a straight, branched or cyclic $C_1$-$C_{20}$ monovalent hydrocarbon group which may contain a heteroatom, $x^a$ and $X^b$ are each independently hydrogen, fluorine or trifluoromethyl, at least one of $X^a$ and $X^b$ is fluorine or trifluoromethyl, and $k^1$ is an integer of 1 to 4.

2. The sulfonium salt of claim 1 wherein $L^1$ is a sulfonyl bond.

3. The sulfonium salt of claim 2 wherein $L^2$ is a single bond and $A^1$ is hydrogen, fluorine or trifluoromethyl.

4. A photoacid generator comprising the sulfonium salt of claim 1.

5. A chemically amplified resist composition comprising the photoacid generator of claim 4.

6. The resist composition of claim 5, further comprising a polymer comprising recurring units having the formula (2) and recurring units having the formula (3) as base resin:

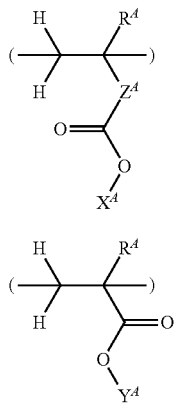

wherein $R^A$ is hydrogen, fluorine, methyl or trifluoromethyl, $Z^A$ is a single bond, phenylene group, naphthylene group or —C(=O)—O—Z'—, Z' is a straight, branched or cyclic $C_1$-$C_{10}$ alkylene group which may contain a hydroxyl radical, ether bond, ester bond or lactone ring, or phenylene group or naphthylene group, $X^A$ is an acid labile group, and $Y^A$ is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

7. The resist composition of claim 5, further comprising a photoacid generator other than the photoacid generator of claim 4.

8. The resist composition of claim 7 wherein the other photoacid generator has the formula (4) or (5):

(4)

wherein $R^{100}$, $R^{200}$ and $R^{300}$ are each independently a straight, branched or cyclic $C_1$-$C_{20}$ monovalent hydrocarbon group which may contain a heteroatom, any two or more of $R^{100}$, $R^{200}$ and $R^{300}$ may bond together to form a ring with the sulfur atom to which they are attached, $X^-$ is an anion selected from the formulae (4A) to (4D)

(4A)

(4B)

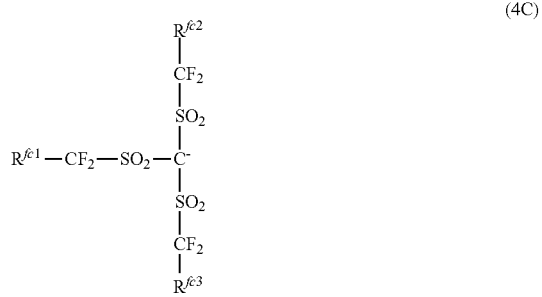
(4C)

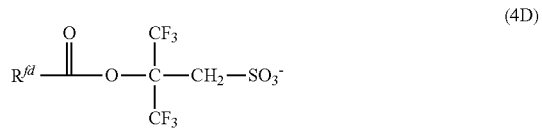
(4D)

wherein $R^{fa}$, $R^{fb1}$, $R^{fb2}$, $R^{fc1}$, $R^{fc2}$ and $R^{fc3}$ are each independently fluorine or a straight, branched or cyclic $C_1$-$C_{40}$ monovalent hydrocarbon group which may contain a heteroatom, or a pair of $R^{fb1}$ and $R^{fb2}$, or $R^{fc1}$ and $R^{fc2}$ may bond together to form a ring with the carbon atom to which they are attached and any intervening atoms, $R^{fd}$ is a straight, branched or cyclic $C_1$-$C_{40}$ monovalent hydrocarbon group which may contain a heteroatom,

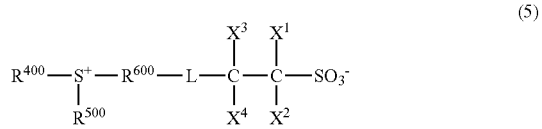
(5)

wherein $R^{400}$ and $R^{500}$ are each independently a straight, branched or cyclic $C_1$-$C_{30}$ monovalent hydrocarbon group which may contain a heteroatom, $R^{600}$ is a straight, branched or cyclic $C_1$-$C_{30}$ divalent hydrocarbon group which may contain a heteroatom, any two or more of $R^{400}$, $R^{500}$ and $R^{600}$ may bond together to form a ring with the sulfur atom to which they are attached, L is a single bond or a straight, branched or cyclic $C_1$-$C_{20}$ divalent hydrocarbon group which may contain a heteroatom, $X^1$, $X^2$, $X^3$ and $X^4$ are each independently hydrogen, fluorine or trifluoromethyl, at least one of $X^1$, $X^2$, $X^3$ and $X^4$ is fluorine or trifluoromethyl.

9. The resist composition of claim 4, further comprising a compound having the formula (6) or (7):

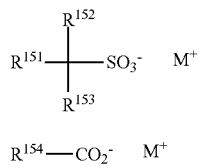

(6)

(7)

wherein $R^{151}$, $R^{152}$ and $R^{153}$ are each independently hydrogen, halogen exclusive of fluorine, or a straight, branched or cyclic $C_1$-$C_{40}$ monovalent hydrocarbon group which may contain a heteroatom, any two or more of $R^{151}$, $R^{152}$ and $R^{153}$ may bond together to form a ring with the carbon atom to which they are attached, $R^{154}$ is a straight, branched or cyclic $C_1$-$C_{40}$ monovalent hydrocarbon group which may contain a heteroatom, and $M^+$ is an onium cation.

10. The resist composition of claim 5, further comprising a quencher.

11. The resist composition of claim 5, further comprising a surfactant which is insoluble or substantially insoluble in water and soluble in alkaline developer, and/or a surfactant which is insoluble or substantially insoluble in water and alkaline developer.

12. A pattern forming process comprising the steps of applying the resist composition of claim 5 onto a substrate, prebaking to form a resist film, exposing a selected region of the resist film to KrF excimer laser, ArF excimer laser, EB or EUV, baking, and developing the exposed resist film in a developer.

13. The pattern forming process of claim 12 wherein the developing step uses an alkaline aqueous solution as the developer, thereby forming a positive pattern in which an exposed region of the resist film is dissolved away and an unexposed region of the resist film is not dissolved.

14. The pattern forming process of claim 12 wherein the developing step uses an organic solvent as the developer, thereby forming a negative pattern in which an unexposed region of the resist film is dissolved away and an exposed region of the resist film is not dissolved.

15. The pattern forming process of claim 14 wherein the organic solvent is at least one solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

16. The process of claim 12 wherein the exposure step is carried out by immersion lithography while a liquid having a refractive index of at least 1.0 is held between the resist film and a projection lens.

17. The process of claim 16, further comprising the step of coating a protective film on the resist film prior to the exposure step, wherein immersion lithography is carried out while the liquid is held between the protective film and the projection lens.

* * * * *